(12) United States Patent
Zhang et al.

(10) Patent No.: US 11,161,827 B2
(45) Date of Patent: Nov. 2, 2021

(54) CATALYTIC SYSTEMS FOR STEREOSELECTIVE SYNTHESIS OF CHIRAL AMINES BY ENANTIODIVERGENT RADICAL C—H AMINATION

(71) Applicant: Trustees of Boston College, Chestnut Hill, MA (US)

(72) Inventors: Xiao-Xiang Zhang, Newton, MA (US); Kai Lang, Boston, MA (US)

(73) Assignee: The Trustees of Boston College, Chesnut Hill (MA)

( * ) Notice: Subject to any disclaimer, the term of this patent is extended or adjusted under 35 U.S.C. 154(b) by 0 days.

(21) Appl. No.: 16/840,879

(22) Filed: Apr. 6, 2020

(65) Prior Publication Data

US 2020/0317627 A1    Oct. 8, 2020

Related U.S. Application Data

(60) Provisional application No. 62/829,713, filed on Apr. 5, 2019.

(51) Int. Cl.
| | | |
|---|---|---|
| *B01J 23/75* | (2006.01) | |
| *C07D 285/10* | (2006.01) | |
| *C07D 487/22* | (2006.01) | |
| *B01J 31/18* | (2006.01) | |

(52) U.S. Cl.
CPC .......... *C07D 285/10* (2013.01); *B01J 31/183* (2013.01); *C07D 487/22* (2013.01); *B01J 2231/4283* (2013.01); *B01J 2531/845* (2013.01)

(58) Field of Classification Search
CPC .................................................. B01J 2531/845
See application file for complete search history.

(56) References Cited

PUBLICATIONS

Hu et al. Angew. Chem. Int. Ed. 2019, 58, 2670-2674 (Year: 2019).*
Lang et al. J. Am. Chem. Soc. 2019, 141, 12388-12396 (Year: 2019).*
Kim et al. Arch. Pharm. Res. vol. 2003, 26, 9-14 (Year: 2003).*
Ichinose et al. Angew. Chem. Int. Ed. 2011, 50, 9884-9887 (Year: 2011).*
Dzik et al. J. Am. Chem. Soc. 2010, 132, 10891-10902 (Year: 2010).*

* cited by examiner

*Primary Examiner* — Matthew P Coughlin
(74) *Attorney, Agent, or Firm* — Lei Fang; Smith Tempel Blaha LLC

(57) ABSTRACT

In one aspect, the disclosure relates to a mode of asymmetric induction in radical processes based on sequential combination of enantiodifferentiative H-atom abstraction and stereoretentive radical substitution. Also disclosed is an asymmetric system for stereoselective synthesis of strained 5-membered cyclic sulfamides via radical 1,5-C—H amination of sulfamoyl azides. The disclosed metalloradical system can control the degree and sense of asymmetric induction in the catalytic radical C—H amination in a systematic manner. The disclosed system is applicable to a broad scope of substrates with different types of $C(sp^3)$—H bonds and exhibits reactivity and selectivity, providing access to both enantiomers of useful 5-membered cyclic sulfamides in a highly enantioenriched form. Also disclosed are catalysts useful in these processes. This abstract is intended as a scanning tool for purposes of searching in the particular art and is not intended to be limiting of the present disclosure.

8 Claims, 34 Drawing Sheets

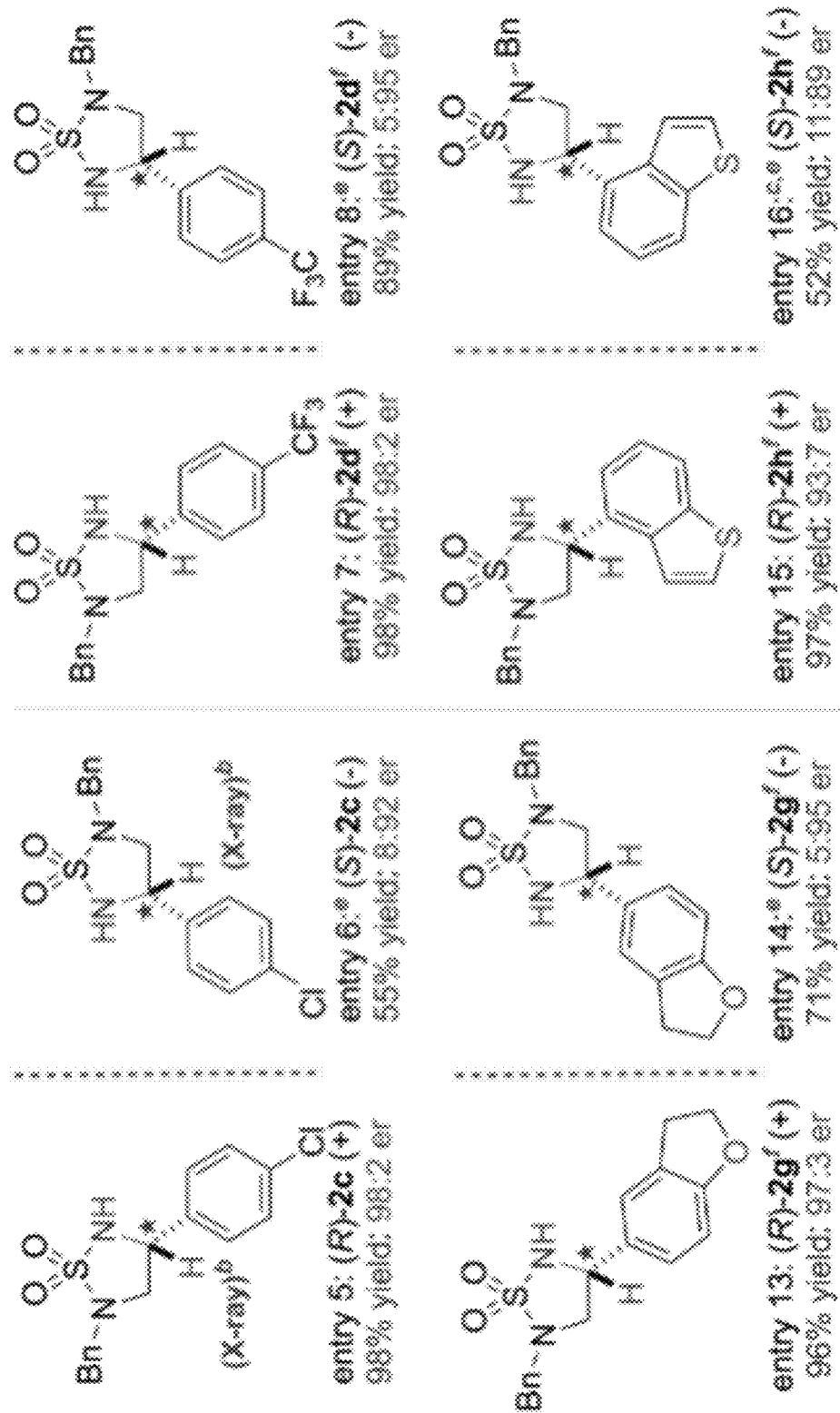
FIG. 2A, cont.

Amination by [Co(P5)] only entry 29:[c,e] (R)-2o[f] (−)
53% yield; 93:7 er entry 30: (R)-2p[f] (+)
94% yield; 98:2 er entry 31: (R)-2q[f] (+)
95% yield; 97:3 er entry 32:[e] (R)-2r[f] (+)
95% yield; 93:7 er

Amination by [Co(P4)] only entry 33:[c] (S,S)-2s (−)
(X-ray)[f]
80% yield; 7:93 er entry 34: (S)-2t[f]
88% yield; dr = 10:90 entry 35:[c,e] (S)-2u[f] (−)
41% yield; 9:91 er

FIG. 2B, cont.

*Traditional Heterocyclization: RA-HAA (Widely Established)*

*Alternative Heterocyclization: HAA-RS (Inherently Limited)*

*Metalloradical Heterocyclization: HAA-RS (Newly Emerged)*

*Chiral Metalloradicals for Asymmetric Heterocyclization*

[Co(P1)] (P1: 3,5-Di$^t$Bu-Hu(C$_4$)Phyrin)  [Co(P2)] (P2: 2,6-DiMeO-Hu(C$_4$)Phyrin)
[Co(P3)] (P3: 3,5-Di$^t$Bu-Hu(C$_6$)Phyrin)  [Co(P4)] (P4: 2,6-DiMeO-Hu(C$_6$)Phyrin)
[Co(P5)] (P5: 3,5-Di$^t$Bu-Hu(C$_8$)Phyrin)  [Co(P6)] (P6: 2,6-DiMeO-Hu(C$_8$)Phyrin)
[Co(P7)] (P7: 3,5-Di$^t$Bu-Hu(C$_{10}$)Phyrin)  [Co(P8)] (P8: 2,6-DiMeO-Hu(C$_{10}$)Phyrin)

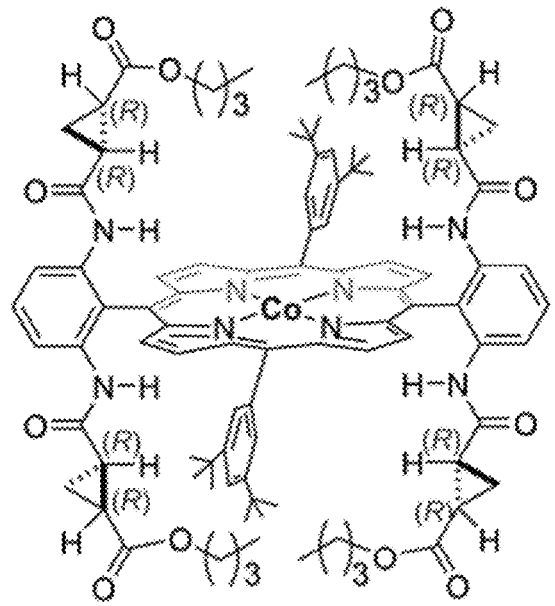
[Co(P10)] in MTBE
95% yield
er of 2a (R:S): 54:46
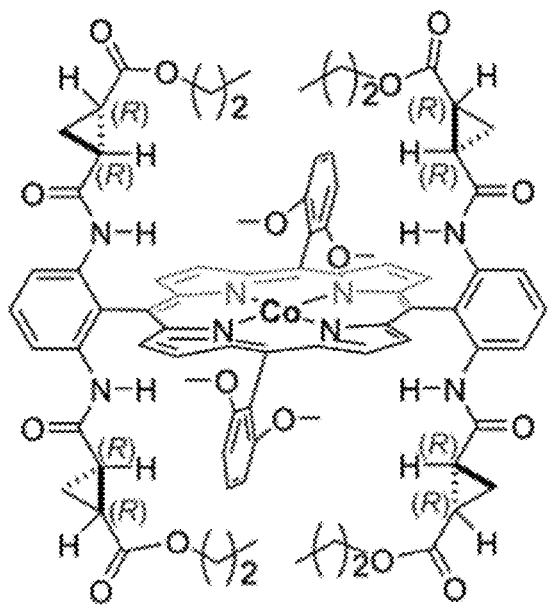
[Co(P11)] in MTBE
89% yield
er of 2a (R:S): 23:77
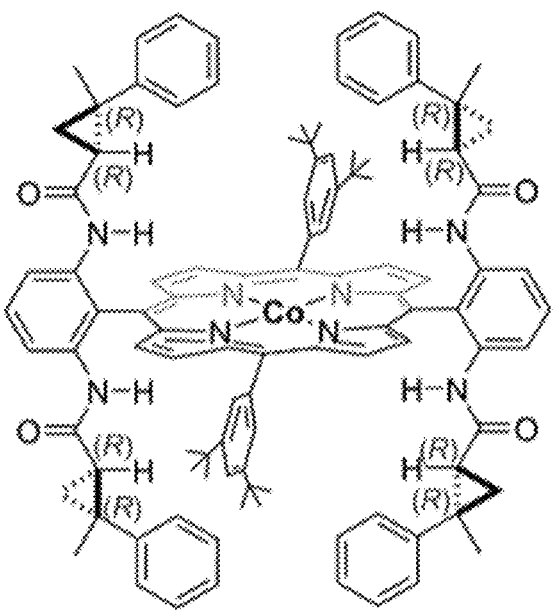
[Co(P14)] in MTBE
95% yield
er of 2a (R:S): 75:25
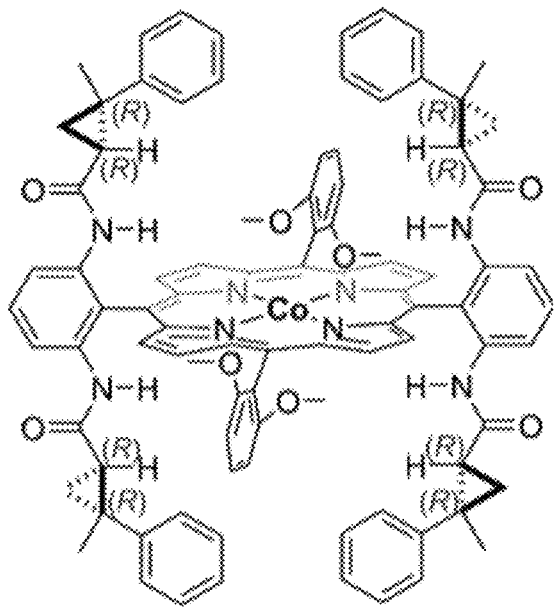
[Co(P15)] in MTBE
92% yield
er of 2a (R:S): 74:26
FIG. 6A, cont.

Bridged Catalysts

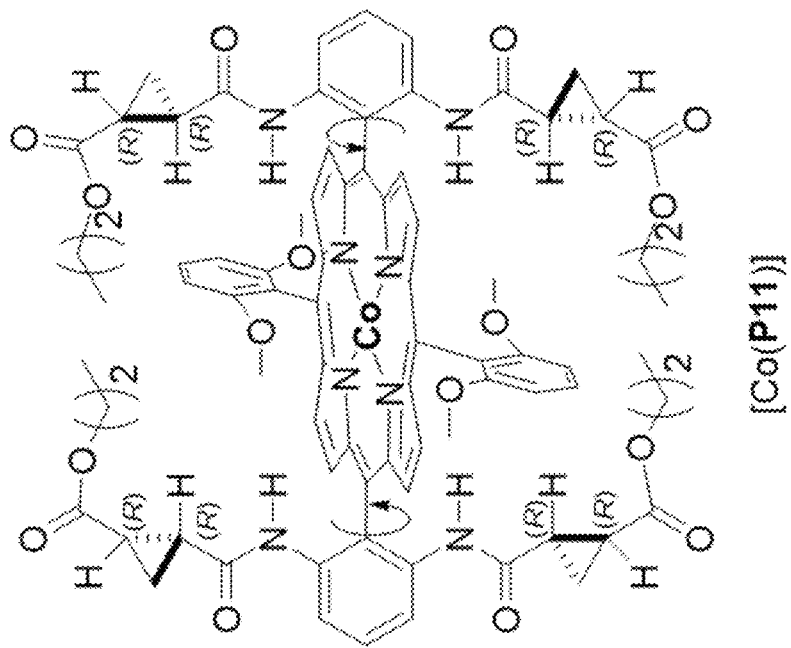
[Co(P11)]
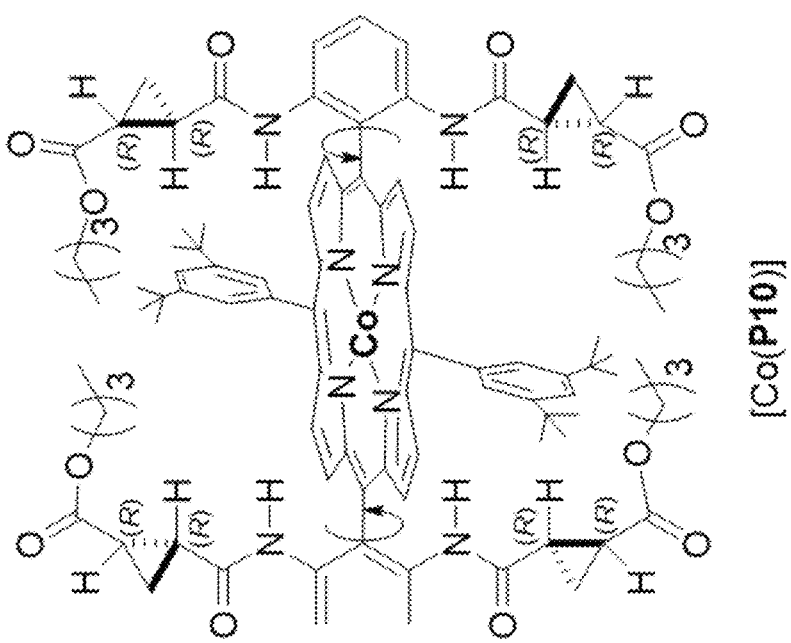
[Co(P10)]
FIG. 6B, cont.

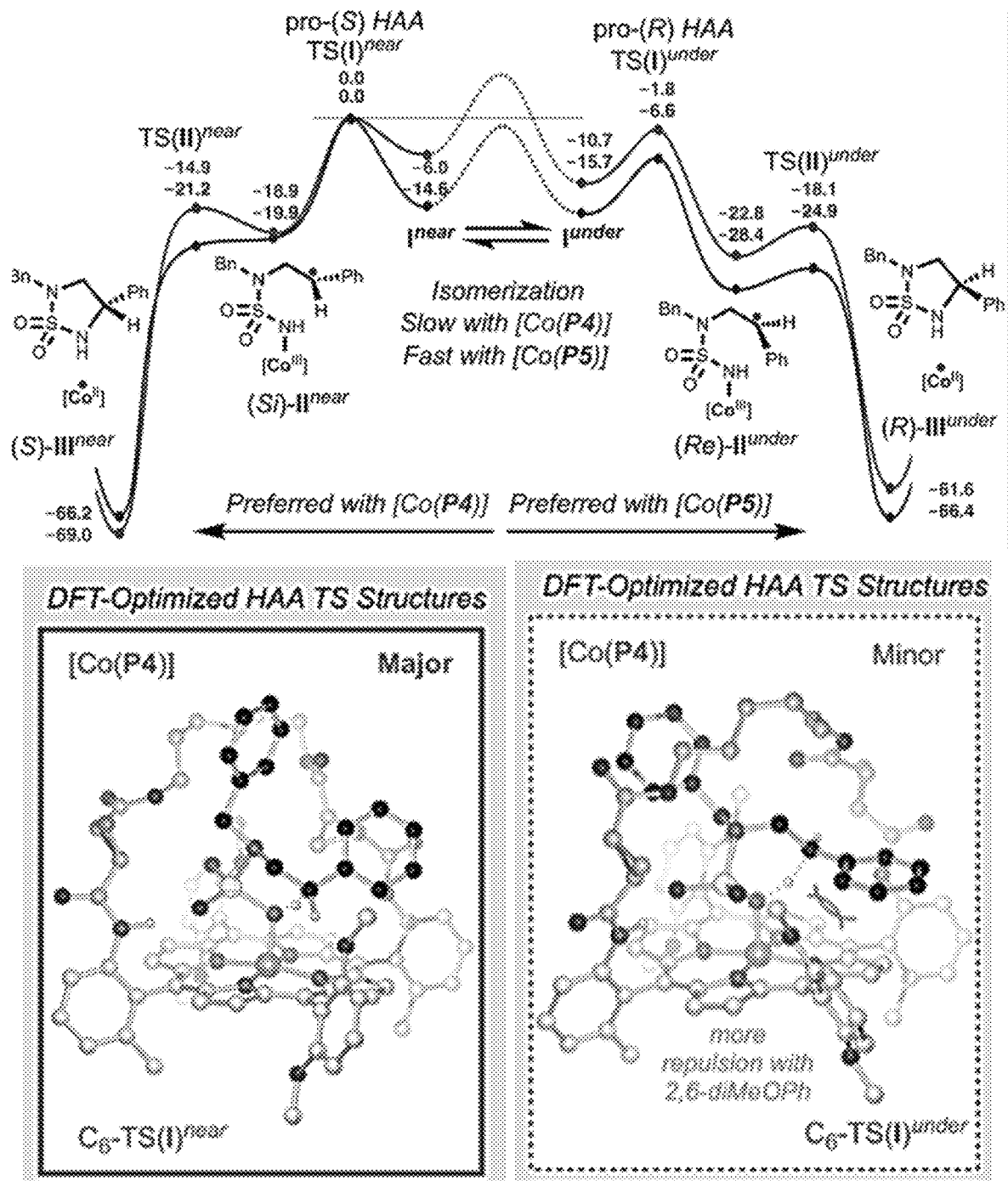
FIG. 7A, cont.

Method Demonstrated for Converting Cyclic Sulfamides into Diamines

Examples of Biologically Important Molecules Containing Vicinal Diamine Motifs

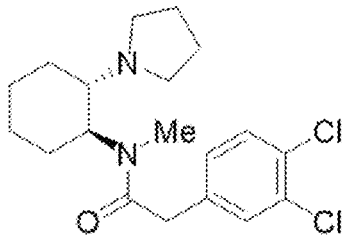
U-50488 (κ Agonist)

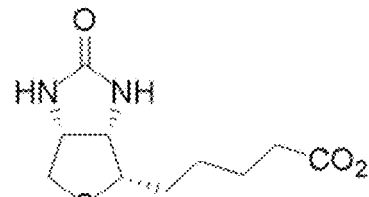
Biotin: Vitamin B₇

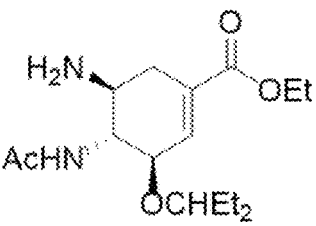
Tamiflu® (Antiviral Drug)

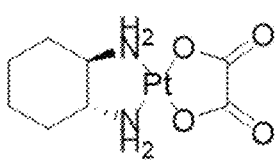
Eloxatin® (Anticancer Drug)

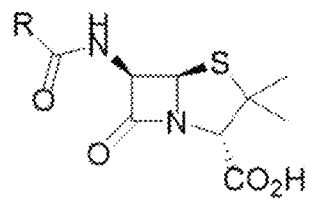
Penicillins (Antibiotics)

FIG. 8C

Selected Examples of Enantiomers of Vicinal Diamine Motifs for Entirely Different Therapeutic Possibilities

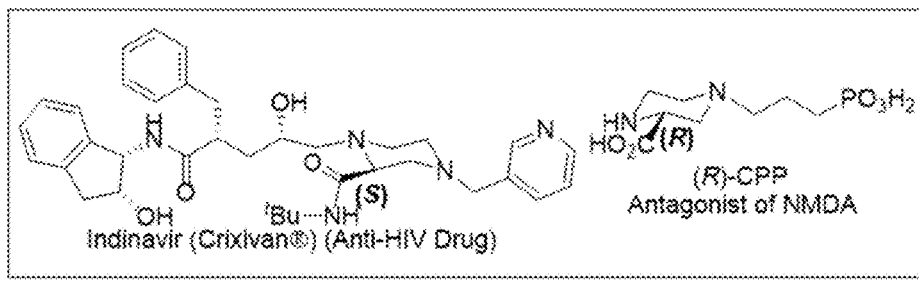

Indinavir (Crixivan®) (Anti-HIV Drug)   (R)-CPP Antagonist of NMDA

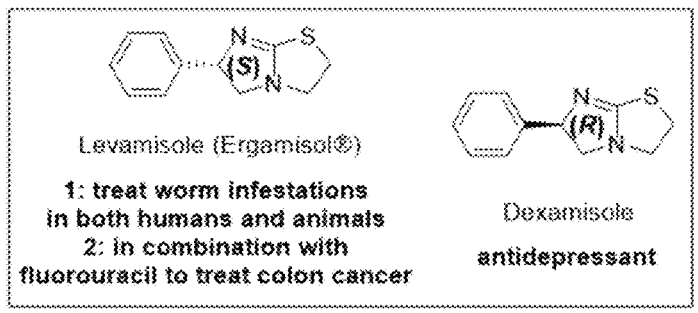

Levamisole (Ergamisol®)
1: treat worm infestations in both humans and animals
2: in combination with fluorouracil to treat colon cancer Dexamisole
antidepressant

FIG. 8D at RT

α-Co(III)-aminyl radical I

From Experimental: $g_{iso}$: 2.00753

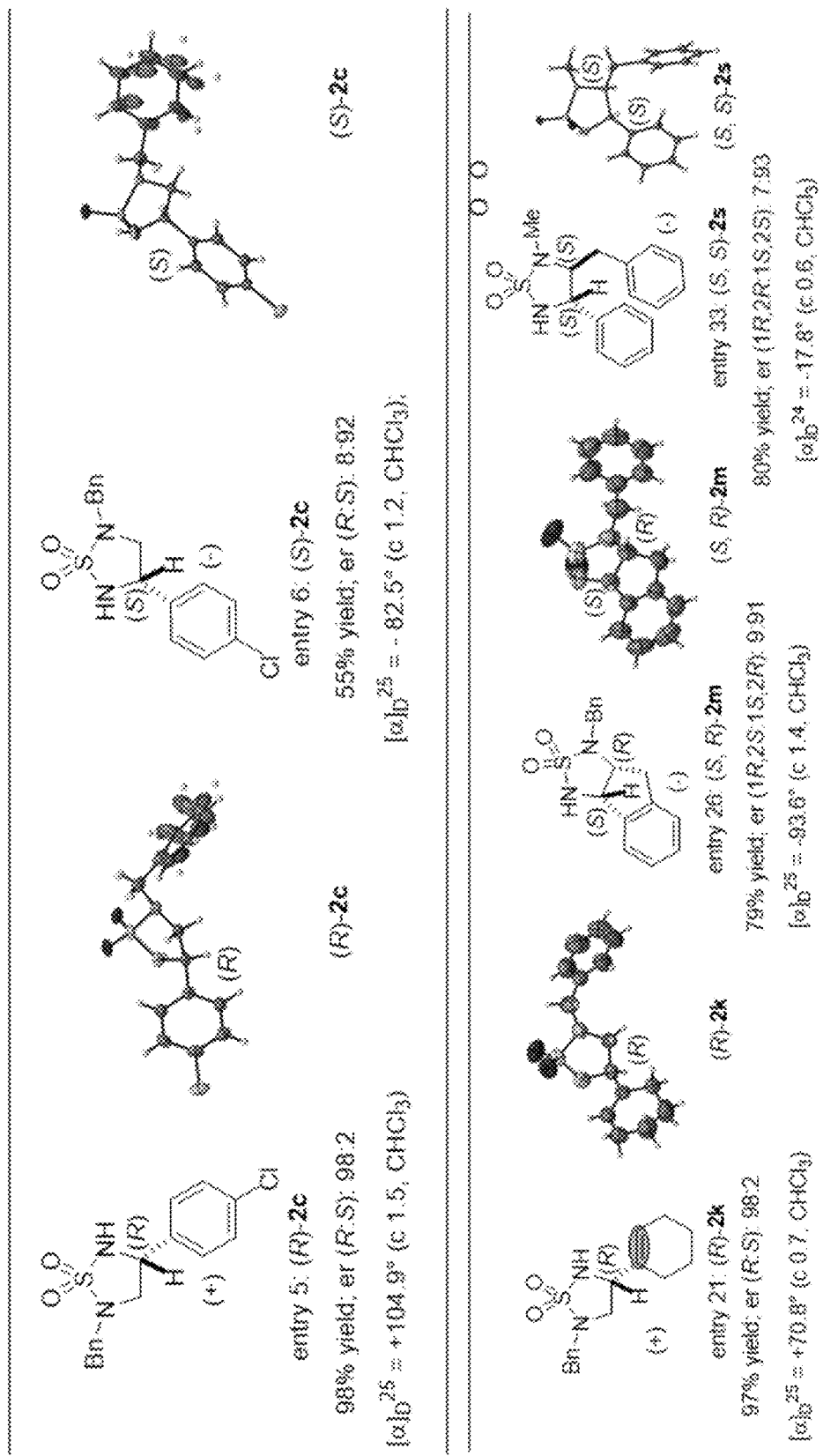
FIG. 11, cont.

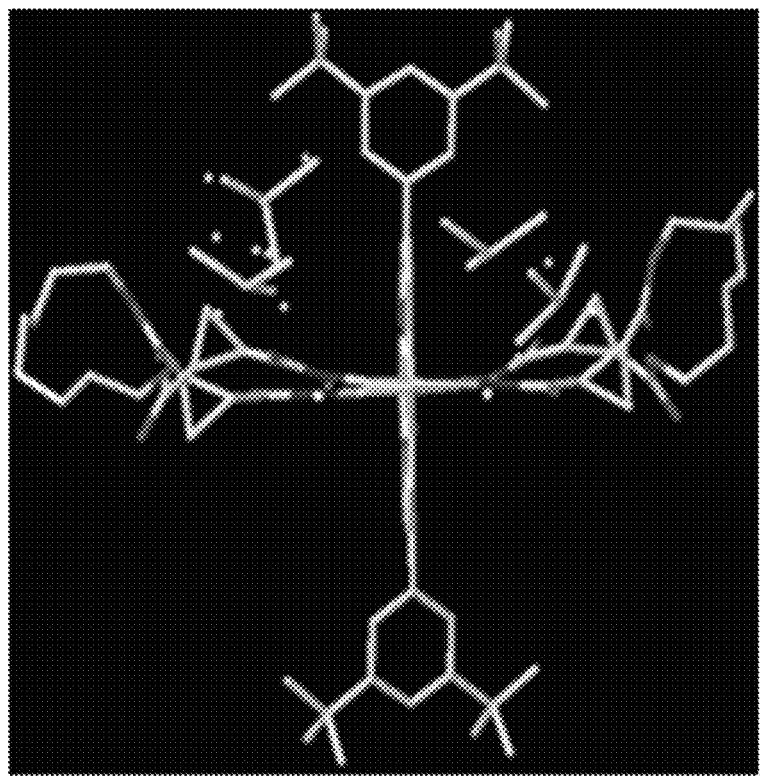
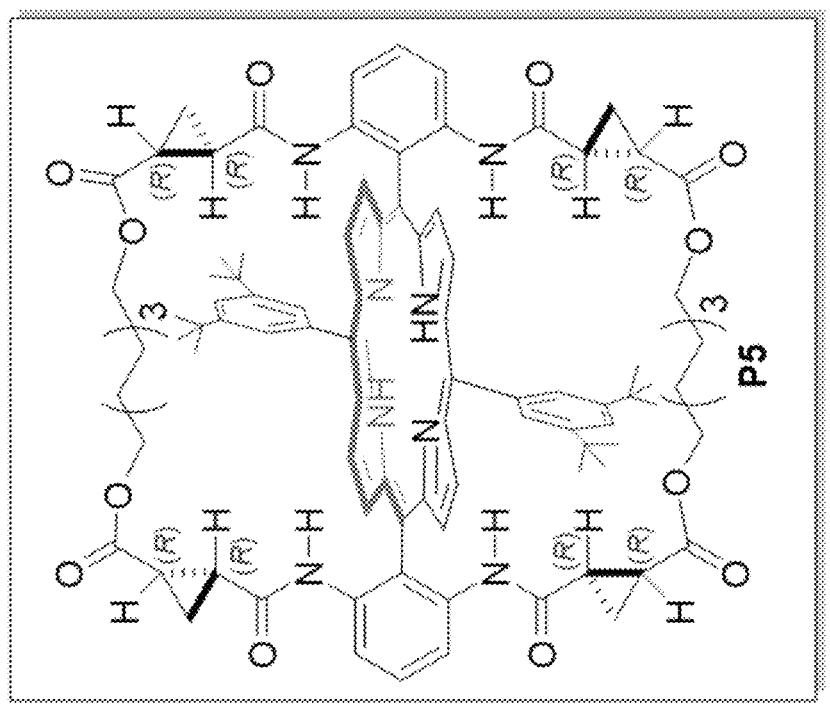
FIG. 12, cont.

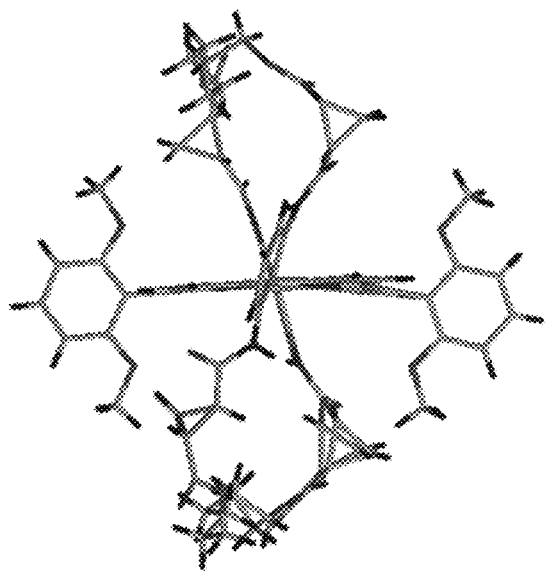
P4 (1)
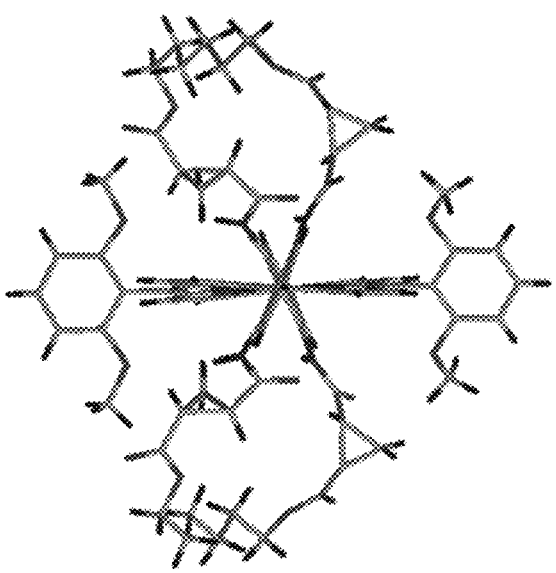
P4 (2)
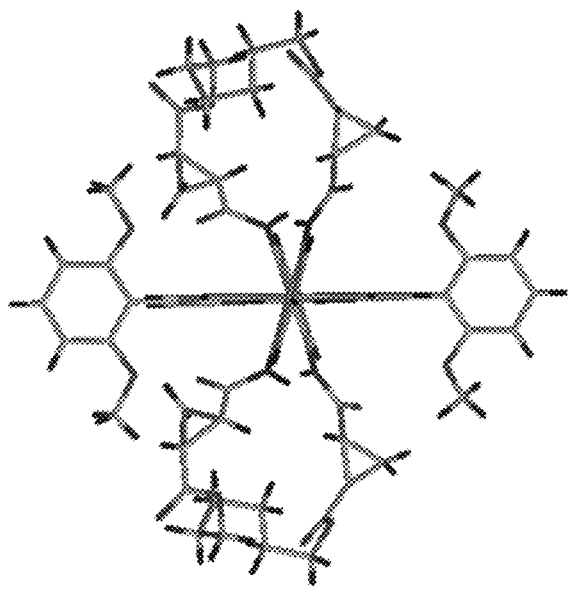
P4 (3)
FIG. 12, cont.

Step 1: Synthesis of Catalyst Building Blocks

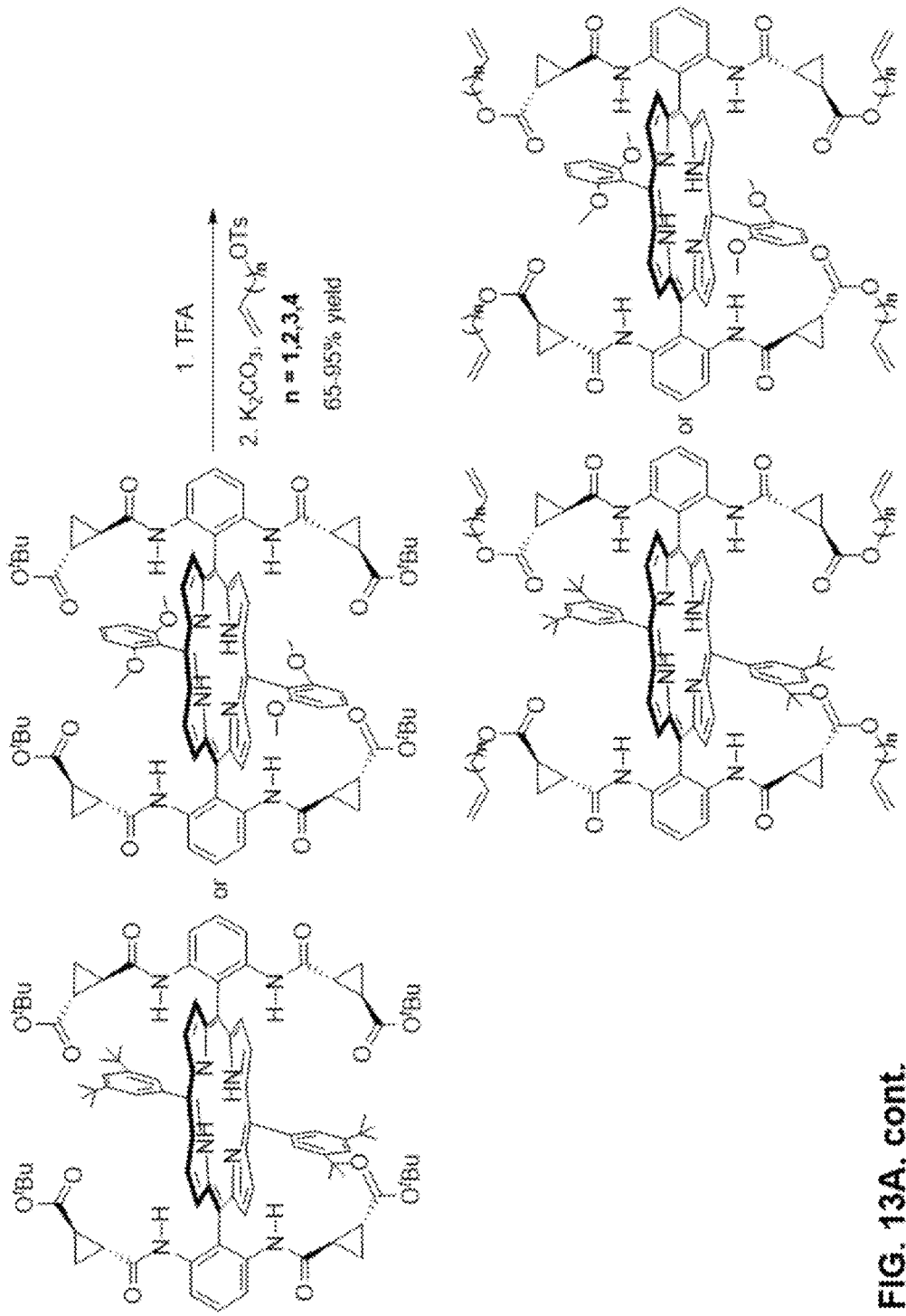
FIG. 13A, cont.

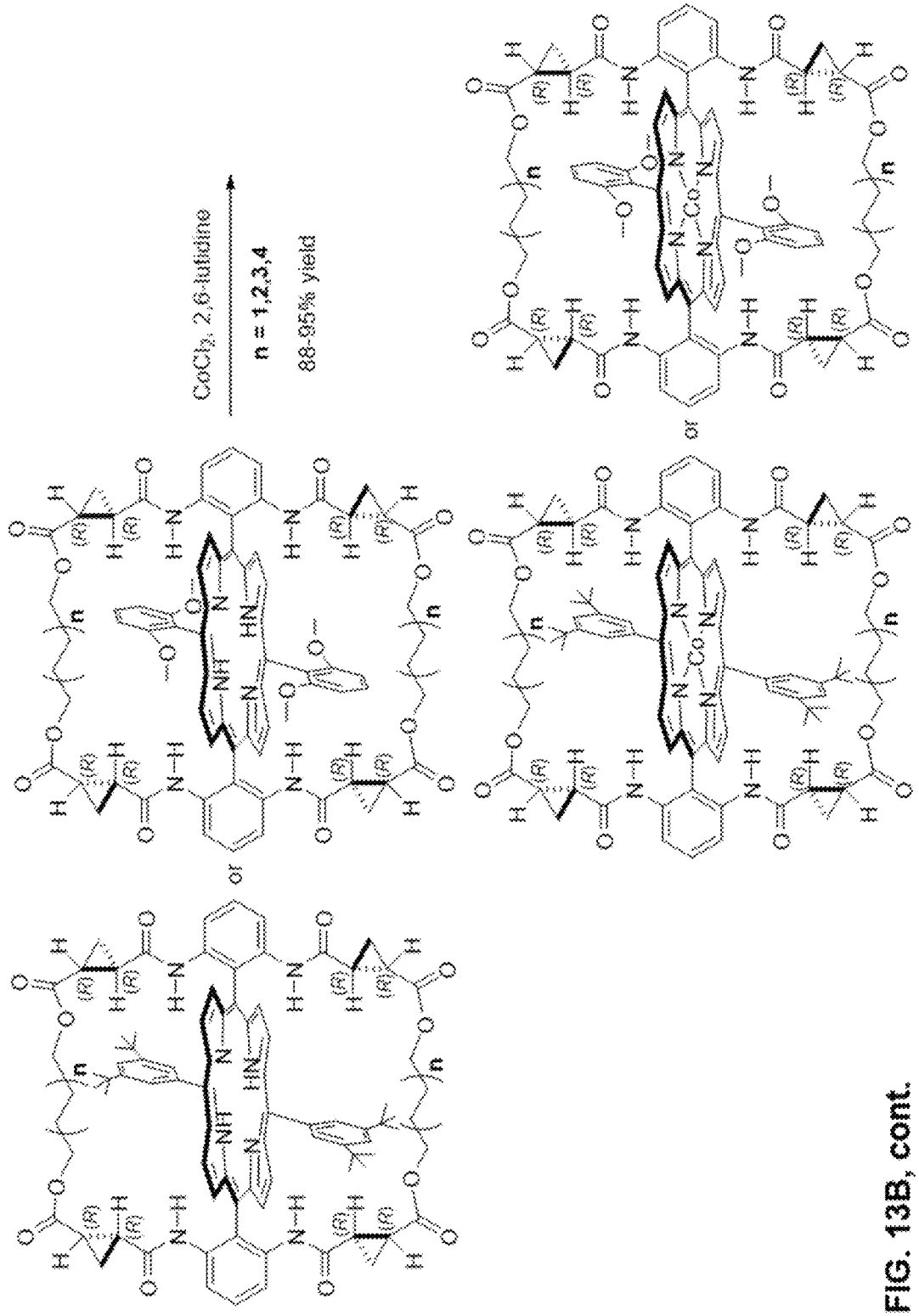
FIG. 13B, cont.

CATALYTIC SYSTEMS FOR STEREOSELECTIVE SYNTHESIS OF CHIRAL AMINES BY ENANTIODIVERGENT RADICAL C—H AMINATION

CROSS-REFERENCE TO RELATED APPLICATIONS

This application claims the benefit of U.S. Provisional Application No. 62/829,713, filed on Apr. 5, 2019.

STATEMENT REGARDING FEDERALLY SPONSORED RESEARCH OR DEVELOPMENT

This invention was made with U.S. Government support under grant number R01 GM098777 awarded by the National Institutes of Health and grant number CHE1624216 awarded by the National Science Foundation. The U.S. government has certain rights in the invention.

FIELD OF INVENTION

The present invention is directed to catalytic systems for stereoselective synthesis of chiral amines by enantiodivergent radical C—H amination.

BACKGROUND

Aminyl radicals have been increasingly explored as synthetic intermediates for the formation of C—N bonds. Among important applications, the N-centered radicals have been commonly employed in intramolecular fashion for construction of N-heterocyclic structures, primarily via radical addition (RA) to unsaturated π-bonds in combination with H-atom abstraction (HAA). Although mechanistically appealing, the alternative heterocyclization that is based on the association of H-atom abstraction (HAA) and radical substitution (RS) has been seldom documented. While activation of C—H bonds by aminyl radicals via intramolecular H-atom abstraction is typically facile, the subsequent C—N bond formation via homolytic radical substitution at the nitrogen center by the resulting alkyl radicals is inherently difficult. The well-known Hofmann-Löffler-Freytag (HLF) reaction obviates this inherent challenge to achieve C—N bond formation by switching the substitution step from radical to nucleophilic pathway. One potential direct solution to this fundamental problem would be the utilization of α-metalloaminyl radicals $R(L_nM)N$· instead of free aminyl radicals RR'N· (Scheme 1c). In view of the lower strength and higher polarity of M-N than C—N bonds, the otherwise difficult radical substitution would become both thermodynamically possible and kinetically feasible, especially with the generation of stable metalloradicals ($L_nM$·). Furthermore, this metalloradical-based approach for radical heterocyclization has a possibility to be turned over catalytically with a promise of controlling enantioselectivity as illustrated with two potential modes of asymmetric induction.

Homolytic radical reactions have vast synthetic potentials and could impact the practice of organic synthesis, which has been dominated by heterolytic ionic reactions. Despite recent advancements, the enduring issue of enantioselectivity remains largely unaddressed for most radical reactions. Engineering reactions to be enantioselective may be particularly important for applications such as drug development, since numerous biologically active molecules possess one or more sterogenic centers (see FIG. 8A-D).

Intramolecular C—H amination via metal-catalyzed nitrene transfer represents a general approach for stereoselective construction of chiral N-heterocycles through direct functionalization of ubiquitous C—H bonds in organic molecules. Despite recent progresses, the development of chiral catalysts for asymmetric intramolecular amination is still limited. In particular, catalytic asymmetric intramolecular 1,5-C—H amination to synthesize optically active 5-membered cyclic sulfamides remains to be developed.

Ideally, a method for catalytic asymmetric intramolecular 1,5-C—H amination for synthesis of optically active 5-membered cyclic sulfamides would be capable of controlling the degree and sense of asymmetric induction in a systematic manner, would be applicable to a broad scope of substrates with different types of $C(sp^3)$—H bonds, and would be reactive and selective in providing target compounds in a highly enantioenriched form. These needs and other needs are satisfied by the present disclosure.

SUMMARY

In accordance with the purpose(s) of the present disclosure, as embodied and broadly described herein, the disclosure, in one aspect, relates to a mode of asymmetric induction in radical processes that is based on sequential combination of enantiodifferentiative H-atom abstraction (HAA) and stereoretentive radical substitution (RS). Also disclosed is an asymmetric system for stereoselective synthesis of the strained 5-membered cyclic sulfamides via radical 1,5-C—H amination of sulfamoyl azides. The disclosed Co(II)-based metalloradical system has been shown to have an unusual capability of controlling both the degree and sense of asymmetric induction in the catalytic radical C—H amination in a systematic manner. The disclosed system is applicable to a broad scope of substrates with different types of $C(sp^3)$—H bonds and exhibits a remarkable profile of reactivity and selectivity, providing access to both enantiomers of useful 5-membered cyclic sulfamides in a highly enantioenriched form. Also disclosed are catalysts useful in the disclosed processes.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 2A shows intramolecular enantiodivergent radical 1,5-C—H amination of sulfamoyl azides via Co(II) based metalloradical catalysis. FIG. 2B shows additional examples of intramolecular enantioselective radical 1,5-C—H amination of sulfamoyl azides via Co(II) based metalloradical catalysis.

FIG. 3A shows widely-established traditional heterocyclization using radical addition and H-atom abstraction. FIG. 3B shows inherently limited alternative heterocyclization using H-atom abstraction and radical substitution. FIG. 3C shows newly emerged metalloradical heterocyclization using H-atom abstraction and radical substitution. FIG. 3D shows chiral metalloradicals for asymmetric heterocyclization.

In FIG. 4A, a catalytic pathway for asymmetric radical 1,5-C—H amination is proposed. In FIG. 4B, potential dual enantioselectivity via enantiodifferentiative H-atom abstraction is proposed.

FIG. 5A shows structures of Co(II) complexes of bridged $D_2$-symmetric chiral amidoporphyrins utilized in the reactions described in FIG. 5B. FIG. 5B shows the relationship between bridge length and relative enantiodivergence for intramolecular radical 1,5-C—H amination by Co(II) complexes of bridged $D_2$-symmetric chiral amidoporphyrins.

FIG. 6A show exemplary catalysts useful in the methods disclosed herein. FIG. 6B shows systematic control of degree and sense of asymmetric induction for intramolecular radical 1,5-C—H amination of sulfamoyl azide 1a by [Co(HuPhyrin)].

FIG. 7A shows DFT-optimized stereochemical models of enantiodifferentiative H-atom by [Co(P4)]. FIG. 7B shows DFT-optimized stereochemical models of enantiodifferentiative H-atom by [Co(P5)].

FIG. 8C shows examples of biologically important molecules containing vicinal diamine motifs. FIG. 8D shows selected examples of enantiomers of vicinal diamine motifs for different therapeutic possibilities.

FIG. 13A shows synthesis of catalyst building blocks and synthesis of ester amidoporphyrins. FIG. 13B shows synthesis of bridged amidoporphyrins and synthesis of Co(II) based bridged amidoporphyrins.

Figure 1:
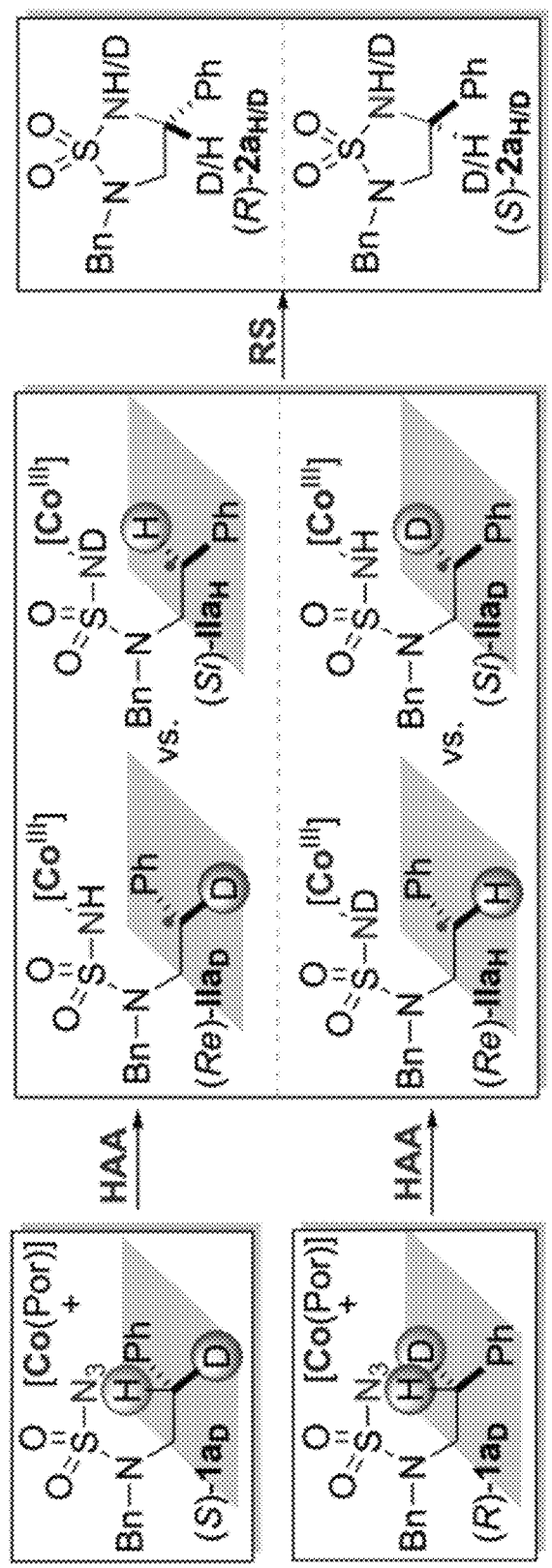
FIG. 1 shows kinetic isotope effect (KIE) studies on catalytic C—H amination of enantiopure isotopomeric azides via Co(II)-based metalloradical catalysis.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of".

As used in the specification and the appended claims, the singular forms "a," "an" and "the" include plural referents unless the context clearly dictates otherwise. Thus, for example, reference to "a catalyst," "a diastereomer," or "a chiral product," includes, but is not limited to, mixtures of two or more such catalysts, diastereomers, or chiral products, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of a catalyst refers to an amount that is sufficient to achieve the desired improvement in the property modulated by the formulation component, e.g. achieving the desired level of modulus. The specific level in terms of wt % in a composition required as an effective amount will depend upon a variety of factors including the desired product stereoisomer, length of catalyst bridge and/or lack thereof, scale of the reaction, and the like.

As used herein, the terms "optional" or "optionally" means that the subsequently described event or circumstance can or cannot occur, and that the description includes instances where said event or circumstance occurs and instances where it does not.

Unless otherwise specified, temperatures referred to herein are based on atmospheric pressure (i.e. one atmosphere).

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_6$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "A$^1$," "A$^2$," "A$^3$," and "A$^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "alkanediyl" as used herein, refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —$CH_2$— (methylene), —$CH_2CH_2$—, —$CH_2C(CH_3)_2CH_2$—, and —$CH_2CH_2CH_2$— are non-limiting examples of alkanediyl groups.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$—$OA^2$ or —$OA^1$—$(OA^2)_a$—$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptenyl, cyclooctenyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) and —N(-alkyl)$_2$, where alkyl is a described herein. Representative examples include, but are not limited to, methylamino group, ethylamino group, propylamino group, isopropylamino group, butylamino group, isobutylamino group, (sec-butyl)amino group, (tert-butyl) amino group, pentylamino group, isopentylamino group, (tert-pentyl)amino group, hexylamino group, dimethylamino group, diethylamino group, dipropylamino group, diisopropylamino group, dibutylamino group, diisobutylamino group, di(sec-butyl)amino group, di(tert-butyl) amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula —(A$^1$O(O)C-A$^2$-C(O)O)$_a$— or —(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula —(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen" or "halide," as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl" as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl" as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxy" as used herein is represented by the formula —OH.

The term "ketone" as used herein is represented by the formula A$^1$C(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —N$_3$.

The term "nitro" as used herein is represented by the formula —NO$_2$.

The term "nitrile" or "cyano" as used herein is represented by the formula —CN.

The term "silyl" as used herein is represented by the formula —SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S═O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," . . . "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH═CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^•$, —(haloR$^•$), —(CH$_2$)$_{0-2}$OH, —(CH$_2$)$_{0-2}$OR$^•$, —(CH$_2$)$_{0-2}$CH(OR$^•$)$_2$; —O(haloR$^•$), —CN, —N$_3$, —(CH$_2$)$_{0-2}$C(O)R$^•$, —(CH$_2$)$_{0-2}$C(O)OH, —(CH$_2$)$_{0-2}$C(O)OR$^•$, —(CH$_2$)$_{0-2}$SR$^•$, —(CH$_2$)$_{0-2}$SH, —(CH$_2$)$_{0-2}$NH$_2$, —(CH$_2$)$_{0-2}$NHR$^•$, —(CH$_2$)$_{0-2}$NR$^•_2$, —NO$_2$, —SiR$^•_3$, —OSiR$^•_3$, —C(O)SR$^•$, —(C$_{1-4}$ straight or branched alkylene)C(O)OR$^•$, or —SSR$^•$ wherein each R$^•$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include ═O and ═S.

Suitable divalent substituents on a saturated carbon atom of an "optionally substituted" group include the following: ═O, ═S, ═NNR*$_2$, ═NNHC(O)R*, ═NNHC(O)OR*, ═NNHS(O)$_2$R*, ═NR*, ═NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R˙, -(haloR˙), —OH, —OR˙, —O(haloR˙), —CN, —C(O)OH, —C(O)OR˙, —NH₂, —NHR˙, —NR˙₂, or —NO₂, wherein each R˙ is unsubstituted or where preceded by "halo" is substituted only with one or more halogens, and is independently $C_{1-4}$ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†₂, —C(O)R†, —C(O)OR†, —C(O)C(O)R†, —C(O)CH₂C(O)R†, —S(O)₂R†, —S(O)₂NR†₂, —C(S)NR†₂, —C(NH)NR†₂, or —N(R†)S(O)₂R†; wherein each R† is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R˙, -(haloR˙), —OH, —OR˙, —O(haloR˙), —CN, —C(O)OH, —C(O)OR˙, —NH₂, —NHR˙, —NR˙₂, or —NO₂, wherein each R˙ is unsubstituted or where preceded by "halo" is substituted only with one or more halogens, and is independently $C_{1-4}$ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

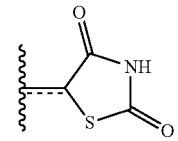

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more sterogenic centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^{2}H$, $^{3}H$, $^{13}C$, $^{14}C$, $^{15}N$, $^{18}O$, $^{17}O$, $^{35}S$, $^{18}F$, and $^{36}Cl$, respectively. Compounds further comprise prodrugs thereof and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

It is also appreciated that certain compounds described herein can be present as an equilibrium of tautomers. For example, ketones with an α-hydrogen can exist in an equilibrium of the keto form and the enol form.

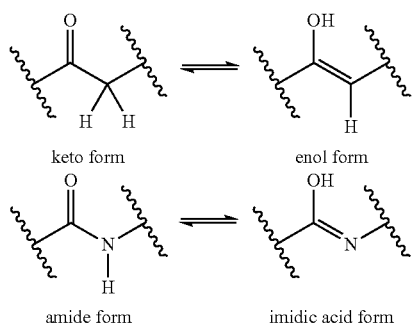

keto form        enol form amide form        imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

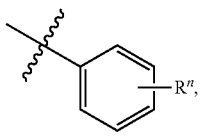

which is understood to be equivalent to a formula:

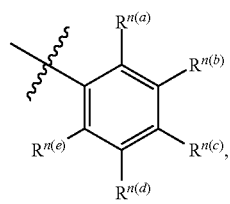

wherein n is typically an integer. That is, $R^n$ is understood to represent five independent substituents, $R^{n(a)}$, $R^{n(b)}$, $R^{n(c)}$, $R^{n(d)}$, and $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B—F, C-D, C-E, and C—F are considered disclosed. Likewise, any subset or combination of these is also disclosed. Thus, for example, the sub-group of A-E, B—F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

In various aspects, it is contemplated herein that the disclosed compounds further comprise their biosteric equivalents. The term "bioisosteric equivalent" refers to compounds or groups that possess near equal molecular shapes and volumes, approximately the same distribution of electrons, and which exhibit similar physical and biological properties. Examples of such equivalents are: (i) fluorine vs. hydrogen, (ii) oxo vs. thia, (iii) hydroxyl vs. amide, (iv) carbonyl vs. oxime, (v) carboxylate vs. tetrazole. Examples of such bioisosteric replacements can be found in the literature and examples of such are: (i) Burger A, *Relation of chemical structure and biological activity*; in Medicinal Chemistry Third ed., Burger A, ed.; Wiley-Interscience; New York, 1970, 64-80; (ii) Burger, A.; "Isosterism and bioisosterism in drug design"; *Prog. Drug Res.* 1991, 37, 287-371; (iii) Burger A, "Isosterism and bioanalogy in drug design", *Med. Chem. Res.* 1994, 4, 89-92; (iv) Clark R D, Ferguson A M, Cramer R D, "Bioisosterism and molecular diversity", *Perspect. Drug Discovery Des.* 1998, 9/10/11, 213-224; (v) Koyanagi T, Haga T, "Bioisosterism in agrochemicals", *ACS Symp. Ser.* 1995, 584, 15-24; (vi) Kubinyi H, "Molecular similarities. Part 1. Chemical structure and biological activity", *Pharm. Unserer Zeit* 1998, 27, 92-106; (vii) Lipinski C A.; "Bioisosterism in drug design"; *Annu. Rep. Med. Chem.* 1986, 21, 283-91; (viii) Patani G A, LaVoie E J, "Bioisosterism: A rational approach in drug design", *Chem. Rev.* (Washington, D.C.) 1996, 96, 3147-3176; (ix) Soskic V, Joksimovic J, "Bioisosteric approach in the design of new dopaminergic/serotonergic ligands", *Curr. Med. Chem.* 1998, 5, 493-512 (x) Thornber C W, "Isosterism and molecular modification in drug design", *Chem. Soc. Rev.* 1979, 8, 563-80.

In further aspects, bioisosteres are atoms, ions, or molecules in which the peripheral layers of electrons can be considered substantially identical. The term bioisostere is usually used to mean a portion of an overall molecule, as opposed to the entire molecule itself. Bioisosteric replacement involves using one bioisostere to replace another with the expectation of maintaining or slightly modifying the biological activity of the first bioisostere. The bioisosteres in this case are thus atoms or groups of atoms having similar size, shape and electron density. Preferred bioisosteres of esters, amides or carboxylic acids are compounds containing two sites for hydrogen bond acceptance. In one embodiment, the ester, amide or carboxylic acid bioisostere is a 5-membered monocyclic heteroaryl ring, such as an optionally substituted 1H-imidazolyl, an optionally substituted oxazolyl, 1H-tetrazolyl, [1,2,4]triazolyl, or an optionally substituted [1,2,4]oxadiazolyl.

In various aspects, the disclosed compounds can possess at least one center of asymmetry, they can be present in the form of their racemates, in the form of the pure enantiomers and/or diastereomers or in the form of mixtures of these enantiomers and/or diastereomers. The stereoisomers can be present in the mixtures in any arbitrary proportions. In some aspects, provided this is possible, the disclosed compounds can be present in the form of the tautomers.

Thus, methods which are known per se can be used, for example, to separate the disclosed compounds which possess one or more sterogenic centers and occur as racemates into their optical isomers, i.e., enantiomers or diastereomers. The separation can be effected by means of column separation on chiral phases or by means of recrystallization from an optically active solvent or using an optically active acid or base or by means of derivatizing with an optically active reagent, such as an optically active alcohol, and subsequently cleaving off the residue.

Control of Enantioselectivity Using Metalloradical Catalysis (MRC)

Control of enantioselectivity remains a major challenge in radical chemistry. In one aspect, the emergence of metalloradical catalysis (MRC) offers a conceptually new strategy for addressing this and other outstanding issues. Further in this aspect, through the employment of $D_2$-symmetric chiral amidoporphyrins as the supporting ligands, Co(II)-based MRC has enabled the development of new catalytic systems for asymmetric radical transformations with a unique profile of reactivity and selectivity. In one aspect, disclosed herein are new-generation $D_2$-symmetric amidoporphyrins HuPhyrin with cavity chiral environment that is tunable by distal bridging provides the Co-centered d-radicals with the added potentiality to address challenging issues that require exquisite control of fundamental radical processes. In a further aspect, with asymmetric 1,5-C—H amination of sulfamoyl azides, the enantiocontrol of which has proven difficult, the judicious use of HuPhyrin ligand by tuning the bridge length and other remote non-chiral elements as disclosed herein allows for controlling both the degree and sense of asymmetric induction in a systematic manner. In one aspect, this effort leads to successful development of new Co(II)-based catalytic systems that are highly effective for enantiodivergent radical 1,5-C—H amination, producing both enantiomers of the strained 5-membered cyclic sulfamides with excellent enantioselectivities. In a further aspect, detailed deuterium labeling studies, together with DFT computation, have revealed an unprecedented mode of asymmetric induction that consists of enantiodifferentiative H-atom abstraction (HAA) and stereoretentive radical substitution (RS).

In one aspect, among recent strategies for addressing enantioselectivity in radical reactions, metalloradical catalysis (MRC) offers a conceptually different approach for achieving stereoselective radical reactions by exploiting metal-centered radicals for catalytic generation of metal-stabilized organic radicals that undergo subsequent radical transformations under the catalyst control. In a further aspect, disclosed herein are Co(II) complexes of porphyrins, as stable 15e metalloradicals, that have shown the unusual capability of activating organic azides to generate the fundamentally new α-Co(III)-aminyl radicals. Further in this aspect, with the employment of $D_2$-symmetric chiral amidoporphyrins as the supporting ligands, the α-metalloaminyl radicals can undergo radical addition and H-atom abstraction as well as radical substitution, leading to the development of new catalytic processes for selective radical transformations. In a further aspect, the aforementioned radical heterocyclization strategy has been recently demonstrated for the construction of strained 5-membered cyclic sulfamides from sulfamoyl azides, which was difficult by the concerned ionic pathway (see FIGS. 3A-D for a comparison of pathways).

Figure 4A:
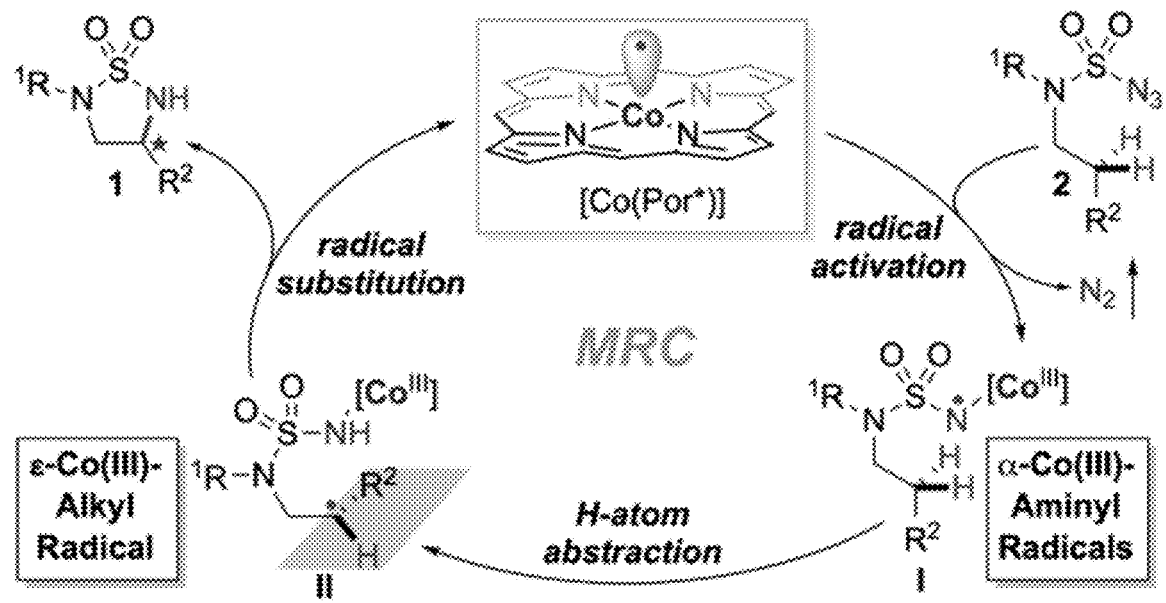
FIGS. 4A-4B show pathways toward enantiodivergence for intramolecular radical 1,5-C—H amination by Co(II) complexes of bridged $D_2$-symmetric chiral amidoporphyrins.
Figure 4B:
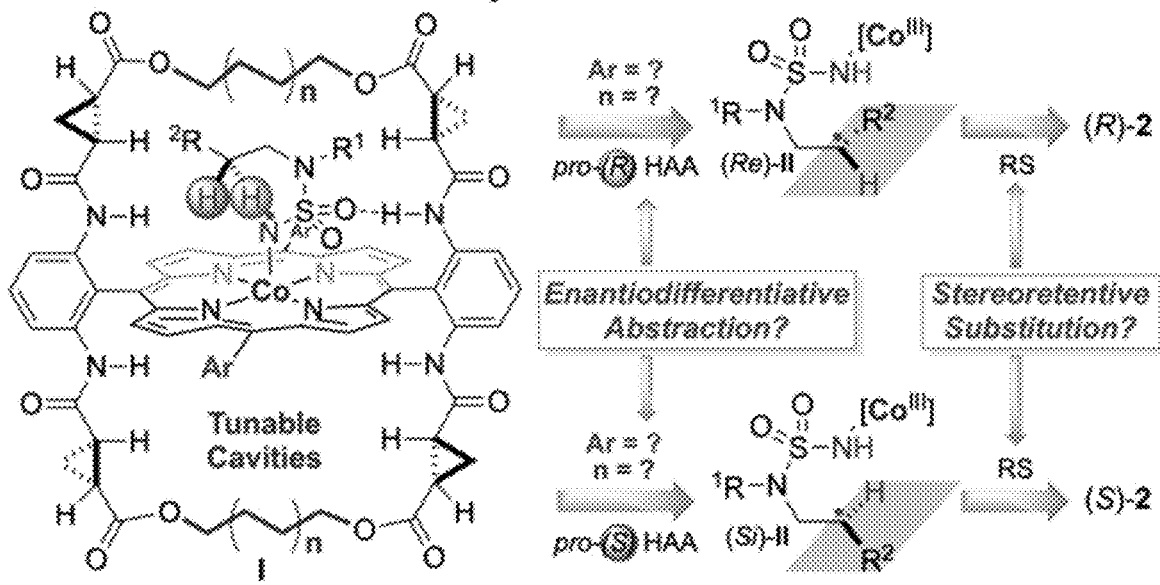

In one aspect, disclosed herein is an asymmetric version of the catalytic process, which makes use of the possibility of controlling enantioselectivity via both modes of asymmetric induction. In the course of pursuing the common Mode B for asymmetric induction with Co(II) complexes of existing open $D_2$-symmetric chiral amidoporphyrins, the recent introduction of new-generation $D_2$-symmetric chiral amidoporphyrins HuPhyrin, which contain bridges across two chiral amide units on both sides of the porphyrin plane where the metal-centered d-radical is situated inside a chiral cavity, prompted, in one aspect, exploration of the rare Mode A for asymmetric induction. In a further aspect, under the support of HuPhyrin ligand with a proper cavity environment, it was hypothesized that the corresponding α-Co(III)-aminyl radical I could be governed for enantiodifferentiative H-atom abstraction (HAA) of either pro-(R) or -(S) hydrogen. In a further aspect, if the newly-created facial chirality in the resulting ε-Co(III)-alkyl radical could be conformationally stabilized by the geometric constraints inside the confined space, the subsequent intramolecular radical substitution (RS) could be enabled stereoretentive, forming 5-membered cyclic sulfamides with the enantioselectivity that is predetermined in the HAA step (see FIGS. 4A-B).

In one aspect, disclosed herein is catalyst engineering by fine-tuning the length of the distal bridge in combination with the remote meso-aryl substituents might allow achieving enantiodivergence for the catalytic radical process, which would be desirable considering that both enantiomers of a chiral catalyst are not always accessible from available chiral sources. In another aspect, with this type of unprecedented radical amination realized, it is fundamentally appealing and practically useful as the resulting 5-membered cyclic sulfamides and related vicinal diamines in both (R)- and (S)-configurations are common structural motifs in biologically important molecules.

In one aspect, disclosed herein is the development of a Co(II)-based metalloradical system with the support of a new type of bridged $D_2$-symmetric chiral amidoporphyrins HuPhyrin for asymmetric intramolecular 1,5-C—H amination of sulfamoyl azides. In a further aspect, using HuPhyrin with varied bridge length and different substituents, both the degree and sense of asymmetric induction in the Co(II)-catalyzed amination can be effectively controlled in a systematic way. In one aspect, disclosed herein are two optimal catalysts, which differ only by the remote non-chiral components, that can catalyze the efficient formation of the strained 5-membered cyclic sulfamides as the opposite enantiomers, respectively. In a further aspect, this enantiodivergent process is applicable to a broad scope of substrates. Also disclosed herein are mechanistic studies that support an unprecedented mode of asymmetric induction that consists of enantiodifferentiative HAA and stereoretentive RS.

In some aspects, other metals can be used in place of cobalt. In one aspect, the metal can be cobalt, zinc, aluminum, magnesium, nickel, copper, manganese, iron, germanium, tin, molybdenum, ruthenium, or a combination thereof. Exemplary methods for synthesizing catalysts useful herein are provided in the examples.

In another aspect, disclosed herein is a method for the stereoselective synthesis of a chiral sulfamide, the method comprising contacting a sulfamoyl azide substrate with the catalysts disclosed herein, in a solvent. In one aspect, the solvent can be methyl tert-butyl ether (MTBE). In another aspect, the method can be conducted at an elevated temperature such as, for example, 40° C. In still another aspect, in addition to a chiral sulfamide, the method produces molecular nitrogen. In some aspects, the method is performed in the presence of molecular sieves having a pore size of about 4 Å.

In some aspects, the method disclosed herein produces chiral sulfamides wherein the ratio of (R) enantiomer to the ratio of (S) enantiomer at a given chiral center is from about 5:95 to about 95:5, or is about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, or about 95:5, or a combination of any of the foregoing values, or a range encompassing any of the foregoing values. In some aspects, the chiral sulfamides have a single stereogenic carbon, or have two or more stereogenic carbons. In aspects when two or more stereogenic carbons are present, the stereocenters can have the same (i.e., both are (R) or both are (S)) or different stereochemistries. In some aspects, when two or more stereogenic carbons are present, the methods disclosed herein will produce more of a particular diastereomer compared to other diastereomers.

REFERENCES

1. Alberti, M. N. et al., Stereochemistry of the singlet oxygenation of simple alkenes: a stereospecific transformation. Org. Lett. 10, 3997-4000 (2008).
2. Burg, F., et al., Site- and enantioselective C—H oxygenation catalyzed by a chiral manganese porphyrin complex with a remote binding site. Angew. Chem. Int. Ed. 57, 2953-2957 (2018).
3. Chen, Y. et al., Bromoporphyrins as versatile synthons for modular construction of chiral porphyrins: cobalt-catalyzed highly enantioselective and diastereoselective cyclopropanation. J. Am. Chem. Soc. 126, 14718-14719 (2004).
4. Chen, Y. et al., Cobalt-catalyzed asymmetric cyclopropanation of electron-deficient olefins. J. Am. Chem. Soc. 129, 12074-12075 (2007).
5. Collet, F. et al., Catalytic C—H amination: the stereoselectivity issue. Chem. Soc. Rev. 40, 1926-1936 (2011).
6. Cramer, C. J. et al., Density functional theory for transition metals and transition metal chemistry. Phys. Chem. Chem. Phys. 11, 10757-10816 (2009).
7. Dick, A. R., et al., Transition metal catalyzed oxidative functionalization of carbon-hydrogen bonds. Tetrahedron 62, 2439-2463 (2006).
8. Doyle, M. P. Exceptional selectivity in cyclopropanation reactions catalyzed by chiral cobalt(II)-porphyrin catalysts. Angew. Chem., Int. Ed. 48, 850-852 (2009).
9. Escorihuela, J. et al., New advances in dual stereocontrol for asymmetric reactions. Chem. Soc. Rev. 42, 5595-5617 (2013).
10. Ganssuer, A., et al., Angew. Chem. Int. Ed. 38, 2909-2910 (1999).
11. Gellman, S. H. Foldamers: a manifesto. Acc. Chem. Res. 31, 173-180 (1998).
12. Goswami, M., et al., Characterization of porphyrin-Co(III)-'nitrene radical' species relevant in catalytic nitrene transfer reactions. J. Am. Chem. Soc. 137, 5468-5479 (2015).
13. Groves, J. T., et al., Asymmetric hydroxylation by a chiral iron porphyrin. J. Am. Chem. Soc. 111, 8537-8538 (1989).
14. Hu, Y., et al., Modular construction of D2-symmetric chiral bridged-amidoporphyrins for Co(II)-based metalloradical catalysis: catalyst engineering via distal bridging Angew. Chem., Int. Ed. 58, 2670-2674 (2019).
15. Jiang, H., et al., Asymmetric radical bicyclization of allyl azidoformates via Cobalt(II)-based metalloradical catalysis. J. Am. Chem. Soc. 139, 9164-9167 (2017).
16. Johnson, M. D. Bimolecular homolytic displacement of transition-metal complexes from carbon. Acc. Chem. Res. 16, 343-349 (1983).
17. Kainz, Q. M., et al., Asymmetric copper-catalyzed C—N cross-couplings induced by visible light. Science 351, 681-684 (2016).
18. Kawade, R. K. et al., Gold-catalyzed annulations of allenes with N-hydroxyanilines to form indole derivatives with benzaldehyde as a promoter. Org. Biomol. Chem. 12, 737-740 (2014).
19. Kern, N., et al., Enantioselective cyclizations and cyclization cascades of samarium ketyl radicals. Nat. Chem. 9, 1198-1204 (2017).
20. Lanigan, R. M. et al., Direct synthesis of amides from carboxylic acids and amines using B(OCH2CF3)3. J. Org. Chem. 78, 4512-4523 (2013).
21. Li, C., et al., Catalytic radical process for enantioselective amination of $C(sp^3)$—H bonds. Angew. Chem., Int. Ed. 57, 16837-16841 (2018).
22. Lu, H. et al, Selective intramolecular C—H amination through the metalloradical activation of azides: synthesis of 1,3-diamines under neutral and nonoxidative conditions. Angew. Chem., Int. Ed. 49, 10192-10196 (2010).
23. Lu, H., et al., Intramolecular 1,5-$C(sp^3)$—H radical amination via Co(II)-based metalloradical catalysis for five-membered cyclic sulfamides. Chem. Sci. 7, 6934-6939 (2016).
24. Lu, Q., et al., Radical enantioselective $C(sp^3)$—H functionalization. Angew. Chem., Int. Ed. 56, 49-51 (2017).
25. Mace, N. et al., Unveiling latent α-iminocarbene reactivity for intermolecular cascade reactions through alkyne oxidative amination. Angew. Chem., Int. Ed. 52, 5836-5839 (2013).
26. Rono, L. J., et al., Enantioselective photoredox catalysis enabled by proton-coupled electron transfer: development of an asymmetric aza-pinacol cyclization. J. Am. Chem. Soc. 135, 17735-17738 (2013).
27. Sathiyaraj, E. et al, Synthesis and spectral studies on Pb(II) dithiocarbamate complexes containing benzyl and furfuryl groups and their use as precursors for PbS nanoparticles. Spectrochim Acta A 97, 575-581 (2012).
28. Shengule, S. R. et al., Highly diastereoselective N-acyliminium ion cyclization reactions of a tethered furan. Tetrahedron 68, 10280-10285 (2012).
29. Sibi, M. P., et al., Enantioselective radical processes. Chem. Rev. 103, 3263-3295 (2003).
30. Studer, A., et al., Catalysis of radical reactions: a radical chemistry perspective. Angew. Chem., Int. Ed. 55, 58-102 (2016).

31. Suarez, A. I. O., et al., Complexes with nitrogen-centered radical ligands: classification, spectroscopic features, reactivity, and catalytic applications. Angew. Chem., Int. Ed. 52, 12510-12529 (2013).
32. Viso, A., et al. α,β-diamino acids: biological significance and synthetic approaches. Chem. Rev. 105, 3167-3196 (2005).
33. Walton, J. C. Homolytic substitution: a molecular ménage à trois. Acc. Chem. Res. 31, 99-107 (1998).
34. Wang, J., et al. Dynamic control of chiral space in a catalytic asymmetric reaction using a molecular motor. Science 331, 1429-1432. (2011).
35. Wendlandt, A. E., et al., Quaternary stereocentres via an enantioconvergent catalytic SN reaction. Nature 556, 447-451 (2018).
36. Wenzel, M. et al., Synthese von ferrocen-bzw. rutthenocen-amphetamin-analoga und ihre markierung mit 2H bzw. 103Ru. J. Labelled Comp. Radiopharm 25, 121-131 (1988).
37. Wolff, M. E. Cyclization of N-halogenated amines (The Hofmann-Löffler reaction). Chem. Rev. 63, 55-64 (1963).
38. Xiong, T., et al., New amination strategies based on nitrogen-centered radical chemistry. Chem. Soc. Rev. 45, 3069-3087 (2016).
39. Xu, X. et al., Highly asymmetric intramolecular cyclopropanation of acceptor-substituted diazoacetates by Co(II)-based metalloradical catalysis: iterative approach for development of new-generation catalysts. J. Am. Chem. Soc. 133, 15292-15295 (2011).
40. Zard, S. Z. Recent progress in the generation and use of nitrogen-centred radicals. Chem. Soc. Rev. 37, 1603-1618 (2008).

ASPECTS

Aspect 1. A catalyst for the stereoselective synthesis of chiral sulfamides, the catalyst comprising Formula I:

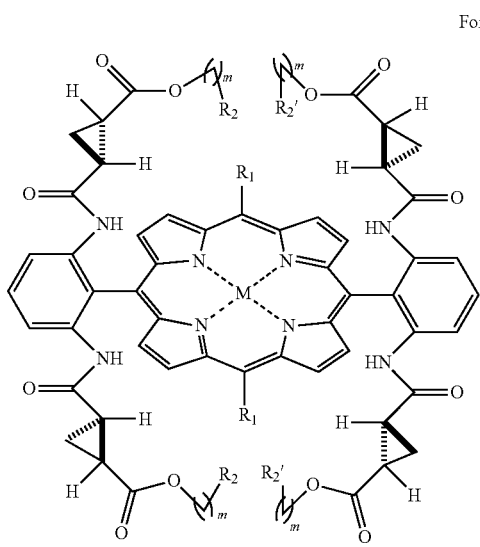

Formula I

Aspect 2. The catalyst of aspect 1, wherein $R_1$ comprises

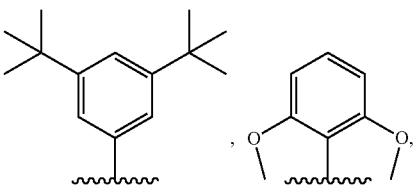 [SMILES: *c1cc(C(C)(C)C)cc(C(C)(C)C)c1 ; *c1c(OC)cccc1OC]

or a combination thereof.

Aspect 3. The catalyst of aspect 1 or 2, wherein stereocenters in the catalyst have the (R) configuration.

Aspect 4. The catalyst of any of aspects 1-3, wherein M comprises cobalt, zinc, aluminum, magnesium, nickel, copper, manganese, iron, germanium, tin, molybdenum, ruthenium, or a combination thereof.

Aspect 5. The catalyst of any of aspects 1-3, wherein M comprises cobalt.

Aspect 6. The catalyst of any of aspects 1-5, wherein each $R_2$ and $R_2'$ independently comprise a methyl group.

Aspect 7. The catalyst of aspect 6, wherein m is 2 or 3.

Aspect 8. The catalyst of aspect 7, wherein m is 3 and $R_1$ comprises

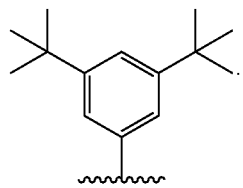

Aspect 9. The catalyst of aspect 6, wherein m is 2 and $R_1$ comprises

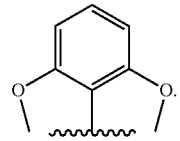 [SMILES: *c1c(OC)cccc1OC]

Aspect 10. The catalyst of any of aspects 1-5, wherein m is 1 and each $R_2$ and $R_2'$ is independently —CH$_2$— and each $R_2$ is chemically linked to an adjoining $R_2'$ with a bridge comprising a structure

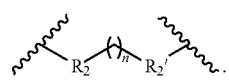

Aspect 11. The catalyst of aspect 10, wherein m is 1 and n is from 0 to 6.

Aspect 12. The catalyst of aspect 11, wherein n is 0 and $R_1$ comprises

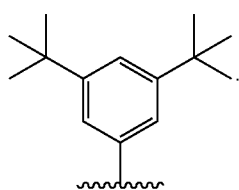

Aspect 13. The catalyst of aspect 11, wherein n is 2 and $R_1$ comprises

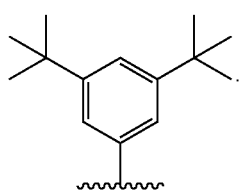

Aspect 14. The catalyst of aspect 11, wherein n is 4 and $R_1$ comprises

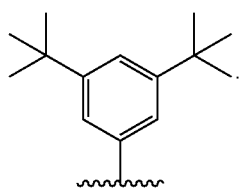

Aspect 15. The catalyst of aspect 11, wherein n is 6 and $R_1$ comprises

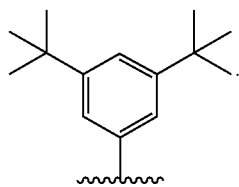

Aspect 16. The catalyst of aspect 11, wherein n is 0 and $R_1$ comprises

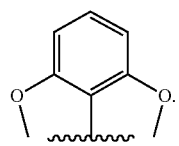

Aspect 17. The catalyst of aspect 11, wherein n is 2 and $R_1$ comprises

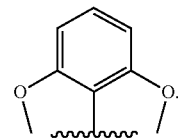 [SMILES: *c1c(OC)cccc1OC]

Aspect 18. The catalyst of aspect 11, wherein n is 4 and $R_1$ comprises

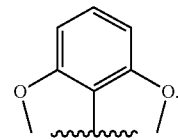 [SMILES: *c1c(OC)cccc1OC]

Aspect 19. The catalyst of aspect 11, wherein n is 6 and $R_1$ comprises

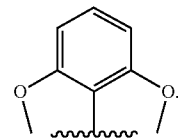 [SMILES: *c1c(OC)cccc1OC]

Aspect 20. A method for the stereoselective synthesis of a chiral sulfamide, the method comprising contacting a sulfamoyl azide substrate with the catalyst of any of aspects 1-19 in a solvent.

Aspect 21. The method of aspect 20, wherein the solvent comprises methyl tert-butyl ether (MTBE).

Aspect 22. The method of aspect 20 or 21, wherein the method is conducted at 40° C.

Aspect 23. The method of any of aspects 20-22, wherein the method further produces molecular nitrogen.

Aspect 24. The method of any of aspects 20-23, further comprising contacting the substrate and the catalyst with molecular sieves.

Aspect 25. The method of aspect 24, wherein the molecular sieves comprise a pore size of about 4 Å.

Aspect 26. The method of any of aspects 20-25, wherein the substrate comprises Formula II:

Formula II

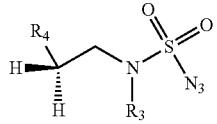

Aspect 27. The method of aspect 26, wherein $R_3$ comprises a benzoyl group, an isopropyl group, —$(CH_2)_3$-Ph, methyl, or a combination thereof.

Aspect 28. The method of aspect 26, wherein $R_4$ comprises -Ph,

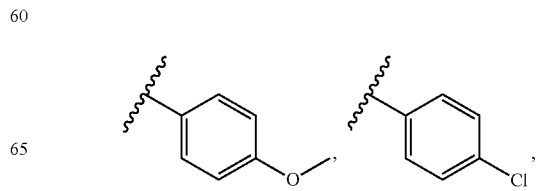

-continued

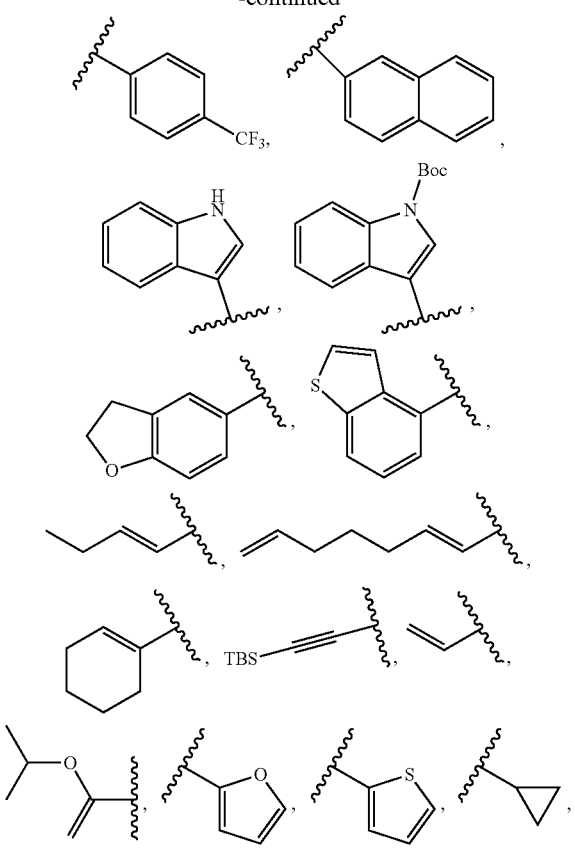

a nucleoside derivative, a metallocene derivative, or a combination thereof.

Aspect 29. The method of aspect 28, wherein the nucleoside derivative comprises

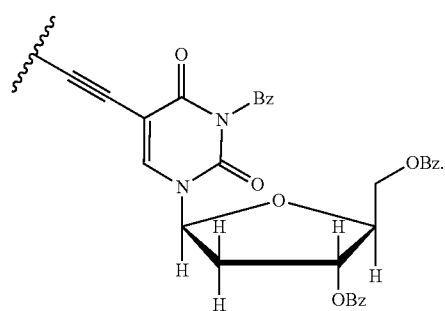

Aspect 30. The method of aspect 28, wherein the metallocene derivative comprises

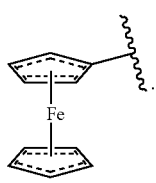

Aspect 31. The method of aspect 26, wherein the substrate comprises

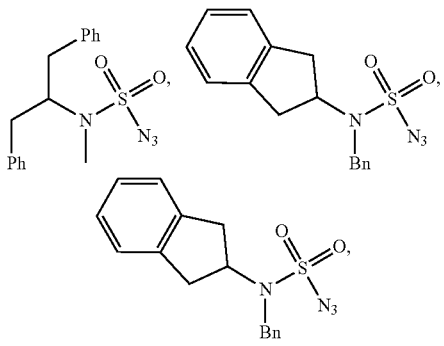

or a combination thereof.

Aspect 32. The method of any of aspects 20-30, wherein the chiral sulfamide comprises the following structures:

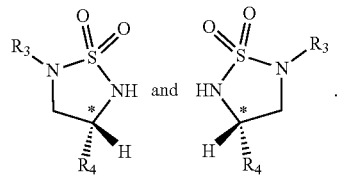

Aspect 33. The method of aspect 31, wherein the chiral sulfamide comprises

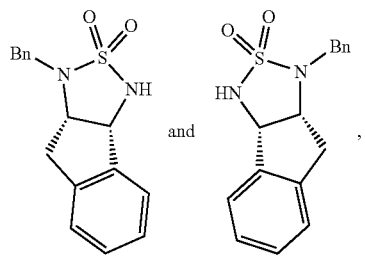

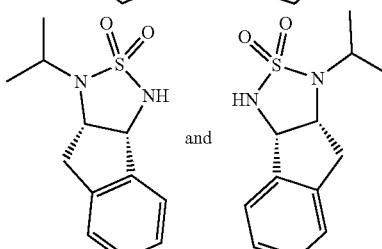

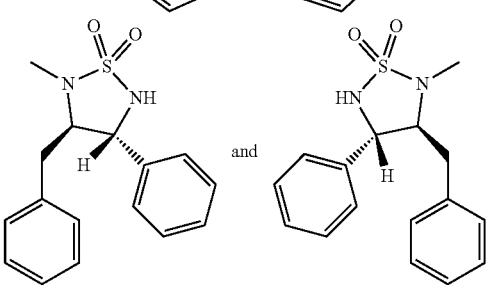

or a combination thereof.

Aspect 34. The method of aspect 32 or 33, wherein the ratio of (R) enantiomer at * to (S) enantiomer at * is from about 5:95 to about 95:5.

31

Aspect 35. The method of aspect 32 or 33, wherein the ratio of (R) enantiomer at * to (S) enantiomer at * is from about 35:65 to about 65:35.

Aspect 36. The method of aspect 32 or 33, wherein the ratio of (R) enantiomer at * to (S) enantiomer at * is from about 45:55 to about 55:45.

Aspect 37. A composition comprising a chiral sulfamide produced by the method of any of aspects 20-36.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Materials and Methods

General Considerations

Unless otherwise noted, all reactions were carried out under a nitrogen atmosphere in oven-dried glassware following standard Schlenk techniques. Gas tight syringes were used to transfer liquid reagents and solvents in catalytic reactions. Solvent was freshly distilled/degassed prior to use unless otherwise noted. Thin layer chromatography was performed on Merck TLC plates (silica gel 60 F254), visualizing with UV-light 254 nm or 365 nm fluorescence quenching, and cerium ammonium-molybdate (CAM) stain (ammonium pentamolybdate, cerium(IV) sulfate, sulfuric acid aqueous solution). Flash column chromatography was performed with ICN silica gel (60 Å, 230-400 mesh, 32-63 μm).

Materials

Commercial reagents were purchased from Sigma Aldrich, Acros, Alfa Aesar, Strem, Oakwood Products Inc., TCI, or Matrix Scientific and used as received with the following exceptions. Dichloromethane was distilled under nitrogen from calcium hydride. Tetrahydrofuran (THF) and toluene were distilled under nitrogen from sodium benzophenone ketyl. 1,4-Dioxane (inhibitor free, ACS reagent grade >99%) was freshly distilled from Na under an atmosphere of dry $N_2$ prior to use. Anhydrous cobalt(II) chloride, palladium(II) acetate, and 9,9-dimethyl-4,5-bis(diphenylphosphino)xanthenes (Xantphos) were purchased from Strem.

Instrumentation

Proton nuclear magnetic resonance ($^1$H NMR) spectra and carbon nuclear magnetic resonance ($^{13}$C NMR) spectra were recorded on a Varian 600-MHz, Bruker 500-MHz, Bruker 400-MHz instrument. Chemical shifts for protons are reported in parts per million downfield from tetramethylsilane and are referenced to residual protium in the NMR solvent ($CHCl_3$=7.26 ppm, $(CH_3)_2CO$=2.05 ppm, $(CH_3)_2SO$=2.5 ppm). Chemical shifts for carbon are reported in parts per million downfield from tetramethylsilane and are referenced to the carbon resonances of the solvent residual peak ($CDCl_3$=77.00 ppm). Infrared spectra were measured with a Nicolet Avatar 320 spectrometer with a Smart S8 Miracle accessory, HPLC measurements were carried out on a Shimadzu HPLC system with Chiralcel OD-H, AD-H and IC. GC measurements were carried out on a Shimadzu GCMS system with a Dex-CB column. Optical rotations were measured on a Rudolph Research Analytical AUTO-POL® IV digital polarimeter. High-resolution mass spectra were obtained on an Agilent 6220 using electrospray ionization time-of-flight (ESI-TOF). The X-ray diffraction data were collected using Bruker-AXS SMART-APEXII CCD diffractometer (CuKα, λ=1.54178 Å) and Bruker D8 Venture PHOTON 100 CMOS system equipped with a Cu KαINCOATEC Imus micro-focus source (λ=1.54178 Å).

Example 2: Synthesis and Characterization of Catalyst Building Blocks

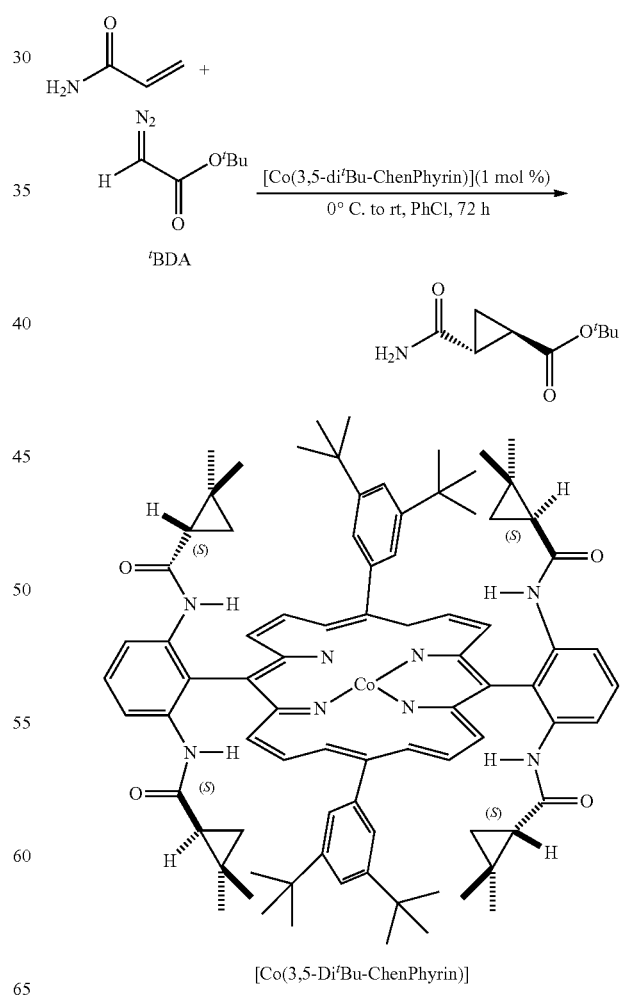

[Co(3,5-Di$^t$Bu-ChenPhyrin)]

(1R,2R)-tert-butyl 2-carbamoylcyclopropanecarboxylate was synthesized according to a previously reported procedure. (S)—[Co(3,5-di$^t$Bu-ChenPhyrin)] (400 mg, 0.3 mmol, 0.01 equiv), acryl amide (10.6 g, 150 mmol, 5 equiv) and DMAP (1.83 g, 15 mmol, 0.5 equiv) were placed in an oven dried resealable Schlenk tube. The tube was capped with a Teflon screw cap, evacuated, and backfilled with nitrogen. The screw cap was replaced with a rubber septum. Chlorobenzene (100 mL) was added via syringe. After the solution was cooled to 0° C., tBDA (4.4 mL, 30 mmol, 1 equiv) was added dropwise followed by the addition of 20 mL of chlorobenzene. The tube was purged with nitrogen for 1 min and sealed with Teflon screwcap. The reaction mixture was warmed up to r.t. and stirred for three days. After the reaction finished, the resulting mixture was purified by silica gel column chromatography (eluent: Hexanes/EtOAc 4:1) to give tert-butyl (1R, 2R)-2-carbamoylcyclopropane-1-carboxylate (5.2 g, 93%), TLC R$_f$=0.25 (Hexanes/EtOAc 3:1) in 98% ee. The following recrystallization gave >99% ee. $^1$H NMR (400 MHz, CDCl$_3$) δ ppm 5.84 (s, 1H), 5.76 (s, 1H), 2.07 (ddd, J=3.8, 5.8, 9.5 Hz, 1H), 1.93 (ddd, J=3.8, 5.7, 9.4 Hz, 1H), 1.44 (s, 9H), 1.38 (ddd, J=3.7, 5.7, 9.3 Hz, 1H), 1.28 (ddd, J=3.7, 5.8, 9.4 Hz, 1H); $^{13}$CNMR (125 MHz, CDCl$_3$) δ ppm 173.0, 171.7, 81.2, 28.1, 23.1, 23.0, 14.9; GC (DCB, 5° C./min): Major t=12.95 min., Minor t=11.77 min.

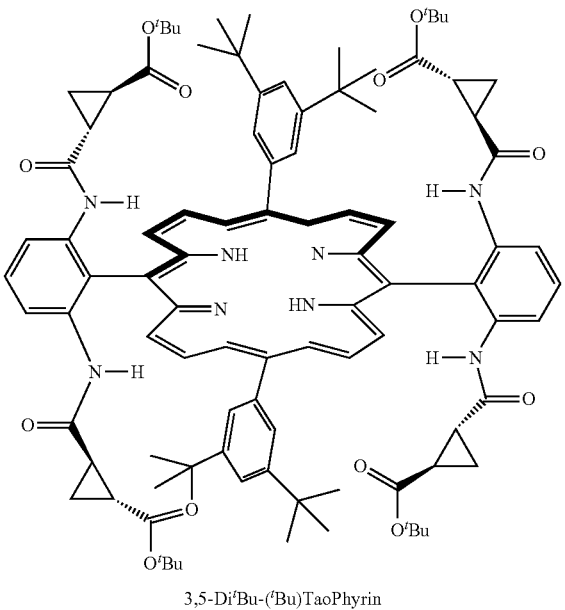

3,5-Di$^t$Bu-($^t$Bu)TaoPhyrin

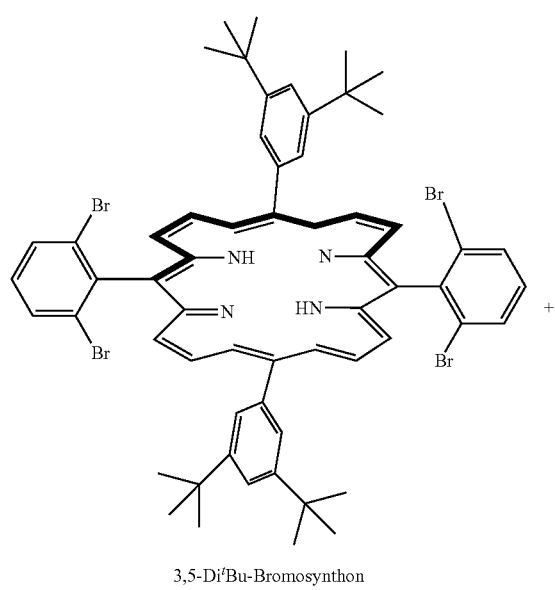

3,5-Di$^t$Bu-Bromosynthon

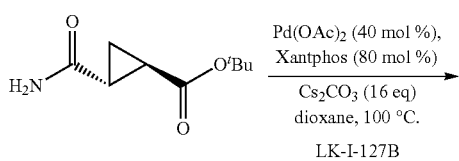

LK-I-127B

Representative procedure for the synthesis of (3,5-Di$^t$Bu-Tao($^t$Bu)Phyrin). 3,5-Di$^t$Bu-Bromosynthon (686 mg, 0.59 mmol, 1 equiv), the above synthesized chiral amide (tert-butyl (1R,2R)-2-carbamoylcyclopropane-1-carboxylate) (1.76 g, 9.5 mmol, 16 equiv), Pd(OAc)$_2$ (53 mg, 0.236 mmol, 0.4 equiv), Xantphos (274 mg, 0.47 mmol, 0.8 equiv) and Cs$_2$CO$_3$ (3.1 g, 9.5 mmol, 16 equiv) were placed in an oven dried Schlenk tube. The tube was capped with a Teflon screw cap, evacuated, and backfilled with nitrogen. Under positive nitrogen atmosphere, the screw cap was replaced with a rubber septum. Dioxane (60 mL) was added via syringe and the tube was purged with nitrogen for 1 min and sealed with Teflon screwcap. Reaction mixture was stirred at 100° C. for three days prior to being cooled to r.t. The reaction mixture was filtered through a short pad of Celite. The solvent was removed and the residue was purified by silica gel column chromatography (eluent: Hexanes/EtOAc 4:1) to give the title compound (820 mg, 88%); TLC R$_f$=0.35 (Hexanes/EtOAc 4:1). $^1$H NMR (500 MHz, CDCl$_3$) δ ppm 9.02 (d, J=4.6 Hz, 4H), 8.79 (d, J=4.6 Hz, 4H), 8.53 (s, 4H), 8.16 (d, J=1.2 Hz, 4H), 7.87-7.81 (m, 4H), 6.66 (s, 4H), 1.85-1.76 (m, 4H), 1.59-1.50 (m, 40H), 1.01 (s, 36H), 0.57-0.40 (m, 8H), −2.43 (s, 2H); $^{13}$C NMR (100 MHz, CDCl3) δ ppm 170.7, 168.7, 149.2, 140.0, 139.0, 130.3, 130.2, 123.2, 121.6, 121.2, 117.0, 107.0, 106.9, 80.7, 35.1, 31.7, 27.7, 24.1, 22.8, 15.1; HRMS (ESI) Calcd. for C$_{96}$H$_{114}$N$_8$NaO$_{12}^+$ [M+Na]$^+$: 1593.8448, Found: 1593.8510; UV-vis (CHCl$_3$), λ$_{max}$ nm (log ε): 421 (5.27), 517 (4.77), 552 (4.37), 592 (4.27), 648 (4.18). (Note: To build up enough materials, multiple runs were conducted.)

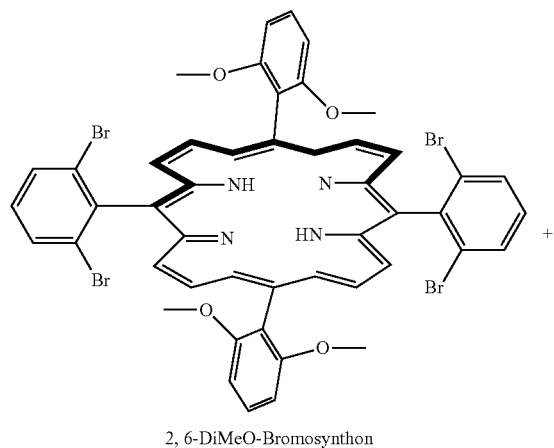

2,6-DiMeO-Bromosynthon

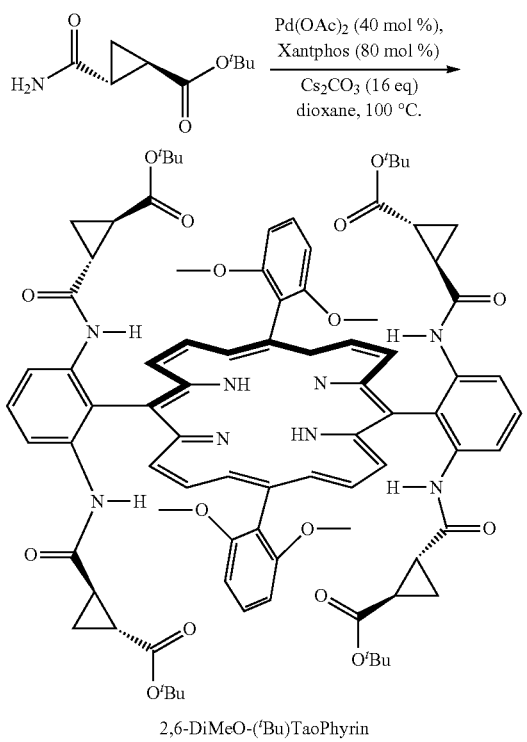

2,6-DiMeO-(tBu)TaoPhyrin

Representative procedure for the synthesis of (2,6-DiMeO-Tao($^t$Bu)Phyrin). 2,6-DiMeO-Bromosynthon (800 mg, 0.76 mmol, 1 equiv), the above synthesized chiral amide (tert-butyl (1R,2R)-2-carbamoylcyclopropane-1-carboxylate) (2.25 g, 12 mmol, 16 equiv), Pd(OAc)$_2$ (68 mg, 0.3 mmol, 0.4 equiv), Xantphos (356 mg, 0.61 mmol, 0.8 equiv) and 052003 (3.9 g, 12 mmol, 16 equiv) were placed in an oven dried Schlenk tube. The tube was capped with a Teflon screw cap, evacuated, and backfilled with nitrogen. Under positive nitrogen atmosphere, the screw cap was replaced with a rubber septum. Dioxane (80 mL) was added via syringe and the tube was purged with nitrogen for 1 min and sealed with Teflon screwcap. The reaction mixture was stirred at 100° C. for three days prior to being cooled to r.t. The reaction mixture was filtered through a short pad of Celite. The solvent was removed and the residue was purified by silica gel column chromatography (eluent: Hexanes/EtOAc 2:1) to give the title compound (757 mg, 68%); TLC R$_f$=0.30 (Hexanes/EtOAc 2:1). $^1$H NMR (500 MHz, CDCl$_3$) δ ppm 8.87 (d, J=4.8 Hz, 4H), 8.73 (d, J=4.7 Hz, 4H), 8.46 (br, 4H), 7.89-7.72 (m, 4H), 7.04 (d, J=8.5 Hz, 4H), 6.74 (s, 4H), 3.54 (s, 12H), 1.85 (ddd, J=3.9, 5.7, 9.3 Hz, 4H), 1.01 (s, 36H), 0.96-0.92 (m, 4H), 0.60-0.54 (m, 8H), 2.42 (s, 2H); $^{13}$C NMR (100 MHz, CDCl$_3$) δ ppm 170.5, 168.9, 160.3, 139.0, 130.9, 130.2, 121.9, 118.6, 117.8, 114.1, 106.4, 104.2, 80.6, 55.9, 27.7, 24.0, 22.8, 14.9; HRMS (ESI) m/z Calcd. for C$_{84}$H$_{91}$N$_8$O$_{16}^+$ [M+H]$^+$: 1467.6548, Found: 1467.6509; UV-vis (CHCl$_3$) λ$_{max}$ nm (log ε): 421 (5.53), 515 (4.34), 545 (3.81), 590 (3.85), 643 (3.55). (Note: To build up enough materials, multiple runs were conducted.)

Example 3: General Procedure A (Synthesis of Ester Amidoporphyrins)

Figure 13A:
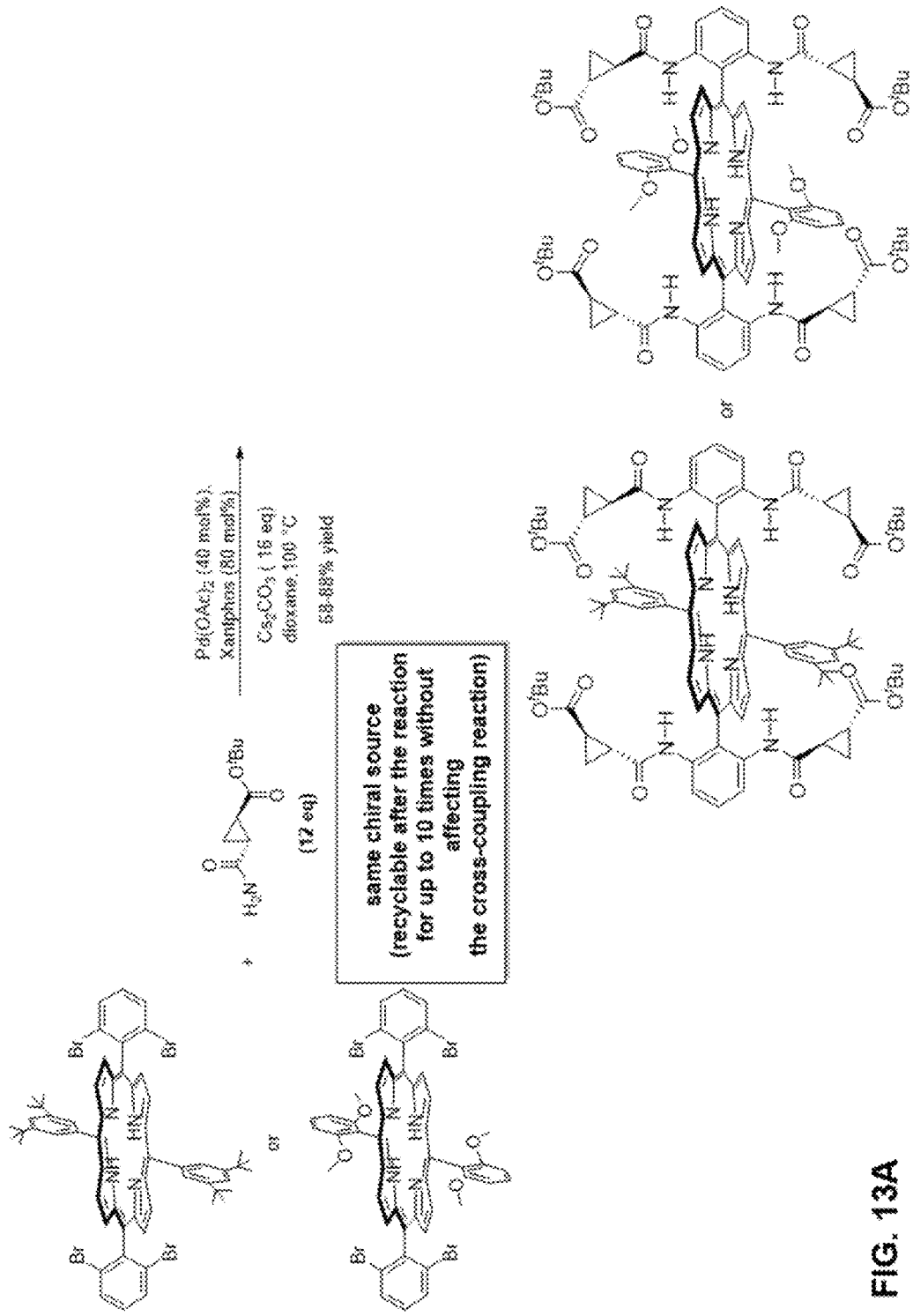
FIGS. 13A-13B show a summary of library synthesis of Co(II) based bridged amidoporphyrins.

TFA (100 equiv) was added to a solution of the above synthesized 3,5-Di$^t$Bu-Tao($^t$Bu)Phyrin (1 equiv) or 2,6-DiMeO-Tao($^t$Bu)Phyrin (1 equiv) in DCM (0.5 M) at 0° C. Then the reaction mixture was slowly warmed up to room temperature and stirred overnight. After the evaporation of all the volatiles, the residue was dissolved in DMF (0.1 M). K$_2$CO$_3$ (50 equiv) was added, followed by the addition of alkylating reagents (16 equiv). The reaction mixture was heated at 100° C. for 12 h. After cooling to the room temperature, the reaction mixture was diluted with EtOAc and water. The organic layer was separated and washed with brine 5 times. The organic solvent was removed under vacuum and the resulting oil was then purified by silica gel column chromatography (Conditions were given below) to afford the pure TaoPhyrin derivatives. (The reaction can be easily scaled up to 800 mg scale.) Example synthetic schemes for ester amidoporphyrins are shown in FIG. 13A.

Characterization of Ester Amidoporphyrins

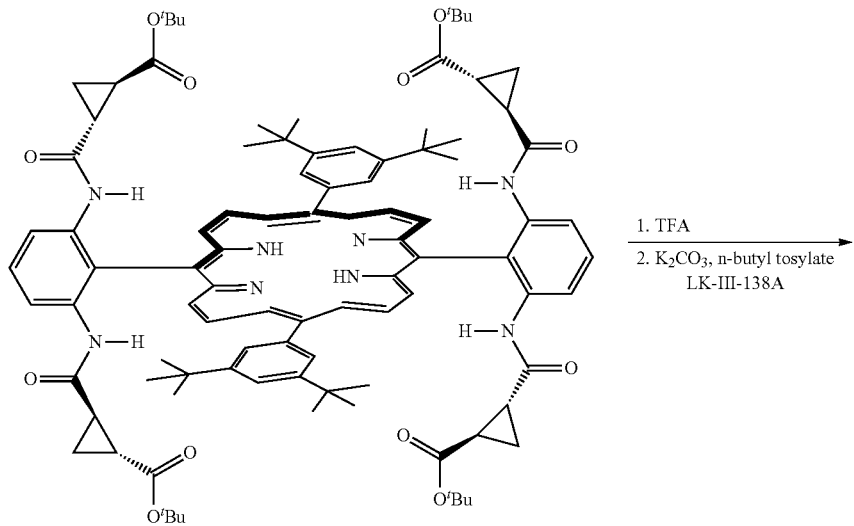

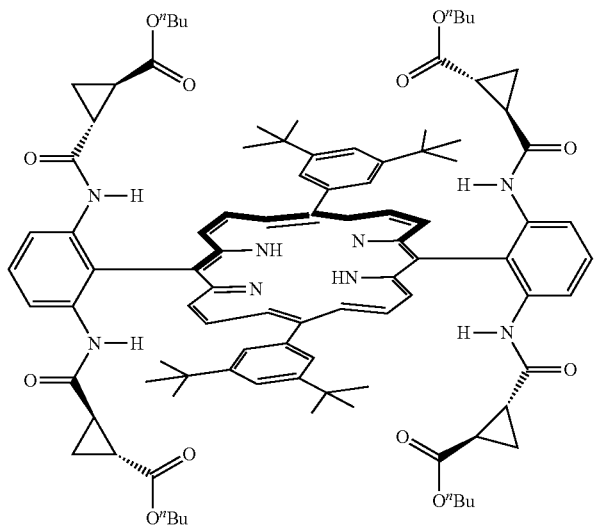

P10

(3,5-Di$^t$Bu-Tao(nBu)Phyrin) (P10) was synthesized following General Procedure A using n-butyl 4-methylbenzenesulfonate as the alkylating reagent and 3,5-Di$^t$Bu-Tao($^t$Bu)Phyrin (48 mg, 0.031 mmol) as catalyst building block, purified by silica gel column chromatography (eluent: Hexanes/EtOAc 6:1) to give the title compound in 82% yield (40 mg); TLC R$_f$=0.35 (Hexanes/EtOAc 4:1). $^1$H NMR (500 MHz, CDCl$_3$) δ ppm 9.03 (d, J=5.3 Hz, 4H), 8.79 (d, J=5.3 Hz, 4H), 8.65-8.39 (m, 4H), 8.19 (d, J=1.5 Hz, 4H), 7.90-7.77 (m, 4H), 6.68 (br. s., 4H), 3.64-3.46 (m, 8H), 1.87-1.85 (m, 4H), 1.57 (s, 36H), 1.24-1.21 (m, 8H), 1.13-0.94 (m, 12H), 0.65-0.63 (t, J=7.2 Hz, 12H), 0.62-0.60 (m, 4H), 0.55-0.37 (m, 4H), −2.46 (s, 2H); $^{13}$C NMR (100 MHz, CDCl$_3$) δ ppm 171.7, 168.3, 149.2, 140.0, 139.0, 133.7, 130.4, 130.3, 129.7, 123.3, 121.6, 116.8, 106.7, 64.5, 35.1, 31.7, 30.2, 24.5, 21.7, 18.7, 15.2, 13.4; HRMS (ESI) m/z Calcd. for C$_{96}$H$_{115}$N$_8$O$_{12}^+$ [M+H]$^+$: 1571.8629, Found: 1571.8658; UV-vis (CHCl$_3$), λ$_{max}$ nm (log ε): 422 (5.33), 522 (4.09), 560 (3.54), 598 (3.55), 652 (3.31).

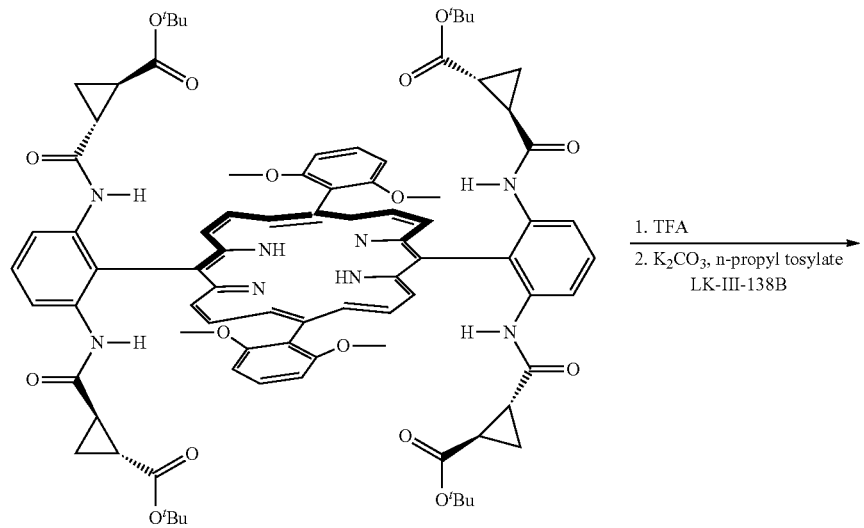

1. TFA
2. K₂CO₃, n-propyl tosylate
LK-III-138B

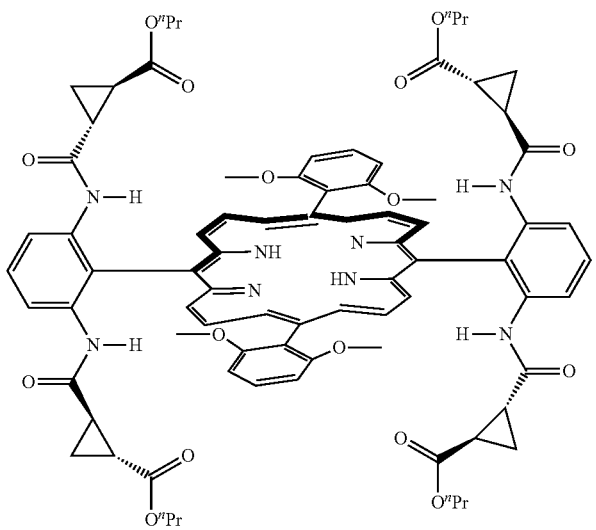

P11

(2,6-DiMeO-Tao(nPr)Phyrin) (P11) was synthesized following General Procedure A using n-propyl 4-methylbenzenesulfonate as the alkylating reagent and 2,6-DiMeO-Tao (ᵗBu)Phyrin (76 mg, 0.052 mmol) as catalyst building block, purified by silica gel column chromatography (eluent: Hexanes/EtOAc 3:1) to give the title compound in 82% yield (60 mg); TLC $R_f$=0.30 (Hexanes/EtOAc 2:1). $^1$H NMR (500 MHz, CDCl$_3$) δ ppm 8.87 (d, J=4.6 Hz, 4H), 8.72 (d, J=4.6 Hz, 4H), 8.47 (br. s., 4H), 7.83 (t, J=8.4 Hz, 2H), 7.78 (t, J=8.4 Hz, 2H), 7.04 (d, J=9.2 Hz, 4H), 6.76 (br. s., 4H), 3.55 (s, 12H), 3.54-3.46 (m, 8H), 1.96-1.85 (m, 4H), 1.36-1.17 (m, 8H), 1.13-0.95 (m, 4H), 0.60 (m, 20H), −2.42 (s, 2H); $^{13}$C NMR (100 MHz, CDCl$_3$) δ ppm 171.3, 168.5, 160.3, 138.9, 130.9, 130.3, 118.4, 117.6, 114.1, 106.3, 104.2, 66.0, 55.9, 24.4, 21.7, 21.5, 14.9, 10.0; HRMS (ESI) m/z Calcd. for $C_{80}H_{83}N_8O_{16}^+$[M+H]$^+$: 1411.5922, Found: 1411.5939; UV-vis (CHCl$_3$), $\lambda_{max}$ nm (log ε): 424 (5.54), 514 (4.53), 556 (3.80), 590 (4.04), 644 (3.68).

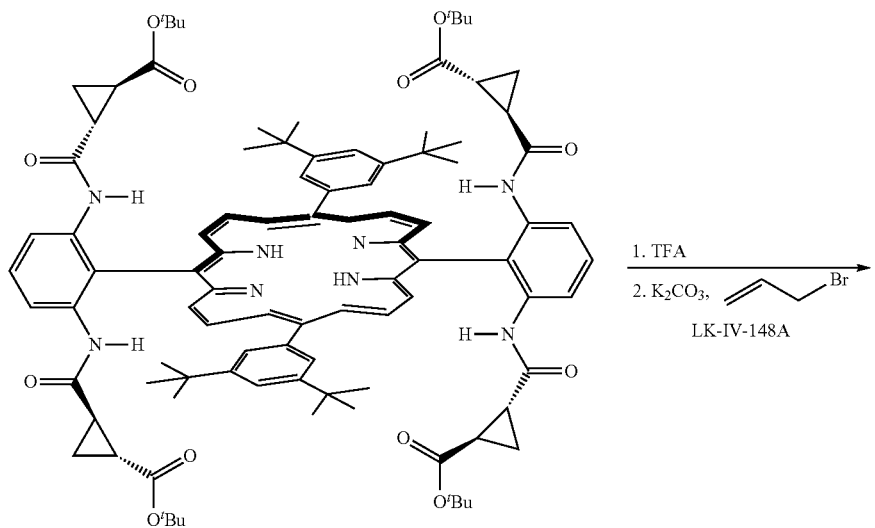

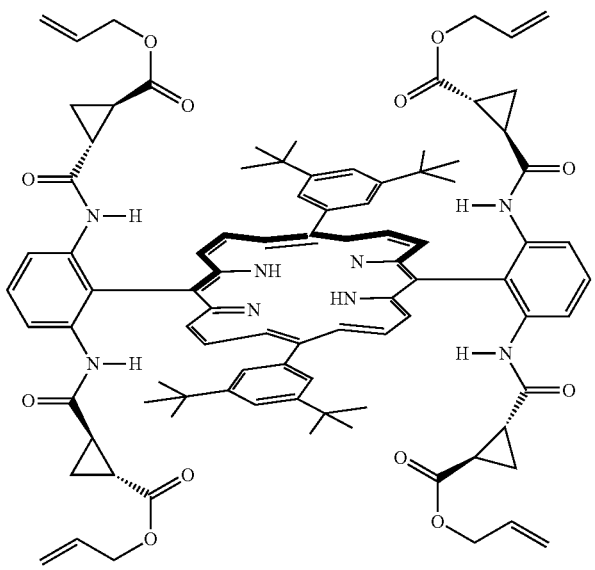

(3,5-Di'Bu-Tao(Allyl)Phyrin) was synthesized following General Procedure A at 80° C. using allyl bromide as the alkylating reagent and 3,5-Di'Bu-Tao('Bu)Phyrin (139 mg, 0.088 mmol) as catalyst building block, purified by silica gel column chromatography (eluent: Hexanes/EtOAc 6:1) to give the title compound in 90% yield (120 mg); TLC $R_f$=0.35 (Hexanes/EtOAc 4:1). $^1$H NMR (500 MHz, CDCl$_3$) δ ppm 9.09 (d, J=4.6 Hz, 4H), 8.84 (d, J=4.6 Hz, 4H), 8.59 (d, J=8.1 Hz, 4H), 8.23 (d, J=1.7 Hz, 4H), 7.97-7.85 (m, 4H), 6.74 (br. s., 4H), 5.53-5.37 (m, 4H), 5.01-4.82 (m, 8H), 4.03 (dd, J=4.6, 15.0 Hz, 8H), 1.93-1.85 (m, 4H), 1.56 (s, 36H), 1.18-1.11 (m, 4H), 0.65 (br. s., 4H), 0.56 (br. s., 4H), −2.42 (s, 2H); $^{13}$C NMR (100 MHz, CDCl$_3$) δ ppm 171.3, 168.1, 149.2, 140.0, 139.0, 131.4, 130.5, 130.2, 123.3, 121.6, 118.1, 117.0, 107.0, 65.1, 35.1, 31.8, 24.6, 21.6, 15.2; HRMS (ESI) m/z Calcd. for $C_{92}H_{98}N_8NaO_{12}^+$ [M+Na]$^+$: 1529.7196, Found: 1529.7243; UV-vis (CHCl$_3$), $\lambda_{max}$ nm (log ε): 422 (5.33), 516 (4.11), 550 (3.68), 590 (3.61), 646 (3.45).

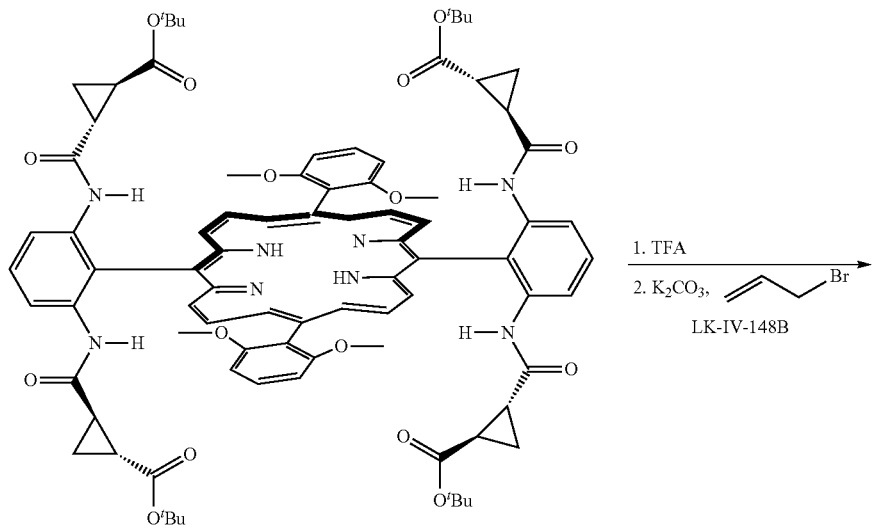

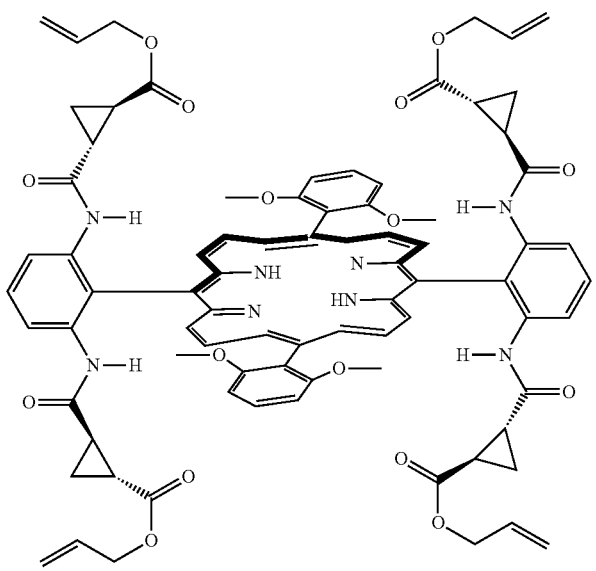

(2,6-DiMeO-Tao(Allyl)Phyrin) was synthesized following General Procedure A at 80° C. using allyl bromide as the alkylating reagent and 2,6-DiMeO-Tao(tBu)Phyrin (139 mg, 0.095 mmol) as catalyst building block, purified by silica gel column chromatography (eluent: Hexanes/EtOAc 3:1) to give the title compound in 75% yield (100 mg); TLC $R_f$=0.30 (Hexanes/EtOAc 2:1). $^1$H NMR (500 MHz, CDCl$_3$) δ ppm 8.90 (d, J=4.6 Hz, 4H), 8.74 (d, J=4.6 Hz, 4H), 8.48 (d, J=4.6 Hz, 4H), 7.90-7.79 (m, 4H), 7.08 (d, J=8.7 Hz, 4H), 6.82 (br. s., 4H), 5.56-5.36 (m, 4H), 5.08-4.68 (m, 8H), 3.98 (d, J=6.9 Hz, 8H), 3.58 (s, 12H), 1.85 (br. s, 4H), 1.03 (br. s, 4H), 0.62 (br. s, 4H), 0.53 (br. s., 4H), −2.42 (br. s, 2H); $^{13}$C NMR (125 MHz, CDCl$_3$) δ ppm 170.9, 168.4, 160.3, 138.9, 131.6, 131.0, 130.3, 121.7, 118.4, 118.0, 117.6, 114.2, 106.3, 104.3, 65.1, 55.9, 24.5, 21.6, 14.9; HRMS (ESI) m/z Calcd. for $C_{80}H_{75}N_8O_{16}^+$ [M+H]$^+$: 1403.5296, Found: 1403.5332; UV-vis (CHCl$_3$), $\lambda_{max}$ nm (log ε): 422 (5.26), 514 (4.10), 548 (3.48), 588 (3.60), 6.44 (3.16).

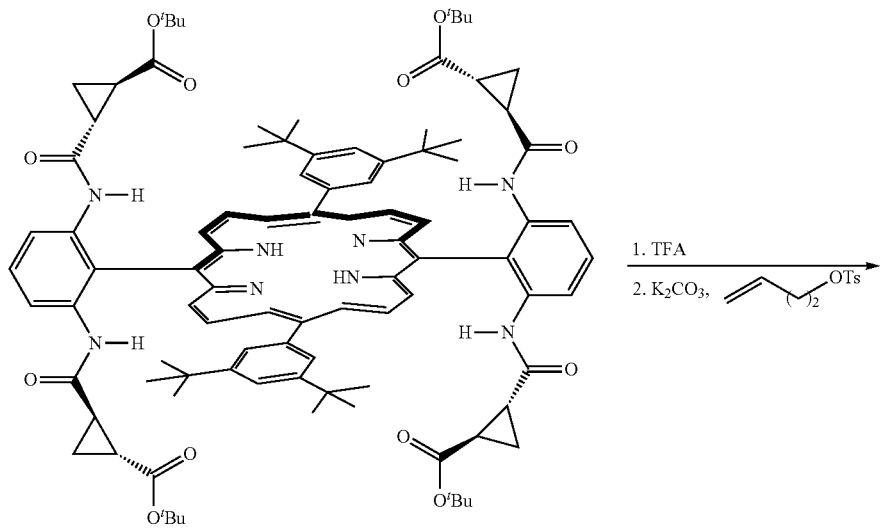

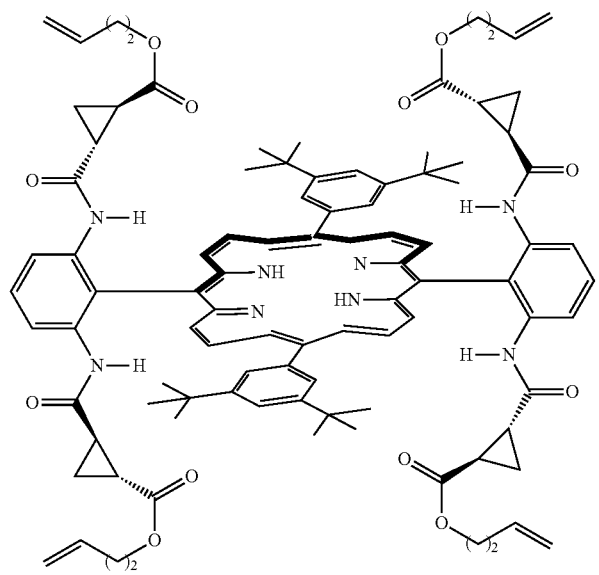

(3,5-Di'Bu-Tao(But-3-en-1-yl)Phyrin) was synthesized following General Procedure A using but-3-en-1-yl 4-methylbenzenesulfonate as the alkylating reagent and 3,5-Di'Bu-Tao('Bu)Phyrin (190 mg, 0.121 mmol) as catalyst building block, purified by silica gel column chromatography (eluent: Hexanes/EtOAc 6:1) to give the title compound in 95% yield (180 mg); TLC $R_f$=0.35 (Hexanes/EtOAc 4:1). $^1$H NMR (500 MHz, CDCl$_3$) δ ppm 9.07 (d, J=4.6 Hz, 4H), 8.83 (d, J=5.2 Hz, 4H), 8.63-8.55 (m, 4H), 8.21 (d, J=1.7 Hz, 4H), 7.90 (t, J=2.0 Hz, 2H), 7.87 (t, J=8.7 Hz, 2H), 6.70 (s, 4H), 5.44-5.33 (m, 4H), 4.80-4.66 (m, 8H), 3.83-3.47 (m, 8H), 2.18-1.95 (m, 8H), 1.88 (ddd, J=3.8, 5.3, 8.8 Hz, 4H), 1.59 (s, 36H), 1.12 (ddd, J=4.0, 5.5, 9.0 Hz, 4H), 0.69-0.60 (m, 4H), 0.56-0.47 (m, 4H), −2.43 (s, 2H); $^{13}$C NMR (125 MHz, CDCl3) δ ppm 171.6, 168.3, 149.3, 140.0, 139.0, 133.5, 130.5, 130.3, 123.3, 121.7, 117.0, 116.8, 106.8, 63.5, 35.2, 32.6, 31.8, 24.6, 21.7, 15.2; HRMS (ESI) m/z Calcd. for $C_{96}H_{106}N_8NaO_{12}^+$ [M+Na]$^+$: 1585.7822, Found: 1585.7854. UV-vis (CHCl$_3$), $\lambda_{max}$ nm (log ε): 422 (5.26), 516 (4.08), 552 (3.81), 592 (3.60), 648 (3.50).

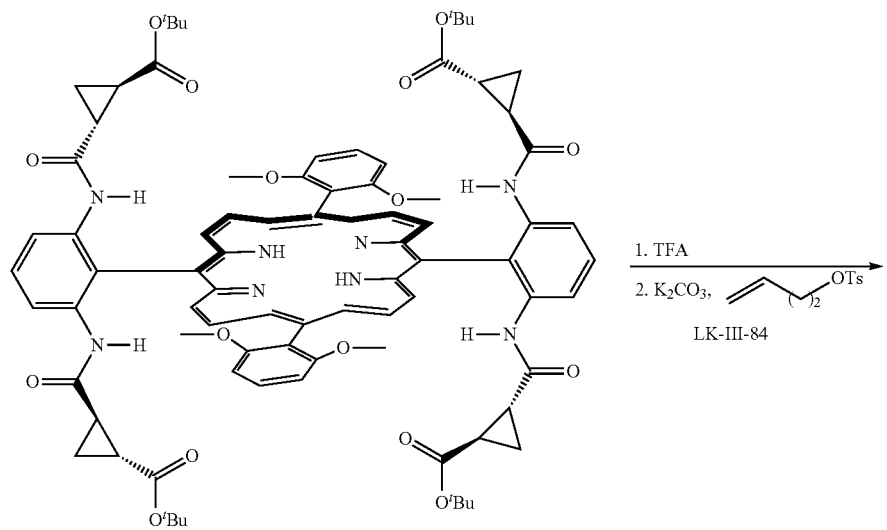

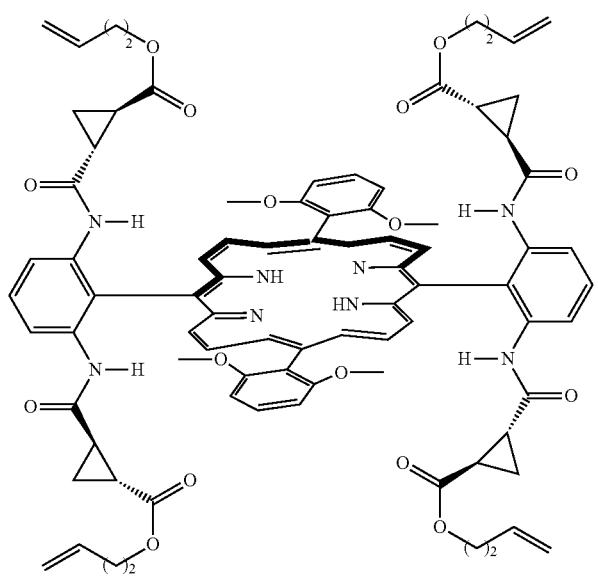

(2,6-DiMeO-Tao(But-3-en-1-yl)Phyrin) was synthesized following General Procedure A using but-3-en-1-yl 4-methylbenzenesulfonate as the alkylating reagent and 2,6-DiMeO-Tao($^t$Bu)Phyrin (270 mg, 0.184 mmol) as catalyst building block, purified by silica gel column chromatography (eluent: Hexanes/EtOAc 3:1) to give the title compound in 70% yield (188 mg); TLC Rf=0.30 (Hexanes/EtOAc 2:1). $^1$H NMR (500 MHz, CDCl$_3$) δ ppm 8.88 (d, J=4.6 Hz, 4H), 8.72 (d, J=4.6 Hz, 4H), 8.48 (d, J=4.6 Hz, 4H), 7.83 (t, J=8.4 Hz, 2H), 7.78 (t, J=8.8 Hz, 2H), 7.04 (d, J=8.4 Hz, 4H), 6.75 (br. s., 4H), 5.63-5.25 (m, 4H), 4.86-4.68 (m, 8H), 3.62-3.52 (m, 8H), 3.55 (s, 12H), 1.97 (d, J=5.3 Hz, 8H), 1.92-1.83 (m, 4H), 1.10-0.99 (m, 4H), 0.65-0.58 (m, 8H), −2.42 (s, 2H); $^{13}$C NMR (100 MHz, CDCl$_3$) δ ppm 171.2, 168.4, 160.3, 138.9, 133.5, 130.9, 130.3, 118.4, 117.5, 116.9, 114.2, 106.3, 104.2, 63.4, 55.9, 32.6, 24.4, 21.7, 14.9; HRMS (ESI) m/z Calcd. for C$_{84}$H$_{83}$N$_8$O$_{16}$$^+$[M+H]$^+$: 1459.5922, Found: 1459.5950; UV-vis (CHCl$_3$) λ$_{max}$ nm (log ε): 424 (5.26), 514 (4.20), 546 (3.59), 588 (3.71), 644 (3.27).

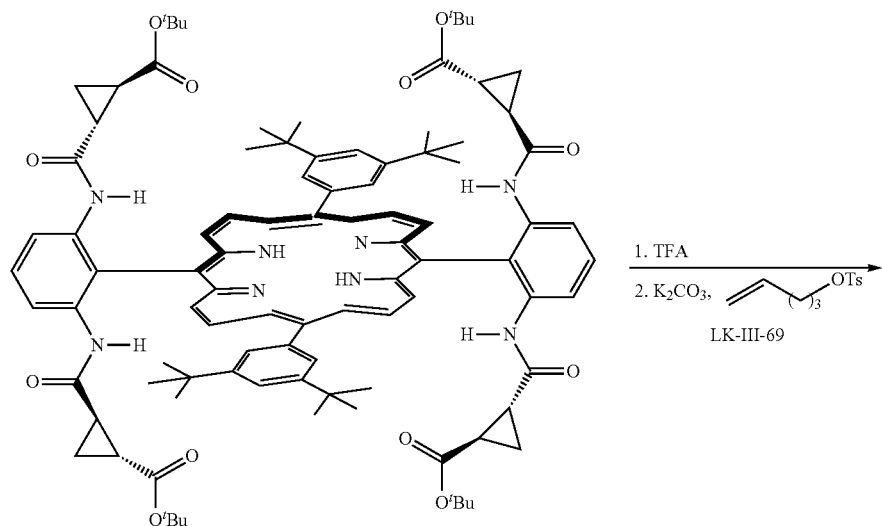

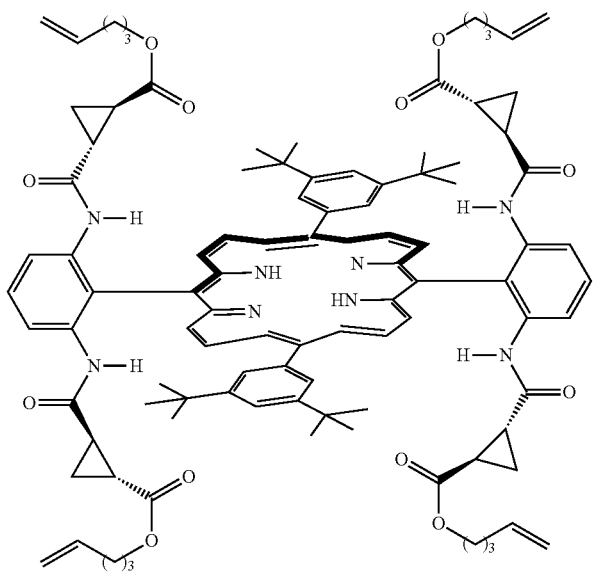

(3,5-Di'Bu-Tao(Pent-4-en-1-yl)Phyrin) was synthesized following General Procedure A using pent-4-en-1-yl 4-methyl benzenesulfonate as the alkylating reagent and 3,5-Di'Bu-Tao('Bu)Phyrin (235 mg, 0.150 mmol) as catalyst building block, purified by silica gel column chromatography (eluent: Hexanes/EtOAc 6:1) to give the title compound in 70% yield (170 mg); TLC $R_f$=0.35 (Hexanes/EtOAc 4:1). $^1$H NMR (500 MHz, CDCl$^3$) δ ppm 9.08 (d, J=4.6 Hz, 4H), 8.84 (d, J=4.6 Hz, 4H), 8.60 (d, J=8.1 Hz, 4H), 8.23 (d, J=1.7 Hz, 4H), 7.91 (t, J=1.7 Hz, 2H), 7.89 (t, J=8.4 Hz, 2H), 6.73 (s, 4H), 5.67-5.44 (m, 4H), 4.82-4.62 (m, 8H), 3.70-3.47 (m, 8H), 1.91 (ddd, J=3.8, 5.3, 8.8 Hz, 4H), 1.86-1.76 (m, 8H), 1.61 (s, 36H), 1.44-1.33 (m, 8H), 1.14 (ddd, J=4.0, 5.1, 8.8 Hz, 4H), 0.68-0.62 (m, 4H), 0.57-0.50 (m, 4H), -2.41 (s, 2H); $^{13}$C NMR (125 MHz, CDCl$_3$) δ ppm 171.7, 168.3, 149.3, 140.0, 139.0, 137.1, 130.5, 130.3, 123.4, 121.6, 116.8, 115.1, 106.8, 64.1, 35.2, 31.8, 29.7, 27.4, 24.6, 21.7, 15.3; HRMS (ESI) m/z Calcd. for $C_{100}H_{114}N_8NaO_{12}^+$[M+Na]$^+$: 1641.8448, Found: 1641.8433; UV-vis (CHCl$_3$), $\lambda_{max}$ nm (log ε): 422 (5.46), 516 (4.22), 550 (3.84), 590 (3.74), 646 (3.55).

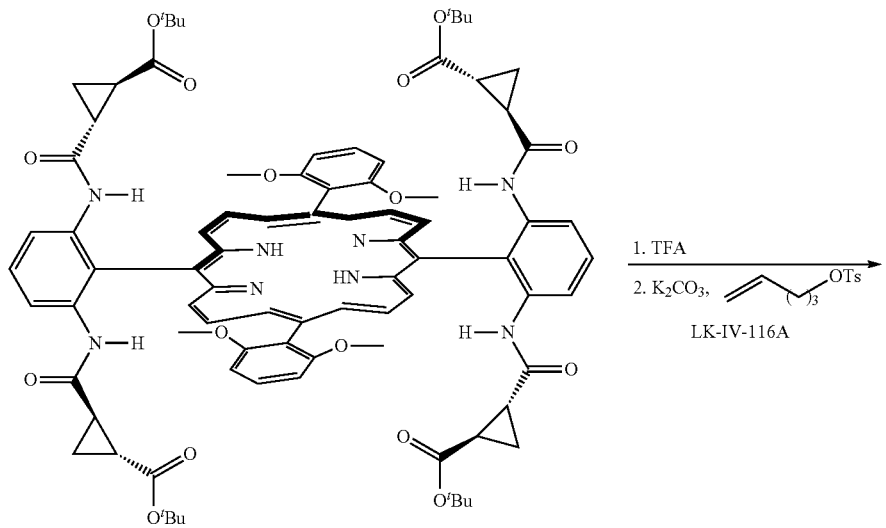

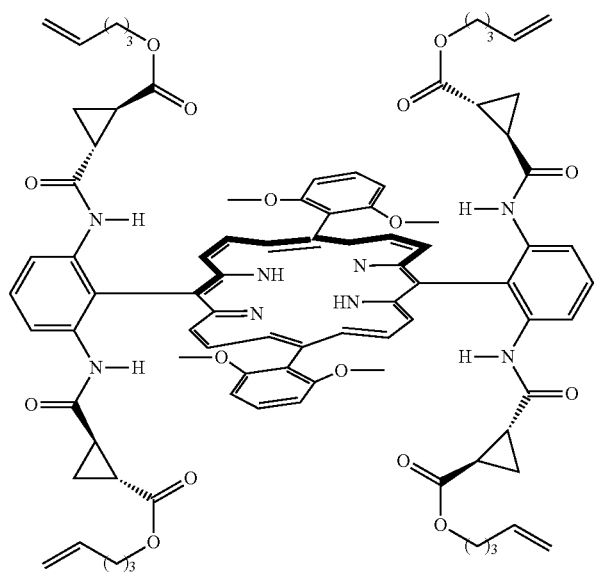

(2,6-DiMeO-Tao(Pent-4-en-1-yl)Phyrin) was synthesized following General Procedure A using pent-4-en-1-yl 4-methyl benzenesulfonate as the alkylating reagent and 2,6-DiMeO-Tao($^t$Bu)Phyrin (75 mg, 0.051 mmol) as catalyst building block, purified by silica gel column chromatography (eluent: Hexanes/EtOAc 3:1) to give the title compound in 90% yield (70 mg); TLC $R_f$=0.30 (Hexanes/EtOAc 2:1). $^1$H NMR (500 MHz, CDCl$_3$) δ ppm 8.87 (d, J=4.6 Hz, 4H), 8.72 (d, J=4.0 Hz, 4H), 8.47 (br. s., 4H), 7.83 (t, J=8.4 Hz, 2H), 7.78 (t, J=8.4 Hz, 2H), 7.04 (d, J=8.7 Hz, 4H), 6.76 (br. s., 4H), 5.59-5.45 (m, 4H), 4.85-4.73 (m, 8H), 3.72-3.40 (m, 8H), 3.54 (s, 12H), 1.91 (td, J=4.6, 8.8 Hz, 4H), 1.79 (d, J=6.4 Hz, 8H), 1.40-1.30 (m, 8H), 1.09-0.97 (m, 4H), 0.70-0.55 (m, 8H), −2.43 (s, 2H); $^{13}$C NMR (125 MHz, CDCl$_3$) δ ppm 171.4, 168.5, 160.3, 138.9, 137.2, 131.0, 130.3, 118.4, 117.6, 115.1, 114.2, 110.0, 106.3, 104.2, 64.0, 55.9, 29.7, 27.4, 24.4, 21.7, 15.0; HRMS (ESI) m/z Calcd. for C$_{88}$H$_{91}$N$_8$O$_{16}^+$ [M+H]$^+$: 1515.6548, Found: 1515.6579; UV-vis (CHCl$_3$), λ$_{max}$ nm (log ε): 424 (5.28), 514 (4.25), 546 (3.64), 588 (3.75), 642 (3.34).

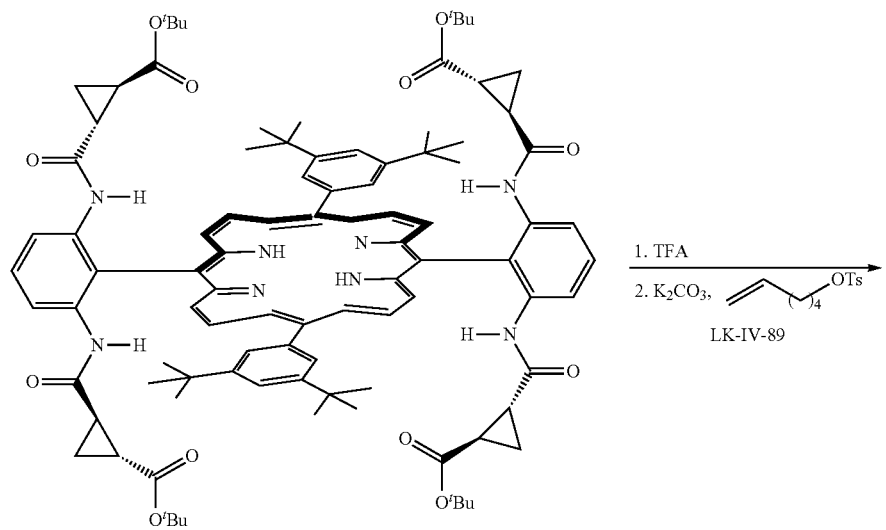

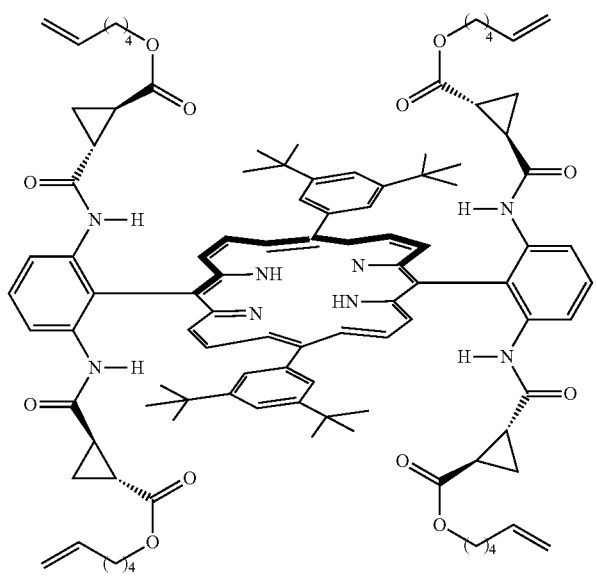

(3,5-Di$^t$Bu-Tao(Hex-5-en-1-yl)Phyrin) was synthesized following General Procedure A using hex-5-en-1-yl 4-methylbenzenesulfonate as the alkylating reagent and 3,5-Di$^t$Bu-Tao($^t$Bu)Phyrin (64 mg, 0.041 mmol) as catalyst building block, purified by silica gel column chromatography (eluent: Hexanes/EtOAc 6:1) to give the title compound in 66% yield (45 mg); TLC R$_f$=0.35 (Hexanes/EtOAc 4:1). $^1$H NMR (500 MHz, CDCl$_3$) δ ppm 9.04 (d, J=4.6 Hz, 4H), 8.79 (d, J=4.6 Hz, 4H), 8.63-8.48 (m, 4H), 8.19 (s, 4H), 7.85 (d, J=12.4 Hz, 4H), 6.68 (br. s., 4H), 5.63-5.51 (m, 4H), 4.87-4.74 (m, 8H), 3.63-3.44 (m, 8H), 1.92-1.77 (m, 12H), 1.57 (s, 36H), 1.25-1.22 (m, 8H), 1.18-1.04 (m, 12H), 0.66-0.56 (m, 4H), 0.54-0.42 (m, 4H), 2.46 (s, 2H); $^{13}$C NMR (125 MHz, CDCl$_3$) δ ppm 171.8, 168.3, 149.2, 140.0, 139.0, 138.6, 138.0, 130.5, 130.3, 123.3, 121.6, 114.7, 64.6, 35.2, 33.5, 33.0, 31.8, 27.6, 24.8, 21.7, 15.3; HRMS (ESI) m/z Calcd. for C$_{104}$H$_{123}$%$_{O12+}$[M+H]$^+$: 1675.9255, Found: 1675.9187; UV-vis (CHCl$_3$), λ$_{max}$ nm (log ε): 424 (5.27), 516 (4.08), 552 (3.67), 590 (3.59), 646 (3.41).

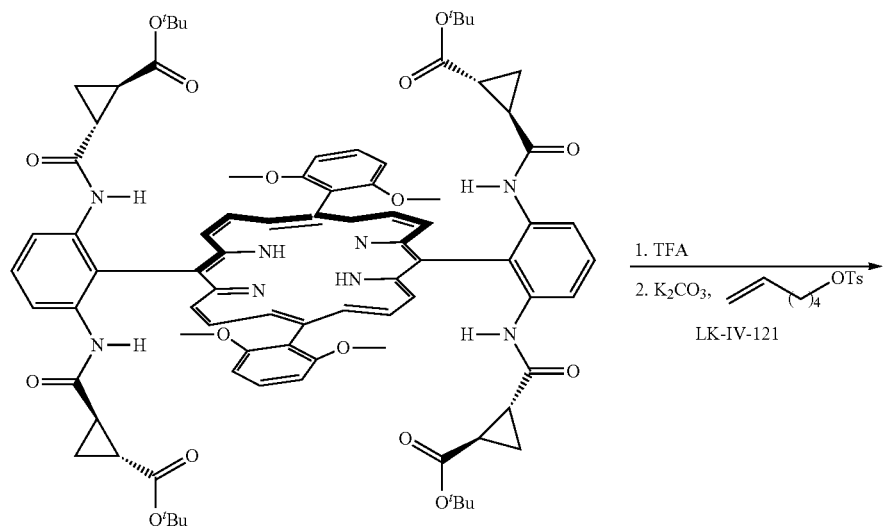

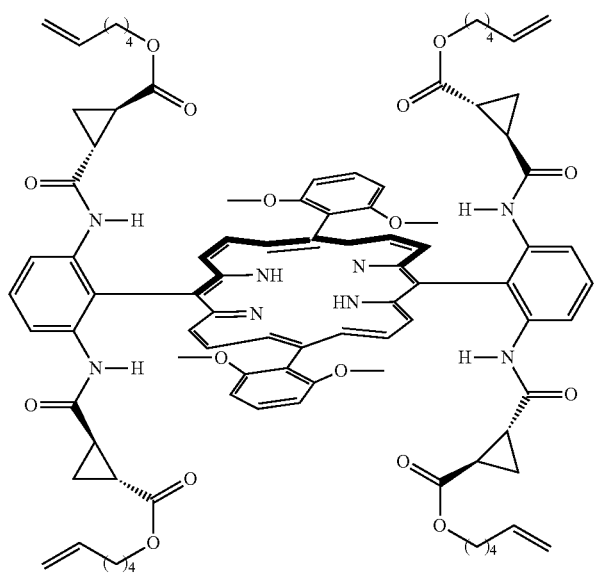

(2,6-DiMeO-Tao(Hex-5-en-1-yl)Phyrin) was synthesized following General Procedure A using hex-5-en-1-yl 4-methylbenzenesulfonate as the alkylating reagent and 2,6-DiMeO-Tao($^t$Bu)Phyrin (62 mg, 0.042 mmol) as catalyst building block, purified by silica gel column chromatography (eluent: Hexanes/EtOAc 4:1) to give the title compound in 65% yield (43 mg); TLC $R_f$=0.30 (Hexanes/EtOAc 3:1). $^1$H NMR (500 MHz, CDCl$_3$) δ ppm 8.87 (d, J=4.6 Hz, 4H), 8.72 (d, J=4.6 Hz, 4H), 8.46 (br. s., 4H), 7.83 (t, J=8.5 Hz, 2H), 7.78 (t, J=8.5 Hz, 2H), 7.04 (d, J=8.7 Hz, 4H), 6.75 (br. s., 4H), 5.59 (d, J=6.9 Hz, 4H), 4.87-4.78 (m, 8H), 3.58 (br. s., 4H), 3.55 (s, 12H), 1.91 (td, J=4.6, 8.8 Hz, 4H), 1.83 (d, J=6.4 Hz, 8H), 1.36-1.21 (m, 12H), 1.15 (d, J=6.4 Hz, 8H), 1.08-0.97 (m, 4H), 0.60 (br. s., 8H), −2.42 (s, 2H); $^{13}$C NMR (125 MHz, CDCl$_3$) δ ppm 171.4, 168.5, 162.6, 160.3, 138.9, 138.1, 131.0, 130.3, 118.4, 117.6, 115.2, 114.7, 114.2, 104.3, 64.5, 55.9, 33.1, 27.7, 24.9, 24.4, 21.7, 15.0; HRMS (ESI) m/z Calcd. for $C_{92}H_{99}N_8O_{16}^+$[M+H]$^+$: 1571.7174, Found: 1571.7114; UV-vis (CHCl$_3$), $\lambda_{max}$ nm (log ε): 422 (5.13), 516 (4.06), 546 (3.47), 590 (3.56), 644 (3.22).

Example 4: General Procedure B (Synthesis of Bridged Amidoporphyrins)

Figure 12:
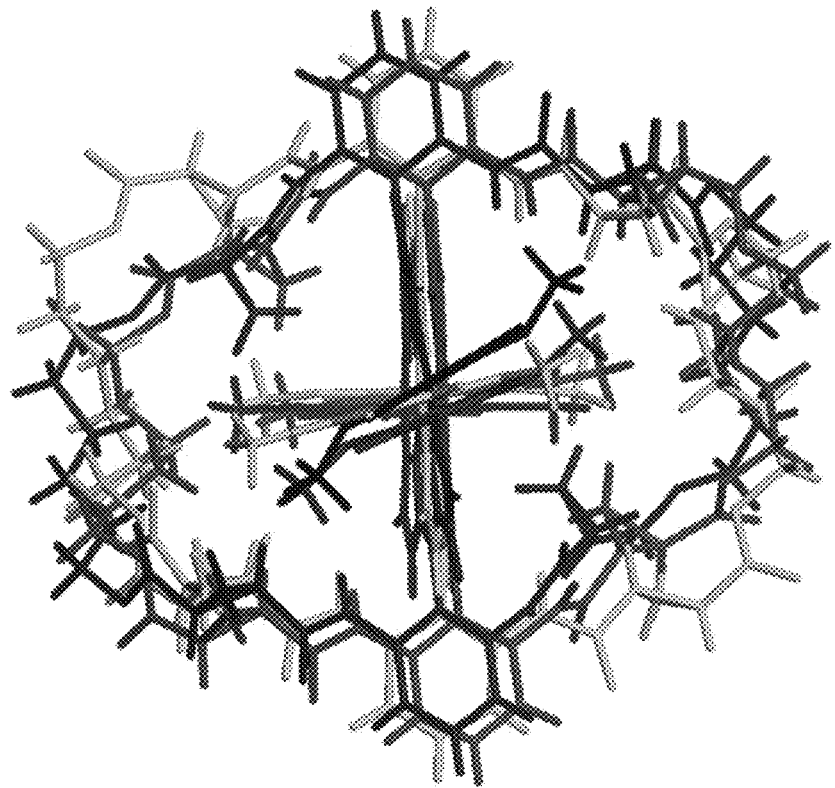
FIG. 12 shows a summary of structures of compounds useful in the disclosed methods confirmed by X-ray structural data.
Figure 12:
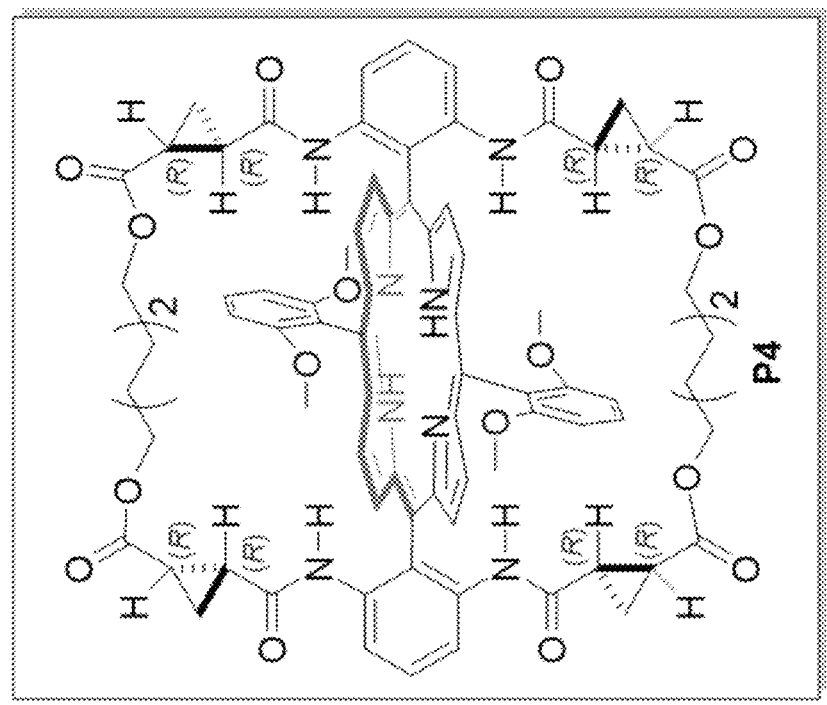
Figure 13B:
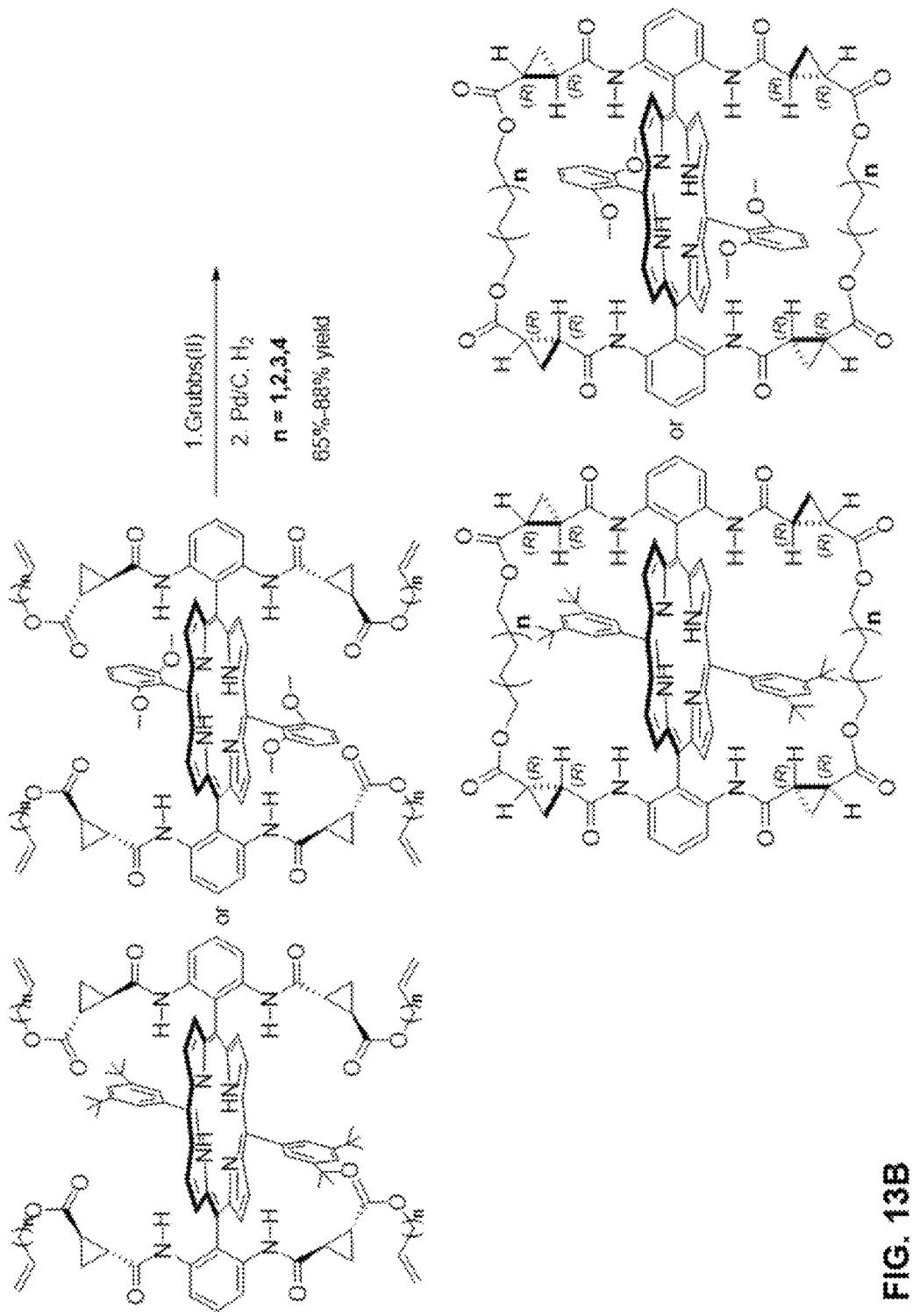

Three-dimensional structures of selected amidoporphyrins as determined by X-ray crystallography are shown in FIG. 12. Example synthetic schemes for bridged amidoporphyrins are shown in FIG. 13B.

Under nitrogen atmosphere, Grubbs 2nd generation catalyst (0.1 equiv) was added to a solution of the above synthesized porphyrins with olefin side chains (1 equiv) in DCM (0.001 M). The reaction mixture was stirred at 40° C. for 12 hours. The reaction mixture was directly poured onto a pad of silica gel (Hexanes/EtOAc=1:1) to afford the mixture of trans-cis olefin metathesis isomers. The solvent was removed and the residue was dissolved in EtOAc-toluene (V/V 2/1, 0.02 M) in the presence of 10% Pd/C (1 mg per mg of porphyrin). Hydrogen gas was bubbled through the reaction mixture until the reaction was completed (typically for 30 min). The reaction mixture was pass through a short pad of Celite, the filtrate was concentrated and purified by silica gel column chromatography (Conditions were given below) to afford the desired product. (The reaction can be easily scaled up to 500 mg scale.) Characterization of Bridged Amidoporphyrins

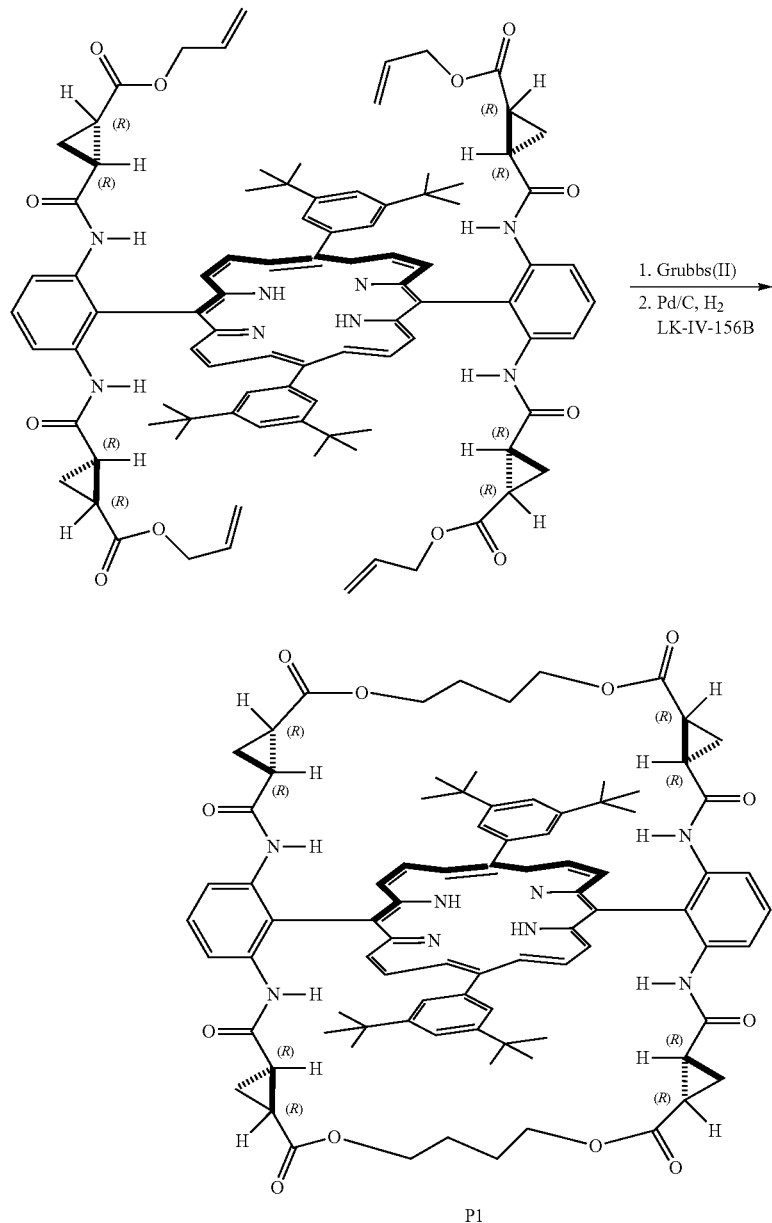

(3,5-Di$^t$Bu-Hu(C$_4$)Phyrin) (P1) was synthesized following General Procedure B from (3,5-Di$^t$BuTao-(Allyl)Phyrin) (73 mg, 0.049 mmol), purified by silica gel column chromatography (eluent: Hexanes/EtOAc 3:1) to give the title compound in 85% yield (60 mg); TLC R$_f$=0.35 (Hexanes/EtOAc 2:1). $^1$H NMR (500 MHz, CDCl$_3$) δ ppm 9.14 (d, J=5.2 Hz, 4H), 8.92 (d, J=4.6 Hz, 4H), 8.45 (d, J=8.7 Hz, 4H), 8.14 (d, J=1.7 Hz, 4H), 7.95-7.89 (m, 4H), 6.63 (s, 4H), 3.63-3.54 (m, 4H), 3.37-3.28 (m, 4H), 1.80 (ddd, J=4.0, 5.5, 9.0 Hz, 4H), 1.61 (s, 36H), 1.08-1.02 (m, 4H), 0.95-0.89 (m, 8H), 0.69 (dd, J=4.6, 8.7 Hz, 4H), 0.66-0.57 (m, 4H), −2.53 (s, 2H); $^{13}$C NMR (125 MHz, CDCl$_3$) δ ppm 170.6, 168.1, 149.6, 139.4, 138.8, 130.6, 130.0, 123.2, 123.0, 122.1, 118.6, 108.1, 64.0, 35.1, 31.7, 24.6, 23.7, 22.0, 14.9; HRMS (ESI) m/z Calcd. for C$_{88}$H$_{94}$N$_8$NaO$_{12}{}^+$ [M+Na]$^+$: 1477.6883, Found: 1477.6867; UV-vis (CHCl$_3$), λ$_{max}$ nm (log ε): 424 (5.29), 514 (3.97), 552 (3.67), 590 (3.55), 644 (3.36).

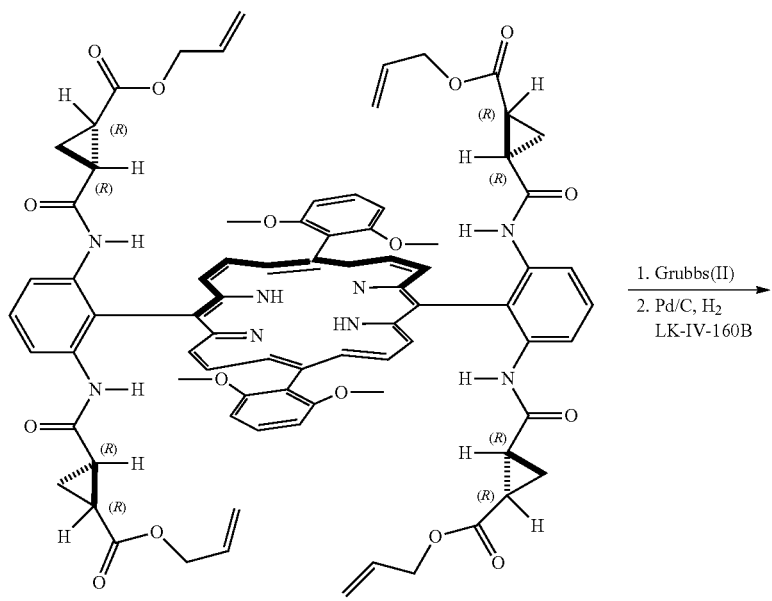

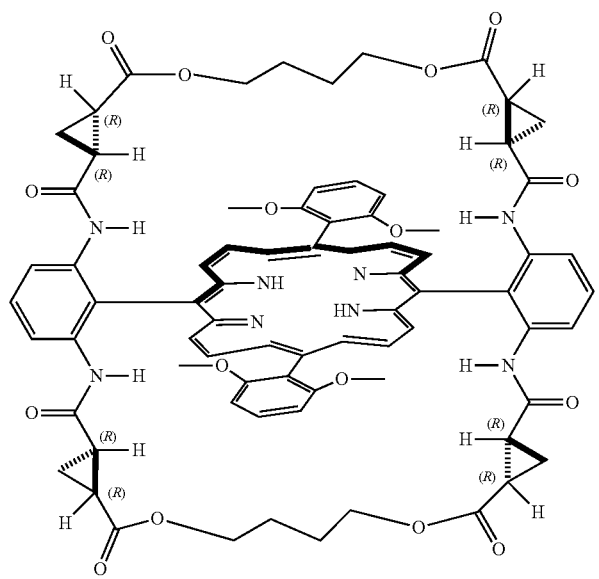

P2

(2,6-DiMeO-Hu(C$_4$)Phyrin) (P2) was synthesized following General Procedure B from (2,6-DiMeO-Tao(Allyl)Phyrin) (89 mg, 0.063 mmol), purified by silica gel column chromatography (eluent: Hexanes/EtOAc 2:1) to give the title compound in 82% yield (70 mg); TLC R$_f$=0.2 (Hexanes/EtOAc 1:1). $^1$H NMR (500 MHz, CDCl$_3$) δ ppm 8.98 (d, J=4.6 Hz, 4H), 8.82 (d, J=4.6 Hz, 4H), 8.46 (d, J=8.7 Hz, 4H), 7.92-7.83 (m, 4H), 7.12 (d, J=8.7 Hz, 4H), 6.67 (s, 4H), 3.67-3.59 (m, 12H), 3.60-3.49 (m, 4H), 3.35-3.26 (m, 4H), 1.88 (ddd, J=4.0, 5.5, 9.0 Hz, 4H), 1.03 (td, J=4.6, 8.8 Hz, 4H), 0.98-0.84 (m, 8H), 0.78-0.64 (m, 4H), 0.58 (td, J=4.6, 8.8 Hz, 4H), −2.50 (s, 2H); $^{13}$C NMR (125 MHz, CDCl$_3$) δ ppm 170.6, 168.2, 160.2, 138.9, 131.3, 130.5, 122.5, 118.3, 117.8, 114.2, 107.0, 104.4, 64.1, 56.1, 24.6, 23.8, 22.2, 14.8; HRMS (ESI) m/z Calcd. for C$_{76}$H$_{71}$N$_8$O$_{16}^+$ [M+H]$^+$: 1351.4983, Found: 1351.4970; UV-vis (CHCl$_3$), λ$_{max}$ nm (log ε): 422 (5.11), 514 (4.06), 544 (3.42), 586 (3.58), 640 (3.10).

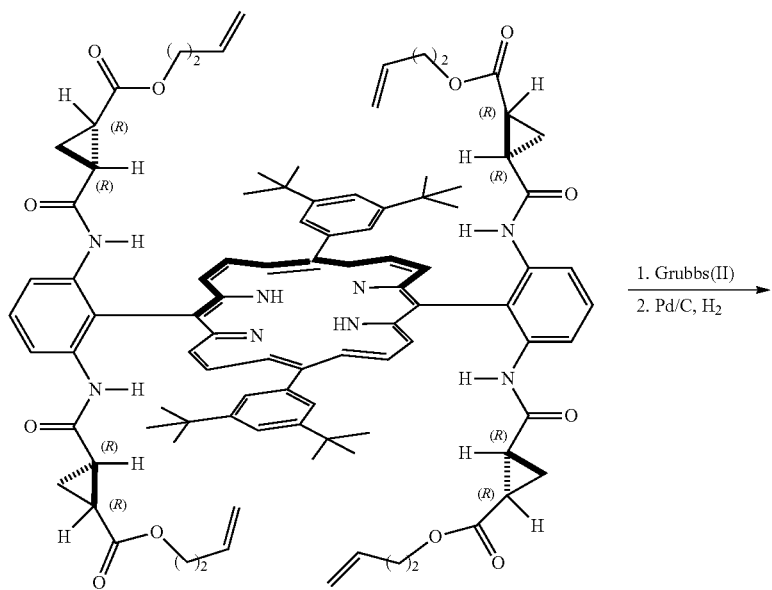

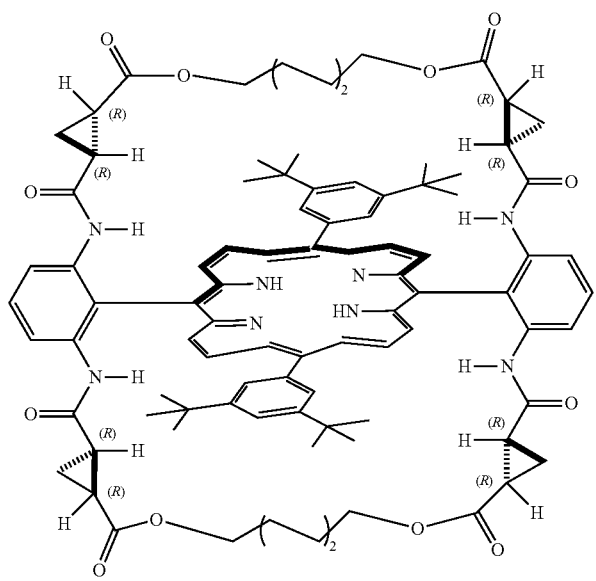

P3

(3,5-Di$^t$Bu-Hu(C$_6$)Phyrin) (P3) was synthesized following General Procedure B from (3,5-Di$^t$Bu-Tao(But-3-en-1-yl)Phyrin) (168 mg, 0.107 mmol), purified by silica gel column chromatography (eluent: Hexanes/EtOAc 3:1) to give the title compound in 80% yield (130 mg); TLC R$_f$=0.37 (Hexanes/EtOAc 2:1). $^1$H NMR (400 MHz, CDCl$_3$) δ ppm 9.05 (d, J=4.6 Hz, 4H), 8.85 (d, J=4.6 Hz, 4H), 8.41 (d, J=8.3 Hz, 4H), 8.11 (d, J=1.4 Hz, 4H), 7.94-7.79 (m, 4H), 6.64 (s, 4H), 3.62-3.56 (m, 4H), 3.50-3.44 (m, 4H), 1.92-1.88 (m, 4H), 1.57 (s, 36H), 1.07 (dd, J=3.7, 8.8 Hz, 4H), 1.01-0.90 (m, 8H), 0.78 (d, J=2.8 Hz, 8H), 0.67-0.49 (m, 8H), 2.55 (s, 2H); $^{13}$C NMR (100 MHz, CDCl$_3$) δ ppm 171.1, 168.3, 149.4, 139.8, 138.7, 130.5, 130.4, 130.3, 130.2, 123.3, 122.4, 121.9, 118.6, 107.7, 64.3, 35.1, 31.8, 27.3, 24.2, 23.9, 22.1, 15.1; HRMS (ESI) m/z Calcd. for C$_{92}$H$_{102}$N$_8$NaO$_{12}$$^+$[M+Na]$^+$: 1533.7515, Found: 1533.7542; UV-vis (CHCl$_3$), λ$_{max}$ nm (log ε): 424 (5.43), 518 (4.22), 554 (3.83), 590 (3.73), 646 (3.58).

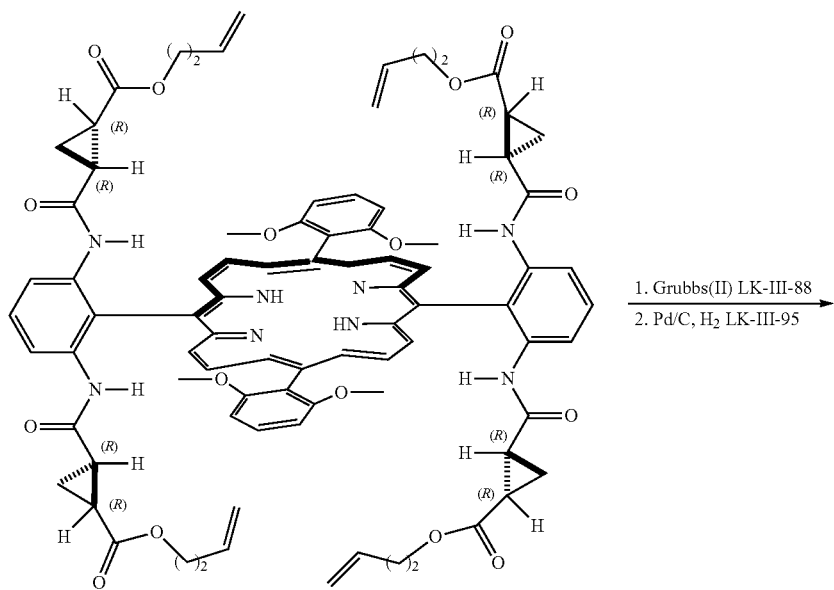

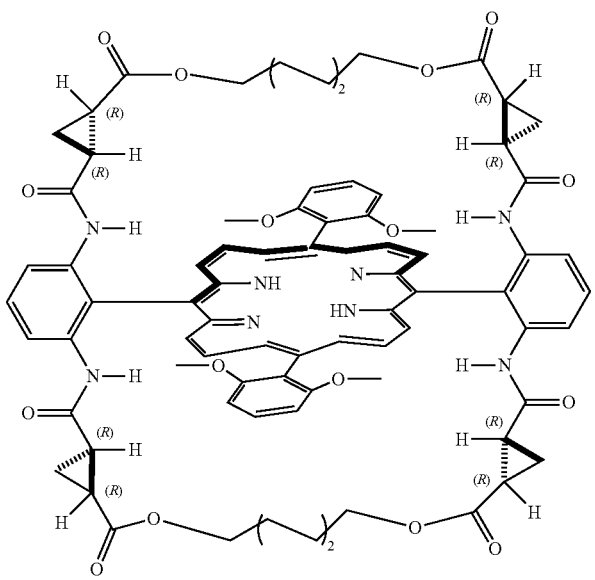

P4

(2,6-DiMeO-Hu(C₆)Phyrin) (P4) was synthesized following General Procedure B from (2,6-DiMeO-Tao(But-3-en-1-yl)Phyrin) (171 mg, 0.117 mmol), purified by silica gel column chromatography (eluent: Hexanes/EtOAc 2:1) to give the title compound in 85% yield (140 mg); TLC $R_f$=0.2 (Hexanes/EtOAc 1:1). $^1$H NMR (500 MHz, CDCl₃) δ pm 8.88 (d, J=4.6 Hz, 4H), 8.76 (d, J=4.6 Hz, 4H), 8.35 (d, J=8.4 Hz, 4H), 7.83 (t, J=8.4 Hz, 2H), 7.79 (t, J=8.5 Hz, 2H), 7.05 (d, J=8.6 Hz, 4H), 6.70 (s, 4H), 3.64 (dt, J=7.0, 10.6 Hz, 4H), 3.54 (s, 12H), 3.44-3.38 (m, 4H), 1.98-1.90 (m, 4H), 1.06 (dt, J=4.4, 8.8 Hz, 4H), 1.00-0.88 (m, 8H), 0.80-0.65 (m, 12H), 0.57 (dd, J=6.8, 10.9 Hz, 4H), −2.50 (s, 2H); $^{13}$C NMR (100 MHz, CDCl₃) δ ppm 170.8, 168.3, 160.2, 138.6, 131.1, 130.3, 122.6, 118.9, 118.3, 114.2, 106.8, 104.3, 64.1, 55.9, 27.4, 24.4, 23.8, 22.1, 14.7; HRMS (ESI) m/z Calcd. for $C_{80}H_{79}N_8O_{16}^+$ [M+H]⁺: 1407.5614, Found: 1407.5642; UV-vis (CHCl₃) $\lambda_{max}$ nm (log ε): 422 (5.26), 516 (4.08), 548 (3.52), 588 (3.59), 644 (3.23).

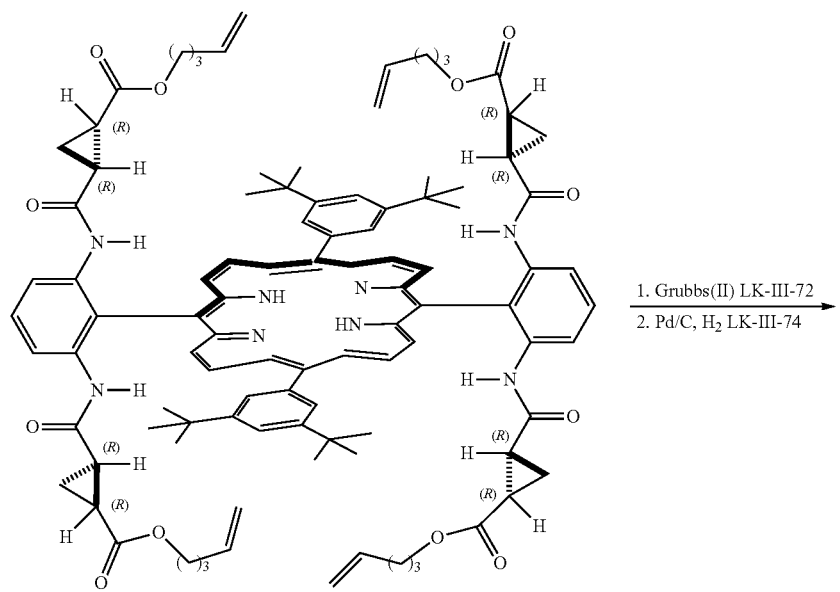
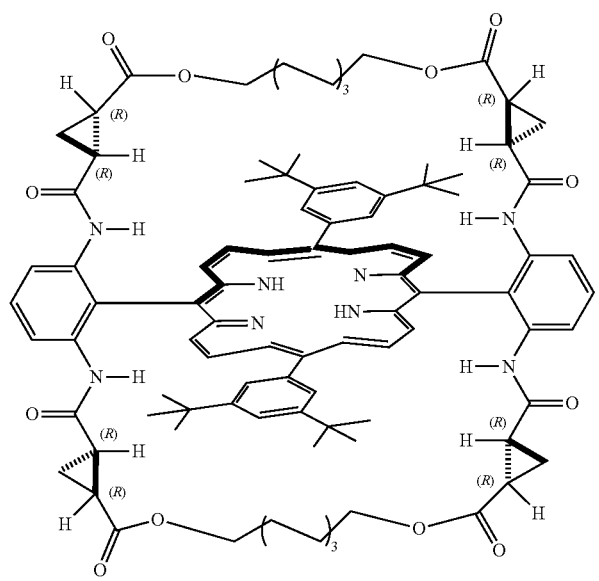
P5

(3,5-Di'Bu-Hu(C$_8$)Phyrin) (P5) was synthesized following General Procedure B from (3,5-Di'Bu-Tao(Pent-4-en-1-yl)Phyrin) (158 mg, 0.098 mmol), purified by silica gel column chromatography (eluent: Hexanes/EtOAc 3:1) to give the title compound in 88% yield (135 mg); TLC R$_f$=0.37 (Hexanes/EtOAc 2:1). $^1$H NMR (500 MHz, CDCl$_3$) δ ppm 9.02 (d, J=4.6 Hz, 4H), 8.80 (d, J=4.7 Hz, 4H), 8.47 (d, J=8.0 Hz, 4H), 8.15 (s, 4H), 7.88-7.81 (m, 4H), 6.64 (s, 4H), 3.72-3.61 (m, 4H), 3.58-3.50 (m, 4H), 1.94-1.84 (m, 4H), 1.56 (s, 36H), 1.25-1.15 (m, 4H), 1.12-1.00 (m, 8H), 0.94-0.80 (m, 16H), 0.65-0.52 (m, 8H), −2.49 (s, 2H); $^{13}$C NMR (125 MHz, CDCl$_3$) δ ppm 171.5, 168.4, 149.3, 140.0, 138.8, 130.5, 130.2, 123.3, 121.7, 117.8, 107.1, 63.8, 35.2, 31.8, 27.3, 26.8, 24.1, 21.9, 15.3; HRMS (ESI) m/z Calcd. for C$_{96}$H$_{110}$N$_8$NaO$_{12}^+$ [M+Na]$^+$1589.8341, Found: 1589.8372; UV-vis (CHCl$_3$), λ$_{max}$ nm (log ε): 424 (5.17), 518 (4.05), 552 (3.67), 592 (3.57), 646 (3.43).

R$_f$=0.3 (Hexanes/EtOAc/DCM 1:1:1). $^1$H NMR (500 MHz, CDCl$_3$) δ ppm 8.90 (d, J=4.6 Hz, 4H), 8.77 (d, J=4.0 Hz, 4H), 8.40 (d, J=8.1 Hz, 4H), 7.82 (t, J=8.4 Hz, 2H), 7.78 (t, J=8.4 Hz, 2H), 7.09 (d, J=8.4 Hz, 4H), 6.81 (br. s., 4H), 3.74-3.59 (m, 4H), 3.59-3.41 (m, 16H), 2.03-1.89 (m, 4H), 1.23-1.04 (m, 12H), 0.89-0.76 (m, 16H), 0.70-0.65 (m, 4H), 0.64-0.55 (m, 4H), −2.39 (s, 2H); $^{13}$C NMR (125 MHz, CDCl$_3$) δ ppm 171.1, 168.4, 160.3, 138.6, 130.9, 130.2, 122.5, 118.9, 118.4, 114.1, 106.5, 104.2, 64.0, 55.8, 27.2, 27.0, 24.2, 24.0, 21.8, 14.8; HRMS (ESI) m/z Calcd. for C$_{84}$H$_{87}$N$_8$O$_{18}^+$[M+H]$^+$: 1463.6235, Found: 1463.6278; UV-vis (CHCl$_3$), λ$_{max}$ nm (log ε): 424 (5.17), 516 (4.17), 550 (3.64), 590 (3.68), 644 (2.34).

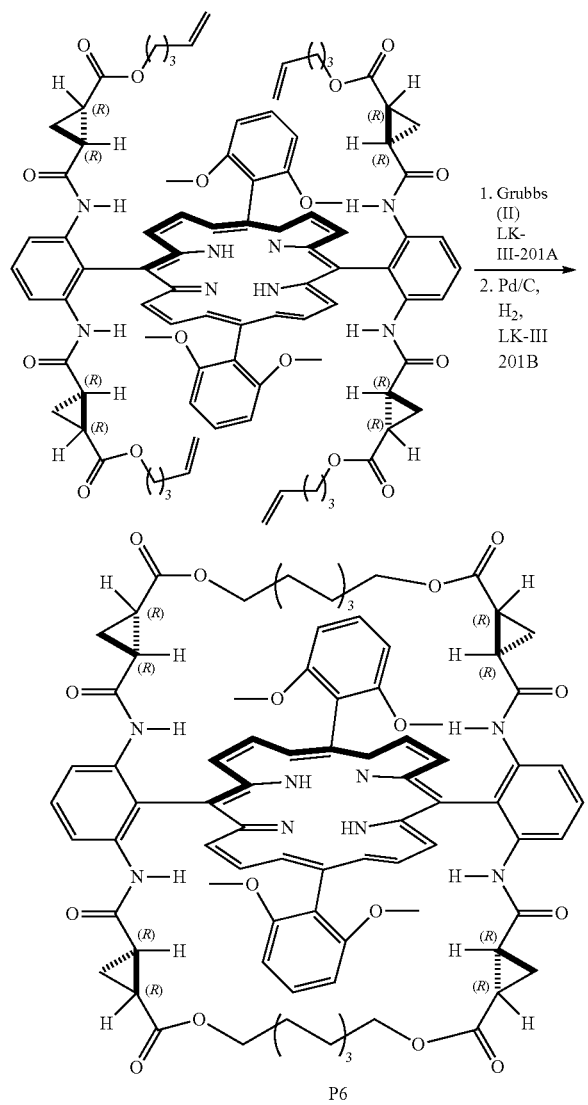

P6

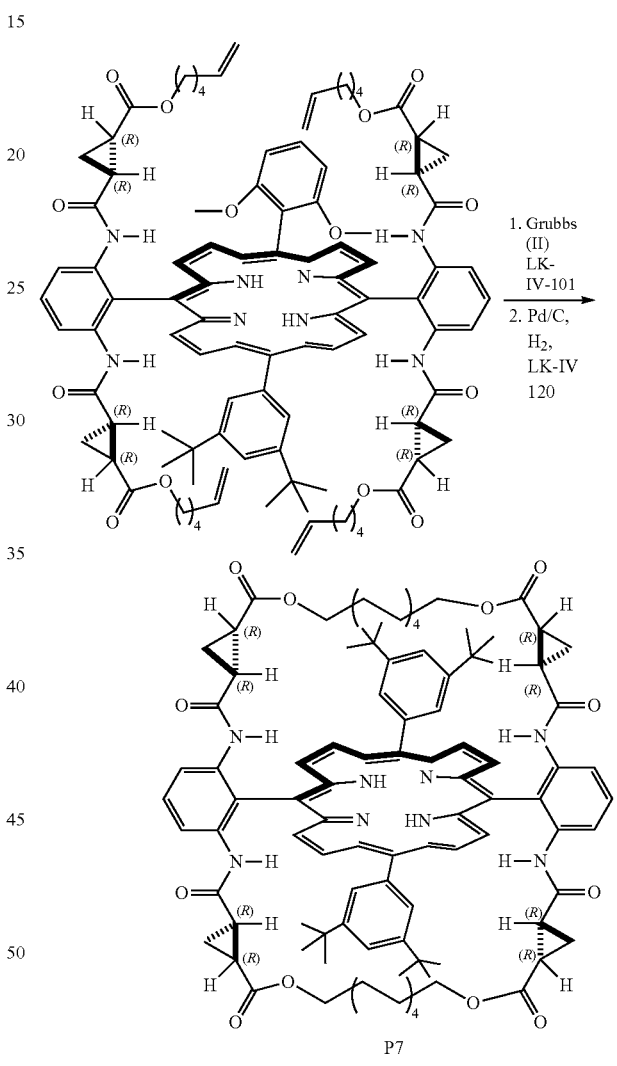

P7

(2,6-DiMeO-Hu(C$_8$)Phyrin) (P6) was synthesized following General Procedure B from (2,6-DiMeOTao(Pent-4-en-1-yl)Phyrin) (59 mg, 0.039 mmol), purified by silica gel column chromatography (eluent: Hexanes/EtOAc/DCM 2:1:1) to give the title compound in 74% yield (42 mg); TLC (3,5-Di'Bu-Hu(C$_{10}$)Phyrin) (P7) was synthesized following General Procedure B from (3,5-Di'Bu-Tao(Hex-5-en-1-yl)Phyrin) (40 mg, 0.024 mmol), purified by silica gel column chromatography (eluent: Hexanes/EtOAc 5:1) to give the title compound in 65% yield (25 mg); TLC R$_1$=0.35 (Hexanes/EtOAc 4:1). $^1$H NMR (500 MHz, CDCl$_3$) δ ppm 9.03 (d, J=4.9 Hz, 4H), 8.80 (d, J=4.6 Hz, 4H), 8.56-8.41 (m, 4H), 8.17 (s, 4H), 7.90-7.80 (m, 4H), 6.68 (s, 4H), 3.77-3.67 (m, 4H), 3.57-3.45 (m, 4H), 1.94-1.86 (m, 4H), 1.60-1.55 (m, 36H), 1.36-1.24 (m, 12H), 1.06 (d, J=8.7 Hz, 4H), 0.99-0.85 (m, 20H), 0.58 (br. s., 8H), −2.48 (s, 2H); $^{13}$C NMR (125 MHz, CDCl$_3$) δ ppm 171.6, 168.4, 149.3, 140.0, 138.9, 130.9, 130.4, 130.2, 128.8, 123.2, 121.6, 107.7, 63.9, 35.1, 31.8, 27.5, 27.3, 26.7, 24.2, 24.0, 21.8, 15.3; HRMS (ESI) m/z Calcd for $C_{100}H_{119}N_8O_{12}^+$ [M+H]$^+$: 1623.8942, Found: 1623.8916; UV-vis (CHCl$_3$), $\lambda_{max}$ nm (log ε): 424 (5.32), 518 (4.07), 552 (3.66), 592 (3.56), 646 (3.40).

1519.6814; UV-vis (CHCl$_3$), $\lambda_{max}$ nm (log ε): 422 (5.22), 516 (4.11), 548 (3.50), 588 (3.62), 644 (3.21).

Example 5: General Procedure C (Synthesis of Co(II) Based, Open and Bridged Amidoporphyrins)

The desired porphyrin starting material (1 equiv) and CoCl$_2$ (8 equiv) were placed in an oven dried Schlenk tube. The tube was capped with a Teflon screw cap, evacuated, and backfilled with nitrogen. The screw cap was replaced with a rubber septum. 2,6-Lutidine (4 equiv) and THF (0.05 M) were added and the tube was purged with nitrogen for 1 min and sealed with Teflon screwcap. The reaction mixture was stirred at 100° C. for 12 h prior to being cooled to r.t. The reaction mixture was diluted with DCM and washed with brine. The organic layer was separated, dried, and concentrated. The residue was purified by silica gel column chromatography (eluent: Hexanes/EtOAc 1:1) to give the title compound.

Characterization of Co(II) Based, Open and Bridged Amidoporphyrins

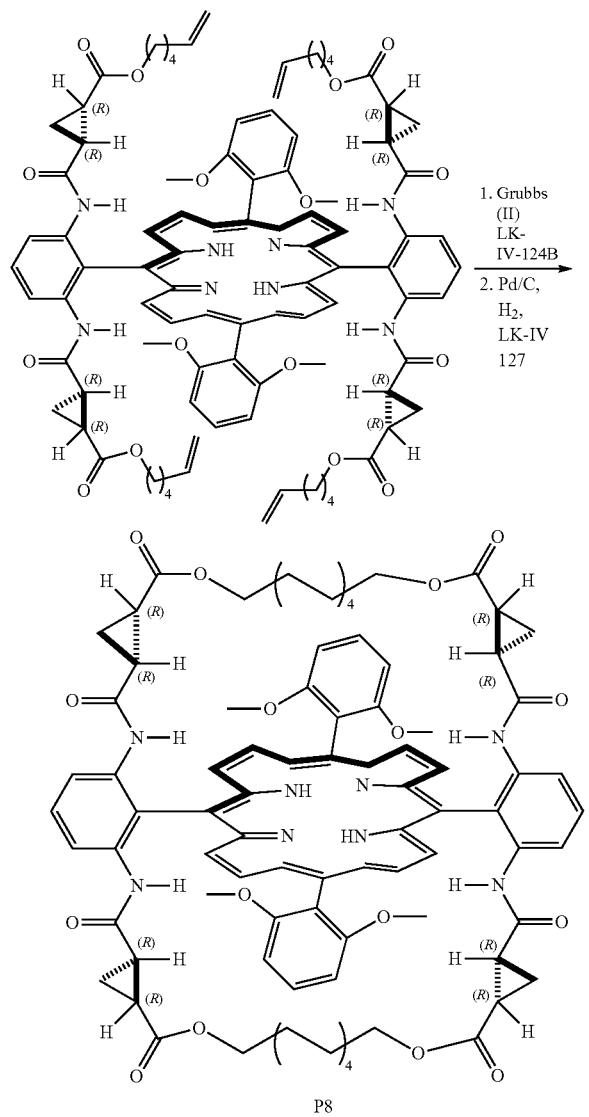

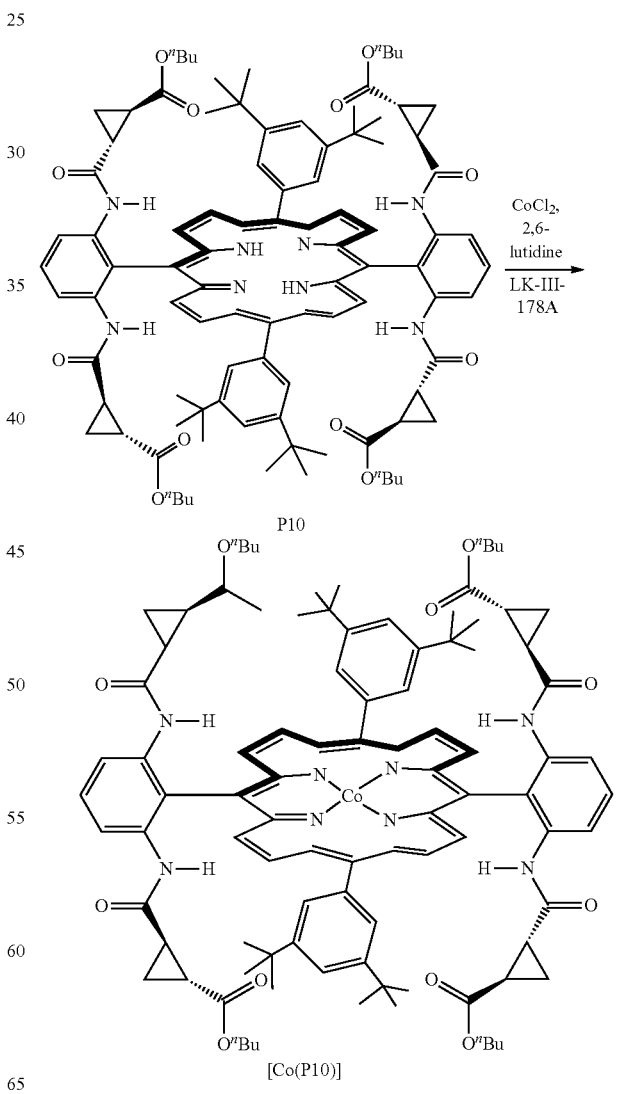

(2,6-DiMeO-Hu(C$_{10}$)Phyrin) (P8) was synthesized following General Procedure B from (2,6-DiMeO-Tao(Hex-5-en-1-yl)Phyrin) (40 mg, 0.025 mmol), purified by silica gel column chromatography (eluent: Hexanes/EtOAc 4:1) to give the title compound in 67% yield (26 mg); TLC R$_f$=0.2 (Hexanes/EtOAc 3:1). $^1$H NMR (500 MHz, CDCl$_3$) δ ppm 8.86 (d, J=4.6 Hz, 4H), 8.72 (d, J=4.3 Hz, 4H), 8.39 (d, J=7.5 Hz, 4H), 7.83 (t, J=8.5 Hz, 2H), 7.79 (t, J=8.5 Hz, 2H), 7.05 (d, J=8.4 Hz, 4H), 6.74 (br. s., 4H), 3.62 (t, J=6.6 Hz, 8H), 3.55 (s, 12H), 1.94 (ddd, J=3.9, 5.5, 8.8 Hz, 4H), 1.34-1.14 (m, 12H), 1.04 (ddd, J=3.9, 5.2, 8.8 Hz, 4H), 0.99-0.83 (m, 20H), 0.67 (br. s., 4H), 0.57 (br. s., 4H), −2.41 (s, 2H); $^{13}$C NMR (125 MHz, CDCl$_3$) δ ppm 187.6, 171.3, 168.5, 160.3, 138.7, 130.9, 130.2, 118.5, 114.1, 106.4, 104.2, 63.9, 55.9, 27.5, 27.4, 26.8, 24.2, 24.1, 21.7, 15.0; HRMS (ESI) m/z Calcd. for $C_{88}H_{95}N_8O_{16}^+$ [M+H]$^+$: 1519.6861, Found:

[Co(3,5-Di'Bu-Tao(nBu)Phyrin)] ([Co(P10)]) was synthesized in 95% yield (32 mg) following General Procedure C from (3,5-Di'Bu-Tao(nBu)Phyrin) (P10) (33 mg, 0.021 mol). HRMS (ESI) m/z Calcd. for $C_{96}H_{113}CoN_8O_{12}^+$ [M+H]$^+$: 1628.7804, Found: 1628.7886; UV-vis (CHCl$_3$), $\lambda_{max}$ nm (log ε): 438 (5.26), 550 (4.24).

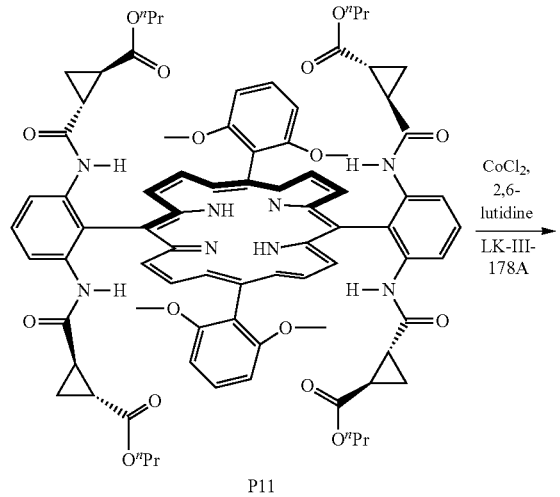

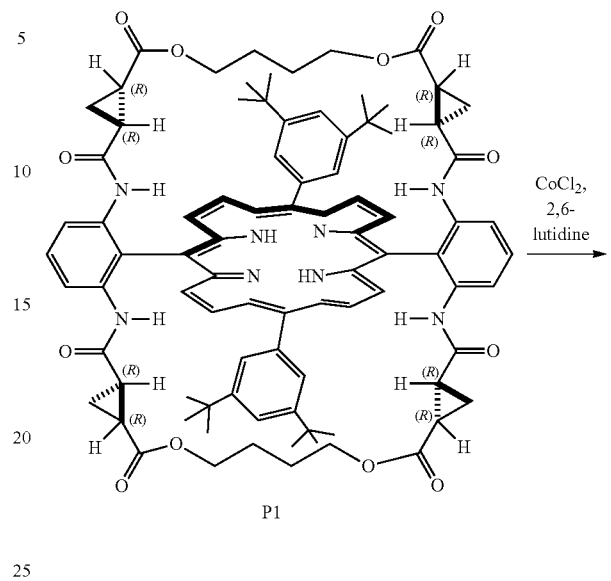

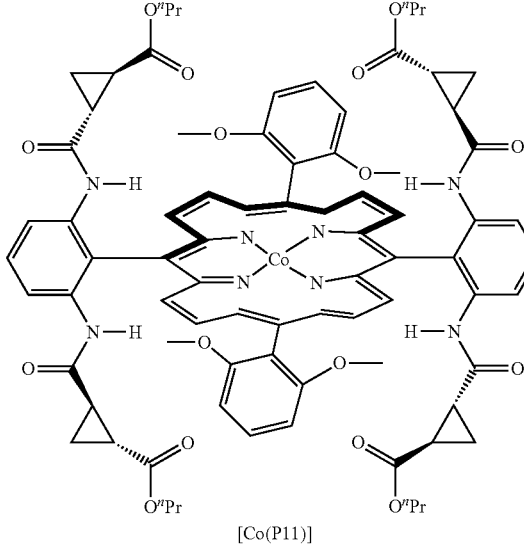

[Co(2,6-DiMeO-Tao(nPr)Phyrin)] ([Co(P11)]) was synthesized in 88% yield (26 mg) following General Procedure C from (2,6-DiMeO-Tao(nPr)Phyrin) (P11) (28 mg, 0.02 mmol). HRMS (ESI) m/z Calcd. for $C_{80}H_{81}CoN_8O_{16}^+$ [M+H]$^+$: 1468.5097, Found: 1468.5096; UV-vis (CHCl$_3$), $\lambda_{max}$ nm (log ε): 436 (5.21), 546 (4.24), 662 (3.71).

[Co(3,5-Di'Bu-Hu(C$_4$)Phyrin)] ([Co(P1)]) was synthesized in 84% yield (40 mg) following General Procedure C from (3,5-Di'Bu-Hu(C$_4$)Phyrin) (P1) (46 mg, 0.032 mmol). HRMS (ESI) m/z Calcd. for $C_{88}H_{93}CoN_8O_{12}^+$ [M+H]$^+$: 1512.6239, Found: 1512.6259; UV-vis (CHCl$_3$), $\lambda_{max}$ nm (log ε): 438 (4.78), 546 (3.84), 662 (3.49).

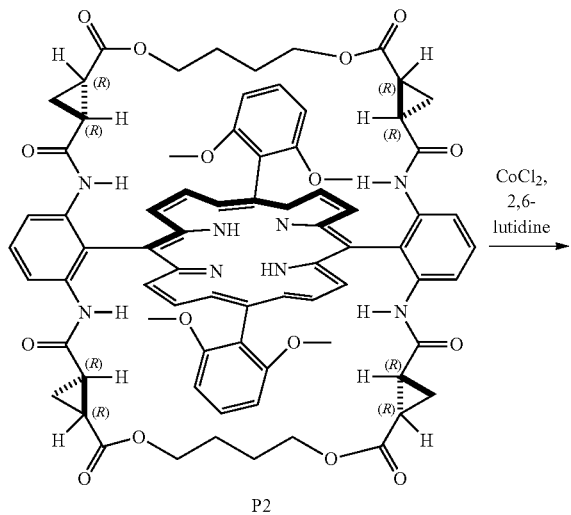

P2

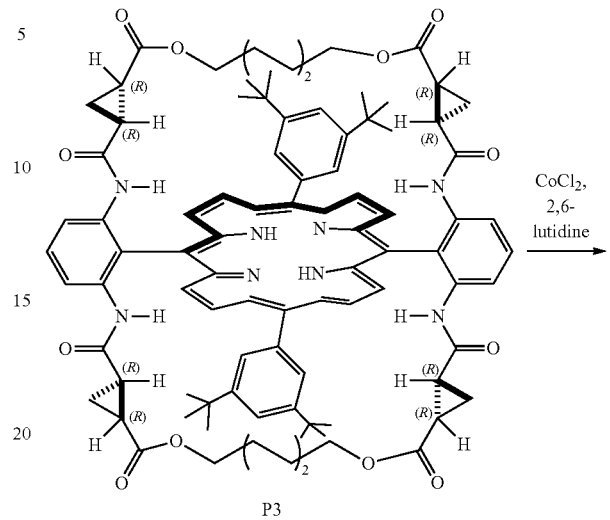

P3

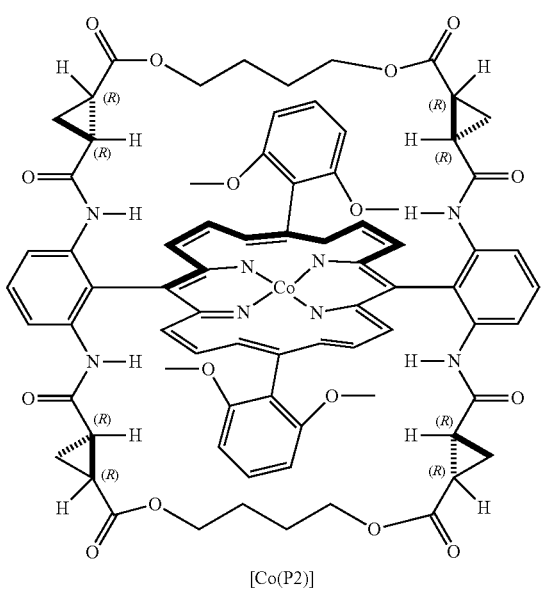

[Co(P2)]

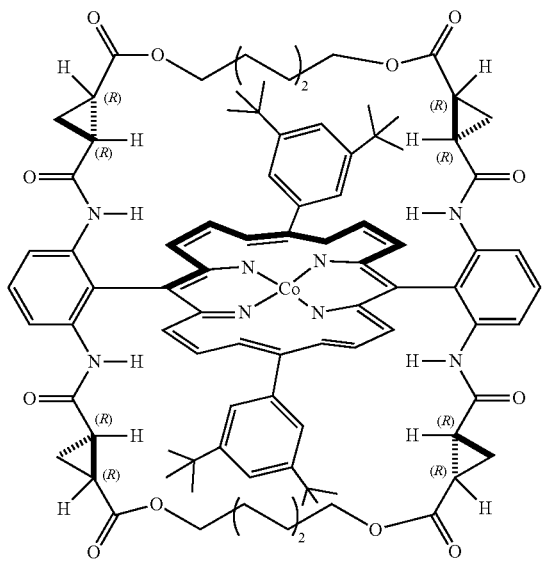

[Co(P3)]

[Co(2,6-DiMeO-Hu(C$_4$)Phyrin)] ([Co(P2)]) was synthesized in 90% yield (55 mg) following General Procedure C from (2,6-DiMeO-Hu(C$_4$)Phyrin) (P2) (58 mg, 0.043 mmol). HRMS (ESI) m/z Calcd. for $C_{76}H_{69}CoN_8O_{16}^+$ [M+H]$^+$: 1408.4158, Found: 1408.4120; UV-vis (CHCl$_3$), $\lambda_{max}$ nm (log ε): 432 (4.85), 542 (3.96), 658 (3.21).

[Co(3,5-Di$^t$Bu-Hu(C$_6$)Phyrin)] ([Co(P3)]) was synthesized in 90% yield (170 mg) following General Procedure C from (3,5-Di$^t$Bu-Hu(C$_6$)Phyrin) (P3) (182 mg, 0.121 mmol). HRMS (ESI) m/z Calcd. for $C_{92}H_{101}CoN_8O_{12}^+$ [M+H]$^+$: 1568.6865, Found: 1568.6894; UV-vis (CHCl$_3$), $\lambda_{max}$ nm (log ε): 436 (5.01), 548 (4.03), 660 (3.31).

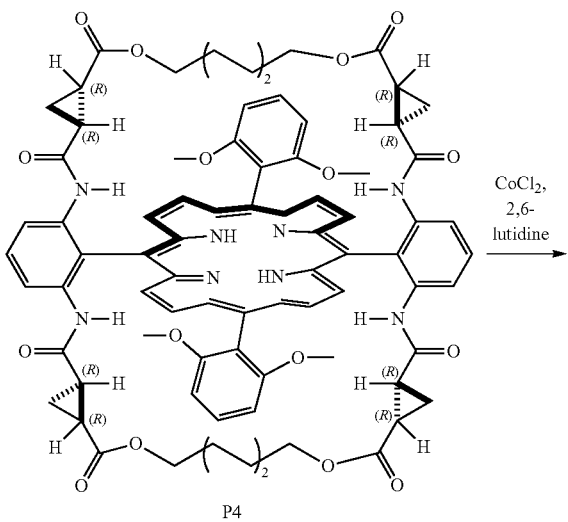

P4

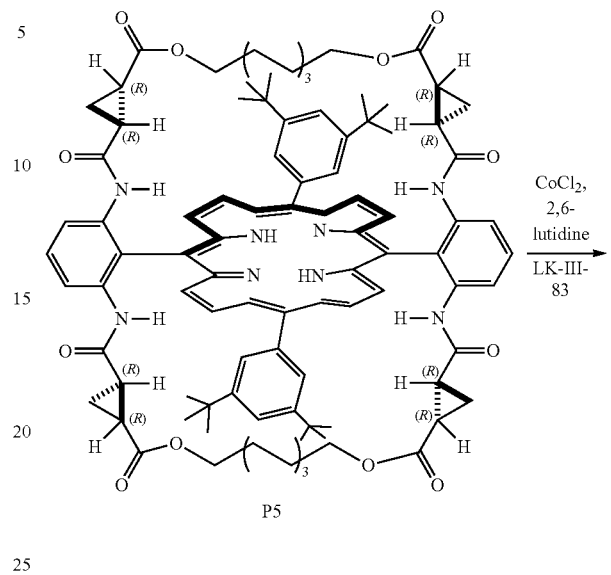

P5

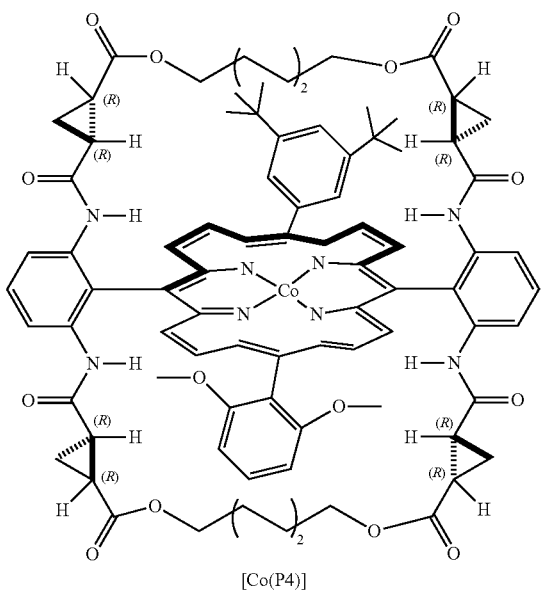

[Co(P4)]

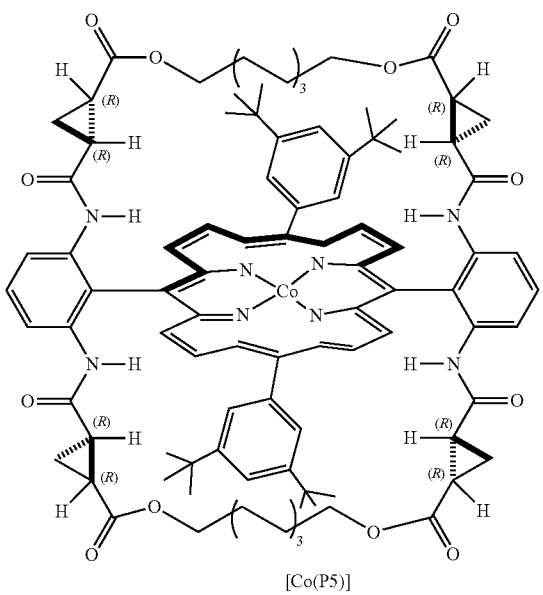

[Co(P5)]

[Co(2,6-DiMeO-Hu(C$_6$)Phyrin)] ([Co(P4)]) was synthesized in 95% yield (50 mg) following General Procedure C from (2,6-DiMeO-Hu(C$_6$)Phyrin) (P4) (51 mg, 0.036 mmol). HRMS (ESI) m/z Calcd. for $C_{80}H_{77}CoN_8O_{16}^+$ [M+H]$^+$: 1464.4784, Found: 1464.4754; UV-vis (CHCl$_3$) $\lambda_{max}$ nm (log ε): 434 (4.92), 544 (3.94), 646 (3.26). (The reaction can be easily scaled up to 400 mg scale).

[Co(3,5-Di$^t$Bu-Hu(C$_8$)Phyrin)] ([Co(P5)]) was synthesized in 91% yield (128 mg) following General Procedure C from (3,5-Di$^t$Bu-Hu(C$_8$)Phyrin) (P5) (136 mg, 0.086 mmol). HRMS (ESI) m/z Calcd. for $C_{96}H_{109}CoN_8O_{12}^+$ [M+H]$^+$: 1624.7491, Found: 1624.7521; UV-vis (CHCl$_3$), $\lambda_{max}$ nm (log ε): 436 (4.97), 550 (3.97), 668 (3.38). (The reaction can be easily scaled up to 500 mg scale).

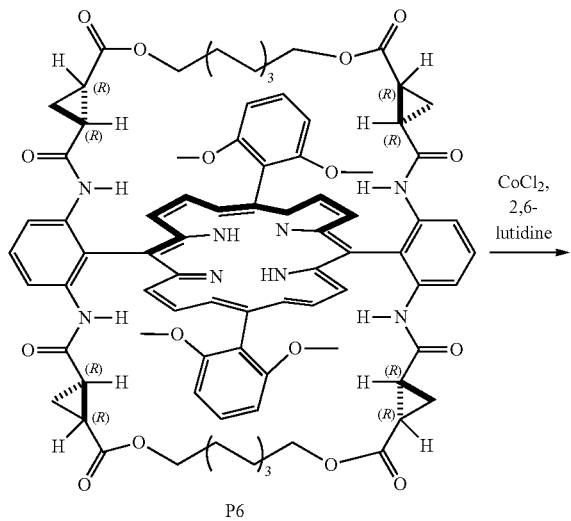

P6

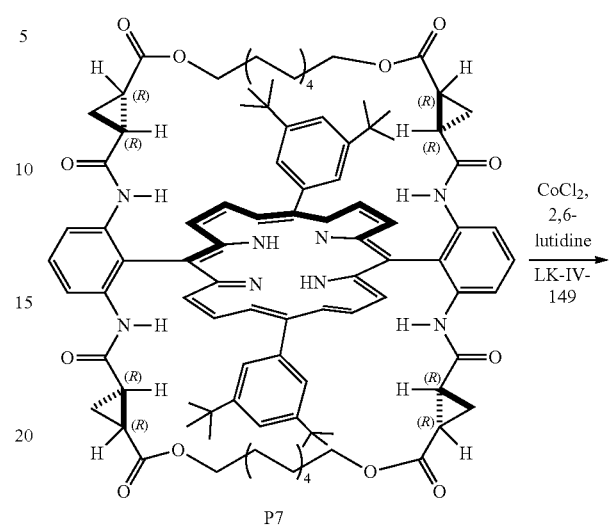

P7

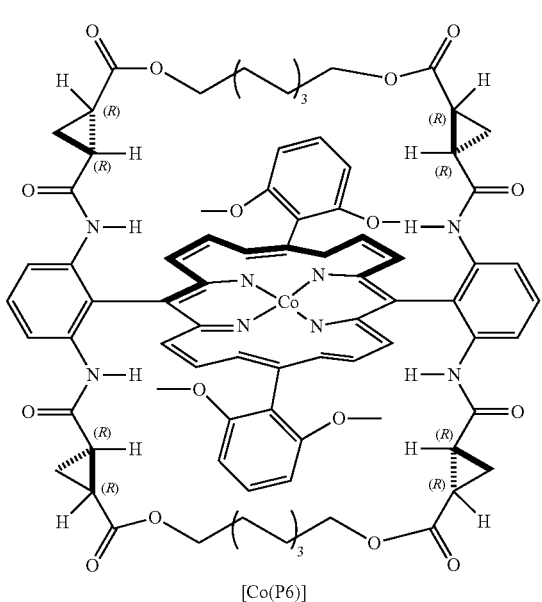

[Co(P6)]

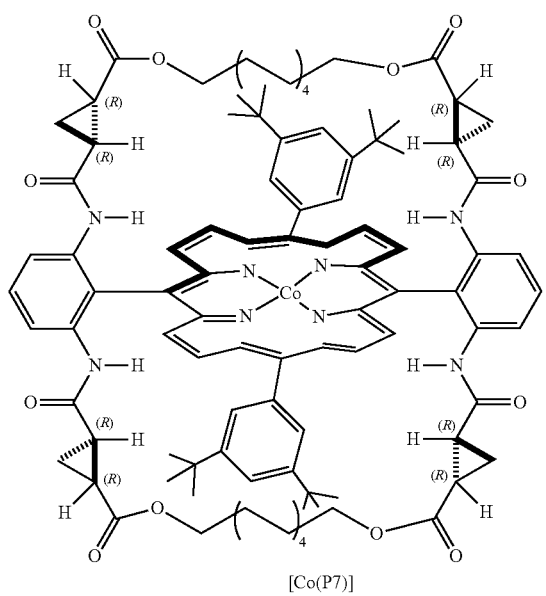

[Co(P7)]

[Co(2,6-DiMeO-Hu(C$_8$)Phyrin)] ([Co(P6)]) was synthesized in 95% yield (50 mg) following General Procedure C from (2,6-DiMeO-Hu(C$_8$)Phyrin) (P6) (51 mg, 0.035 mmol). HRMS (ESI) m/z Calcd. for $C_{84}H_{85}CoN_8O_{16}^+$ [M+H]$^+$: 1520.5410, Found: 1520.5432; UV-vis (CHCl$_3$), $\lambda_{max}$ nm (log ε): 436 (5.05), 544 (4.08), 668 (3.41).

[Co(3,5-Di$^t$Bu-Hu(C$_{10}$)Phyrin)] ([Co(P7)]) was synthesized in 92% yield (17 mg) following General Procedure C from (3,5-Di$^t$Bu-Hu(C$_{10}$)Phyrin) (P7) (18 mg, 0.011 mmol). HRMS (ESI) m/z Calcd. for $C_{100}H_{117}CoN_8O_{12}^+$ [M+H]$^+$, 1680.8117, Found: 1680.8033; UV-vis (CHCl$_3$), $\lambda_{max}$ nm (log ε): 438 (4.91), 550 (3.94), 670 (3.37).

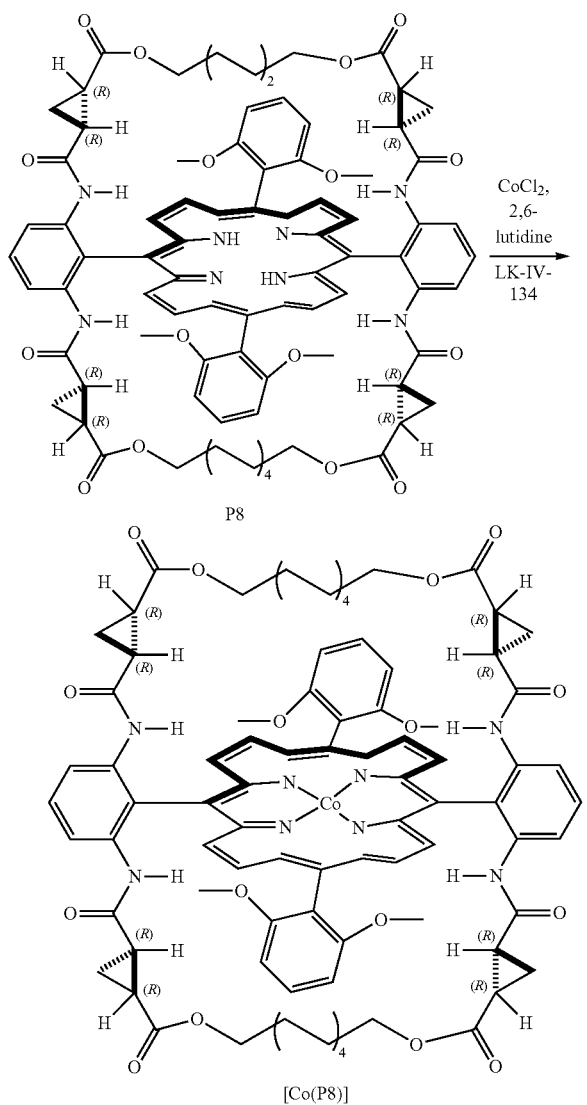

P8

[Co(P8)]

[Co(2,6-DiMeO-Hu(C$_{10}$)Phyrin)] ([Co(P8)]) was synthesized in 90% yield (18 mg) following General Procedure C from (2,6-DiMeO-Hu(C$_{10}$)Phyrin) (P8) (19 mg, 0.013 mmol). HRMS (ESI) m/z Calcd. for $C_{88}H_{93}CoN_8O_{16}^+$ [M+H]$^+$: 1576.6036, Found: 1576.5922; UV-vis (CHCl$_3$), $\lambda_{max}$ nm (log ε): 436 (4.88), 546 (3.91), 670 (3.35).

Example 6: General Procedure D (Amine Synthesis)
Procedure D1 (SN$_2$ Amination)

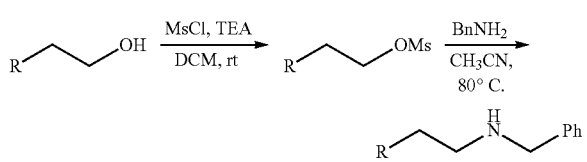

Methanesulfonyl chloride (0.58 mL, 7.5 mmol) was added to a round bottom flask containing alcohol precursor (5 mmol) in DCM (15 mL), followed by the addition of triethyl amine (1.41 mL, 10 mmol). The precipitate was formed immediately. The reaction mixture was stirred at room temperature for 1 or 2 hours until the alcohol was fully consumed based on TLC. DCM (30 mL) was added and the reaction mixture was washed with water (50 mL). The aqueous solution was extracted by DCM (3×20 mL). The combined organic layer was dried over anhydrous sodium sulfate. The solvent was removed and CH$_3$CN (20 mL) was added, followed by the benzyl amine (10 mmol) and the reaction was heated at 80° C. for 6 hours. Then the solvent was removed and the residue was purified by silica gel column chromatography (gradient elution: Hexanes/EtOAc 8:1 to 1:1) to give the desired amine products, which were used directly for the next step.

Procedure D2 (Reductive Amination)

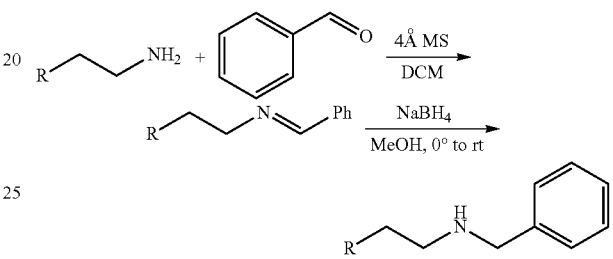

Oven-dried 4 Å molecular sieves (1.0 g) were added to a solution of primary amine (5 mmol) and benzaldehyde (0.53 mL, 5 mmol) in dichloromethane (30 mL). The reaction mixture was stirred for 2 hours at room temperature. Then the solvent was removed under reduced pressure and MeOH (25 mL) was added into the residue. The reaction mixture was cooled to 0° C., followed by the addition of NaBH$_4$ (570 mg, 15 mmol) in several portions. After the reaction became less vigorous, the reaction was slowly warmed up to room temperature and stirred for another hour. Then the solvent was removed and the residue was purified by silica gel column chromatography (gradient elution: Hexanes/EtOAc 8:1 to 1:1) to give the desired amine products, which were used directly for the next step.

Procedure D3 (Amide Reduction)

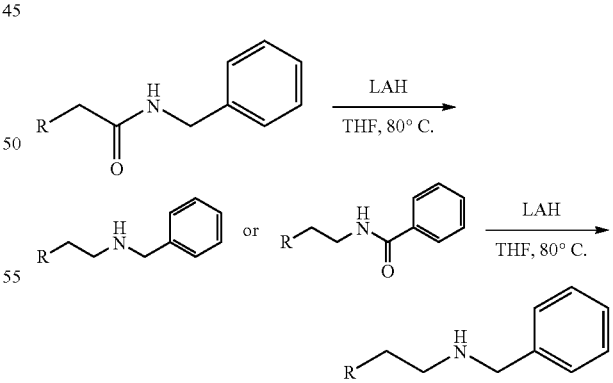

LiAlH$_4$ (1.5 mmol) was added to a sealed tube containing amide (5 mmol) in newly distilled anhydrous THF (15 mL). The reaction mixture was heated to 80° C. for 2 days. After quenching the excess amount of LiAlH$_4$ following the Fieser method, the reaction mixture was filtrated through a short pad of Celite. Then the solvent was removed and the residue was purified by silica gel column chromatography (gradient elution: Hexanes/EtOAc 8:1 to 1:1) to give the desired amine products, which were used directly for the next step.

Characterization of Amines

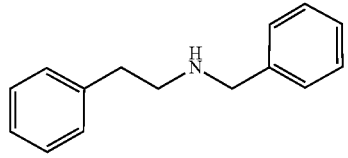 [SMILES: c1ccc(CCNCc2ccccc2)cc1]

N-Benzyl-2-phenylethan-1-amine was prepared in 75% yield (790 mg) as yellow oil through General Procedure D2 from 2-phenylethan-1-amine (commercially available, cas: 64-04-0) (605 mg, 5 mmol). $^1$H NMR (500 MHz, CDCl$_3$) δ ppm 7.44-7.24 (m, 10H), 3.88 (s, 2H), 3.03-2.96 (m, 2H), 2.94-2.87 (m, 2H), 1.50 (br. s., 1H); $^{13}$C NMR (125 MHz, CDCl$_3$) δ ppm 140.4, 140.1, 128.8, 128.5, 128.1, 127.0, 126.2, 54.0, 50.7, 36.5; HRMS (ESI) m/z Calcd. for C$_{15}$H$_{18}$N$^+$ [M+H]$^+$: 212.1434, Found: 212.1429; IR (neat, cm$^{-1}$): 2923, 2815, 1736, 1602, 1494, 1452, 1240, 733, 696.

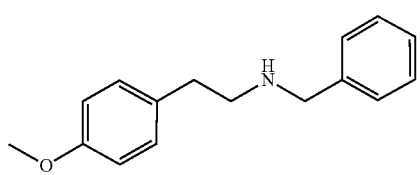 [SMILES: COc1ccc(CCNCc2ccccc2)cc1]

N-Benzyl-2-(4-methoxyphenyl)ethan-1-amine was prepared in 82% yield (980 mg) as yellow oil through General Procedure D1 from 2-(4-methoxyphenyl)ethan-1-ol (commercially available, cas: 702-23-8) (760 mg, 5 mmol). $^1$H NMR (500 MHz, CDCl$_3$) δ ppm 7.42-7.27 (m, 5H), 7.22-7.16 (m, 2H), 6.93-6.87 (m, 2H), 3.87 (s, 2H), 3.85 (s, 3H), 2.98-2.91 (m, 2H), 2.87-2.80 (m, 2H), 1.57 (br. s., 1H); $^{13}$C NMR (125 MHz, CDCl$_3$) δ ppm 158.1, 140.4, 132.1, 129.7, 128.4, 128.2, 127.0, 113.9, 55.3, 53.9, 50.8, 35.5; HRMS (ESI) m/z Calcd. for C$_{16}$H$_{20}$NO$^+$ [M+H]$^+$: 242.1539, Found: 242.1527; IR (neat, cm$^{-1}$): 2932, 2834, 1611, 1583, 1511, 1453, 1244, 907, 727, 697.

LK-III-242

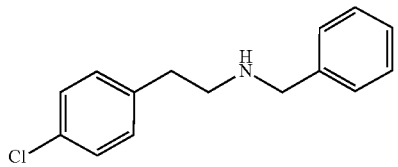

N-Benzyl-2-(4-chlorophenyl)ethan-1-amine was prepared in 86% yield (1.05 g) as yellow oil through General Procedure D1 from 2-(4-chlorophenyl)ethan-1-ol (commercially available, cas: 1875-88-3) (780 mg, 5 mmol). $^1$H NMR (500 MHz, CDCl$_3$) δ ppm 7.41-7.20 (m, 7H), 7.17-7.12 (m, 2H), 3.81 (s, 2H), 2.91-2.87 (m, 2H), 2.83-2.77 (m, 2H), 1.61 (br. s., 1H); $^{13}$C NMR (125 MHz, CDCl$_3$) δ ppm 140.1, 138.5, 131.9, 130.1, 128.6, 128.4, 128.1, 127.0, 53.9, 50.3, 35.7; HRMS (ESI) m/z Calcd. for C$_{15}$H$_{17}$ClN$^+$ [M+H]$^+$: 246.1044, Found: 248.1041; IR (neat, cm-1): 2925, 2817, 1668, 1599, 1491, 1453, 1089, 1014, 730, 697.

LK-III-292D

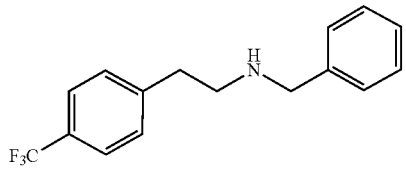

N-Benzyl-2-(4-(trifluoromethyl)phenyl)ethan-1-amine was prepared in 70% yield (976 mg) as yellow oil through General Procedure D1 from 2-(4-(trifluoromethyl)phenyl)ethan-1-ol (commercially available, cas: 2968-93-6) (950 mg, 5 mmol). $^1$H NMR (500 MHz, CDCl$_3$) δ ppm 7.56 (d, J=8.3 Hz, 2H), 7.39-7.24 (m, 7H), 3.83 (s, 2H), 2.99-2.92 (m, 2H), 2.93-2.84 (m, 2H), 1.41 (br. s., 1H); $^{13}$C NMR (125 MHz, CDCl$_3$) δ ppm 144.2, 140.1, 129.0, 128.5 (q, J=32.5 Hz), 128.4, 128.0, 127.0, 125.3 (q, J=3.8 Hz), 124.3 (q, J=270.0 Hz), 53.8, 50.1, 36.2; HRMS (ESI) m/z Calcd. for C$_{16}$H$_{17}$F$_3$N$^+$ [M+H]$^+$: 280.1308, Found: 280.1306; IR (neat, cm$^{-1}$): 2928, 1618, 1454, 1323, 1066, 907, 730, 698.

LK-III-260B

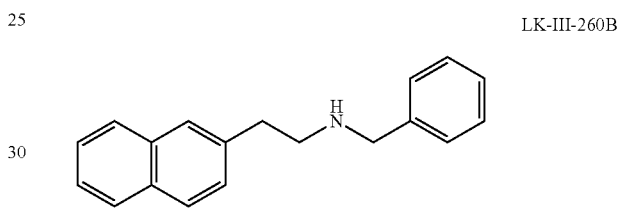

N-Benzyl-2-(naphthalen-2-yl)ethan-1-amine was prepared in 74% yield (970 mg) as yellow oil through General Procedure D3 from N-benzyl-2-(naphthalen-2-yl)acetamide (1.37 g, 5 mmol) which was prepared using 2-(naphthalen-2-yl)acetic acid (commercially available, cas: 581-96-4) and benzylamine. $^1$H NMR (500 MHz, CDCl$_3$) δ ppm 7.93-7.77 (m, 3H), 7.66 (s, 1H), 7.51-7.40 (m, 2H), 7.38-7.19 (m, 6H), 3.83 (s, 2H), 3.01 (s, 4H), 1.55 (br. s., 1H); $^{13}$C NMR (125 MHz, CDCl$_3$) δ ppm 140.2, 137.5, 133.5, 132.1, 128.4, 128.1, 128.0, 127.6, 127.4, 127.3, 127.0, 126.9, 126.0, 125.3, 53.9, 50.3, 36.4; HRMS (ESI) m/z Calcd. for C$_{19}$H$_{20}$N$^+$ [M+H]$^+$: 262.1590, Found: 262.1589; IR (neat, cm$^{-1}$): 2924, 2853, 1728, 1601, 1552, 1260, 1077, 907, 730, 647.

LK-III-60C

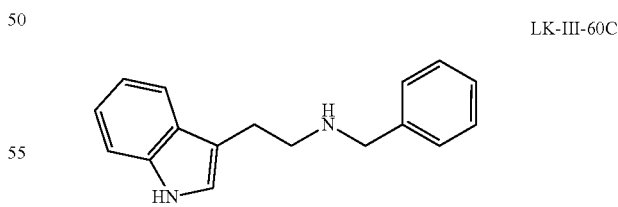

N-Benzyl-2-(1H-indol-3-yl)ethan-1-amine was prepared in 83% yield (1.04 g) as yellow oil through General Procedure D2 from Tryptamine (commercially available, cas: 61-54-1) (800 mg, 5 mmol). $^1$H NMR (500 MHz, CDCl$_3$) δ ppm 8.15 (br. s., 1H), 7.68 (d, J=7.8 Hz, 1H), 7.40 (d, J=7.8 Hz, 1H), 7.37-7.27 (m, 5H), 7.27-7.22 (m, 1H), 7.20-7.13 (m, 1H), 7.05 (d, J=2.0 Hz, 1H), 3.88 (s, 2H), 3.15-3.01 (m, 4H), 1.62 (br. s., 1H); $^{13}$C NMR (125 MHz, CDCl$_3$) δ ppm 140.3, 136.3, 128.3, 128.1, 127.4, 126.8, 122.0, 121.9, 119.2, 118.9, 114.0, 111.1, 53.9, 49.4, 25.8; HRMS (ESI) m/z Calcd. for $C_{17}H_{19}N_2^+$ [M+H]$^+$: 251.1543, Found: 215.1543; IR (neat, cm$^{-1}$): 3457, 3055, 2917, 2836, 1618, 1454, 735, 696.

LK-III-160

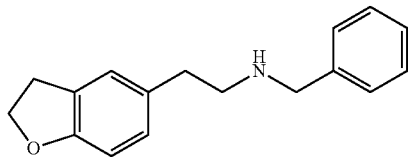

N-Benzyl-2-(2,3-dihydrobenzofuran-5-yl)ethan-1-amine was prepared in 65% yield (822 mg) as yellow oil through General Procedure D3 from N-benzyl-2-(2,3-dihydrobenzofuran-5-yl)acetamide (1.34 g, 5 mmol) which was prepared using 2-(2,3-dihydrobenzofuran-5-yl)acetic acid (commercially available, cas: 69999-16-2) and benzylamine following a published procedure. $^1$H NMR (500 MHz, CDCl$_3$) δ ppm 7.43-7.21 (m, 5H), 7.04 (s, 1H), 6.99-6.88 (m, 1H), 6.75-6.67 (m, 1H), 4.64-4.51 (m, 2H), 3.89-3.77 (m, 2H), 3.28-3.12 (m, 2H), 2.95-2.82 (m, 2H), 2.81-2.69 (m, 2H), 1.77 (br. s., 1H); $^{13}$C NMR (125 MHz, CDCl$_3$) δ ppm 159.7, 140.2, 131.8, 128.5, 128.4, 128.1, 127.5, 127.4, 125.2, 109.1, 71.4, 53.9, 50.9, 35.7, 29.7; HRMS (ESI) m/z Calcd. for $C_{17}H_{20}NO^+$ [M+H]$^+$: 254.1539, Found: 254.1527; IR (neat, cm$^{-1}$): 2893, 2854, 1613, 1490, 1242, 982, 728, 698.

k0I-593

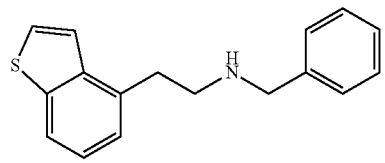

N-Benzyl-2-(benzo[b]thiophen-4-yl)ethan-1-amine was prepared in 59% yield (340 mg) as yellow oil through General Procedure D3 from N-benzyl-2-(benzo[b]thiophen-4-yl)acetamide (600 mg, 2.1 mmol) which was prepared using 2-(benzo[b]thiophen-4-yl)acetic acid (commercially available, cas: 2635-75-8) and benzylamine following a published procedure. $^1$H NMR (600 MHz, CDCl$_3$) δ ppm 7.75 (d, J=8.1 Hz, 1H), 7.33-7.21 (m, 8H), 7.19 (d, J=7.1 Hz, 1H), 3.82 (s, 2H), 3.18 (t, J=7.2 Hz, 2H), 3.01 (t, J=7.2 Hz, 2H), 1.49 (br. s., 1H); $^{13}$C NMR (150 MHz, CDCl$_3$) δ ppm 140.4, 140.3, 139.0, 135.1, 128.5, 128.2, 127.1, 126.2, 124.5, 124.4, 121.9, 120.8, 54.0, 50.0, 34.7; HRMS (ESI) m/z Calcd. for $C_{17}H_{18}NS^+$ [M+H]$^+$: 268.1154, Found: 268.1155; IR (neat, cm$^{-1}$): 2818, 1452, 1411, 1105, 907, 729, 698.

LK-II-285B

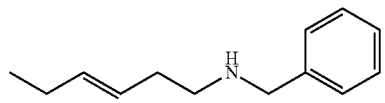

(E)-N-Benzylhex-3-en-1-amine was prepared in 65% yield (614 mg) as yellow oil through General Procedure D1 from (E)-hex-3-en-1-ol (commercially available, cas: 928-97-2) (500 mg, 5 mmol). $^1$H NMR (500 MHz, CDCl$_3$) δ ppm 7.42-7.35 (m, 4H), 7.34-7.28 (m, 1H), 5.64-5.56 (m, 1H), 5.46-5.38 (m, 1H), 3.86 (s, 2H), 2.75-2.70 (m, 2H), 2.28 (dq, J=1.0, 6.8 Hz, 2H), 2.13-2.01 (m, 2H), 1.74 (br. s., 1H), 1.02 (t, J=7.5 Hz, 3H); $^{13}$C NMR (125 MHz, CDCl$_3$) δ ppm 140.3, 134.3, 128.4, 128.2, 127.0, 126.4, 53.9, 48.9, 33.0, 25.7, 13.9; HRMS (ESI) m/z Calcd. for $C_{13}H_{20}N^+$[M+H]$^+$: 190.1590, Found: 190.1601; IR (neat, cm$^{-1}$): 2960, 2929, 1453, 1404, 1286, 966, 732, 697.

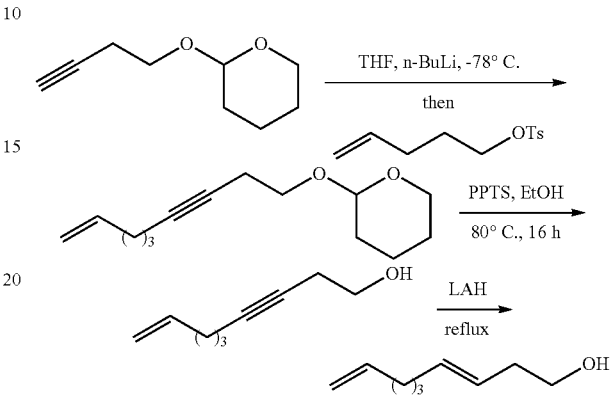

2-(But-3-yn-1-yloxy)tetrahydro-2H-pyran (1.7 g, 11 mmol) was dissolved into THF (10 mL) under nitrogen atmosphere and cooled down to −78° C. n-BuLi (2.5 M solution in Hexane) (4.8 mL, 12.1 mmol) was added slowly into this solution and the reaction mixture was warmed up to room temperature and stirred for 30 min. Then the reaction solution was cooled down to −78° C. Pent-4-en-1-yl 4-methylbenzenesulfonate (2.9 g, 12.1 mmol) in THF (5 mL) was added slowly into the alkenyllithium solution and the reaction was heated up to reflux for 24 h. The solvent was removed and the residue was purified by silica gel column chromatography (eluent: Hexanes/EtOAc 30:1), to give 2-(non-8-en-3-yn-1-yloxy)tetrahydro-2H-pyran as colorless oil, TLC Rf=0.7 (Hexanes/EtOAc 9:1) (1.0 g, 65% yield).

2-(Non-8-en-3-yn-1-yloxy)tetrahydro-2H-pyran (1.0 g, 4.5 mmol) was dissolved into ethanol (40 mL). PPTS (150 mg, 0.6 mmol) was added. The reaction mixture was stirred at 80° C. for 16 h. The solvent was removed and the residue was purified by silica gel column chromatography (eluent: Hexanes/EtOAc 8:1) to give non-8-en-3-yn-1-ol as colorless oil, TLC R$_f$=0.5 (Hexanes/EtOAc 8:1) (620 mg, 98% yield). $^1$H NMR (500 MHz, CDCl$_3$) δ ppm 5.79 (tdd, J=6.6, 10.3, 17.1 Hz, 1H), 5.03 (qd, J=1.6, 17.1 Hz, 1H), 5.00-4.95 (m, 1H), 3.68 (t, J=6.4 Hz, 2H), 2.43 (tt, J=2.4, 6.4 Hz, 2H), 2.22-2.16 (m, 2H), 2.16-2.08 (m, 2H), 1.89 (s, 1H), 1.59 (quin, J=7.2 Hz, 2H); $^{13}$C NMR (125 MHz, CDCl$_3$) δ ppm 137.9, 115.1, 82.3, 76.6, 61.4, 32.8, 28.1, 23.2, 18.1.

(E)-Nona-3,8-dien-1-ol was prepared according to the following procedure. A solution of non-8-en-3-yn-1-ol (500 mg, 3.62 mmol) was added to a cold (0° C.) suspension of LiAlH$_4$ (412 mg, 10.8 mmol) in a mixture of diglyme (5.5 mL) and THF (1.6 mL). The reaction mixture was heated to reflux for 72 h. The reaction was quenched using H$_2$O (0.4 mL) followed by 10% NaOH (0.4 mL) and H$_2$O (1.2 mL). Then the reaction mixture was poured into 10% HCl and extracted with pentane (3×40 mL). The combined organic layer was concentrated under high vacuum to give (E)-nona-3,8-dien-1-ol, as a colorless oil (450 mg, 90% yield). $^1$H NMR (500 MHz, CDCl$_3$) δ ppm 5.79 (tdd, J=6.7, 10.2, 17.1 Hz, 1H), 5.59-5.47 (m, 1H), 5.45-5.30 (m, 1H), 4.99 (qd, J=1.6, 17.1 Hz, 1H), 4.96-4.91 (m, 1H), 3.64-3.57 (m, 2H), 2.26 (q, J=6.4 Hz, 2H), 2.12-2.00 (m, 4H), 1.99 (s, 1H), 1.51-1.43 (m, 2H).

LK-III-216

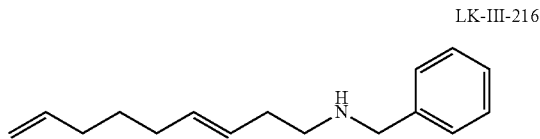 [SMILES: C=CCCC/C=C/CCNCc1ccccc1]

(E)-N-Benzylnona-3,8-dien-1-amine was prepared in 50% yield (300 mg) as yellow oil through General Procedure D1 from (E)-nona-3,8-dien-1-ol (364 mg, 2.6 mmol). $^1$H NMR (500 MHz, CDCl$_3$) δ ppm 7.39-7.31 (m, 4H), 7.29-7.22 (m, 1H), 5.81 (tdd, J=6.6, 10.3, 17.1 Hz, 1H), 5.55-5.46 (m, 1H), 5.43-5.34 (m, 1H), 5.01 (qd, J=1.6, 17.1 Hz, 1H), 4.98-4.92 (m, 1H), 3.80 (s, 2H), 2.68 (t, J=6.8 Hz, 2H), 2.23 (q, J=6.8 Hz, 2H), 2.10-1.98 (m, 4H), 1.46 (quin, J=7.5 Hz, 2H), 1.39 (br. s., 1H); $^{13}$C NMR (125 MHz, CDCl$_3$) δ ppm 140.5, 138.8, 132.2, 128.4, 128.1, 127.9, 126.8, 114.5, 53.9, 48.9, 33.2, 33.1, 32.0, 28.7; HRMS (ESI) m/z Calcd. for C$_{16}$H$_{24}$N$^+$[M+H]$^+$: 230.1903, Found: 230.1895; IR (neat, cm$^{-1}$): 2924, 2840, 1640, 1453, 968, 908, 730, 690.

LK-III-189

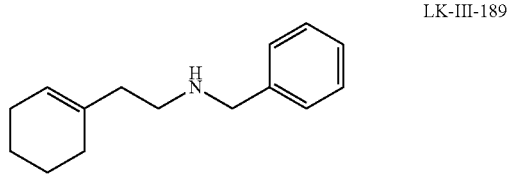 [SMILES: C1=C(CCNCc2ccccc2)CCCC1]

N-Benzyl-2-(cyclohex-1-en-1-yl)ethan-1-amine was prepared in 84% yield (900 mg) as yellow oil through General Procedure D2 from 2-(cyclohex-1-en-1-yl)ethan-1-amine (commercially available, cas: 3399-73-3) (625 mg, 5 mmol). $^1$H NMR (500 MHz, CDCl$_3$) δ ppm 7.37-7.29 (m, 4H), 7.29-7.21 (m, 1H), 5.50-5.45 (m, 1H), 3.81 (s, 2H), 2.71 (t, J=7.1 Hz, 2H), 2.18 (t, J=7.1 Hz, 2H), 2.04-1.96 (m, 2H), 1.92-1.84 (m, 2H), 1.66-1.59 (m, 2H), 1.59-1.53 (m, 2H), 1.47 (br. s., 1H); $^{13}$C NMR (125 MHz, CDCl$_3$) δ ppm 140.5, 135.4, 128.4, 128.1, 126.8, 122.8, 53.9, 46.9, 38.3, 28.1, 25.3, 23.0, 22.5; HRMS (ESI) m/z Calcd. for C$_{15}$H$_{22}$N$^+$ [M+H]$^+$: 216.1747, Found: 216.1742; IR (neat, cm$^{-1}$): 2923, 2833, 2855, 1494, 1452, 1114, 907, 728, 697.

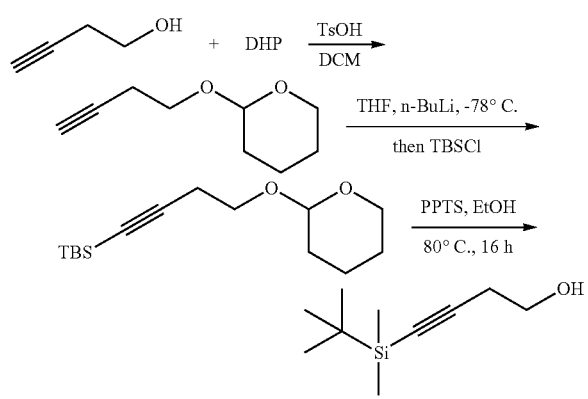

Under nitrogen atmosphere, p-toluenesulfonic acid (63 mg, 0.33 mmol) was added to a round-bottom flask containing but-3-yn-1-ol (2.52 mL, 33 mmol) in DCM (36 mL) followed by the slow addition of dihydropyran (3.2 mL, 35 mmol). The reaction mixture was stirred for 2 hours at room temperature until the consumption of but-3-yn-1-ol based on TLC. Then the solvent was removed and the residue was purified by silica gel column chromatography (eluent: Hexanes/EtOAc 30:1) to give 2-(but-3-yn-1-yloxy)tetrahydro-2H-pyran as colorless oil, TLC R$_f$=0.3 (Hexanes/EtOAc 9:1) (5.1 g, 99% yield).

The above DHP protected alkyne (1.5 g, 10 mmol) was dissolved into THF (10 mL) under nitrogen atmosphere and cooled down to −78° C. n-BuLi (2.5 M solution in Hexane) (4.3 mL, 10.7 mmol) was added slowly into this solution and the reaction mixture was warmed up to room temperature and stirred for 30 min. Then the reaction solution was cooled down to −78° C. tert-butyldimethylsilyl chloride (1.6 g, 10.6 mmol) in THF (5 mL) was added slowly into the alkenyllithium solution and the reaction was warmed up to room temperature and stirred for 3 h. The solvent was removed and the residue was purified by silica gel column chromatography (eluent: Hexanes/EtOAc 30:1) to give tert-butyldimethyl(4-((tetrahydro-2H-pyran-2-yl)oxy)but-1-yn-1-yl)silane as colorless oil, TLC R$_f$=0.6 (Hexanes/EtOAc 9:1) (1.2 g, 46% yield). $^1$H NMR (500 MHz, CDCl$_3$) δ ppm 4.66 (t, J=3.4 Hz, 1H), 3.89 (ddd, J=2.9, 8.7, 11.4 Hz, 1H), 3.82 (td, J=7.2, 9.7 Hz, 1H), 3.61-3.40 (m, 2H), 2.53 (t, J=7.1 Hz, 2H), 1.83 (dd, J=3.4, 9.3 Hz, 1H), 1.75-1.66 (m, 1H), 1.63-1.56 (m, 2H), 1.55-1.45 (m, 2H), 0.92 (s, 9H), 0.07 (s, 6H); $^{13}$C NMR (125 MHz, CDCl$_3$) δ ppm 104.5, 98.6, 83.6, 65.7, 61.9, 30.5, 26.0, 25.4, 21.4, 19.2, 16.5, 4.5.

tert-butyldimethyl(4-((tetrahydro-2H-pyran-2-yl)oxy)but-1-yn-1-yl)silane (1.2 g, 4.4 mmol) was dissolved into ethanol (40 mL). PPTS (150 mg, 0.6 mmol) was added. The reaction mixture was stirred at 80° C. for 16 h. The solvent was removed and the residue was purified by silica gel column chromatography (eluent: Hexanes/EtOAc 16:1) to give 4-(tert-butyldimethylsilyl)but-3-yn-1-ol as colorless oil, TLC R$_f$=0.4 (Hexanes/EtOAc 8:1) (800 mg, 98% yield). $^1$H NMR (500 MHz, CDCl$_3$) δ ppm 3.71 (t, J=6.4 Hz, 2H), 2.50 (t, J=6.4 Hz, 2H), 2.01 (s, 1H), 0.92 (s, 9H), 0.09 (s, 6H); $^{13}$C NMR (125 MHz, CDCl$_3$) δ ppm 103.8, 85.1, 61.0, 26.0, 24.2, 16.4, −4.52.

LK-III-204

N-Benzyl-4-(tert-butyldimethylsilyl)but-3-yn-1-amine was prepared in 36% yield (402 mg) as yellow oil through General Procedure D1 from the above synthesized 4-(tert-butyldimethylsilyl)but-3-yn-1-ol (750 mg, 4.1 mmol). $^1$H NMR (500 MHz, CDCl$_3$) δ ppm 7.40-7.29 (m, 4H), 7.29-7.24 (m, 1H), 3.83 (s, 2H), 2.80 (t, J=6.6 Hz, 2H), 2.48 (t, J=6.6 Hz, 2H), 1.88 (br. s., 1H), 0.93 (s, 9H), 0.10 (s, 6H); $^{13}$C NMR (125 MHz, CDCl$_3$) δ ppm 140.0, 128.4, 128.1, 127.0, 105.5, 84.2, 53.3, 47.4, 26.1, 20.9, 16.5, −4.5; HRMS (ESI) m/z Calcd. for C$_{17}$H$_{28}$NSi$^+$ [M+H]$^+$: 274.1986, Found: 274.1977; IR (neat, cm$^{-1}$): 2952, 2927, 2855, 2171, 1461, 1249, 809, 836, 824, 732, 697.

LK-III-238

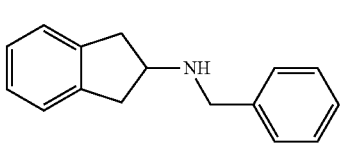

N-Benzyl-2,3-dihydro-1H-inden-2-amine was prepared in 38% yield (420 mg) as yellow oil through General Procedure D1 from 2,3-dihydro-1H-inden-2-ol (commercially available, cas: 4254-29-9) (690 mg, 5 mmol). $^1$H NMR (400 MHz, CDCl$_3$) δ ppm 7.38-7.29 (m, 4H), 7.28-7.22 (m, 1H), 7.22-7.16 (m, 2H), 7.16-7.07 (m, 2H), 3.86 (s, 2H), 3.68 (quin, J=6.8 Hz, 1H), 3.17 (dd, J=7.2, 15.4 Hz, 2H), 2.81 (dd, J=6.8, 15.4 Hz, 2H), 1.57 (br. s., 1H); $^{13}$C NMR (125 MHz, CDCl$_3$) δ ppm 141.7, 140.3, 128.4, 128.2, 127.0, 126.4, 124.7, 59.0, 52.3, 40.0; HRMS (ESI) m/z Calcd. for C$_{16}$H$_{18}$N$^+$ [M+H]$^+$: 224.1434, Found: 224.1430; IR (neat, cm$^{-1}$): 2932, 2835, 1603, 1453, 1124, 738, 697.

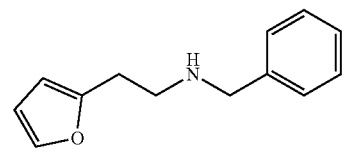 [SMILES: c1ccc(CNCCc2ccco2)cc1]

N-Benzyl-2-(furan-2-yl)ethan-1-amine was prepared in 57% yield as yellow oil through General Procedure D2 from 2-(furan-2-yl)ethan-1-amine (222 mg, 2 mmol) (synthesized according to a published procedure). $^1$H NMR (500 MHz, CDCl$_3$) b 7.36-7.29 (m, 5H), 7.28-7.22 (m, 1H), 6.30 (dd, J=2.0, 2.9 Hz, 1H), 6.12-6.01 (m, 1H), 3.82 (s, 2H), 2.97-2.91 (m, 2H), 2.89-2.83 (m, 2H), 1.61 (br. s., 1H); $^{13}$C NMR (125 MHz, CDCl$_3$) δ ppm 154.1, 141.2, 140.2, 128.4, 128.1, 127.0, 110.2, 105.8, 53.7, 47.5, 28.7; HRMS (ESI) m/z Calcd. for C$_{13}$H$_{16}$NO$^+$ [M+H]$^+$: 202.1226, Found: 202.1205; IR (neat, cm$^{-1}$): 2923, 2821, 1496, 1453, 1157, 873, 729, 697, 599.

LK-III-169

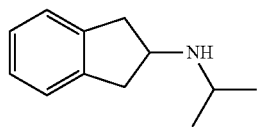

N-Isopropyl-2,3-dihydro-1H-inden-2-amine was prepared in 50% yield (437 mg) as yellow oil through General Procedure D1 between 2,3-dihydro-1H-inden-2-ol (commercially available, cas: 4254-29-9) (690 mg, 5 mmol) and propan-2-amine. $^1$H NMR (500 MHz, CDCl$_3$) δ ppm 7.24-7.18 (m, 2H), 7.18-7.13 (m, 2H), 3.76 (quin, J=7.3 Hz, 1H), 3.19 (dd, J=7.3, 15.7 Hz, 2H), 3.00 (td, J=6.4, 12.6 Hz, 1H), 2.74 (dd, J=7.1, 15.7 Hz, 2H), 1.48 (br. s., 1H), 1.11 (d, J=6.4 Hz, 6H); $^{13}$C NMR (125 MHz, CDCl$_3$) δ ppm 141.8, 126.4, 124.7, 57.0, 46.6, 40.3, 23.2; HRMS (ESI) m/z Calcd. for C$_{12}$H$_{18}$N$^+$ [M+H]$^+$: 176.1434, Found: 176.1437; IR (neat, cm$^{-1}$): 2963, 2837, 1617, 1459, 1173, 908, 728, 640.

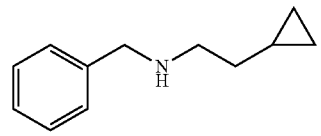 [SMILES: c1ccc(CNCCC2CC2)cc1]

N-Benzyl-2-cyclopropylethan-1-amine was prepared in 58% yield (1.02 g) as yellow oil through General Procedure D1 from 2-cyclopropylethan-1-ol (commercially available, cas: 2566-44-1) (500 mg, 5.8 mmol). $^1$H NMR (600 MHz, CDCl$_3$) δ ppm 7.36-7.30 (m, 3H), 7.27-7.23 (m, 2H), 3.81 (s, 2H), 2.74 (t, J=7.1 Hz, 2H), 1.43 (dd, J=14.1, 7.0 Hz, 2H), 1.40 (br.s, 1H), 0.75-0.64 (m, 1H), 0.48-0.40 (m, 2H), 0.09-0.03 (m, 2H); $^{13}$C NMR (150 MHz, CDCl$_3$) δ ppm 140.7, 128.5, 128.2, 127.0, 54.3, 49.7, 35.2, 9.0, 4.3; HRMS (ESI) m/z Calcd. for C$_{12}$H$_{18}$N$^+$ [M+H]$^+$: 176.1434, Found: 176.1422; IR (neat, cm$^{-1}$): 2915, 1453, 751.

LK-III-176

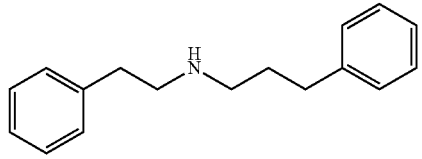

N-Phenethyl-3-phenylpropan-1-amine was prepared in 83% yield (1.0 g) as yellow oil through General Procedure D1 between 3-phenylpropan-1-ol (commercially available, cas: 122-97-4) (680 mg, 5 mmol) and 2-phenylethan-1-amine (commercially available, cas: 64-04-0) (1.2 g, 10 mmol). $^1$H NMR (500 MHz, CDCl$_3$) δ ppm 7.39-7.11 (m, 10H), 2.93-2.87 (m, 2H), 2.86-2.79 (m, 2H), 2.66 (td, J=7.5, 14.4 Hz, 4H), 1.83 (td, J=7.5, 15.0 Hz, 2H), 1.23 (br. s., 1H); $^{13}$C NMR (125 MHz, CDCl$_3$) δ ppm 142.1, 140.1, 128.7, 128.4, 128.3, 128.2, 126.1, 125.7, 51.1, 49.2, 36.3, 33.6, 31.6; HRMS (ESI) m/z Calcd. for C$_{17}$H$_{22}$N$^+$ [M+H]$^+$: 240.1747, Found: 240.1738; IR (neat, cm$^{-1}$): 2931, 2856, 1602, 1495, 1453, 908, 728, 697.

N-Methyl-1,3-diphenylpropan-2-amine was synthesized according to the following method: At room temperature, Ti(OiPr)$_4$ (1.5 mL, 5.2 mmol) was added to a 1,3-diphenylpropanone (commercially available, cas: 102-04-5) (1.0 g, 4.7 mmol) DCM solution (20 mL), followed by the addition of MeNH$_2$ (3.5 mL, 7 mmol, 2 M in MeOH). The reaction mixture was stirred for 1 hour and the solvent was removed. The residue was dissolved into MeOH (20 mL) and cooled to 0° C. Then NaBH$_4$ (0.53 g, 14.1 mmol) was added to this solution and the reaction mixture was slowly warmed up to room temperature and stirred for 2 hours. Then the solvent was removed and the residue was purified by silica gel column chromatography (gradient elution: Hexanes/EtOAc 8:1 to 1:1) to give the desired amine product as yellow oil (600 mg, 56% yield). 1H NMR (500 MHz, CDCl$_3$) δ ppm 7.38-7.12 (m, 10H), 3.01-2.91 (m, 1H), 2.82-2.73 (m, 2H), 2.71-2.62 (m, 2H), 2.42 (s, 3H); $^{13}$C NMR (125 MHz, CDCl$_3$) δ ppm 139.5, 129.3, 128.4, 126.2, 62.8, 40.2, 34.2;

HRMS (ESI) m/z Calcd. for $C_{16}H_{20}N^+[M+H]^+$: 226.1590, Found: 226.1576; IR (neat, cm$^{-1}$): 2930, 2851, 1737, 1601, 1494, 1452, 748, 697.

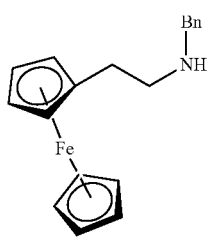

N-Benzyl-2-(ferrocenyl)ethan-1-amine was prepared in 63% yield (340 mg) as yellow oil through General Procedure D2 from 2-(ferrocenyl)ethan-1-amine (390 mg, 1.7 mmol) (synthesized according to a published procedure). $^1$H NMR (600 MHz, CDCl$_3$) δ ppm 7.36-7.24 (m, 5H), 4.10 (s, 7H), 4.07 (s, 2H), 3.81 (s, 2H), 2.79 (t, J=7.0 Hz, 2H), 2.58 (t, J=7.0 Hz, 2H), 1.61 (br. s., 1H); $^{13}$C NMR (150 MHz, CDCl$_3$) δ ppm 140.3, 128.4, 128.1, 126.9, 86.5, 68.5, 68.3, 67.3, 53.9, 50.4, 30.1; HRMS (ESI) m/z Calcd. for $C_{19}H_{22}FeN^+$ [M+H]$^+$: 320.1102, Found: 320.1110; IR (neat, cm$^{-1}$): 1739, 1365, 1229, 1217.

Example 7: General Procedure E (Synthesis of Sulfamoyl Azide 1)

Sulphuryl Azide ($N_3SO_2N_3$) was prepared according to a reported procedure without further optimization. Sulfuryl chloride (9.72 mL, 120 mmol) was added dropwise for 1 h to a solution of sodium azide (29.25 g, 450 mmol) and pyridine (19.44 mL, 250 mmol) in acetonitrile (600 mL) at 0° C. Then the reaction mixture was stirred for one hour at room temperature followed by the addition of 100 mL DCM. The mixture was poured into ice-cold water and extracted with DCM (3×100 mL). The combined organic layer was washed sequentially with hydrochloric acid (1 mol/L in H$_2$O), water, potassium hydroxide (1 mol/L in H$_2$O), hydrochloric acid (1 mol/L in H$_2$O), and water. After drying (Na$_2$SO$_4$), the sulphuryl azide solution was used directly for the further reaction. This solution (0.3 M in DCM) can be stored in the refrigerator at −20° C. for at least six months without significant decomposition.

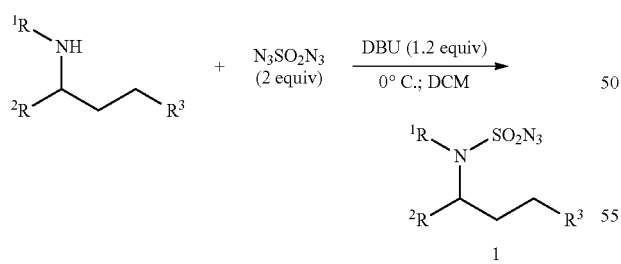

A mixture of amine (1 equiv) and DBU (1.2 equiv) in DCM was added dropwise via pipette to a solution of $N_3SO_2N_3$ (2 equiv, 0.3 M in DCM) at 0° C. After the reaction was completed based on TLC (~ 1 h), the majority of the solvent was removed under reduced pressure at room temperature. Purification of this mixture by silica gel column chromatography (Conditions are given below.) afforded the sulfamoyl azide. Note: Some azides could be explosive and should be handled carefully.

Characterization of Sulfamoyl Azides (1a-1u)

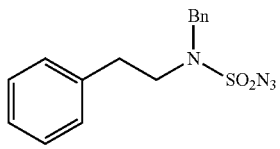

1a

N-Benzyl-2-phenylethan-1-sulfamoyl azide (1a) was obtained in 88% yield (560 mg) as colorless oil through General Procedure E from N-benzyl-2-phenylethan-1-amine starting from 2 mmol scale, purified by silica gel column chromatography (eluent: Hexanes/EtOAc 40:1), TLC R$_f$=0.6 (Hexanes/EtOAc 8:1). $^1$H NMR (500 MHz, CDCl$_3$) δ ppm 7.44-7.37 (m, 2H), 7.37-7.32 (m, 2H), 7.32-7.26 (m, 2H), 7.26-7.20 (m, 2H), 7.10 (d, J=6.8 Hz, 2H), 4.43 (s, 2H), 3.48-3.40 (m, 2H), 2.88-2.81 (m, 2H); $^{13}$C NMR (100 MHz, CDCl$_3$) δ ppm 137.6, 134.5, 129.0, 128.8, 128.7, 128.6, 128.5, 126.8, 53.0, 50.0, 34.4; IR (neat, cm$^{-1}$): 2123, 1380, 1204, 1164, 734, 697.

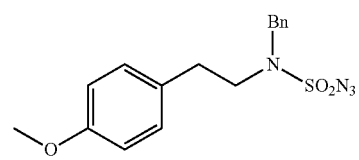

1b

N-Benzyl-2-(4-methoxyphenyl)ethan-1-sulfamoyl azide (1 b) was obtained in 85% yield (294 mg) as colorless oil through General Procedure E from N-benzyl-2-(4-methoxyphenyl)ethan-1-amine starting from 1 mmol scale, purified by silica gel column chromatography (eluent: Hexanes/EtOAc 40:1), TLC R$_f$=0.3 (Hexanes/EtOAc 8:1). $^1$H NMR (400 MHz, CDCl$_3$) δ ppm 7.55-7.26 (m, 5H), 7.08-6.94 (m, 2H), 6.86-6.69 (m, 2H), 4.39 (s, 2H), 3.76 (s, 3H), 3.44-3.26 (m, 2H), 2.87-2.66 (m, 2H); $^{13}$C NMR (125 MHz, CDCl$_3$) δ ppm 158.4, 134.5, 129.7, 129.5, 128.9, 128.6, 128.5, 114.1, 55.2, 53.0, 50.2, 33.4; IR (neat, cm$^{-1}$): 2126, 1611, 1513, 1456, 1379, 1205, 1165, 905, 726, 699.

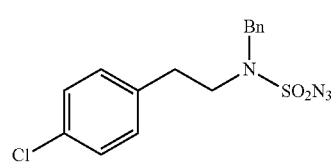

1c

N-Benzyl-2-(4-chlorophenyl)ethan-1-sulfamoyl azide (1c) was obtained in 88% yield (310 mg) as colorless oil through General Procedure E from N-benzyl-2-(4-chlorophenyl) ethan-1-amine starting from 1 mmol scale, purified by silica gel column chromatography (eluent: Hexanes/EtOAc 40:1), TLC R$_f$=0.4 (Hexanes/EtOAc 8:1). $^1$H NMR (400 MHz, CDCl$_3$) δ ppm 7.42-7.13 (m, 7H), 7.06-6.86 (m, 2H), 4.39 (s, 2H), 3.50-3.28 (m, 2H), 2.88-2.66 (m, 2H); $^{13}$C NMR (100 MHz, CDCl$_3$) δ ppm 136.0, 134.3, 132.6, 130.1, 129.0, 128.8, 128.6, 53.2, 49.9, 33.8; IR (neat, cm$^{-1}$): 2128, 1493, 1380, 1264, 1167, 733, 703, 610, 593.

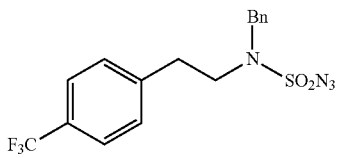
1d

N-Benzyl-2-(4-(trifluoromethyl)phenyl)ethan-1-sulfamoyl azide (1d) was obtained in 90% yield (355 mg) as colorless oil through General Procedure E from N-benzyl-2-(4-(trifluoromethyl)phenyl)ethan-1-amine starting from 1 mmol scale, purified by silica gel column chromatography (eluent: Hexanes/EtOAc 40:1), TLC $R_f$=0.7 (Hexanes/EtOAc 8:1). $^1$H NMR (600 MHz, CDCl$_3$) δ ppm 7.51 (d, J=8.0 Hz, 2H), 7.40-7.36 (m, 3H), 7.33-7.28 (m, 2H), 7.15 (d, J=8.0 Hz, 2H), 4.42 (s, 2H), 3.57-3.33 (m, 2H), 2.95-2.78 (m, 2H); $^{13}$C NMR (150 MHz, CDCl$_3$) δ ppm 141.6, 134.2, 129.2 (q, J=32.0 Hz), 129.1, 129.0, 128.7, 128.6, 125.6 (q, J=3.0 Hz), 124.1 (q, J=272.0 Hz), 53.4, 49.8, 34.3; $^{19}$F NMR (470 MHz, CFCl$_3$, CDCl$_3$) δ ppm −63.05 (s, 3F); IR (neat, cm$^{-1}$): 2128, 1619, 1380, 1325, 1264, 1123, 1067, 733, 702, 609, 593.

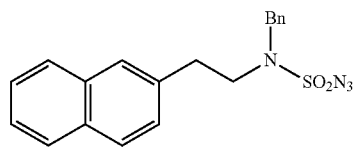
1e

N-Benzyl-2-(naphthalen-2-yl)ethan-1-sulfamoyl azide (1e) was obtained in 80% yield (292 mg) as colorless wax through General Procedure E from N-benzyl-2-(naphthalen-2-yl)ethan-1-amine starting from 1 mmol scale, purified by silica gel column chromatography (eluent: Hexanes/EtOAc 40:1), TLC $R_f$=0.7 (Hexanes/EtOAc 8:1). $^1$H NMR (500 MHz, CDCl$_3$) δ ppm 7.88-7.70 (m, 3H), 7.54 (s, 1H), 7.53-7.41 (m, 2H), 7.41-7.13 (m, 6H), 4.44 (s, 2H), 3.53 (t, J=7.8 Hz, 2H), 3.01 (t, J=7.8 Hz, 2H); $^{13}$C NMR (125 MHz, CDCl$_3$) δ ppm 135.0, 134.5, 133.5, 132.3, 128.9, 128.7, 128.6, 128.4, 127.7, 127.5, 127.3, 126.9, 126.2, 125.7, 53.1, 50.0, 34.6; IR (neat, cm$^{-1}$): 2124, 1600, 1496, 1455, 1378, 1206, 1164, 907, 751, 1 730, 609, 591.

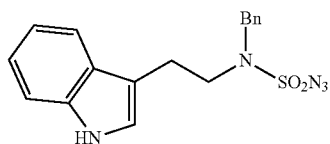

N-Benzyl-2-(1H-indol-3-yl)ethan-1-sulfamoyl azide was obtained in 87% yield (620 mg) as yellow wax through General Procedure E from N-benzyl-2-(1H-indol-3-yl)ethan-1-amine starting from 2 mmol scale, purified by silica gel column chromatography (eluent: Hexanes/EtOAc 8:1), TLC $R_f$=0.25 (Hexanes/EtOAc 8:1). $^1$H NMR (500 MHz, CDCl$_3$) δ ppm 7.99 (br. s., 1H), 7.45-7.31 (m, 7H), 7.21 (dt, J=1.0, 7.6 Hz, 1H), 7.15-7.07 (m, 1H), 6.98 (d, J=2.4 Hz, 1H), 4.47 (s, 2H), 3.61-3.41 (m, 2H), 3.10-2.94 (m, 2H); $^{13}$C NMR (125 MHz, CDCl$_3$) δ ppm 136.2, 134.6, 128.9, 128.7, 128.5, 127.0, 122.3, 122.2, 119.6, 118.5, 111.8, 111.2, 53.1, 49.1, 24.2.

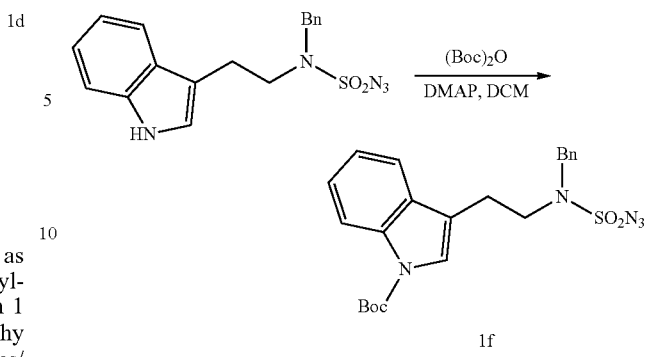
1f

N-Benzyl-2-(1-(tert-butoxycarbonyl)-1H-indol-3-yl)ethan-1-sulfamoyl azide (1f) was obtained according to the following procedure. DMAP (12 mg, 0.1 mmol) and (Boc)$_2$O (231 mg, 1.2 mmol) were added to a solution of N-benzyl-2-(1H-indol-3-yl)ethan-1-sulfamoyl azide (355 mg, 1 mmol) in DCM (4 mL). The reaction mixture was stirred for 2 h. The solvent was removed and the residue was purified by silica gel column chromatography (eluent: Hexanes/EtOAc 40:1), to give N-benzyl-2-(1-(tert-butoxycarbonyl)-1H-indol-3-yl) ethan-1-sulfamoyl azide as colorless wax, TLC $R_f$=0.7 (Hexanes/EtOAc 8:1) (450 mg, 95% yield). $^1$H NMR (500 MHz, CDCl$_3$) δ ppm 8.24-7.98 (m, 1H), 7.44-7.19 (m, 9H), 4.49 (s, 2H), 3.60-3.42 (m, 2H), 3.03-2.85 (m, 2H), 1.68 (s, 9H); $^{13}$C NMR (100 MHz, CDCl$_3$) δ ppm 149.6, 135.4, 134.4, 129.9, 128.9, 128.6, 124.5, 123.4, 122.5, 118.6, 116.2, 115.3, 83.7, 53.4, 48.5, 28.2, 24.0; IR (neat, cm$^{-1}$): 2125, 1728, 1453, 1369, 1161, 1095, 906, 727, 698, 609, 592.

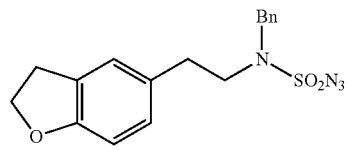
1g

N-Benzyl-2-(2,3-dihydrobenzofuran-5-yl)ethan-1-sulfamoyl azide (1 g) was obtained in 95% yield (340 mg) as colorless wax through General Procedure E from N-benzyl-2-(2,3-dihydrobenzofuran-5-yl)ethan-1-amine starting from 1 mmol scale, purified by silica gel column chromatography (eluent: Hexanes/EtOAc 40:1), TLC $R_f$=0.6 (Hexanes/EtOAc 8:1). $^1$H NMR (600 MHz, CDCl$_3$) δ ppm 7.41-7.35 (m, 3H), 7.32 (d, J=6.8 Hz, 2H), 6.91 (s, 1H), 6.79 (d, J=8.0 Hz, 1H), 6.68 (d, J=8.1 Hz, 1H), 4.54 (t, J=8.7 Hz, 2H), 4.42 (s, 2H), 3.45-3.33 (m, 2H), 3.15 (t, J=8.7 Hz, 2H), 2.79-2.71 (m, 2H); $^{13}$C NMR (100 MHz, CDCl$_3$) δ ppm 158.9, 134.5, 129.4, 128.9, 128.6, 128.5, 128.2, 127.4, 125.2, 109.3, 71.2, 53.0, 50.4, 33.8, 29.7; IR (neat, cm$^{-1}$): 2126, 1735, 1614, 1492, 1264, 1165, 732, 701, 608, 593.

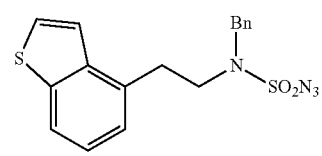
1h

N-Benzyl-2-(benzo[b]thiophen-4-yl)ethan-1-sulfamoyl azide (1h) was obtained in 88% yield (330 mg) as colorless wax through General Procedure E from N-benzyl-2-(benzo[b]thiophen-4-yl)ethan-1-amine starting from 1 mmol scale, purified by silica gel column chromatography (eluent: Hexanes/EtOAc 40:1), TLC $R_f$=0.55 (Hexanes/EtOAc 8:1). $^1$H NMR (600 MHz, CDCl$_3$) δ ppm 7.75 (d, J=8.1 Hz, 1H), 7.42 (d, J=5.5 Hz, 1H), 7.40-7.34 (m, 2H), 7.25-7.15 (m, 2H), 7.24 (dd, J=12.4, 4.7 Hz, 2H), 7.16 (d, J=5.5 Hz, 1H), 7.04 (d, J=7.2 Hz, 1H), 4.42 (s, 2H), 3.47 (t, J=7.9 Hz, 2H), 3.145 (t, J=7.9 Hz, 2H); $^{13}$C NMR (125 MHz, CDCl$_3$) δ ppm 140.4, 138.7, 134.6, 132.5, 129.1, 128.9, 128.8, 126.9, 124.8, 124.5, 121.6, 121.4, 53.6, 49.6, 33.3; IR (neat, cm$^{-1}$): 2122, 1454, 1378, 1164, 760, 592.

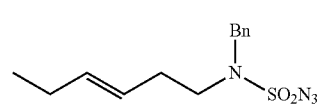

(E)-N-Benzylhex-3-en-1-sulfamoyl azide (1i) was obtained in 89% yield (265 mg) as colorless oil through General Procedure E from (E)-N-benzoylhex-3-en-1-amine starting from 1 mmol scale, purified by silica gel column chromatography (eluent: Hexanes/EtOAc 40:1), TLC $R_f$=0.7 (Hexanes/EtOAc 8:1). $^1$H NMR (400 MHz, CDCl$_3$) δ ppm 7.52-7.31 (m, 5H), 5.62-5.47 (m, 1H), 5.26 (td, J=6.8, 15.2 Hz, 1H), 4.49 (s, 2H), 3.36-3.19 (m, 2H), 2.33-2.21 (m, 2H), 2.06-1.92 (m, 2H), 1.05-0.90 (m, 3H); $^{13}$C NMR (100 MHz, CDCl$_3$) δ ppm 135.6, 134.7, 128.8, 128.5, 128.4, 124.0, 52.6, 48.5, 30.8, 25.5, 13.5; IR (neat, cm-1): 2124, 1496, 1455, 1379, 1204, 1166, 906, 727, 697, 593.

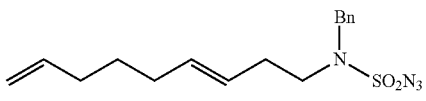

(E)-N-Benzylnona-3,8-dien-1-sulfamoyl azide (1j) was prepared in 95% yield (317 mg) as colorless oil through General Procedure E from (E)-N-benzylnona-3,8-dien-1-amine starting from 1 mmol scale, purified by silica gel column chromatography (eluent: Hexanes/EtOAc 40:1), TLC $R_f$=0.7 (Hexanes/EtOAc 8:1). $^1$H NMR (400 MHz, CDCl$_3$) δ ppm 7.39-7.30 (m, 5H), 5.77 (tdd, J=6.7, 10.3, 16.9 Hz, 1H), 5.43 (td, J=6.7, 15.0 Hz, 1H), 5.29-5.13 (m, 1H), 5.04-4.84 (m, 2H), 4.45 (s, 2H), 3.35-3.12 (m, 2H), 2.22 (q, J=7.2 Hz, 2H), 2.08-1.84 (m, 4H), 1.40 (quin, J=7.5 Hz, 2H); $^{13}$C NMR (100 MHz, CDCl$_3$) δ ppm 138.6, 134.6, 133.7, 128.8, 128.5, 128.4, 125.2, 114.5, 52.6, 48.5, 33.1, 31.9, 30.8, 28.4; IR (neat, cm-1): 2123, 1640, 1496, 1455, 1379, 1204, 1165, 907, 728, 697, 592.

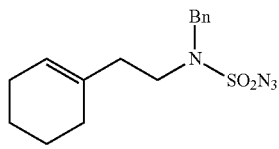

N-Benzyl-2-(cyclohex-1-en-1-yl)ethan-1-sulfamoyl azide (1k) was obtained in 80% yield (255 mg) as colorless oil through General Procedure E from N-benzyl-2-(cyclohex-1-en-1-yl)ethan-1-amine starting from 1 mmol scale, purified by silica gel column chromatography (eluent: Hexanes/EtOAc 40:1), TLC $R_f$=0.7 (Hexanes/EtOAc 8:1). $^1$H NMR (500 MHz, CDCl$_3$) δ ppm 7.48-7.33 (m, 5H), 5.52-5.36 (m, 1H), 4.51 (s, 2H), 3.41-3.22 (m, 2H), 2.26-2.16 (m, 2H), 2.05-1.94 (m, 2H), 1.92-1.80 (m, 2H), 1.65-1.59 (m, 2H), 1.58-1.52 (m, 2H); $^{13}$C NMR (125 MHz, CDCl$_3$) δ ppm 134.7, 133.5, 128.8, 128.5, 128.4, 124.1, 52.3, 47.2, 35.8, 28.1, 25.2, 22.7, 22.1; IR (neat, cm$^{-1}$): 2122, 1381, 1205, 1165, 768, 735, 698.

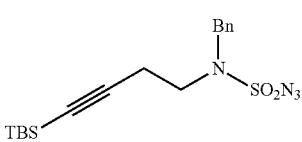

N-Benzyl-4-(tert-butyldimethylsilyl)but-3-yn-1-sulfamoyl azide (1l) was obtained in 82% yield (310 mg) as colorless wax through General Procedure E from N-benzyl-4-(tert-butyldimethylsilyl)but-3-yn-1-amine starting from 1 mmol scale, purified by silica gel column chromatography (eluent: Hexanes/EtOAc 40:1), TLC $R_f$=0.7 (Hexanes/EtOAc 8:1). $^1$H NMR (400 MHz, CDCl$_3$) δ ppm 7.43-7.26 (m, 5H), 4.59 (s, 2H), 3.38 (t, J=7.2 Hz, 2H), 2.50 (t, J=7.2 Hz, 2H), 0.91 (s, 9H), 0.07 (s, 6H); $^{13}$C NMR (100 MHz, CDCl$_3$) δ ppm 134.6, 129.0, 128.5, 103.1, 85.7, 53.2, 47.1, 26.0, 19.6, 16.4, −4.6; IR (neat, cm$^{-1}$): 2176, 2133, 1471, 1456, 1382, 1201, 1165, 837, 809, 774, 736, 596.

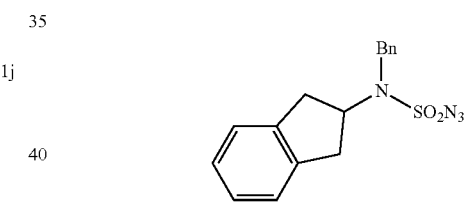

N-Benzyl-2,3-dihydro-1H-inden-2-sulfamoyl azide (1m) was obtained in 70% yield (230 mg) as colorless oil through General Procedure E from N-benzyl-2,3-dihydro-1H-inden-2-amine starting from 1 mmol scale, purified by silica gel column chromatography (eluent: Hexanes/EtOAc 40:1), TLC $R_f$=0.7 (Hexanes/EtOAc 8:1). $^1$H NMR (400 MHz, CDCl$_3$) δ ppm 7.34-7.26 (m, 3H), 7.22-7.05 (m, 6H), 4.89-4.79 (m, 1H), 4.40 (s, 2H), 3.21-3.12 (m, 2H), 3.09-3.00 (m, 2H); 130 NMR (100 MHz, CDCl$_3$) δ ppm 139.7, 136.5, 128.6, 127.8, 127.1, 127.0, 124.4, 60.0, 49.4, 36.6; IR (neat, cm$^{-1}$): 2129, 1421, 1264, 1169, 908, 732, 703.

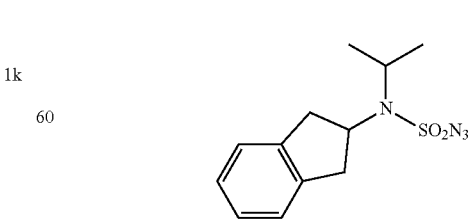

N-Isopropyl-2,3-dihydro-1H-inden-2-sulfamoyl azide (1 m') was obtained in 70% yield (196 mg) as colorless oil through General Procedure E from N-isopropyl-2,3-dihydro-1H-inden-2-amine starting from 1 mmol scale, purified by silica gel column chromatography (eluent: Hexanes/EtOAc 40:1), TLC $R_f$=0.8 (Hexanes/EtOAc 8:1). $^1$H NMR (500 MHz, CDCl$_3$) δ ppm 7.24-7.17 (m, 4H), 4.45 (quin, J=8.8 Hz, 1H), 3.97 (td, J=6.8, 13.7 Hz, 1H), 3.35 (dd, J=9.3, 15.7 Hz, 2H), 3.15 (dd, J=8.3, 15.7 Hz, 2H), 1.38 (d, J=6.8 Hz, 6H); $^{13}$C NMR (125 MHz, CDCl$_3$) δ ppm 139.9, 127.0, 124.5, 57.6, 51.3, 37.2, 21.3; IR (neat, cm$^{-1}$): 2122, 1462, 1369, 1264, 1190, 1147, 733, 703, 642, 619.

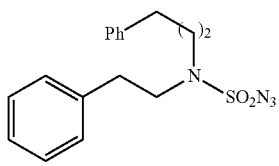

1n

N-Phenethyl-3-phenylpropan-1-azide (1n) was obtained in 90% yield (310 mg) as colorless oil through General Procedure E from N-phenethyl-3-phenylpropan-1-amine starting from 1 mmol scale, purified by silica gel column chromatography (eluent: Hexanes/EtOAc 40:1), TLC $R_f$=0.7 (Hexanes/EtOAc 8:1). $^1$H NMR (400 MHz, CDCl$_3$) δ ppm 7.40-7.30 (m, 4H), 7.30-7.23 (m, 2H), 7.22-7.14 (m, 4H), 3.60-3.44 (m, 2H), 3.35-3.20 (m, 2H), 3.00-2.85 (m, 2H), 2.64 (t, J=7.6 Hz, 2H), 2.03-1.87 (m, 2H); $^{13}$C NMR (100 MHz, CDCl$_3$) δ ppm 140.5, 137.5, 128.7, 128.6, 128.3, 126.9, 126.2, 51.0, 49.3, 34.8, 32.6, 29.3; IR (neat, cm$^{-1}$): 2122, 1603, 1496, 1454, 1379, 1203, 1163, 906, 727, 698, 598.

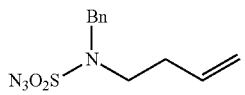

N-Benzyl-2-(vinyl)ethan-1-sulfamoyl azide was obtained in 85% yield (2.1 g) through General Procedure E from N-benzylbut-3-en-1-amine (commercially available, cas: 17150-62-8) (1.5 g, 9.3 mmol). Purified by silica gel column chromatography (eluent: Hexanes/EtOAc 40:1), colorless oil, TLC $R_f$=0.5 (Hexanes/EtOAc 8:1). $^1$H NMR (500 MHz, CDCl$_3$) δ ppm 7.64-7.29 (m, 5H), 5.78-5.58 (m, 1H), 5.17-5.00 (m, 2H), 4.49 (s, 2H), 3.41-3.19 (m, 2H), 2.43-2.22 (m, 2H); $^{13}$C NMR (125 MHz, CDCl$_3$) δ ppm 134.6, 133.8, 128.9, 128.5, 117.8, 52.6, 47.9, 31.9; IR (neat, cm$^{-1}$): 2122, 1377, 1204, 1165, 923, 763, 735, 698.

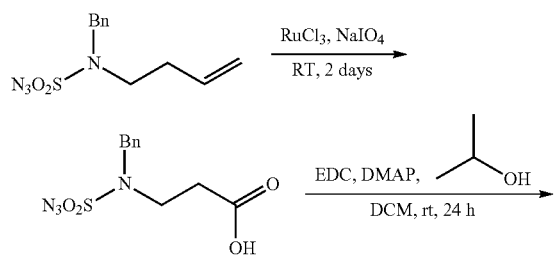

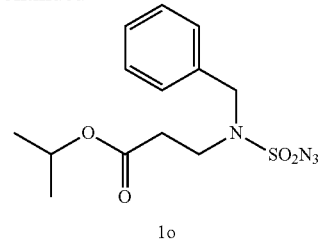

1o

Sodium periodate (2.6 g, 12 mmol) and ruthenium(III) chloride hydrate (60 mg, 0.25 mmol) were added to a solution of N-benzyl-2-(vinyl)ethan-1-sulfamoyl azide (1.6 g, 6 mmol) in CH$_3$CN (3 mL), 0014 (4 mL) and H$_2$O (4 mL). The reaction mixture was stirred for 48 h at room temperature until the consumption of starting material based on TLC. After addition of 50 mL of EtOAc, the reaction mixture was washed by water (80 mL) and the aqueous layer was extracted by EtOAc (3×40 mL). The combined organic layer was dried over anhydrous sodium sulfate. The solvent was removed by vacuum and the residue was purified by silica gel column chromatography (gradient elution: Hexanes/EtOAc 3:1 to 1:1) to give the desired carboxylic acid azide intermediate as yellow oil (1.28 g, 75% yield), TLC $R_1$=0.3 (Hexanes/EtOAc 1:1). $^1$H NMR (500 MHz, CDCl$_3$): δ 7.50-7.32 (m, 5H), 4.50 (s, 2H), 3.54 (t, J=7.3 Hz, 2H), 2.73-2.56 (m, 2H); $^{13}$C NMR (125 MHz, CDCl$_3$) b 176.3, 134.3, 129.1, 128.7, 128.5, 53.6, 44.0, 32.7; IR (neat, cm$^{-1}$): 2129, 1712, 1378, 1266, 1195, 1166, 733, 700.

EDC (180 mg, 1.1 mmol), DMAP (12 mg, 0.1 mmol) and iPrOH (0.8 mL, 10 mmol) were added to a solution of the above carboxylic acid azide (284 mg, 1 mmol) in DCM (10 mL) at 0° C. The reaction mixture was stirred at room temperature for 16 h. The solvent was removed and the residue was purified by silica gel column chromatography (gradient elution: Hexanes/EtOAc 8:1 to 4:1) to give the desired product 1o in 85% yield (277 mg), colorless oil, TLC $R_f$=0.5 (Hexanes/EtOAc 3:1). $^1$H NMR (500 MHz, CDCl$_3$) δ ppm 7.50-7.32 (m, 5H), 4.99 (td, J=6.3, 12.3 Hz, 1H), 4.51 (s, 2H), 3.55 (t, J=7.3 Hz, 2H), 2.57 (t, J=7.3 Hz, 2H), 1.23 (d, J=5.9 Hz, 6H); $^{13}$C NMR (125 MHz, CDCl$_3$) δ ppm 170.3, 134.5, 129.0, 128.6, 128.5, 68.5, 53.3, 44.4, 33.2, 21.8; IR (neat, cm$^{-1}$): 2125, 1726, 1455, 1375, 1196, 1164, 753, 591.

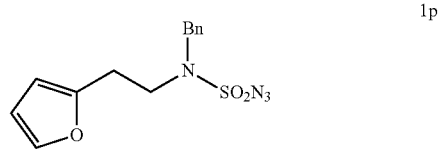

1p

N-Benzyl-2-(furan-2-yl)ethan-1-sulfamoyl azide (1p) was obtained in 90% yield (275 mg) through General Procedure E from N-benzyl-2-(furan-2-yl)ethan-1-amine starting from 1 mmol scale. Purified by silica gel column chromatography (eluent: Hexanes/EtOAc 16:1), colorless oil TLC $R_f$=0.6 (Hexanes/EtOAc 8:1). $^1$H NMR (400 MHz, CDCl$_3$) δ ppm 7.41-7.30 (m, 6H), 6.28 (dd, J=2.0, 3.2 Hz, 1H), 6.05 (dd, J=0.8, 3.2 Hz, 1H), 4.35 (s, 2H), 3.51 (t, J=7.2 Hz, 2H), 2.90 (t, J=7.2 Hz, 2H); $^{13}$C NMR (125 MHz, CDCl$_3$) δ ppm 151.4, 141.6, 134.5, 128.9, 128.5, 128.4, 110.5, 107.0, 52.8, 47.0, 26.8; IR (neat, cm$^{-1}$): 2126, 1379, 1194, 1165, 906, 727.

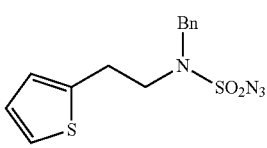

N-Benzyl-2-(thiophen-2-yl)ethan-1-sulfamoyl azide (1q) was obtained in 88% yield (283 mg) through General Procedure E from N-benzyl-2-(thiophen-2-yl)ethan-1-amine (Synthesized according to the known procedure 8), starting from 1 mmol scale. Purified by silica gel column chromatography (eluent: Hexanes/EtOAc 16:1), colorless oil, TLC $R_f$=0.55 (Hexanes/EtOAc 10:1). $^1$H NMR (400 MHz, CDCl$_3$) b 7.42-7.32 (m, 5H), 7.16 (d, J=4.4 Hz, 1H), 6.94-6.91 (m, 1H), 6.78 (d, J=2.8 Hz, 1H), 4.42 (s, 2H), 3.48 (t, J=7.6 Hz, 2H), 3.05 (t, J=8.0 Hz, 2H). $^{13}$C NMR (125 MHz, CDCl$_3$) b 139.6, 134.4, 129.0, 128.6, 128.6, 127.1, 125.7, 124.2, 53.2, 50.0, 28.5; IR (neat, cm$^{-1}$): 2126, 1380, 1204, 1167, 905, 727, 698.

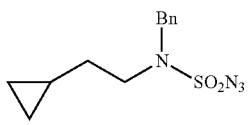

N-Benzyl-2-(cyclopropyl)ethan-1-sulfamoyl azide (1r) was obtained in 75% yield (300 mg) through General Procedure E from N-benzyl-2-cyclopropylethan-1-amine, starting from 1.4 mmol scale. Purified by silica gel column chromatography (eluent: Hexanes/EtOAc 16:1), colorless oil, TLC $R_f$=0.65 (Hexanes/EtOAc 10:1). $^1$H NMR (600 MHz, CDCl$_3$) δ ppm 7.42-7.31 (m, 5H), 4.46 (s, 2H), 3.32-3.28 (m, 2H), 1.45 (dd, J=7.3, 15.2 Hz, 2H), 0.56 (ddd, J=5.1, 7.8, 12.5 Hz, 1H), 0.42 (dt, J=5.1, 5.5 Hz, 2H), 0.03-0.04 (m, 2H); $^{13}$H NMR (150 MHz, CDCl$_3$) δ ppm 134.8, 129.0, 128.7, 128.6, 52.8, 48.8, 32.8, 8.3, 4.5; IR (neat, cm$^{-1}$): 2127, 1383, 1166.

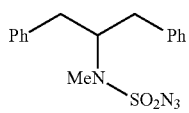

N-Methyl-1,3-diphenylpropan-2-sulfamoyl azide (1s) was obtained in 85% yield (280 mg) through General Procedure E from N-methyl-1,3-diphenylpropan-2-amine starting from 1 mmol scale. Purified by silica gel column chromatography (eluent: Hexanes/EtOAc 16:1), colorless oil TLC $R_f$=0.6 (Hexanes/EtOAc 8:1); $^1$H NMR (500 MHz, CDCl$_3$) δ ppm 7.39-7.31 (m, 4H), 7.30-7.24 (m, 2H), 7.24-7.17 (m, 4H), 4.54-4.40 (m, 1H), 2.95-2.84 (m, 4H), 2.94 (s, 3H); $^{13}$C NMR (125 MHz, CDCl$_3$) δ ppm 137.2, 129.0, 128.7, 127.0, 62.9, 38.1, 30.0; IR (neat, cm$^{-1}$): 2126, 1496, 1454, 1370, 1264, 1201, 1162, 960, 933, 733, 700, 612.

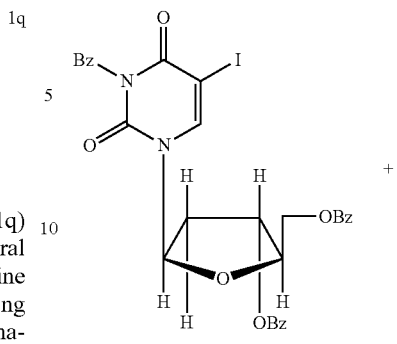

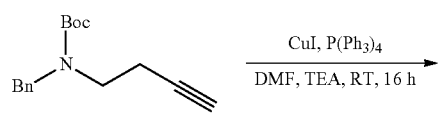

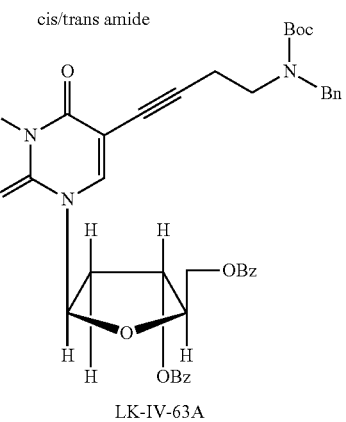

LK-IV-63A

Deoxyuridine-based sulfamoyl azide (1t) was synthesized according to the following procedure. tert-butyl (azidosulfonyl)(but-3-yn-1-yl) carbamate (800 mg, 3.06 mmol), triethylamine (0.42 mL, 3.06 mmol), Pd(PPh$_3$)$_4$ (105 mg, 0.09 mmol) and CuI (35 mg, 0.185 mmol) were added to a solution of 3-N-benzoyl 3',5-di-O-benzoyl-5-iodo-2'-deoxyuridine (1.0 g, 1.53 mmol) in anhydrous DMF (10 mL). The reaction was stirred at room temperature for 24 h. The solution was concentrated in vacuo and the residue was purified by silica gel column chromatography (eluent: Hexanes/EtOAc 7:1) to obtain the product, $R_f$=0.42 (Hexanes/EtOAc 1:1) (812 mg, 68% yield) as yellow solid. $^1$H NMR (500 MHz, CDCl$_3$) δ ppm 8.11-8.01 (m, 4H), 7.92 (d, J=7.8 Hz, 2H), 7.86 (br. s, 1H), 7.70-7.64 (m, 1H), 7.63-7.54 (m, 2H), 7.48 (td, J=7.8, 19.6 Hz, 7H), 7.36-7.29 (m, 2H), 7.26-7.16 (m, 2H), 6.39 (dd, J=5.4, 8.3 Hz, 1H), 5.64 (d, J=6.4 Hz, 1H), 4.85-4.71 (m, 2H), 4.61 (br. s., 1H), 4.54-4.46 (m, 2H), 3.32 (br. s., 1H), 3.23 (br. s., 1H), 2.80 (d, J=11.7 Hz, 1H), 2.46 (d, J=18.1 Hz, 2H), 2.42-2.30 (m, 2H), 1.49 (br. s., 5H), 1.44 (br. s., 4H); HRMS (ESI) Calcd. for $C_{46}H_{43}N_3NaO_{10}^+$ [M+Na]$^+$: 820.2841, Found: 820.2855.

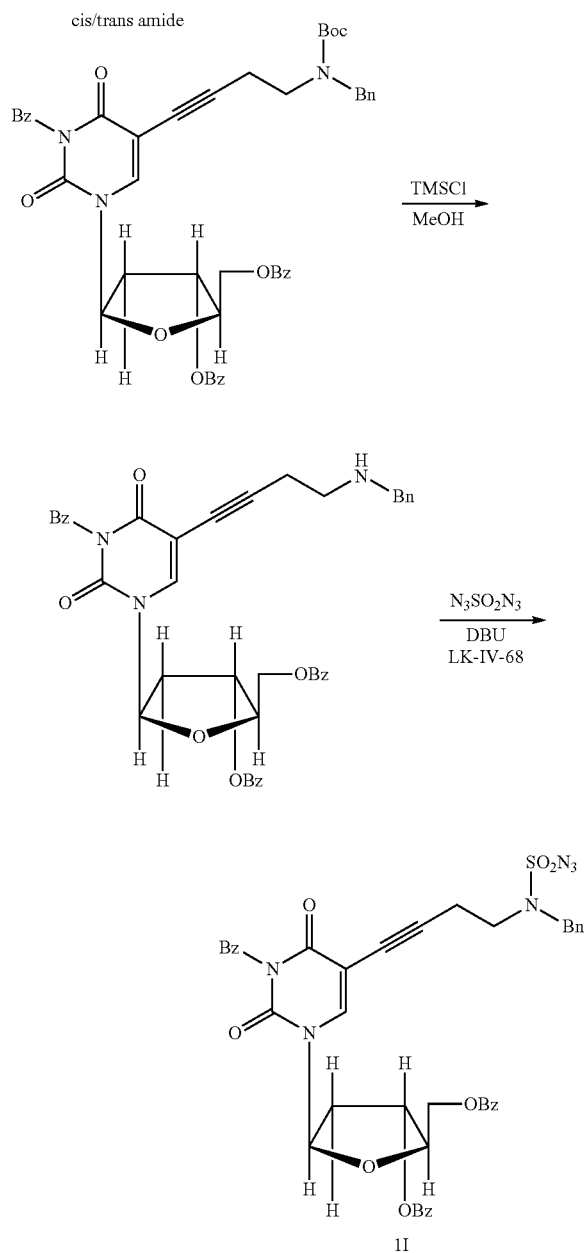

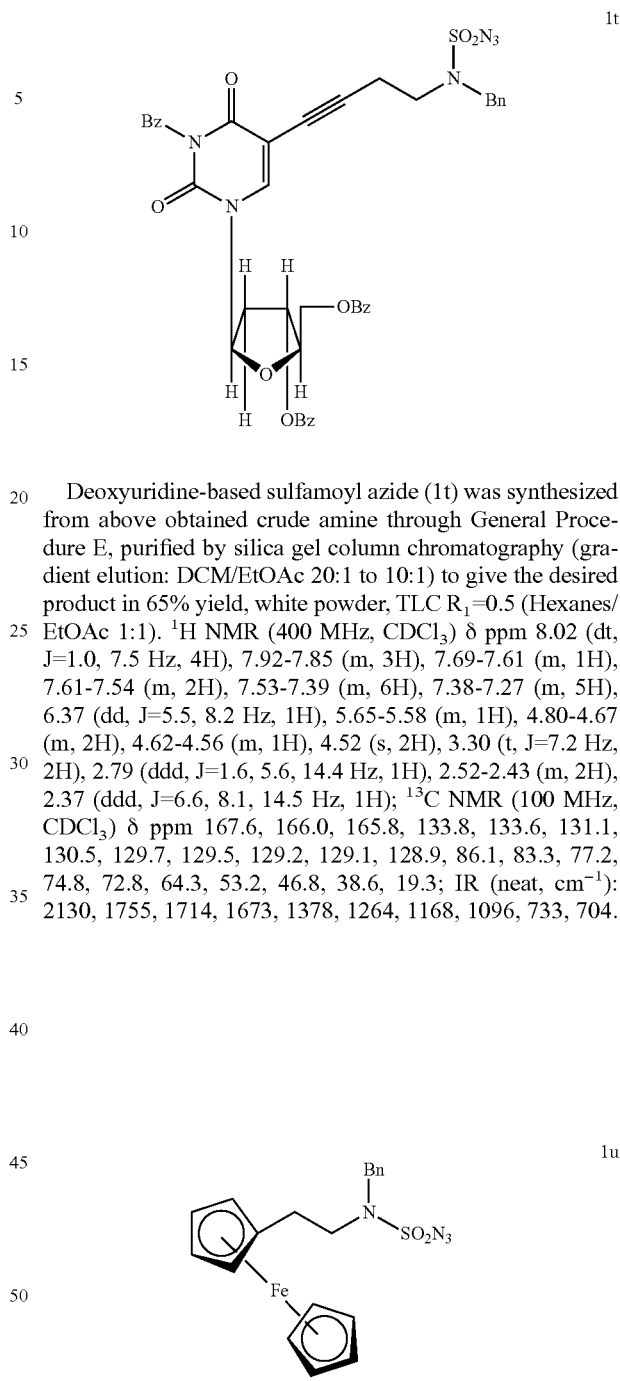

The deprotection of the Boc-substituted substrate was conducted according to the following procedure. The Boc-protected amine (500 mg, 1 mmol) was set to stir in MeOH (10 mL) and DCM (5 mL) in a round-bottom flask and put under a nitrogen atmosphere. The stirring solution was then cooled to 0° C. in an ice bath and then TMSCl (1.26 mL, 10 mmol) was added slowly over the course of 30 minutes. The reaction was allowed to slowly warm to room temperature and left to react for 3 h. After the reaction had completed, all volatiles were removed under reduced pressure. The non-volatile products dissolved in DCM (20 mL), $Et_3N$ (2.0 mL) and brine (20 mL), then extracted with DCM (2×20 mL). The organic extracts were dried over $Na_2SO_4$, filtered, and concentrated under vacuum to give crude amine (350 mg, Yield: about 80%) which was used directly in the next step (Note, this compound is unstable and needs to be converted immediately).

Deoxyuridine-based sulfamoyl azide (1t) was synthesized from above obtained crude amine through General Procedure E, purified by silica gel column chromatography (gradient elution: DCM/EtOAc 20:1 to 10:1) to give the desired product in 65% yield, white powder, TLC $R_1$=0.5 (Hexanes/EtOAc 1:1). $^1$H NMR (400 MHz, $CDCl_3$) δ ppm 8.02 (dt, J=1.0, 7.5 Hz, 4H), 7.92-7.85 (m, 3H), 7.69-7.61 (m, 1H), 7.61-7.54 (m, 2H), 7.53-7.39 (m, 6H), 7.38-7.27 (m, 5H), 6.37 (dd, J=5.5, 8.2 Hz, 1H), 5.65-5.58 (m, 1H), 4.80-4.67 (m, 2H), 4.62-4.56 (m, 1H), 4.52 (s, 2H), 3.30 (t, J=7.2 Hz, 2H), 2.79 (ddd, J=1.6, 5.6, 14.4 Hz, 1H), 2.52-2.43 (m, 2H), 2.37 (ddd, J=6.6, 8.1, 14.5 Hz, 1H); $^{13}$C NMR (100 MHz, $CDCl_3$) δ ppm 167.6, 166.0, 165.8, 133.8, 133.6, 131.1, 130.5, 129.7, 129.5, 129.2, 129.1, 128.9, 86.1, 83.3, 77.2, 74.8, 72.8, 64.3, 53.2, 46.8, 38.6, 19.3; IR (neat, $cm^{-1}$): 2130, 1755, 1714, 1673, 1378, 1264, 1168, 1096, 733, 704.

N-Benzyl-2-(ferrocenyl)ethan-1-sulfamoyl azide (1u) was synthesized from N-benzyl-2-(ferrocenyl)ethan-1-amine (270 mg, 0.85 mmol) through General Procedure E, purified by silica gel column chromatography (gradient elution: Hexanes/EtOAc 20/1) to give the desired product in 94% yield (340 mg) yellow oil, TLC $R_f$=0.65 (Hexanes/EtOAc 8:1). $^1$H NMR (600 MHz, $CDCl_3$) δ ppm 7.43-7.32 (m, 5H), 4.43 (s, 2H), 4.11-4.06 (m, 7H), 4.01 (s, 2H), 3.43-3.32 (m, 2H), 2.62-2.52 (m, 2H); $^{13}$C NMR (150 MHz, $CDCl_3$) δ ppm 134.5, 128.9, 128.6, 128.5, 84.2, 68.7, 68.2, 67.8, 52.9, 49.2, 27.9; IR (neat, cm-1): 2126, 1383, 1208, 1167, 740, 612.

Example 8: General Procedure F (Co(II)-Catalyzed Intramolecular Radical 1,5-C—H Amination)

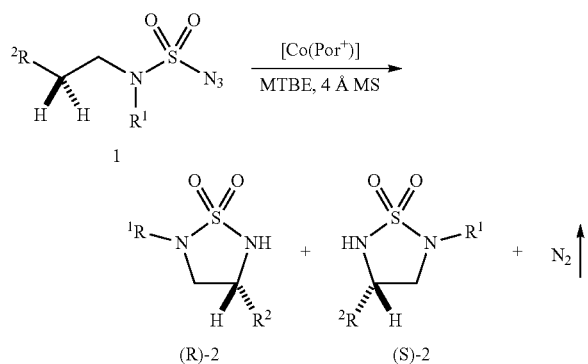

An oven dried Schlenk tube was charged with catalyst (0.002 mmol) or (0.005 mmol) and 4 Å molecular sieves (50 mg). This reaction vessel was evacuated and backfilled with nitrogen several times. The Teflon screw cap was replaced with a rubber septum and the azide substrate (0.1 mmol) was added followed by the addition of 1.0 mL of methyl tert-butyl ether (HPLC plus, residue analysis 99.9% from Aldrich). The Schlenk tube was then purged with nitrogen for 2 minutes and the rubber septum was replaced with a Teflon screw cap. The Schlenk tube was then placed in an oil bath at the indicated temperature while stirring. After the indicated time, the reaction mixture was purified by silica gel column chromatography (Conditions were given previously). The fractions containing product were collected and concentrated by rotary evaporation to obtain the target compound. All the racemic products (for HPLC) were obtained following the same procedure with achiral catalyst [Co(P9)][Co(3,5-Di$^t$Bu-IbuPhyrin)].

Figure 6A:
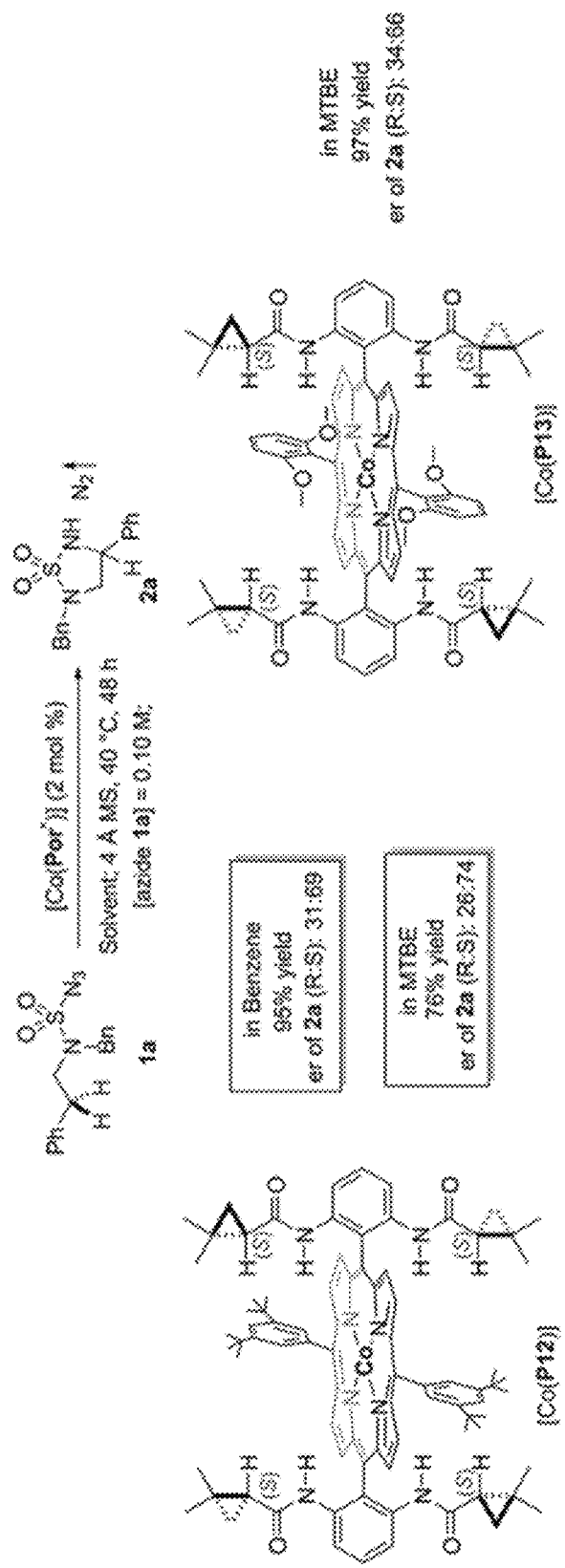
FIGS. 6A-6B show exemplary catalysts and reactions disclosed herein.
Figure 6B:
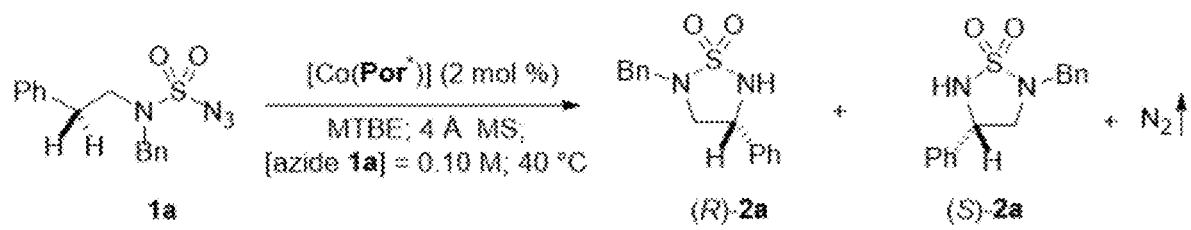
Figure 6B:
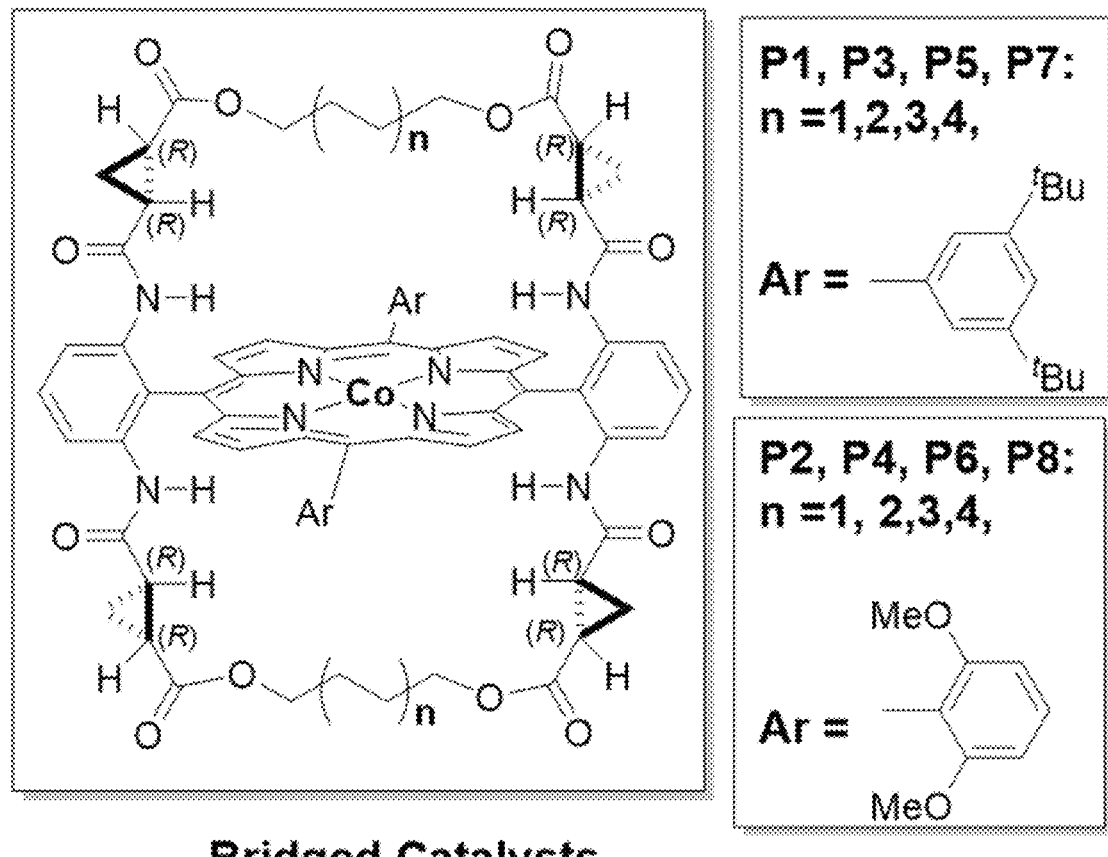

Example 9: Systematic Control of Degree and Sense of Asymmetric Induction for Intramolecular Radical 1,5-C—H Amination of Sulfamoyl Azide 1a Reactions were performed on a 0.1 mmol scale of sulfamoyl azide 1a using 2 mol % of [Co(Por*)] in 1 mL of MTBE at 40° C. Isolated yields and absolute stereochemistries assigned by X-ray crystal structure are shown in Table 1. Enantiomeric ratios (er) were determined by chiral HPLC analysis using an AD-H (amylose tris-(3,5-dimethylphenyl-carbamate)) column. Selected structures and synthetic schemes are presented in FIGS. 6A-B and results are presented in Table 1.

TABLE 1

Systematic Control and Degree and Sense of Asymmetric Induction for Intramolecular Radical 1,5-C—H Amination of sulfamoyl azide 1a by [Co(HuPhyrin)].

| Catalyst | meso-Substituent | Methylene Chain Length | Yield (%) | (R)/(S) | er (R:S) |
|---|---|---|---|---|---|
| [Co(P1)] | 3,5-Di$^t$Bu Phenyl | 4 | 85 | R | 52:48 |
| [Co(P2)] | 2,6-DiMeO Phenyl | 4 | 10 | S | 32:68 |
| [Co(P3)] | 3,5-Di$^t$Bu Phenyl | 6 | 89 | S | 30:70 |

TABLE 1-continued

Systematic Control and Degree and Sense of Asymmetric Induction for Intramolecular Radical 1,5-C—H Amination of sulfamoyl azide 1a by [Co(HuPhyrin)].

| Catalyst | meso-Substituent | Methylene Chain Length | Yield (%) | (R)/(S) | er (R:S) |
|---|---|---|---|---|---|
| [Co(P4)] | 2,6-DiMeO Phenyl | 6 | 68 | S | 6:94 |
| [Co(P5)] | 3,5-Di$^t$Bu Phenyl | 8 | 92 | R | 97:3 |
| [Co(P6)] | 2,6-DiMeO Phenyl | 8 | 76 | R | 62:38 |
| [Co(P7)] | 3,5-Di$^t$Bu Phenyl | 10 | 90 | R | 87:13 |
| [Co(P8)] | 2,6-DiMeO Phenyl | 10 | 95 | S | 36:64 |
| [Co(P10)] | 3,5-Di$^t$Bu Phenyl | Not bridged | 95 | R | 54:46 |
| [Co(P11)] | 2,6-DiMeO Phenyl | Not bridged | 89 | S | 23:77 |

Example 10: Characterization of Sulfamides (2a-2m')

Figure 11:
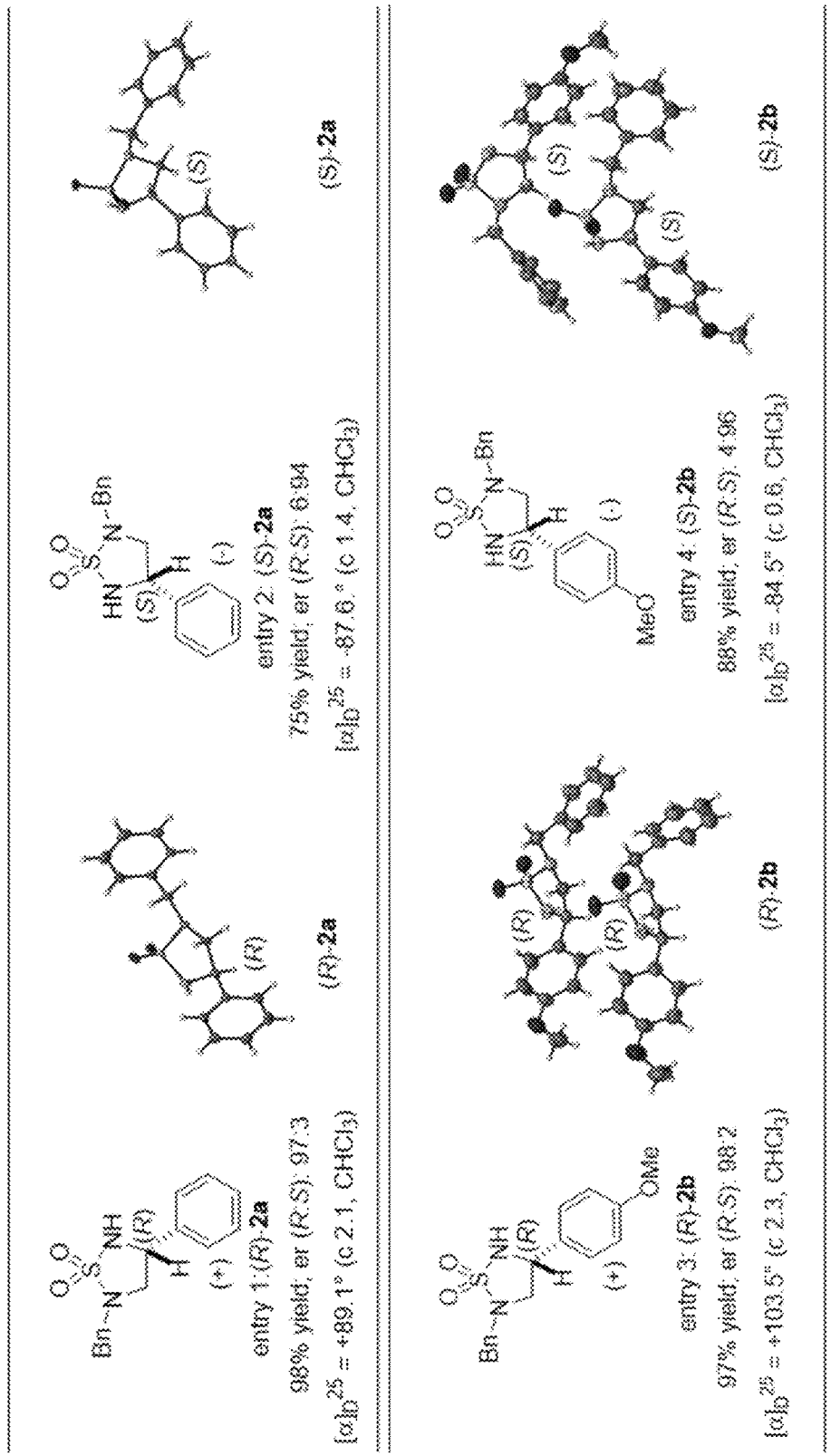
FIG. 11 shows exemplary structures of compounds useful in the disclosed methods confirmed by X-ray structural data.

Three-dimensional structures determined by X-ray crystallography are presented for selected sulfamides in FIG. 11.

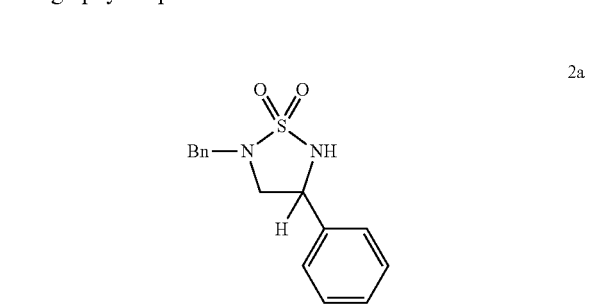

2-Benzyl-4-phenyl-1,2,5-thiadiazolidine 1,1-dioxide (2a) was obtained through General Procedure F. Purified by silica gel column chromatography (eluent: Hexanes/EtOAc 4:1), white solid, TLC $R_f$=0.35 (Hexanes/EtOAc 4:1); For [Co(3,5-Di$^t$Bu-Hu(C$_8$)Phyrin)] ([Co(P5)]), 2 mmol % of catalyst was used (92% yield) and the reaction was run at 40° C. for 48 h; for [Co(2,6-DiMeO-Hu(C$_6$)Phyrin)] ([Co(P4)]), 2 mmol % of catalyst was used and the reaction was run at 40° C. for 48 h (68% yield). $^1$H NMR (400 MHz, CDCl$_3$) δ ppm 7.44-7.26 (m, 10H), 4.85-4.74 (m, 1H), 4.71 (d, J=5.9 Hz, 1H), 4.35, 3.98 (AB q, J=13.3 Hz, each 1H), 3.54 (dd, J=7.2, 9.6 Hz, 1H), 3.11 (dd, J=8.2, 9.4 Hz, 1H); $^{13}$C NMR (125 MHz, CDCl$_3$) δ ppm 138.4, 134.8, 129.0, 128.8, 128.7, 128.2, 126.4, 55.8, 55.1, 50.5; HRMS (ESI) m/z Calcd. for $C_{15}H_{17}N_2O_2S^+$ [M+H]$^+$: 289.1005, Found: 289.0991; IR (neat, cm-1): 1331, 1285, 1153, 1096, 1019, 753, 696, 684; Enantiomeric excess was determined by HPLC with an ADH column (90:10 n-hexane:isopropanol, 0.8 mL/min); R-enantiomer: $t_r$=34.4 min; S-enantiomer: $t_r$=24.7 min; Absolute configurations of both enantiomer products were confirmed by X-ray.

Both reactions were successfully scaled up to 2 mmol without any notable change for enantioselectivities. For [Co(3,5-Di$^t$Bu-Hu(C$_8$)Phyrin)] ([Co(P5)]), 2 mmol % of catalyst was used (98% yield, 97:3 er) and the reaction was run at 40° C. for 48 h; for [Co(2,6-DiMeO-Hu(C$_6$)Phyrin)] ([Co(P4)]), 2 mmol % of catalyst was used and the reaction was run at 40° C. for 48 h (75% yield, 6:94 er).

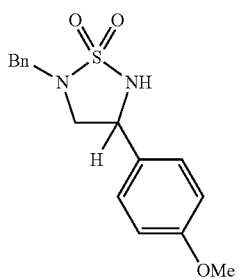

2b

2-Benzyl-4-(4-methoxyphenyl)-1,2,5-thiadiazolidine 1,1-dioxide (2b) was obtained through General Procedure F. Purified by silica gel column chromatography (eluent: Hexanes/EtOAc 4:1), white solid, TLC $R_f$=0.32 (Hexanes/EtOAc 4:1); For [Co(3,5-Di$^t$BuHu-(C$_8$)Phyrin)] ([Co(P5)]), 2 mmol % of catalyst was used (97% yield) for 48 h; for [Co(2,6-DiMeO-Hu(C$_6$)Phyrin)] ([Co(P4)]), 2 mmol % of catalyst was used and the reaction was run at 40° C. for 72 h (88% yield). $^1$H NMR (600 MHz, CDCl$_3$) b 7.39-7.32 (m, 5H), 7.30 (d, J=8.7 Hz, 2H), 6.87 (d, J=8.6 Hz, 2H), 4.74 (dd, J=7.1, 14.5 Hz, 1H), 4.65 (d, J=6.2 Hz, 1H), 4.36, 4.02 (AB q, J=13.6 Hz, each 1H), 3.79 (s, 3H), 3.51 (dd, J=7.1, 9.6 Hz, 1H), 3.16-3.09 (m, 1H); $^{13}$C NMR (150 MHz, CDCl$_3$) δ ppm 160.1, 135.1, 130.4, 128.9, 128.8, 128.3, 127.9, 114.5, 55.7, 55.5, 54.4, 50.6; HRMS (ESI) m/z Calcd. for C$_{16}$H$_{19}$N$_2$O$_3$S$^+$ [M+H]$^+$: 319.1111, Found: 319.1099; IR (neat, cm$^{-1}$): 1613, 1515, 1307, 1264, 1163, 896, 833, 731, 701; Enantiomeric excess was determined by HPLC with an ADH column (90:10 n-hexane:isopropanol, 1.0 mL/min); R-enantiomer: $t_r$=42.0 min; S-enantiomer: $t_r$=25.0 min; Absolute configurations of both enantiomer products were confirmed by X-ray.

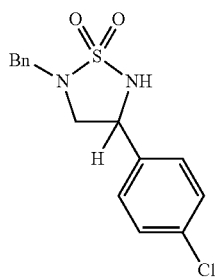

2c

2-Benzyl-4-(4-chlorophenyl)-1,2,5-thiadiazolidine 1,1-dioxide (2c) was obtained through General Procedure F. Purified by silica gel column chromatography (eluent: Hexanes/EtOAc 4:1), white solid, TLC $R_f$=0.3 (Hexanes/EtOAc 4:1); For [Co(3,5-Di$^t$BuHu-(C$_8$)Phyrin)] ([Co(P5)]), 2 mmol % of catalyst was used (98% yield) for 48 h; for [Co(2,6-DiMeO-Hu(C$_6$)Phyrin)] ([Co(P4)]), 5 mmol % of catalyst was used and the reaction was run for 72 h (55% yield). $^1$H NMR (600 MHz, CDCl$_3$) δ ppm 7.38-7.30 (m, 9H), 4.77 (dd, J=7.2, 14.7 Hz, 1H), 4.72 (br. s, 1H), 4.38 3.98 (AB q, J=13.6 Hz, each 1H), 3.56 (dd, J=7.3, 9.7 Hz, 1H), 3.06 (dd, J=8.2, 9.7 Hz, 1H); $^{13}$C NMR (100 MHz, CDCl$_3$) δ ppm 137.0, 134.6, 129.2, 128.8, 128.7, 128.3, 127.8, 55.2, 54.8, 50.5; HRMS (ESI) m/z Calcd. for C$_{15}$H$_{16}$ClN$_2$O$_2$S$^+$ [M+H]$^+$: 323.0616, Found: 323.0595; IR (neat, cm$^{-1}$): 1493, 1455, 1339, 1264, 1153, 1059, 827, 733, 698; Enantiomeric excess was determined by HPLC with an ADH column (90:10 n-hexane:isopropanol, 1.0 mL/min); R-enantiomer: $t_r$=31.2 min; S-enantiomer: $t_r$=19.5 min; Absolute configurations of both enantiomer products were confirmed by X-ray.

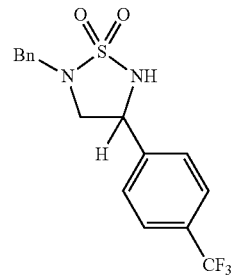

2d

2-Benzyl-4-(4-(trifluoromethyl)phenyl)-1,2,5-thiadiazolidine 1,1-dioxide (2d) was obtained through General Procedure F. Purified by silica gel column chromatography (eluent: Hexanes/EtOAc 4:1), white solid, TLC $R_f$=0.4 (Hexanes/EtOAc 4:1); For [Co(3,5-Di$^t$Bu-Hu(C$_8$)Phyrin)] ([Co(P5)]), 2 mmol % of catalyst was used (98% yield) for 48 h; for [Co(2,6-DiMeO-Hu(C$_6$)Phyrin)] ([Co(P4)]), 5 mmol % of catalyst was used and the reaction was run for 72 h (89% yield). $^1$H NMR (500 MHz, CDCl$_3$) δ ppm 7.63 (d, J=8.1 Hz, 2H), 7.53 (d, J=8.0 Hz, 2H), 7.44-7.30 (m, 5H), 4.97-4.77 (m, 2H), 4.40, 3.96 (AB q, J=13.5 Hz, each 1H), 3.63 (dd, J=5.6, 11.4 Hz, 1H), 3.05 (dd, J=5.8, 11.4 Hz, 1H); $^{13}$C NMR (150 MHz, CDCl$_3$) δ ppm 142.7, 134.7, 131.1 (q, J=33.0 Hz), 129.0, 128.9, 128.5, 126.9, 126.5 (q, J=4.5 Hz), 123.9 (q, J=271.5 Hz), 55.4, 54.8, 50.7; $^{19}$F NMR (470 MHz, CFCl$_3$, CDCl$_3$) δ ppm −63.27 (s, 3F); HRMS (ESI) m/z Calcd. for C$_{16}$H$_{15}$F3N$_2$NaO$_2$S$^+$ [M+Na]$^+$: 379.0699, Found: 379.0721; IR (neat, cm$^{-1}$): 1620, 1496, 1456, 1423, 1400, 1324, 1286, 1153, 1110, 1016, 840, 684, 700, 657; Enantiomeric excess was determined by HPLC with an ADH column (90:10 n-hexane:isopropanol, 1.0 mL/min); R-enantiomer: $t_r$=28.1 min; S-enantiomer: $t_r$=14.5 min; Absolute configurations of the products were determined by analogy.

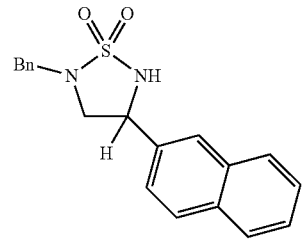

2e

2-Benzyl-4-(naphthalen-2-yl)-1,2,5-thiadiazolidine 1,1-dioxide (2e) was obtained through General Procedure F. Purified by silica gel column chromatography (eluent: Hexanes/EtOAc 4:1), white solid, TLC $R_f$=0.5 (Hexanes/EtOAc 4:1); For [Co(3,5-Di$^t$BuHu-(C$_8$)Phyrin)] ([Co(P5)]), 2 mmol % of catalyst was used (97% yield) for 48 h; for [Co(2,6-DiMeO-Hu(C$_6$)Phyrin)] ([Co(P4)]), mmol % of catalyst was used and the reaction was run at 40° C. for 72 h (53% yield). $^1$H NMR (500 MHz, CDCl$_3$) δ ppm 7.90-7.79 (m, 5H), 7.57-7.47 (m, 2H), 7.43-7.30 (m, 5H), 5.00-4.94 (m, 1H), 4.93-4.88 (m, 1H), 4.42, 4.03 (AB q, J=13.7 Hz, each 1H), 3.64 (dd, J=7.3, 9.8 Hz, 1H), 3.21 (dd, J=8.3, 9.8 Hz, 1H); $^{13}$C NMR (125 MHz, CDCl$_3$) δ ppm 135.6, 134.8, 133.3, 133.0, 129.1, 128.8, 128.7, 128.2, 128.0, 127.7, 126.7, 126.6, 125.7, 123.6, 56.1, 54.9, 50.6; HRMS (ESI) m/z Calcd. for $C_{19}H_{18}N_2NaO_2S^+$ [M+Na]$^+$: 361.0981, Found: 361.0964; IR (neat, cm$^{-1}$): 1724, 1494, 1455, 1378, 1283, 1158, 1122, 1049, 1030, 904, 891, 821, 730, 594; Enantiomeric excess was determined by HPLC with an ADH column (90:10 n-hexane:isopropanol, 1.0 mL/min); R-enantiomer: $t_r$=34.0 min; S-enantiomer: $t_r$=24.0 min; Absolute configurations of the products were determined by analogy.

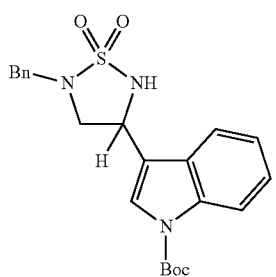

2f tert-butyl 3-(5-benzyl-1,1-dioxido-1,2,5-thiadiazolidin-3-yl)-1H-indole-1-carboxylate (2f) was obtained through General Procedure F. Purified by silica gel column chromatography (eluent: Hexanes/EtOAc 4:1), white solid, TLC $R_f$=0.2 (Hexanes/EtOAc 4:1); For [Co(3,5-Di$^t$Bu-Hu(C$_8$)Phyrin)] ([Co(P5)]), 2 mmol % of catalyst was used (98% yield) for 48 h; for [Co(2,6-DiMeO-Hu(C$_6$)Phyrin)] ([Co(P4)]), 5 mmol % of catalyst was used and the reaction was run at 40° C. for 72 h (92% yield). $^1$H NMR (400 MHz, CDCl$_3$) δ ppm 8.18-8.08 (m, 1H), 7.68 (d, J=7.8 Hz, 1H), 7.58 (s, 1H), 7.42-7.25 (m, 6H), 7.26-7.22 (m, 1H), 5.04 (q, J=7.4 Hz, 1H), 4.67 (d, J=6.6 Hz, 1H), 4.36, 4.11 (AB q, J=13.7 Hz, each 1H), 3.55 (dd, J=7.0, 9.8 Hz, 1H), 3.41 (dd, J=8.2, 9.4 Hz, 1H), 1.64 (s, 9H); $^{13}$C NMR (100 MHz, CDCl$_3$) δ ppm 149.2, 135.8, 134.9, 128.8, 128.7, 128.2, 127.4, 125.2, 124.0, 123.1, 119.2, 117.2, 115.6, 84.4, 53.2, 50.5, 49.5, 28.1; HRMS (ESI) m/z Calcd. for $C_{22}H_{26}N_3O_4S^+$ [M+H]$^+$: 428.1639, Found: 428.1623; IR (neat, cm-1): 1732, 1608, 1571, 1476, 1452, 1368, 1256, 1150, 1093, 732, 697. Enantiomeric excess was determined by HPLC with an ODH column (85:15 n-hexane:isopropanol, 1.0 mL/min); R-enantiomer: $t_r$=25.6 min; S-enantiomer: $t_r$=16.5 min; Absolute configurations of the products were determined by analogy.

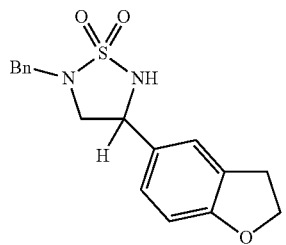

2g

2-Benzyl-4-(2,3-dihydrobenzofuran-5-yl)-1,2,5-thiadiazolidine 1,1-dioxide (2 g) was obtained through General Procedure F. Purified by silica gel column chromatography (eluent: Hexanes/EtOAc 4:1), white solid, TLC $R_f$=0.5 (Hexanes/EtOAc 4:1); For [Co(3,5-Di$^t$Bu-Hu(C$_8$)Phyrin)] ([Co(P5)]), 2 mmol % of catalyst was used (96% yield) for 48 h; for [Co(2,6-DiMeO-Hu(C$_6$)Phyrin)] ([Co(P4)]), 5 mmol % of catalyst was used and the reaction was run for 72 h (71% yield). $^1$H NMR (500 MHz, CDCl$_3$) δ ppm 7.43-7.30 (m, 5H), 7.28 (s, 1H), 7.07 (d, J=8.3 Hz, 1H), 6.73 (d, J=8.3 Hz, 1H), 4.73 (q, J=7.2 Hz, 1H), 4.65 (d, J=6.4 Hz, 1H), 4.58 (t, J=8.6 Hz, 2H), 4.38, 4.02 (AB q, J=13.7 Hz, each 1H), 3.50 (dd, J=7.1, 9.5 Hz, 1H), 3.20 (t, J=8.8 Hz, 2H), 3.12 (dd, J=8.3, 9.8 Hz, 1H); $^{13}$C NMR (125 MHz, CDCl$_3$) δ ppm 160.6, 134.9, 130.2, 128.8, 128.7, 128.2, 126.7, 123.2, 109.4, 71.5, 55.9, 55.3, 50.5, 29.5; HRMS (ESI) m/z Calcd. for $C_{17}H_{19}N_2O_3S^+$ [M+H]$^+$: 331.1111, Found: 331.1135; IR (neat, cm$^{-1}$): 1615, 1493, 1455, 1264, 1162, 731, 697, 597; Enantiomeric excess was determined by HPLC with an ADH column (90:10 n-hexane:isopropanol, 1.0 mL/min); R-enantiomer: $t_r$=43.8 min; S-enantiomer: $t_r$=31.6 min; Absolute configurations of the products were determined by analogy.

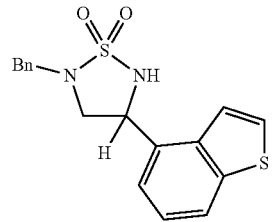

2h

2-Benzyl-4-(benzo[b]thiophen-4-yl)-1,2,5-thiadiazolidine 1,1-dioxide (2h) was obtained through General Procedure F. Purified by silica gel column chromatography (eluent: Hexanes/EtOAc 4:1), white solid, TLC $R_f$=0.5 (Hexanes/EtOAc 3:1); For [Co(3,5-Di$^t$Bu-Hu(C$_8$)Phyrin)] ([Co(P5)]), 2 mmol % of catalyst was used (97% yield) for 48 h; for [Co(2,6-DiMeO-Hu(C$_6$)Phyrin)] ([Co(P4)]), 5 mmol % of catalyst was used and the reaction was run at 40° C. for 72 h (52% yield). $^1$H NMR (500 MHz, acetone-D$_6$) δ ppm 7.95 (d, J=8.1 Hz, 1H), 7.76 (d, J=5.6 Hz, 1H), 7.71 (d, J=5.6 Hz, 1H), 7.66 (d, J=7.4 Hz, 1H), 7.42 (t, J=6.4 Hz, 2H), 7.40-7.39 (m, 1H), 7.36 (t, J=7.3 Hz, 2H), 7.32-7.29 (m, 1H), 6.97 (d, J=6.9 Hz, 1H), 5.47 (dd, J=7.7, 15.1 Hz, 1H), 4.35, 3.98 (AB q, J=13.8 Hz, each 1H), 3.91-3.85 (m, 1H), 3.15 (t, J=9.1 Hz, 1H); $^{13}$C NMR (150 MHz, CDCl$_3$) δ ppm 141.1, 136.8, 134.9, 132.5, 129.0, 128.9, 128.4, 128.0, 124.6, 123.3, 122.5, 120.7, 54.9, 54.2, 50.7; HRMS (ESI) m/z Calcd. for $C_{17}H_{17}N_2O_2S_2^+$ [M+H]$^+$: 345.0726, Found: 345.0726; IR (neat, cm$^{-1}$): 1214, 1164, 750, 668; Enantiomeric excess was determined by HPLC with an ADH column (90:10 n-hexane:isopropanol, 1.0 mL/min); R-enantiomer: $t_r$=32.6 min; S-enantiomer: $t_r$=28.7 min; Absolute configurations of the products were determined by analogy.

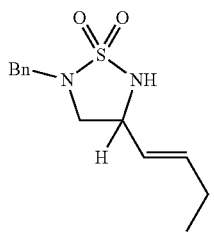

2i (E)-2-Benzyl-4-(but-1-en-1-yl)-1,2,5-thiadiazolidine 1,1-dioxide (2i) was obtained through General Procedure F. Purified by silica gel column chromatography (eluent: Hexanes/EtOAc 4:1), white solid, TLC $R_f$=0.4 (Hexanes/EtOAc 4:1); For [Co(3,5-Di$^t$Bu-Hu(C$_8$)Phyrin)] ([Co(P5)]), 2 mmol % of catalyst was used (93% yield) for 48 h; for [Co(2,6-DiMeO-Hu(C$_6$)Phyrin)] ([Co(P4)]), 5 mmol % of catalyst was used and the reaction was run at 40° C. for 72 h (57% yield). $^1$H NMR (500 MHz, CDCl$_3$) δ ppm 7.45-7.29 (m, 5H), 5.79 (td, J=6.2, 15.5 Hz, 1H), 5.41 (dd, J=7.8, 15.2 Hz, 1H), 4.40 (d, J=5.9 Hz, 1H), 4.28, 4.05 (AB q, J=13.7 Hz, each 1H), 4.19 (quin, J=7.1 Hz, 1H), 3.33 (dd, J=6.8, 9.8 Hz, 1H), 2.99 (dd, J=8.1, 9.5 Hz, 1H), 2.12-1.98 (m, 2H), 0.97 (t, J=7.6 Hz, 3H); $^{13}$C NMR (125 MHz, CDCl$_3$) δ ppm 138.1, 135.1, 128.8, 128.6, 128.1, 125.4, 54.8, 53.4, 50.4, 25.1, 13.0; HRMS (ESI) m/z Calcd. for $C_{13}H_{19}N_2O_2S^+$ [M+H]$^+$: 267.1162, Found: 267.1170; IR (neat, cm$^{-1}$): 1671, 1496, 1455, 1299, 1265, 1163, 1055, 1027, 773, 731, 697; Enantiomeric excess was determined by HPLC with an ADH column (90:10 n-hexane:isopropanol, 0.8 mL/min); R-enantiomer: $t_r$=19.9 min; S-enantiomer: $t_r$=15.9 min; Absolute configurations of the products were determined by analogy.

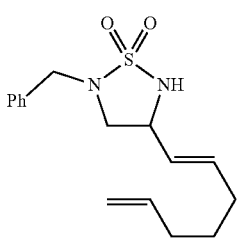

2j (E)-2-Benzyl-4-(hepta-1,6-dien-1-yl)-1,2,5-thiadiazolidine 1,1-dioxide (2j) was obtained through General Procedure F. Purified by silica gel column chromatography (eluent: Hexanes/EtOAc 4:1), white solid, TLC $R_f$=0.4 (Hexanes/EtOAc 4:1); For [Co(3,5-Di$^t$Bu-Hu (C$_8$)Phyrin)] ([Co(P5)]), 2 mmol % of catalyst was used (98% yield) for 48 h; for [Co(2,6-DiMeO-Hu(C$_6$)Phyrin)]([Co(P4)]), 5 mmol % of catalyst was used and the reaction was run at 40° C. for 72 h (58% yield). $^1$H NMR (500 MHz, CDCl$_3$) δ ppm 7.38 (d, J=4.4 Hz, 4H), 7.34 (td, J=3.8, 8.1 Hz, 1H), 5.83-5.70 (m, 2H), 5.44 (dd, J=7.8, 15.2 Hz, 1H), 5.05-4.93 (m, 2H), 4.37 (d, J=6.4 Hz, 1H), 4.29, 4.06 (AB q, J=14.2 Hz, each 1H), 4.24-4.16 (m, 1H), 3.34 (dd, J=6.8, 9.8 Hz, 1H), 2.99 (dd, J=7.8, 9.3 Hz, 1H), 2.13-1.95 (m, 4H), 1.45 (quin, J=7.6 Hz, 2H); $^{13}$C NMR (125 MHz, CDCl$_3$) δ ppm 138.2, 136.2, 135.1, 128.8, 128.6, 128.2, 126.7, 114.9, 54.7, 53.4, 50.4, 33.1, 31.4, 27.9; HRMS (ESI) m/z Calcd. for $C_{16}H_{23}N_2O_2S^+$ [M+H]$^+$: 307.1475, Found: 307.1464; IR (neat, cm$^{-1}$): 1639, 1496, 1455, 1395, 1303, 1266, 1162, 731, 969, 613; Enantiomeric excess was determined by HPLC with an ADH column (95:5 n-hexane:isopropanol, 0.8 mL/min); R-enantiomer: $t_r$=40.2 min; S-enantiomer: $t_r$=30.6 min; Absolute configurations of the products were determined by analogy.

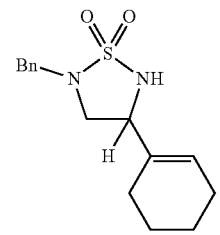

2k

2-Benzyl-4-(cyclohex-1-en-1-yl)-1,2,5-thiadiazolidine 1,1-dioxide (2 k) was obtained through General Procedure F. Purified by silica gel column chromatography (eluent: Hexanes/EtOAc 4:1), white solid, TLC $R_f$=0.4 (Hexanes/EtOAc 4:1); For [Co(3,5-Di$^t$Bu-Hu (C$_8$)Phyrin)] ([Co(P5)]), 2 mmol % of catalyst was used (97% yield) for 48 h; for [Co(2,6-DiMeO-Hu(C$_6$)Phyrin)] ([Co(P4)]), 5 mmol % of catalyst was used and the reaction was run at 40° C. for 72 h (68% yield). $^1$H NMR (500 MHz, CDCl$_3$) δ ppm 7.40-7.36 (m, 4H), 7.36-7.32 (m, 1H), 5.79-5.74 (m, 1H), 4.33, 3.99 (AB q, J=13.7 Hz, each 1H), 4.33-4.32 (m, 1H), 4.17 (q, J=7.5 Hz, 1H), 3.30 (dd, J=7.1, 9.5 Hz, 1H), 3.03 (t, J=8.8 Hz, 1H), 2.11-1.87 (m, 4H), 1.72-1.49 (m, 4H); $^{13}$C NMR (100 MHz, CDCl$_3$) δ ppm 135.1, 133.9, 128.8, 128.6, 128.1, 126.3, 57.8, 51.8, 50.5, 24.9, 23.7, 22.3, 22.1; HRMS (ESI) m/z Calcd. for $C_{15}H_{21}N_2O_2S^+$ [M+H]$^+$: 293.1318, Found: 293.1320; IR (neat, cm$^{-1}$): 1323, 1276, 1152, 909, 755, 698, 684; Enantiomeric excess was determined by HPLC with an ADH column (90:10 n-hexane:isopropanol, 1.0 mL/min); R-enantiomer: $t_r$=17.7 min; S-enantiomer: $t_r$=15.8 min; Absolute configurations of the products were determined by X-ray and analogy.

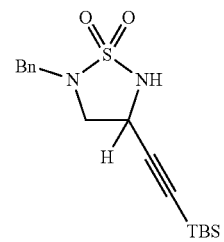

2l

2-Benzyl-4-((tert-butyldimethylsilyl)ethynyl)-1,2,5-thiadiazolidine 1,1-dioxide (2l) was obtained through General Procedure F. Purified by silica gel column chromatography (eluent: Hexanes/EtOAc 4:1), white solid, TLC $R_f$=0.5 (Hexanes/EtOAc 4:1); For [Co(3,5-Di$^t$Bu-Hu(C$_8$)Phyrin)] ([Co(P5)]), 2 mmol % of catalyst was used for 48 h (88% yield); for [Co(2,6-DiMeO-Hu(C$_6$)Phyrin)] ([Co(P4)]), 5 mmol % of catalyst was used and the reaction was run at 40° C. for 72 h (55% yield). $^1$H NMR (400 MHz, CDCl$_3$) δ ppm 7.39-7.27 (m, 5H), 4.50-4.44 (m, 1H), 4.43-4.38 (m, 1H), 4.26-4.14 (m, 2H), 3.43 (dd, J=6.6, 9.8 Hz, 1H), 3.34-3.22 (m, 1H), 0.89 (s, 9H), 0.08 (s, 6H); $^{13}$C NMR (100 MHz, CDCl$_3$) δ ppm 134.8, 128.8, 128.5, 128.2, 100.7, 90.5, 53.8, 50.5, 44.4, 25.9, 16.3, −4.9; HRMS (ESI) m/z Calcd. for $C_{17}H_{27}N_2O_2SSi^+$ [M+H]$^+$: 351.1557, Found: 351.1541; IR (neat, cm$^{-1}$): 1496, 1455, 1471, 1330, 1265, 1168, 839, 824, 810, 777, 733, 698, 622; Enantiomeric excess was determined by HPLC with an ADH column (98:2 n-hexane:isopropanol, 0.8 mL/min); R-enantiomer: t$_r$=46.1 min; S-enantiomer: t$_r$=40.2 min; Absolute configurations of the products were determined by analogy.

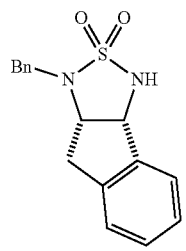

2m

3-Benzyl-3,3a,8,8a-tetrahydro-1H-indeno[1,2-c][1,2,5]thiadiazole 2,2-dioxide (2m) was obtained through General Procedure F. Purified by silica gel column chromatography (eluent: Hexanes/EtOAc 4:1), white solid, TLC R$_f$=0.4 (Hexanes/EtOAc 4:1); For [Co(3,5-Di$^t$Bu-Hu(C$_8$)Phyrin)] ([Co(P5)]), 2 mmol % of catalyst was used (95% yield) for 48 h; for [Co(2,6-DiMeO-Hu(C$_6$)Phyrin)] ([Co(P4)]), 5 mmol % of catalyst was used and the reaction was run for 72 h (79% yield). $^1$H NMR (500 MHz, CDCl$_3$) δ ppm 7.48-7.34 (m, 6H), 7.33-7.25 (m, 2H), 7.14 (d, J=7.3 Hz, 1H), 5.12 (t, J=7.8 Hz, 1H), 4.51 (d, J=14.2 Hz, 1H), 4.35 (d, J=8.3 Hz, 1H), 4.22-4.10 (m, 2H), 3.01-2.89 (m, 1H), 2.88-2.75 (m, 1H); $^{13}$C NMR (125 MHz, CDCl$_3$) δ ppm 141.5, 138.0, 135.1, 130.0, 129.2, 128.8, 128.3, 127.9, 125.5, 125.2, 63.3, 61.0, 50.2, 38.1; HRMS (ESI) m/z Calcd. for $C_{16}H_{17}N_2O_2S^+$ [M+H]$^+$: 301.1005, Found: 301.1001; IR (neat, cm$^{-1}$): 1727, 1496, 1480, 1403, 1321, 1303, 1154, 1029, 786, 738, 701, 620; Enantiomeric excess was determined by HPLC with an ODH column (90:10 n-hexane:isopropanol, 1.0 mL/min); (1R,2S)-enantiomer: t$_r$=27.0 min; (1S,2R)-enantiomer: t$_r$=36.2 min; Absolute configurations of the products were determined by X-ray and analogy.

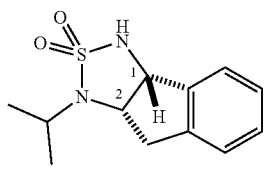

(R, S)-2m'

1-Isopropyl-3,3a,8,8a-tetrahydro-1H-indeno[1,2-c][1,2,5]thiadiazole 2,2-dioxide (2m') was obtained through General Procedure F. Purified by silica gel column chromatography (eluent: Hexanes/EtOAc 4:1), white solid, TLC R$_f$=0.4 (Hexanes/EtOAc 4:1); For [Co(3,5-Di$^t$Bu-Hu(C$_8$)Phyrin)] ([Co(P5)]), 2 mmol % of catalyst was used (61% yield) for 48 h. $^1$H NMR (500 MHz, CDCl$_3$) δ ppm 7.44-7.32 (m, 2H), 7.32-7.21 (m, 2H), 5.08 (t, J=8.1 Hz, 1H), 4.33 (dt, J=5.1, 7.7 Hz, 1H), 4.25 (d, J=8.8 Hz, 1H), 3.77 (td, J=6.6, 13.2 Hz, 1H), 3.42 (dd, J=8.1, 16.9 Hz, 1H), 3.22 (dd, J=5.1, 16.9 Hz, 1H), 1.39 (dd, J=2.2, 6.6 Hz, 6H); $^{13}$C NMR (125 MHz, CDCl$_3$) δ ppm 142.1, 137.6, 130.1, 127.8, 125.6, 125.5, 60.9, 60.2, 48.4, 40.9, 22.2, 20.6; HRMS (ESI) m/z Calcd. for $C_{12}H_{17}N_2O_2S^+$ [M+H]$^+$: 253.1005, Found: 253.1011; IR (neat, cm$^{-1}$): 1627, 1483, 1461, 1391, 1325, 1285, 1175, 1144, 1046, 874, 1017, 751; Enantiomeric excess was determined by HPLC with an ODH column (90:10 n-hexane:isopropanol, 1.0 mL/min); R-enantiomer: t$_r$=29.0 min; S-enantiomer: t$_r$=18.2 min; Absolute configurations of the products were determined by analogy.

Example 11: Ligand Effect on Co(II)-Catalyzed Selective Formation of 5-Membered Ring Structures (Open vs. Bridged Catalysts)

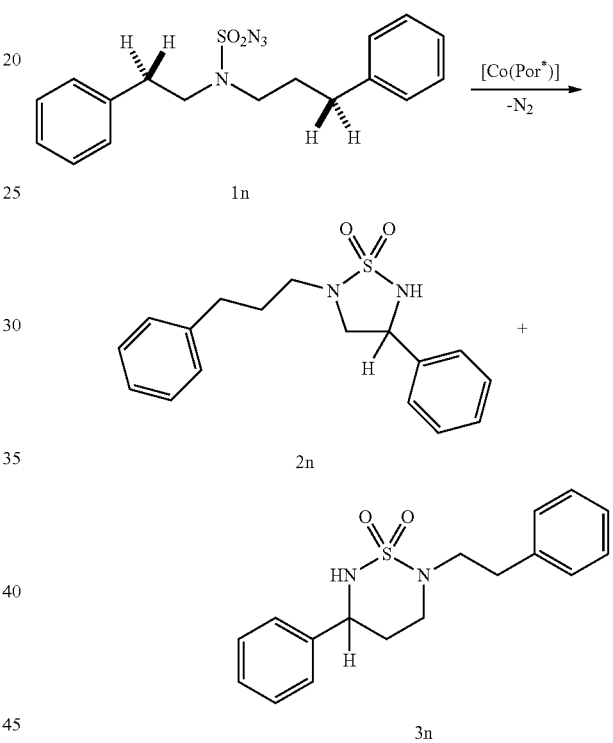

The reaction shown above was performed at room temperature with 5 mol % [Co(Por*)]. Absolute configuration was determined by analogy. Results are given in Table 2 and structures of catalysts are pictured below.

TABLE 2

Ligand Effect on Co(II)-Catalyzed Selective Formation of 5-Membered Ring Structures.

| Catalyst | 2n:3n (1,5/1,6) | er of 2n (R:S) | Er of 3n | Yield (%) |
|---|---|---|---|---|
| [Co(P4)] | >98:2 | 8:92 | ND | 65 |
| [Co(P5)] | >96:4 | 87:13 | ND | 94 |
| [Co(P10)] | 74:26 | 44:56 | 59:41 | 94 |
| [Co(P11)] | 81:19 | 22:78 | 23:77 | 90 |
| [Co(P9)] | 70:30 | — | — | 98 |

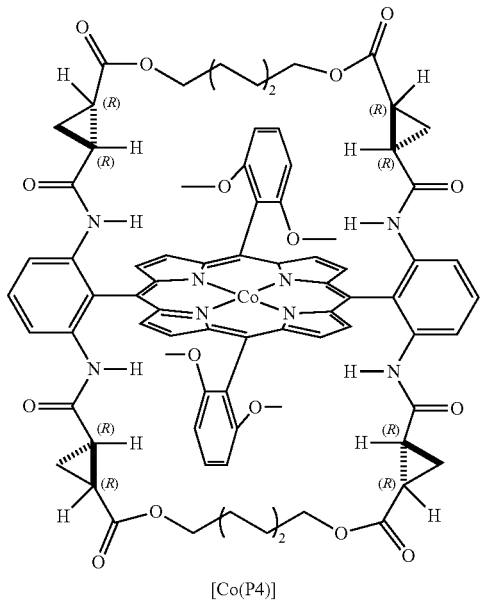
[Co(P4)]
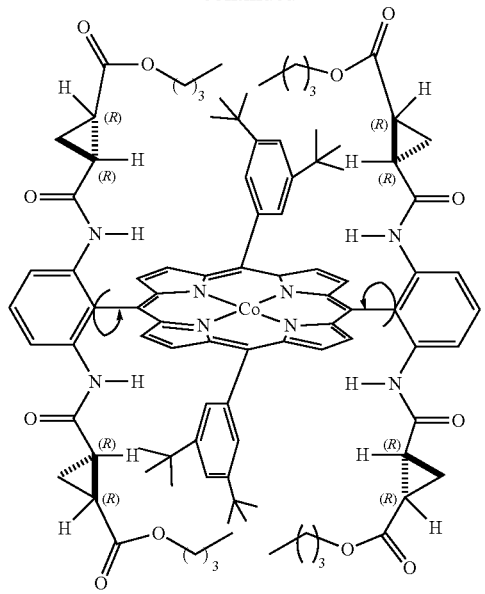
[Co(P10)]
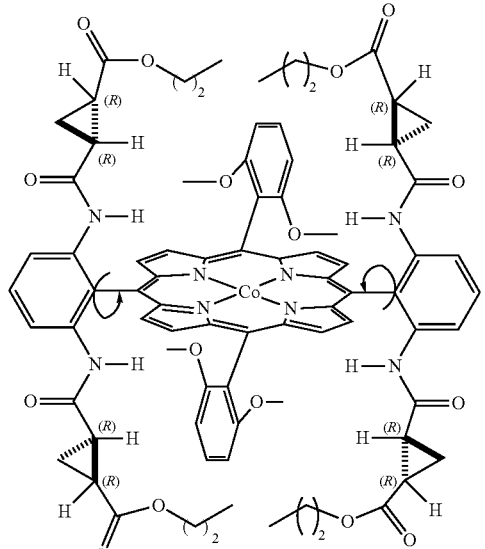
[Co(P11)]
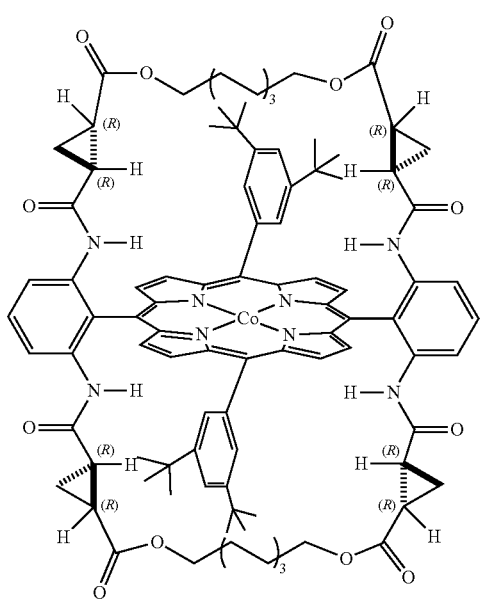
[Co(P5)]
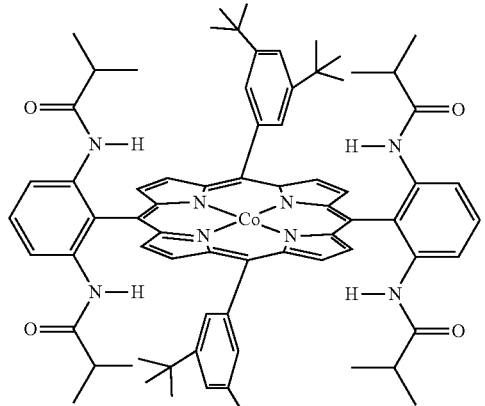
[Co(P9)]

Example 12: Characterization of Sulfamides (2n-2u)

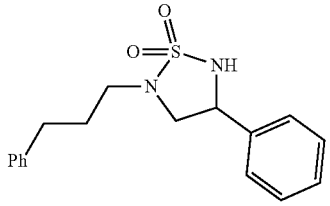

2n

4-Phenyl-2-(3-phenylpropyl)-1,2,5-thiadiazolidine 1,1-dioxide (2n) was obtained through General Procedure F. Purified by silica gel column chromatography (eluent: Hexanes/EtOAc 4:1), white solid, TLC Rf=0.3 (Hexanes/EtOAc 4:1); For [Co(3,5-Di$^t$Bu-Hu (C$_8$)Phyrin)] ([Co(P5)]), 5 mmol % of catalyst was used for 48 h (94% yield); for [Co(2,6-DiMeO-Hu(C$_6$)Phyrin)] ([Co(P4)]), mmol % of catalyst was used and the reaction was run for 72 h (65% yield). $^1$H NMR (500 MHz, CDCl$_3$) δ ppm 7.48-7.34 (m, 5H), 7.33-7.28 (m, 2H), 7.24-7.17 (m, 3H), 4.88-4.77 (m, 1H), 4.61 (d, J=5.4 Hz, 1H), 3.71 (dd, J=6.8, 9.3 Hz, 1H), 3.22 (dd, J=8.3, 9.3 Hz, 1H), 3.16 (td, J=7.3, 12.7 Hz, 1H), 2.99 (td, J=7.1, 12.7 Hz, 1H), 2.74 (t, J=7.6 Hz, 2H), 1.99 (q, J=7.3 Hz, 2H); $^{13}$C NMR (100 MHz, CDCl$_3$) δ ppm 141.0, 138.5, 129.1, 128.8, 128.5, 128.4, 126.4, 126.1, 56.0, 55.8, 46.3, 32.9, 29.3; HRMS (ESI) m/z Calcd. for C$_{17}$H$_{21}$N$_2$O$_2$S$^+$ [M+H]$^+$: 317.1318, Found: 317.1330; IR (neat, cm$^{-1}$): 1602, 1496, 1454, 1286, 1265, 1155, 1028, 733, 698; Enantiomeric excess was determined by HPLC with an ODH column (90:10 n-hexane:isopropanol, 1.0 mL/min); R-enantiomer: t$_r$=63.0 min; S-enantiomer: t$_r$=97.1 min; Absolute configurations of product were determined by analogy.

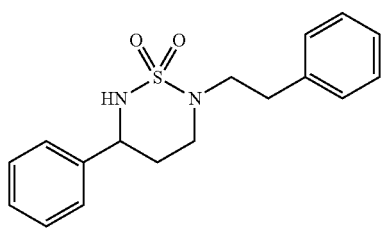

3n

2-Phenethyl-5-phenyl-1,2,6-thiadiazinane 1,1-dioxide (3n) was obtained through General Procedure F together with 2n-a using [Co(3,5-Di$^t$Bu-(nBu)TaoPhyrin)] ([Co(P10)]) (5 mol %) for 48 h and [Co(2,6-DiMeO-(nPr)TaoPhyrin)] ([Co(P11)]) (5 mol %) for 72 h. Purified by silica gel column chromatography (eluent: Hexanes/EtOAc 4:1), white solid, TLC R$_f$=0.5 (Hexanes/EtOAc 4:1). $^1$H NMR (400 MHz, CDCl$_3$) δ ppm 7.43-7.25 (m, 7H), 7.23-7.18 (m, 3H), 4.77-4.65 (m, 1H), 4.05 (d, J=7.4 Hz, 1H), 3.69 (dt, J=3.1, 13.3 Hz, 1H), 3.47-3.32 (m, 2H), 3.31-3.18 (m, 1H), 3.02-2.85 (m, 2H), 2.05-1.88 (m, 1H), 1.87-1.77 (m, 1H); $^{13}$C NMR (125 MHz, CDCl$_3$) δ ppm 139.3, 138.5, 129.0, 128.8, 128.6, 126.6, 126.3, 59.7, 50.8, 49.6, 35.1, 29.5; HRMS (ESI) m/z Calcd. for C$_{17}$H$_{21}$N$_2$O$_2$S$^+$ [M+H]$^+$: 317.1318, Found: 317.1331; IR (neat, cm$^{-1}$): 1728, 1603, 1495, 1456, 1425, 1324, 1295, 1145, 1026, 950, 774, 744, 694; Enantiomeric excess was determined by HPLC with an ODH column (90:10 n-hexane:isopropanol, 1.0 mL/min); enantiomer A: t$_r$=28.5 min; enantiomer: B t$_r$=33.7 min.

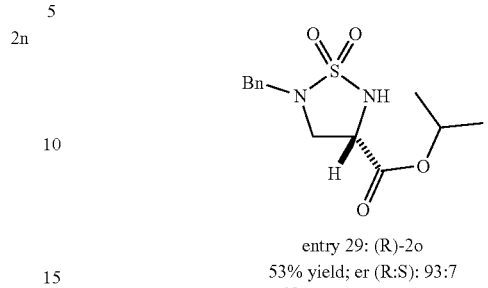

entry 29: (R)-2o
53% yield; er (R:S): 93:7
[α]$_D^{25}$ = -13.9° (c 0.9, CHCl$_3$)

Isopropyl (S)-5-benzyl-1,2,5-thiadiazolidine-3-carboxylate 1,1-dioxide ((R)-2o) was obtained through General Procedure F. Purified by silica gel column chromatography (eluent: Hexanes/EtOAc 4:1), white solid, TLC Rf=0.3 (Hexanes/EtOAc 3:1) with [Co(3,5-Di$^t$Bu-Hu(C$_8$)Phyrin)] ([Co(P5)]). 5 mmol % of catalyst was used and the reaction was run at 40° C. for 72 h (53% yield, er (R:S)=93:7). For [Co(2,6-DiMeO-Hu(C$_6$) Phyrin)] ([Co(P4)]), 5 mmol % of catalyst was used at 40° C. for 72 h (<10% yield). $^1$H NMR (500 MHz, CDCl$_3$) δ ppm 7.41-7.31 (m, 5H), 5.20 (br. s., 1H), 5.12 (td, J=6.4, 12.7 Hz, 1H), 4.33, 3.97 (AB q, J=13.7 Hz, each 1H), 4.13 (br. s., 1H), 3.48-3.38 (m, 2H), 1.27 (dd, J=1.0, 6.4 Hz, 3H), 1.21 (dd, J=1.0, 6.4 Hz, 3H); $^{13}$C NMR (125 MHz, CDCl$_3$) δ ppm 169.3, 134.6, 128.8, 128.4, 128.3, 71.3, 52.9, 50.2, 49.7, 21.6, 21.5; HRMS (ESI) m/z Calcd. for C$_{13}$H$_{18}$N$_2$NaO$_4$S$^+$ [M+Na]$^+$: 321.0879, Found: 321.0856; IR (neat, cm$^{-1}$): 1736, 1455, 1332, 1264, 1170, 1102, 896, 732, 702; Enantiomeric excess was determined by HPLC with an ODH column (97:3 n-hexane:isopropanol, 1.0 mL/min); R-enantiomer: t$_r$=94.7 min; S-enantiomer: t$_r$=80.8 min; Absolute configurations of product were determined by analogy.

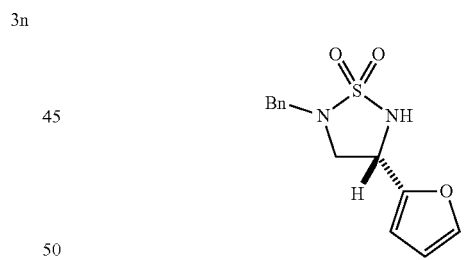

entry 30: (R)-2p
94% yield; er (R:S): 98:2
[α]$_D^{25}$ = +103.5° (c 2.0, CHCl$_3$)

(R)-2-Benzyl-4-(furan-2-yl)-1,2,5-thiadiazolidine 1,1-dioxide ((R)-2p) was obtained through General Procedure F. Purified by silica gel column chromatography (eluent: Hexanes/EtOAc 4:1), white solid, TLC R$_f$=0.3 (Hexanes/EtOAc 4:1) with [Co(3,5-Di$^t$Bu-Hu(C$_8$)Phyrin)] ([Co(P5)]). 2 mmol % of catalyst was used for 48 h (94% yield, er (R:S)=98:2). For [Co(2,6-DiMeO-Hu(C$_6$) Phyrin)] ([Co(P4)]), 5 mmol % of catalyst was used at 40° C. for 72 h (<10% yield). $^1$H NMR (500 MHz, CDCl$_3$) δ ppm 7.55-7.30 (m, 6H), 6.45-6.31 (m, 2H), 4.86 (q, J=7.3 Hz, 1H), 4.76 (d, J=6.4 Hz, 1H), 4.34, 4.14 (AB q, J=13.7 Hz, each 1H), 3.59-3.48 (m, 1H), 3.46-3.33 (m, 1H); $^{13}$C NMR (125 MHz, CDCl₃) b 150.0, 143.2, 134.9, 128.8, 128.6, 128.2, 110.7, 108.5, 52.1, 50.5, 49.7; IR (neat, cm-1): 1332, 1304, 1265, 1166, 731, 699; HRMS (ESI) m/z Calcd. for $C_{13}H_{14}N_2NaO_3S$ [M+Na]⁺: 301.0623, Found: 301.0610; Enantiomeric excess was determined by HPLC with an ADH column (90:10 n-hexane:isopropanol, 1.0 mL/min); R-enantiomer: $t_r$=20.7 min; S-enantiomer: $t_r$=26.5 min; Absolute configurations of product were determined by analogy.

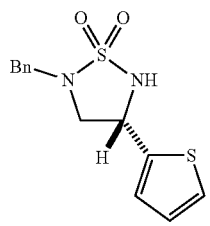

entry 31: (R)-2q
95% yield; er (R:S): 97:3
$[\alpha]_D^{24}$ = +98.4° (c 2.6, CHCl₃)

(R)-2-Benzyl-4-(thiophen-2-yl)-1,2,5-thiadiazolidine 1,1-dioxide ((R)-2q) was obtained through General Procedure F. Purified by silica gel column chromatography (eluent: Hexanes/EtOAc 4:1), white solid, TLC $R_f$=0.25 (Hexanes/EtOAc 4:1) with [Co(3,5-Di$^t$Bu-Hu(C₈)Phyrin)] ([Co(P5)]). 2 mmol % of catalyst was used for 48 h (95% yield, er (R:S)=97:3). For [Co(2,6-DiMeO-Hu(C₆) Phyrin)] ([Co(P4)]), 5 mmol % of catalyst was used at 40° C. for 72 h (<10% yield). ¹H NMR (500 MHz, CDCl₃) δ ppm 7.40-7.29 (m, 5H), 7.29 (d, J=5.0 Hz, 1H), 7.05 (d, J=3.5 Hz, 1H), 6.97-6.95 (m, 1H), 5.06 (q, J=7.0 Hz, 1H), 4.78 (d, J=5.5 Hz, 1H), 4.32, 4.13 (AB q, J=14.0 Hz, each 1H), 3.58 (dd, J=7.0, 10.0 Hz, 1H), 3.30 (dd, J=7.5, 10.0 Hz, 1H); ¹³C NMR (125 MHz, CDCl₃) δ ppm 141.2, 134.8, 128.8, 128.7, 128.3, 127.1, 126.3, 126.0, 55.1, 51.9, 50.4; IR (neat, cm⁻¹): 1455, 1387, 1367, 1300, 1285, 1265, 1155, 1126, 1017, 727; HRMS (ESI) m/z Calcd. For $C_{13}H_{15}N_2O_2S_2$ [M+H]⁺: 295.0575, Found: 295.0570; Enantiomeric excess was determined by HPLC with an ODH column (90:10 n-hexane:isopropanol, 1.0 mL/min); R-enantiomer: $t_r$=33.3 min; S-enantiomer: $t_r$=45.6 min; Absolute configurations of product were determined by analogy.

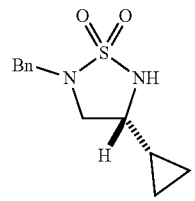

entry 32: (R)-2r
95% yield; er (R:S): 93:7
$[\alpha]_D^{24}$ = +15.0° (c 2.0, CHCl₃)

(R)-2-Benzyl-4-cyclopropyl-1,2,5-thiadiazolidine 1,1-dioxide ((R)-2r) was obtained through General Procedure F. Purified by silica gel column chromatography (eluent: Hexanes/EtOAc 4:1), colorless oil, TLC $R_f$=0.30 (Hexanes/EtOAc 3:1) with [Co(3,5-Di$^t$Bu-Hu(C₈)Phyrin)] ([Co(P5)]). 5 mmol % of catalyst was used for 48 h (95% yield, er (R:S)=93:7). For [Co(2,6-DiMeO-Hu(C₆) Phyrin)] ([Co(P4)]), 5 mmol % of catalyst was used at 40° C. for 72 h (98% yield, er (R:S)=58:42). ¹H NMR (500 MHz, CDCl₃) δ ppm 7.39-7.30 (m, 5H), 4.57 (d, J=3.8 Hz, 1H), 4.23, 4.09 (AB q, J=13.7 Hz, each 1H), 3.37-3.28 (m, 1H), 3.13-3.03 (m, 2H), 1.07-0.97 (m, 1H), 0.63-0.55 (m, 1H), 0.56-0.48 (m, 1H), 0.36 (td, J=4.9, 10.0 Hz, 1H), 0.24-0.17 (m, 1H); ¹³C NMR (125 MHz, CDCl₃) δ ppm 135.3, 128.9, 128.7, 128.3, 57.4, 53.2, 50.5, 14.7, 3.1, 2.5; IR (neat, cm⁻¹): 3247, 1289, 1165; HRMS (ESI) m/z Calcd. For $C_{12}H_{17}N_2O_2S$ [M+H]⁺: 253.1005, Found: 253.1002; Enantiomeric excess was determined by HPLC with an ODH column (90:10 n-hexane:isopropanol, 1.0 mL/min); R-enantiomer: $t_r$=70.9 min; S-enantiomer: $t_r$=76.1 min; Absolute configurations of product were determined by analogy.

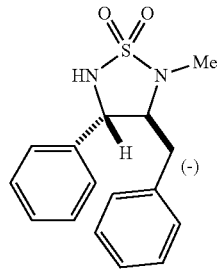

entry 33:(S,S)-2s
80% yield; er (1R,2R;1S,2S): 7:93
$[\alpha]_D^{24}$ = -17.8° (c 0.6, CHCl₃)

(3S,4S)-3-Benzyl-2-methyl-4-phenyl-1,2,5-thiadiazolidine 1,1-dioxide ((S,S)-2s) was obtained through General Procedure F. Purified by silica gel column chromatography (eluent: Hexanes/EtOAc 4:1), white solid, TLC $R_f$=0.35 (Hexanes/EtOAc 4:1) with [Co(2,6-DiMeO-Hu(C₆) Phyrin)] ([Co(P4)]), (2 mol %) at 40° C. for 72 h (80% yield, er (1R,2R:1 S,2S)=7:93). For [Co(3,5-Di$^t$Bu-Hu (C₈)Phyrin)] ([Co(P5)]), 2 mmol % of catalyst was used for 72 h (98% yield, er (1R,2R:1S,2S)=58:42). ¹H NMR (500 MHz, CDCl₃) δ ppm 7.56-7.21 (m, 8H), 7.20-7.09 (m, 2H), 4.64 (d, J=6.4 Hz, 1H), 4.44 (t, J=7.1 Hz, 1H), 3.55 (ddd, J=4.9, 6.4, 7.3 Hz, 1H), 3.14-3.03 (m, 1H), 3.00-2.93 (m, 1H), 2.69 (s, 3H); ¹³C NMR (125 MHz, CDCl₃) δ ppm 138.2, 135.9, 129.6, 128.9, 128.7, 127.2, 127.1, 69.8, 60.5, 36.9, 32.8; IR (neat, cm-1):1603, 1495, 1454, 1298, 1266, 1153, 1028, 750, 735, 698; HRMS (ESI) m/z Calcd. for $C_{16}H_{19}N_2O_2S^+$ [M+H]⁺: 303.1162, Found: 303.1148; Enantiomeric excess was determined by HPLC with an ODH column (90:10 n-hexane:isopropanol, 1.0 mL/min); (1R,2R)-enantiomer: $t_r$=27.7 min; (1S,2S)-enantiomer: $t_r$=35.6 min; Absolute configurations of product were determined by analogy.

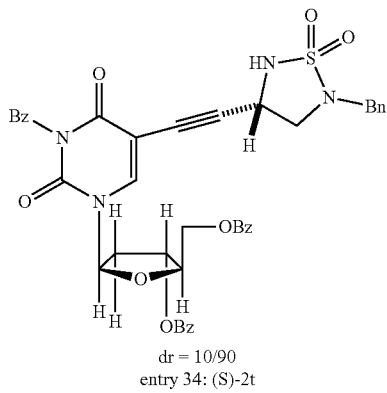

dr = 10/90
entry 34: (S)-2t

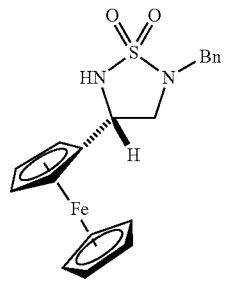

entry 35: (S)-2u
41% yield; er (R:S): 9:91
$[\alpha]_D^{25}$ = -27.4° (c 0.3, CHCl$_3$)

Product ((S)-2t) was obtained through General Procedure F. Purified by silica gel column chromatography (eluent: Hexanes/EtOAc 2:1), white solid, TLC R$_f$=0.45 (Hexanes/EtOAc 1:1) with [Co(2,6-DiMeO-Hu(C$_6$)Phyrin)] ([Co (P4)]), (2 mol %) for 96 h (88% yield, dr=10:90). For [Co(3,5-Di$^t$Bu-Hu (C$_8$)Phyrin)] ([Co(P5)]), 2 mmol % of catalyst was used for 72 h (82% yield, dr=60:40). $^1$H NMR (500 MHz, CDCl$_3$) δ ppm 8.09-8.01 (m, 4H), 7.99 (s, 1H), 7.90 (d, J=8.3 Hz, 2H), 7.72-7.65 (m, 1H), 7.64-7.56 (m, 2H), 7.55-7.44 (m, 6H), 7.40-7.30 (m, 5H), 6.36 (dd, J=5.9, 7.8 Hz, 1H), 5.64 (d, J=6.4 Hz, 1H), 4.83-4.74 (m, 2H), 4.70 (d, J=6.4 Hz, 1H), 4.64 (d, J=1.5 Hz, 1H), 4.45 (q, J=6.5 Hz, 1H), 4.27 (d, J=14.2 Hz, 1H), 4.11 (d, J=13.7 Hz, 1H), 3.38 (dd, J=7.6, 9.5 Hz, 1H), 3.27-3.22 (m, 1H), 2.86 (dd, J=5.4, 14.2 Hz, 1H), 2.39 (td, J=7.3, 14.3 Hz, 1H); $^{13}$C NMR (125 MHz, CDCl$_3$) δ ppm 167.4, 166.0, 165.8, 160.1, 148.0, 142.5, 135.4, 134.7, 133.8, 133.7, 130.9, 130.5, 129.7, 129.6, 129.2, 129.1, 128.8, 128.6, 128.2, 99.1, 89.3, 86.5, 83.4, 76.5, 74.7, 64.2, 53.4, 50.6, 44.1, 38.6; The diastereomeric ratio was determined by both 1H NMR and 13C NMR spectroscopic integration; IR (neat, cm$^{-1}$): 1754, 1712, 1671, 1450, 1315, 1266, 1167, 1095, 1070, 907, 727, 712; HRMS (ESI) m/z Calcd. For O$_{41}$H$_{34}$N$_4$NaO$_{10}$S$^+$[M+Na]$^+$: 797.1888, Found: 797.1842.

(S)-2-Benzyl-4-(ferrocenyl)-1,2,5-thiadiazolidine 1,1-dioxide ((S)-2u) was obtained through General Procedure F. Purified by silica gel column chromatography (eluent: Hexanes/EtOAc 4:1), yellow solid, TLC R$_f$=0.35 (Hexanes/EtOAc 4:1) with [Co(2,6-DiMeO-Hu(C$_6$)Phyrin)] ([Co (P4)]), (5 mol %) at 40° C. for 72 h (41% yield). For [Co(3,5-Di$^t$Bu-Hu (C$_8$)Phyrin)] ([Co(P5)]), 2 mmol % of catalyst was used for 48 h (73% yield, er (R:S)=58:42). 1H NMR (500 MHz, acetone-D$_6$) δ ppm 7.49-7.43 (m, 2H), 7.41-7.36 (m, 2H), 7.34 (d, J=6.8 Hz, 1H), 6.38-6.29 (m, 1H), 4.67-4.63 (m, 1H), 4.32-4.29 (m, 1H), 4.26-4.23 (m, 1H), 4.23, 4.07 (AB q, J=15.0 Hz, each 1H), 4.18 (s, 5H), 4.17-4.15 (m, 2H), 3.62 (dd, J=7.3, 9.8 Hz, 1H), 3.21 (dd, J=8.1, 9.5 Hz, 1H); $^{13}$C NMR (150 MHz, acetone-D$_6$) 127.3, 119.6, 118.8, 78.4, 59.6, 59.3, 59.0, 58.1, 57.4, 45.6, 42.5, 41.4; IR (neat, cm$^{-1}$): 3263, 2921, 2852, 1709, 1576, 1317, 774; HRMS (DART) m/z Calcd. for C$_{19}$H$_{21}$FeN$_2$O$_2$S$^+$ [M+H]$^+$: 397.0668, Found: 397.0679; Enantiomeric excess was determined by HPLC with an ADH column (90:10 n-hexane:isopropanol, 1.0 mL/min); S-enantiomer: t$_1$=42.0 min; R-enantiomer: t$_1$=56.8 min; Absolute configurations of product were determined by analogy.

Example 13: Kinetic Isotope Effects on Catalytic C—H Amination of Enantiopure Isotopomeric Azides Via Co(II)-Based MRC A reaction pathway is shown in FIG. 1. Reactions were performed on a 0.10 mmol scale of sulfamoyl azide (R)-1a$_D$ or (S)-1a$_D$ using 2 mol % of [Co(Por)] in 1 mL of MTBE at 40° C. Catalyst structures are depicted previously. Results are presented in Table 3 below.

TABLE 3

Kinetic Isotope Effects on Catalytic C—H Amination of Enantiopure Isotopomeric Azides via Co(II)-Based MRC.

| Azide | Catalyst | KIE[b] | Re:Si of IIa[c] | ee %[cal, d] | ee %[exp, e] | Yield (%)[a] |
|---|---|---|---|---|---|---|
| (S)-1a$_D$ | [Co(P9)] (achiral) | 23.0 | 96:4 | 92 (R) | 4 (R) | 80 |
| (S)-1a$_D$ | [Co(P4)][f] | 2.0 | 67:33 | 34 (R) | -4 (S) | 64 |
| (S)-1a$_D$ | [Co(P5)] | 96.0 | 99:1 | 98 (R) | 94 (R) | 98 |
| (R)-1a$_D$ | [Co(P9)] (achiral) | 23.0 | 4:96 | -92 (S) | -4 (S) | 85 |
| (R)-1a$_D$ | [Co(P4)]f | 61.0 | 2:98 | -96 (S) | -94 (S) | 80 |
| (R)-1a$_D$ | [Co(P5)] | 0.8 | 57:43 | 14 (R) | 32 (R) | 98 |

[a]Isolated yield.
[b]Ratio of H:D determined by $^1$H-NMR spectroscopy.
[c]Calculated based on the ratio of H:D.
[d]Calculated on the basis of stereoretentive RS.
[e]Determined by chiral HPLC analysis, which offered no separation of (R)-2a$_H$ from (R)-2a$_D$ and (S)-2a$_H$ from (S)-2a$_D$.
[f]5 mol % [Co(P4)].

There was an overlap of N—H proton and chiral benzylic proton for H- vs. D-derivative analysis. This issue was solved by simply adding one drop of D$_2$O to the CDCl$_3$ solution for NH proton exchange. The complete disappearance of NH proton allowed accurate integration (500 MHz machine with cryogenically cooled probe) of benzylic proton and calculation of the ratios of H:D.

For bridged catalysts [Co(P4)] and [Co(P5)], HAA is highly enantioselective, radical substitution is stereoretentive due to either the stereochemistry retention of facial chirality through cavity-like ligand environments or the cavity-favored rapid radical substitution before the rotation/racemization occurs, or the combined effects.

For the achiral open catalyst [Co(P9)], high values of intramolecular KIE (23.0) were consistently obtained from both isotopic enantiomers (S)-1a$_D$ or (R)-1a$_D$, generating the highly enantio-enriched radical intermediates (Re)-IIa$_D$ or (Si)-IIa$_D$. However, the facile rotation of α-C—C bond of radical (Re)-IIa$_D$ or (Si)-IIa$_D$ inside such flexible cavity led to the erosion of enantiopurity in radical intermediates (Re)-IIa$_D$ or (Si)-IIa$_D$. Therefore, the cyclization product 2a$_H$ was obtained with poor enantiomeric ratios.

Example 14: Synthesis and Characterization of Deuterated Azides (S)-1a$_D$, (R)-1a$_D$ and Products 2a$_H$

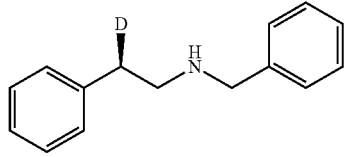 [SMILES: [2H][C@@H](CNCc1ccccc1)c1ccccc1]

(R)—N-Benzyl-2-phenylethan-2-d-1-amine was prepared in 65% yield (550 mg) through General Procedure D1 from (R)-2-phenylethan-2-d-1-ol which was prepared according to a published procedure from (R)-mandelic acid (commercially available, cas: 611-71-2). $^1$H NMR (500 MHz, CDCl$_3$) δ ppm 7.36-7.16 (m, 10H), 3.81 (s, 2H), 2.91 (d, J=7.3 Hz, 2H), 2.85-2.76 (m, 1H); $^{13}$C NMR (125 MHz, CDCl$_3$) δ ppm 140.3, 140.0, 128.7, 128.4, 128.1, 126.9, 126.1, 53.9, 50.5, 36.0 (t, J=18.8 Hz); HRMS (ESI) m/z Calcd. For C$_{15}$H$_{17}$DN$^+$ [M+H]$^+$: 213.1497, Found: 213.1503.

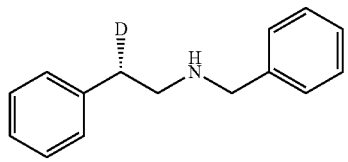 [SMILES: [2H][C@H](CNCc1ccccc1)c1ccccc1]

(S)—N-Benzyl-2-phenylethan-2-d-1-amine was prepared in 45% yield (350 mg) through General Procedure D1 from (S)-2-phenylethan-2-d-1-ol which was prepared according to a published procedure from (S)-mandelic acid (commercially available, cas: 17199-29-0).

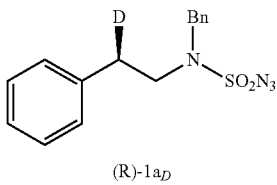

(R)-1a$_D$ (R)—N-Benzyl-2-phenylethan-2-d-1-sulfamoyl azide was obtained in 67% yield (160 mg) as colorless oil through General Procedure E from (R)—N-Benzyl-2-phenylethan-2-d-1-amine starting from 0.75 mmol scale, purified by silica gel column chromatography (eluent: Hexanes/EtOAc 40:1), TLC R$_f$=0.6 (Hexanes/EtOAc 8:1). $^1$H NMR (600 MHz, CDCl$_3$) δ ppm 7.42-7.35 (m, 3H), 7.35-7.31 (m, 2H), 7.31-7.26 (m, 2H), 7.25-7.18 (m, 1H), 7.12-7.05 (m, 2H), 4.42 (s, 2H), 3.42 (d, J=8.3 Hz, 2H), 2.81 (t, J=8.1 Hz, 1H); $^{13}$C NMR (100 MHz, CDCl$_3$) δ ppm 137.5, 134.5, 128.9, 128.7, 128.6, 126.8, 53.0, 49.9, 34.0 (t, J=19.0 Hz). Enantiopurity >99% based on the method used and the product $^1$H NMR (t=35; T$_1$=66; ø=45 C) on a 600 MHz machine. Non-deuterated 1a is <1%, falling into the $^1$H NMR integration error. Therefore, it is a reasonable approximation for the above KIE studies by assuming that the isotopomeric sulfamoyl azides are the only component.

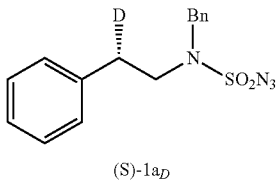

(S)-1a$_D$ (S)—N-Benzyl-2-phenylethan-2-d-1-sulfamoyl azide was obtained in 79% yield (250 mg) as colorless oil through General Procedure E from (S)—N-Benzyl-2-phenylethan-2-d-1-amine starting from 1.0 mmol scale, purified by silica gel column chromatography (eluent: Hexanes/EtOAc 40:1), TLC R$_f$=0.6 (Hexanes/EtOAc 8:1).

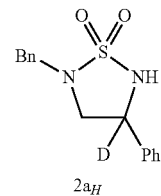

2a$_H$

2-Benzyl-4-phenyl-1,2,5-thiadiazolidine 1,1-dioxide-4d (2a$_H$) was obtained through General Procedure F. Purified by silica gel column chromatography (eluent: Hexanes/EtOAc 4:1), white solid, TLC R$_f$=0.35 (Hexanes/EtOAc 4:1); For [Co(3,5-Di$^t$Bu-Hu(C$_8$)Phyrin)] ([Co(P5)]), 2 mmol % of catalyst was used and the reaction was run at 40° C. for 48 h (98% yield with both (R)-1a$_D$ and (S)-1a$_D$ as starting azides); for [Co(2,6-DiMeOHu—(C$_6$)Phyrin)] ([Co(P4)]), 5 mmol % of catalyst was used and the reaction was run at 40° C. for 48 h (80% yield for (R)-1a$_D$; 64% yield for (S)-1a$_D$); for [Co(3,5-Di$^t$Bu-IbuPhyrin)] ([Co(P9)]), 2 mmol % of catalyst was used and the reaction was run at 40° C. for 48 h (85% yield for (R)-1a$_D$; 80% yield for (S)-1a$_D$). $^1$H NMR (500 MHz, CDCl$_3$) δ ppm 7.48-7.28 (m, 10H), 4.87 (br. s., 1H), 4.38, 4.01 (AB q, J=15.0 Hz, each 1H), 3.56 (d, J=9.8 Hz, 1H), 3.13 (d, J=9.3 Hz, 1H); $^{13}$C NMR (100 MHz, CDCl$_3$) δ ppm 138.3, 134.8, 129.0, 128.8, 128.7, 128.2, 126.4, 55.8-55.1 (m); 55.0, 50.5; HRMS (ESI) m/z Calcd. For C$_{15}$H$_{16}$DN$_2$O$_2$S$^+$ [M+H]$^+$: 290.1068, Found: 290.1055; Enantiomeric excess was determined by HPLC with an ADH column (90:10 n-hexane:isopropanol, 0.8 mL/min); R-enantiomer: t$_r$=34.4 min; S-enantiomer: t$_r$=24.7 min.

Example 15: Experimental Evidence for Radical Mechanism

TEMPO Trapping Experiment

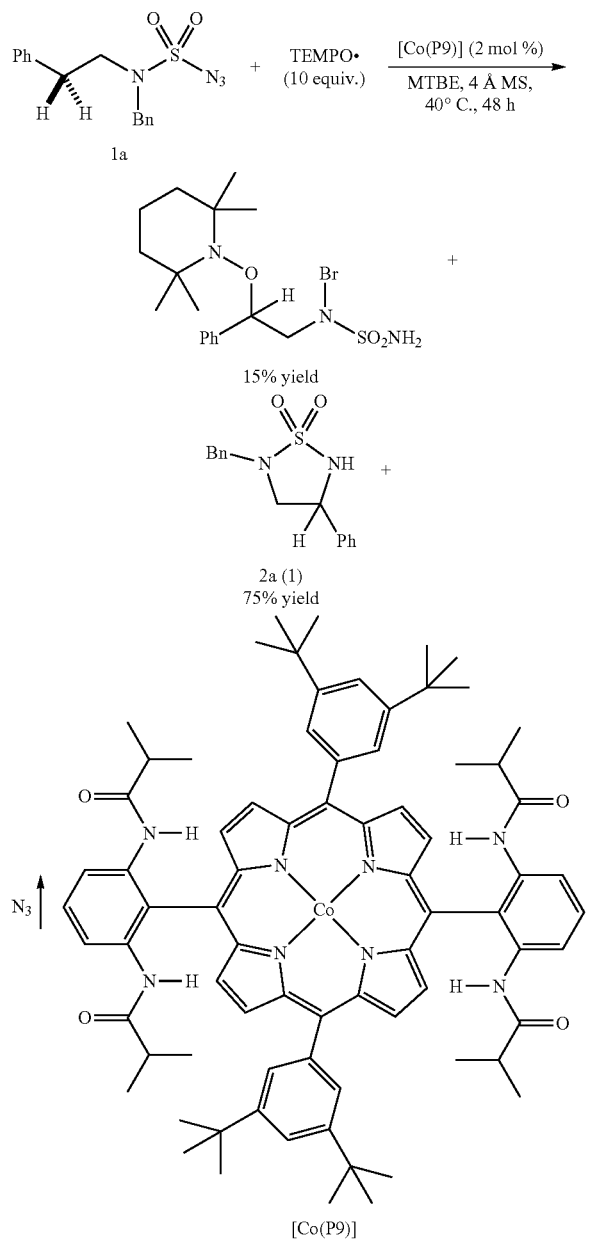

An oven dried Schlenk tube was charged with catalyst [Co(P9)] (0.002 mmol) and 4 Å molecular sieves (50 mg). This reaction vessel was evacuated and backfilled with nitrogen several times. The Teflon screw cap was replaced with a rubber septum and azide 1a (0.1 mmol) was added followed methyl tert-butyl ether (0.5 mL), TEMPO (1 mmol) and the remaining methyl tert-butyl ether (0.5 mL). The Schlenk tube was then purged with nitrogen for 2 minutes and the rubber septum was replaced with a Teflon screw cap. The Schlenk tube was then placed in an oil bath at 40° C. while stirring. After 48 h, the reaction mixture was purified by silica gel column chromatography (eluent: Hexanes/EtOAc 4:1), to give the TEMPO-trapped product in 15% yield as yellow solid (TLC R$_f$=0.15 (Hexanes/EtOAc 1:1)) together with amination product 2a(±) in 75% yield. For TEMPO-trapped product: $^1$H NMR (500 MHz, CDCl$_3$) δ ppm 7.45-7.38 (m, 4H), 7.37-7.28 (m, 6H), 4.86 (dd, J=5.1, 10.5 Hz, 1H), 4.17-4.07 (m, 2H), 3.82-3.75 (m, 1H), 3.73-3.64 (m, 1H), 3.45 (s, 2H), 1.50-1.38 (m, 6H), 1.17-0.93 (m, 12H); $^{13}$C NMR (100 MHz, CDCl$_3$) δ ppm 141.9, 135.6, 128.7, 128.5, 128.3, 128.1, 128.0, 84.4, 77.2, 51.5, 50.6, 40.4, 29.7, 17.1; IR (neat, cm$^{-1}$): 2925, 1554, 1495, 1454, 1333, 1361, 1155, 1132, 1008, 940, 756, 733, 700, 547; HRMS (ESI) m/z Calcd. For C$_{24}$H$_{36}$N$_3$O$_3$S$^+$ [M+H]$^+$: 446.2472, Found: 446.2459.

EPR Experiment

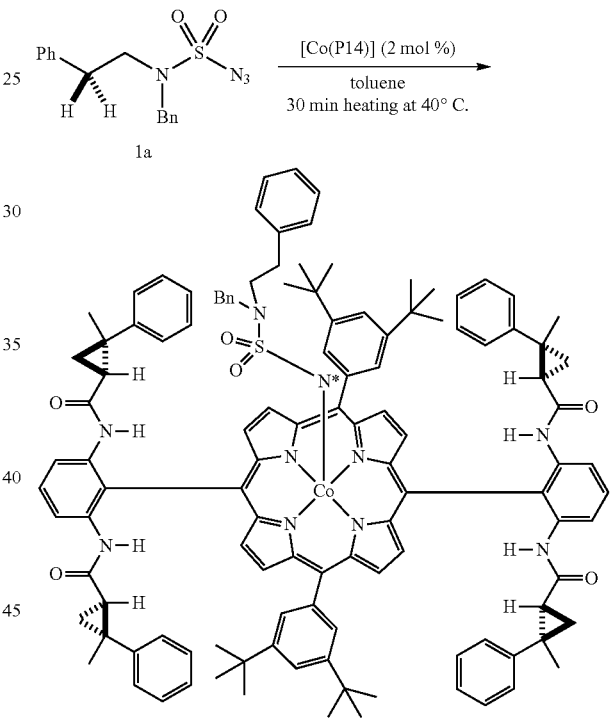

An oven-dried EPR tube was cooled down under nitrogen atmosphere and charged with catalyst [Co(P14)] (0.002 mmol mmol). This EPR tube was then capped with a red rubber septum, which was fastened with parafilm. The tube was evacuated and backfilled with nitrogen three times. Then the sulfamoyl azide 1a (0.1 mmol in 0.4 mL of anhydrous toluene) was added into this tube through a gas-tight syringe. The cap of the EPR tube was further sealed with vacuum grease. The reaction mixture was shaken well followed by the reaction at 40° C. for 30 minutes. Then the sample was ready for EPR experiment at room temperature.

Figure 9A:
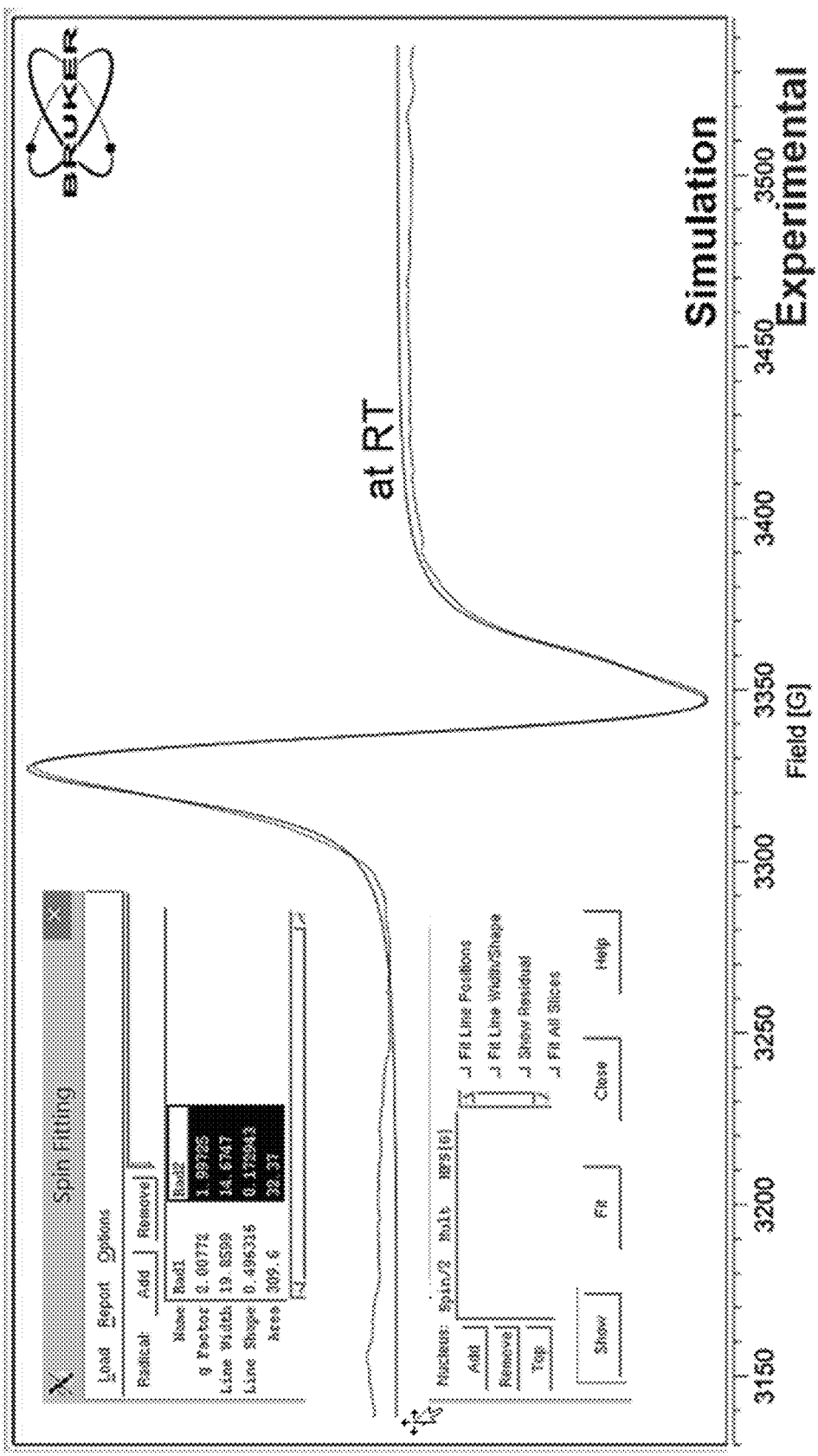
FIG. 9A shows experimental and simulated X-band EPR spectra for α-Co(III)-aminyl radical I in toluene at room temperature.
Figure 9B:
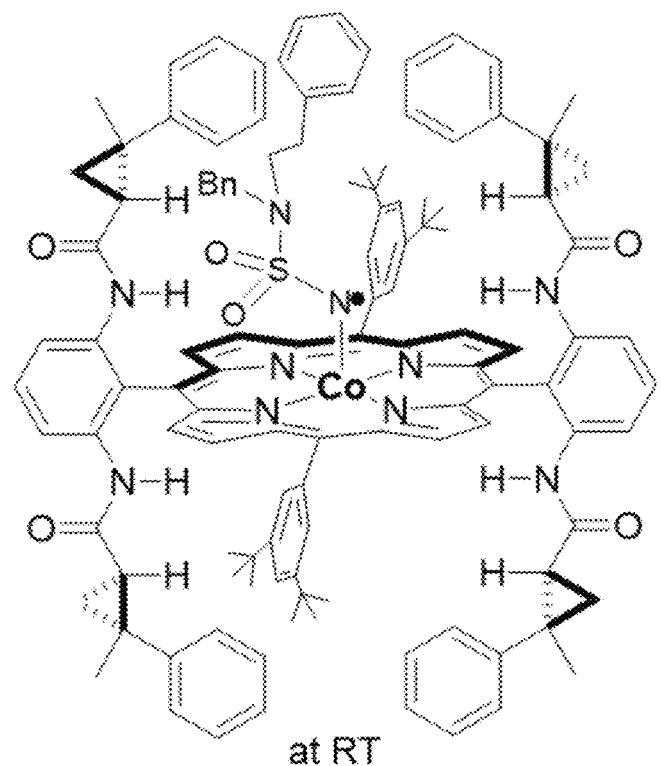
FIG. 9B shows the structure of α-Co(III)-aminyl radical I, with experimental $g_{iso}$=2.00753.
Figure 9C:
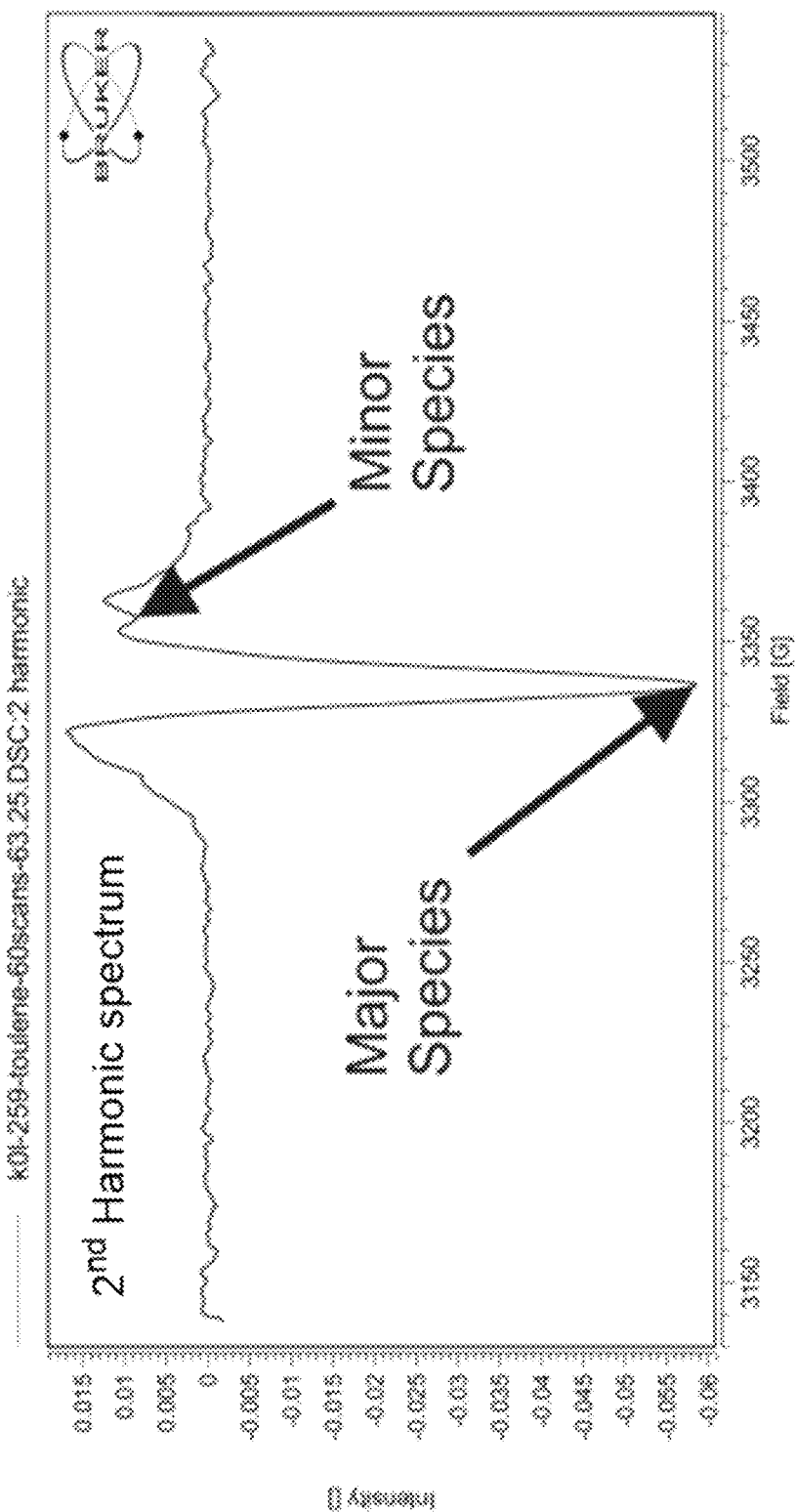
FIG. 9C shows that a second minor species was observed in the EPR spectrum based on the second harmonic spectrum. From simulation: $g_{iso(major)}$=2.00772, $g_{iso(minor)}$=1.99725.

X-band EPR spectra (see FIGS. 9A-C) were recorded on a Bruker EMX-Plus spectrometer (Bruker BioSpin). Simulations of the EPR spectra were performed by using the EPR simulation program SpinFit in Xenon. Experimental X-band EPR spectra of α-Co(III)-Aminyl Radical I in toluene were recorded at room temperature. (Freq=9.42731 GHz; mod. amp.=1 G; microwave power=63.25 mW).

HRMS Experiment
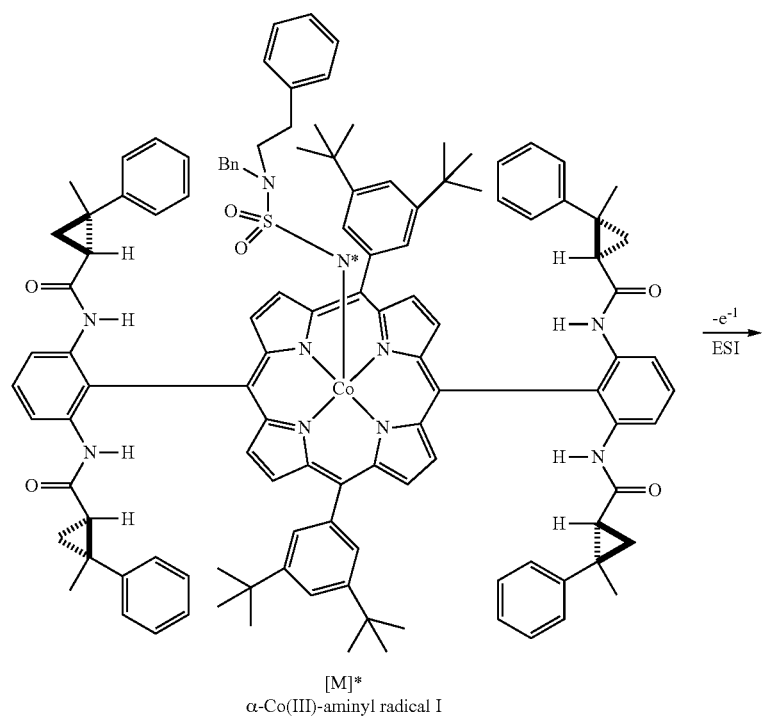
[M]•
α-Co(III)-aminyl radical I
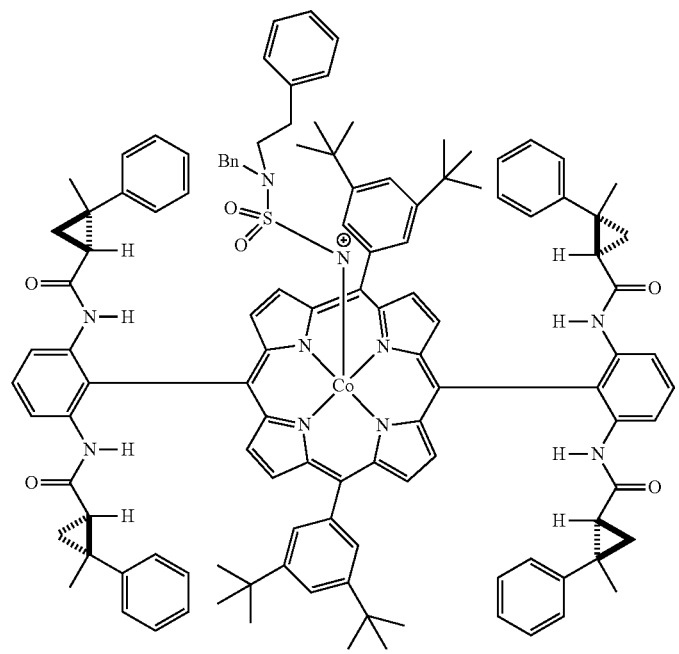
[M]+
Chemical Formula: $C_{119}H_{120}CoN_{16}O_6S^+$
Exact Mass: 1875.8440

Figure 10:
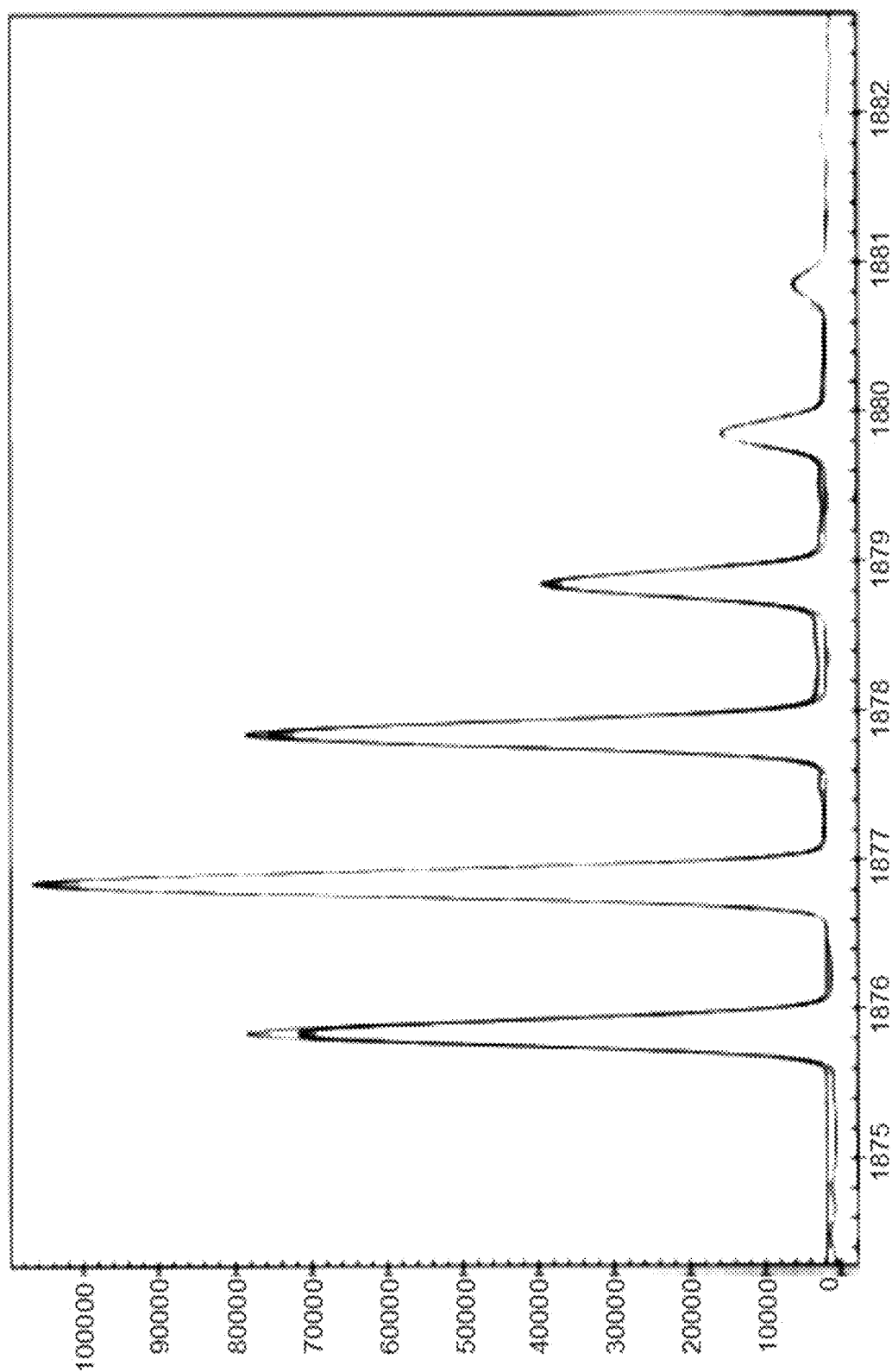
FIG. 10 shows observed and simulated ESI-MS spectra with isotope distribution corresponding to [α-Co(III)-aminyl radical I−e$^{−1}$]$^{+}$ ([M]$^{+}$ m/z=1875.8391).

Through a gas-tight syringe, the same EPR solution was transferred to a sealed HRMS sample vial, which was pre-evacuated and backfilled with nitrogen. The high-resolution mass spectra (CH$_3$CN as solvent for LC-HRMS) (ESI) in the absence of any additives such as formic acids that commonly act as electron carriers for ionization allowed for the detection of the molecular ion signals corresponding to the α-Co(III)-aminyl radical I ([M]$^+$ m/z=1875.8391 (observed)), by the loss of one electron. An example spectrum is presented in FIG. 10.

Example 16: X-Ray Crystallography Methods

The X-ray diffraction data for (R)-2a (LK-3-247C-0m), (S)-2a (lk-3-186c), (R)-2c (LK-3-68B), (S)-2c (LK-3-68C), (S, R)-2m (LK-3-237B-0m), (S, S)-2s (LK_4_13c), P4 (lk_3_95_2nd) and P5 (LK-3-74A) were measured on a Bruker D8 Venture PHOTON 100 CMOS system equipped with a Cu K$_\alpha$ INCOATEC Imus micro-focus source (λ=1.54178 Å). X-ray diffraction data for (R)-2b (LK-3-29A), (S)-2b (LK-3-36-3rd) and (R)-2 k (LK-3-198B), were collected using Bruker-AXS SMART-APEXII CCD diffractometer) using Kα radiation (λ=1.54178 Å). Indexing was performed using APEX2 (Difference Vectors method). Data integration and reduction were performed using SaintPlus 6.01. Absorption correction was performed by multi-scan method implemented in SADABS. Space groups were determined using XPREP implemented in APEX2. The structure was solved using SHELXS-97 (direct methods) and refined using SHELXL-2013 (full-matrix least-squares on F2) contained in APEX2 [1,7], WinGX v1.70.01 and OLEX2. All non-hydrogen atoms were refined anisotropically. Hydrogen atoms of —CH, —CH$_2$, —CH$_3$ groups were placed in geometrically calculated positions and included in the refinement process using riding model with isotropic thermal parameters: Uiso(H)=1.2 Ueq(—CH$_1$—CH$_2$) and Uiso(H)=1.5 Ueq(—CH$_3$).

Example 17: General Procedure for Circular Dichroism Spectra Studies

Figure 14A:
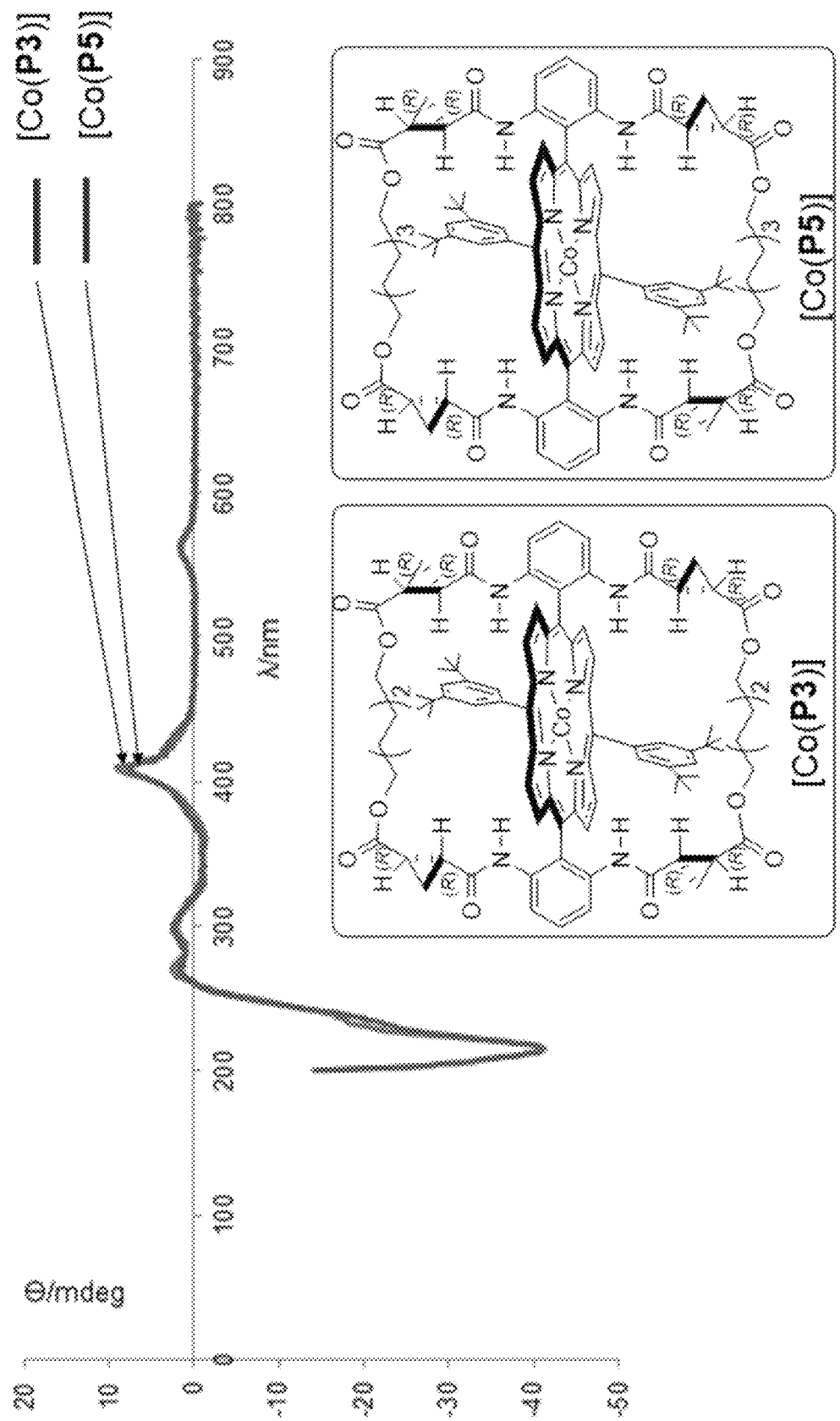
FIG. 14A shows circular dichroism spectra of [Co(P3)] and [Co(P5)] at 25° C.
Figure 14B:
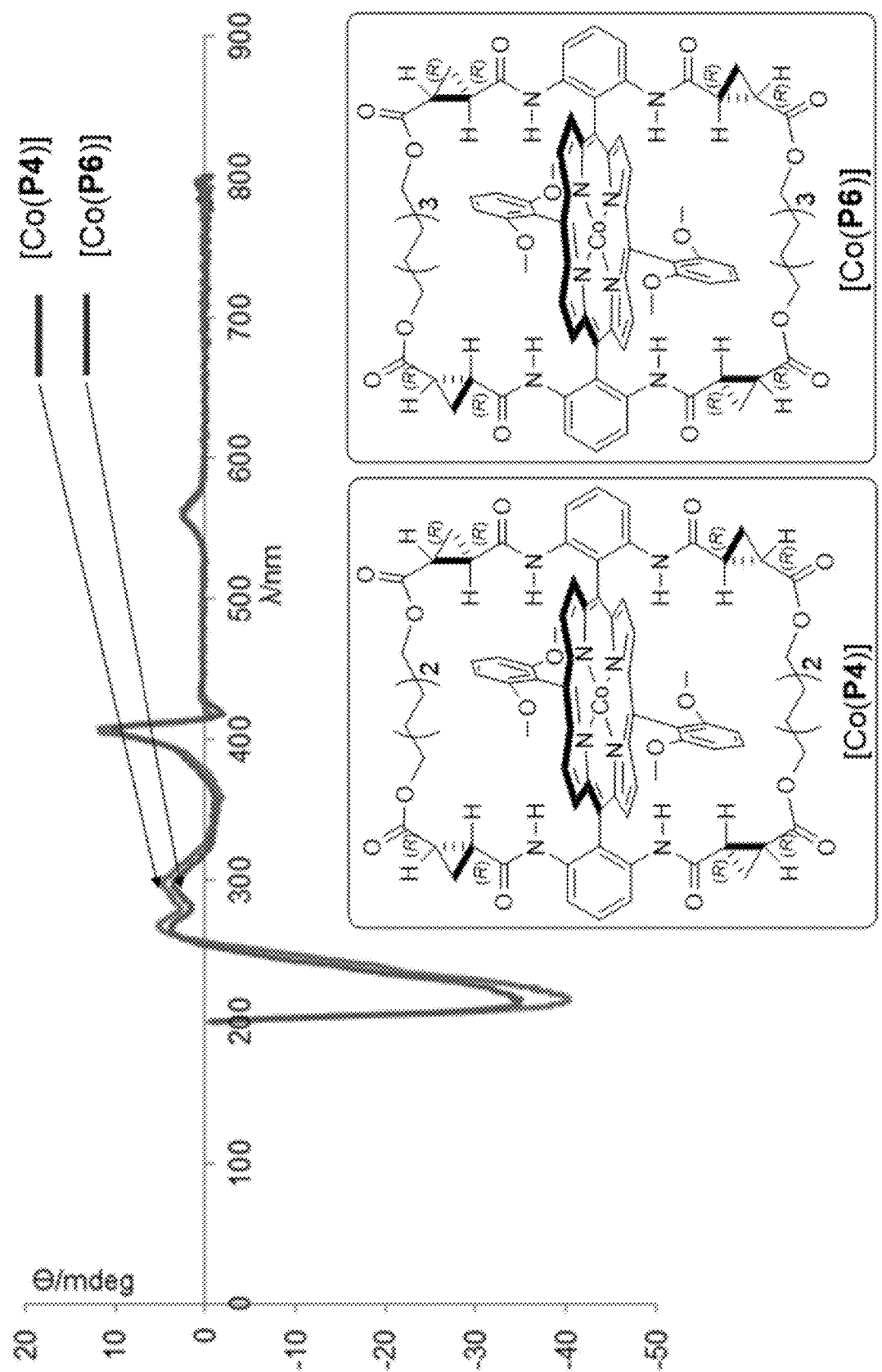
FIG. 14B shows circular dichroism spectra of [Co(P4)] and [Co(P6)] at 25° C. Overlapping spectra are likely indicative of similar chiral conformations of these catalysts.

A stock solution of [Co(II)(D$_2$-Por*)] in CH$_3$CN (6.7× 10$^{-5}$ M) was prepared. This solution was used for CD study at 25° C. The nearly identical CD spectra of [Co(P3)] and [Co(P5)] and of [Co(P4)] and [Co(P6)] suggested that similar types of chiral conformations were adopted by these catalysts. CD spectra are presented in FIGS. 14A-B.

Example 18: Density Functional Theory Calculations

Methods

Initial screening of conformational space: Calculations were performed on a truncated model system, wherein the linker on the bottom side of the porphyrin ring has been reduced to methyl groups ([Co(P4)]$_{model}$ and [Co(P5)]$_{model}$) in order to reduce conformational complexity and cost. Initial screening of the conformational space was performed with molecular mechanics (MMFF) implemented in the Spartan04 software. The critical distances to the hydrogen radical in the HAA transition states have been constrained during the force field calculations (1.30 Å for C . . . H and N . . . H distances). From the initial global screening, a number of relevant modes have been identified (A1-D2) and these have been subjected to a second round of conformational screening with frozen hydrogen bonds between the amide proton of the bridge and one of the O(═S) atoms of the substrate (O$^1$ or O$^2$). A selection of conformers thus obtained has been subjected to DFT calculations performed with the Gaussian 09 suite of programs. Geometries of the radical species (doublet spin state) were optimized in gas phase with the M06L23 functional in combination with the LAN L2DZ basis set, which has been chosen due to the large size of the system. Stationary points were probed through vibrational analysis (1 negative frequency for transition states) and Gibbs free energy corrections were performed under standard conditions (298.15 K, 1.0 atm). Additionally, we probed the performance of various density functionals through single point energy calculations at the geometries optimized at the levels described above by means of the SMD solvation model with benzene as solvent and the larger Def2TZVPP basis set. Since the optimal density functional for the current system is not known we tested three additional state of the art approaches that have been developed over the past decade: ωB97XD, M06, and MN12SX.

Calculations on smaller model systems: To gain a better understanding of the conformational preferences during HAA in absence of the bridge (i.e., by eliminating any strain induced by the bridge), additional model calculations have been performed on a further truncated model system at the M06L/Def2SVP level ([Co]$_{model01}$).

Calculation of free energy surface: In order to construct the free energy surface, we reoptimized the three most stable transition state conformers of the preferred reaction mode (obtained with M06L/LANL2DZ) for both catalyst systems ([Co(P4)]$_{model}$ and [Co(P5)]$_{model}$) with M06L/Def2SVP. From the optimized transition state structures, we performed Intrinsic Reaction Coordinate calculations (IRC) employing the L(ocal) Q(uadratic) A(approximation) method and reoptimized the end points with M06L/Def2SVP.

Calculations of HAA transition states leading to 5- or 6-membered ring product: Finally, we investigated the kinetic selectivity between HAA transition states leading to the 5- or 6-membered ring products, also at the M06L/Def2SVP level ([Co]$_{model02}$).

Challenges and Simplifications

Considering the large complexity of the system under investigation we assumed that the second bridge on the bottom side of the porphyrin ring has little influence on HAA occurring at the top side (i.e., we used a truncated model system).

Due to the large size of the system under investigation we used the small LANL2DZ basis set for geometry optimization, which will lead to significant basis set superposition error. The optimized structures have been subjected to single point energy calculations with the larger Def2TZVPP basis set and four density functionals (ωB97XD, M06, MN12SX and M06L).

As a consequence of the above uncertainties we also focus on chemically meaningful trends rather than relying solely on exact free energy differences between the transition states leading to the major and minor enantiomer (on the order of 2 kcal/mol). That is, the resulting stereochemical model has to be in agreement with characteristic selectivity trends arising from variations of the substrates. In particular the model should account for:

Reactions of sterically hindered substrates (i.e., 1s, 1t and 1u) are selective only with [Co(P4)]. They are facile but nonselective with [Co(P5)].

Low yields are obtained when substrates containing moieties with heteroatoms (ester, 1o; furyl, 1p; and thienyl, 1q) are used in reactions with [Co(P4)]. These reactions proceed smoothly with [Co(P5)].

(c) Significantly higher levels of enantioselectivity are obtained when reactions with substrates containing small alkenyl moieties (1i and 1j) or a cyclopropyl group (1 r) are performed with [Co(P5)] vs. [Co(P4)].

Figure 7A:
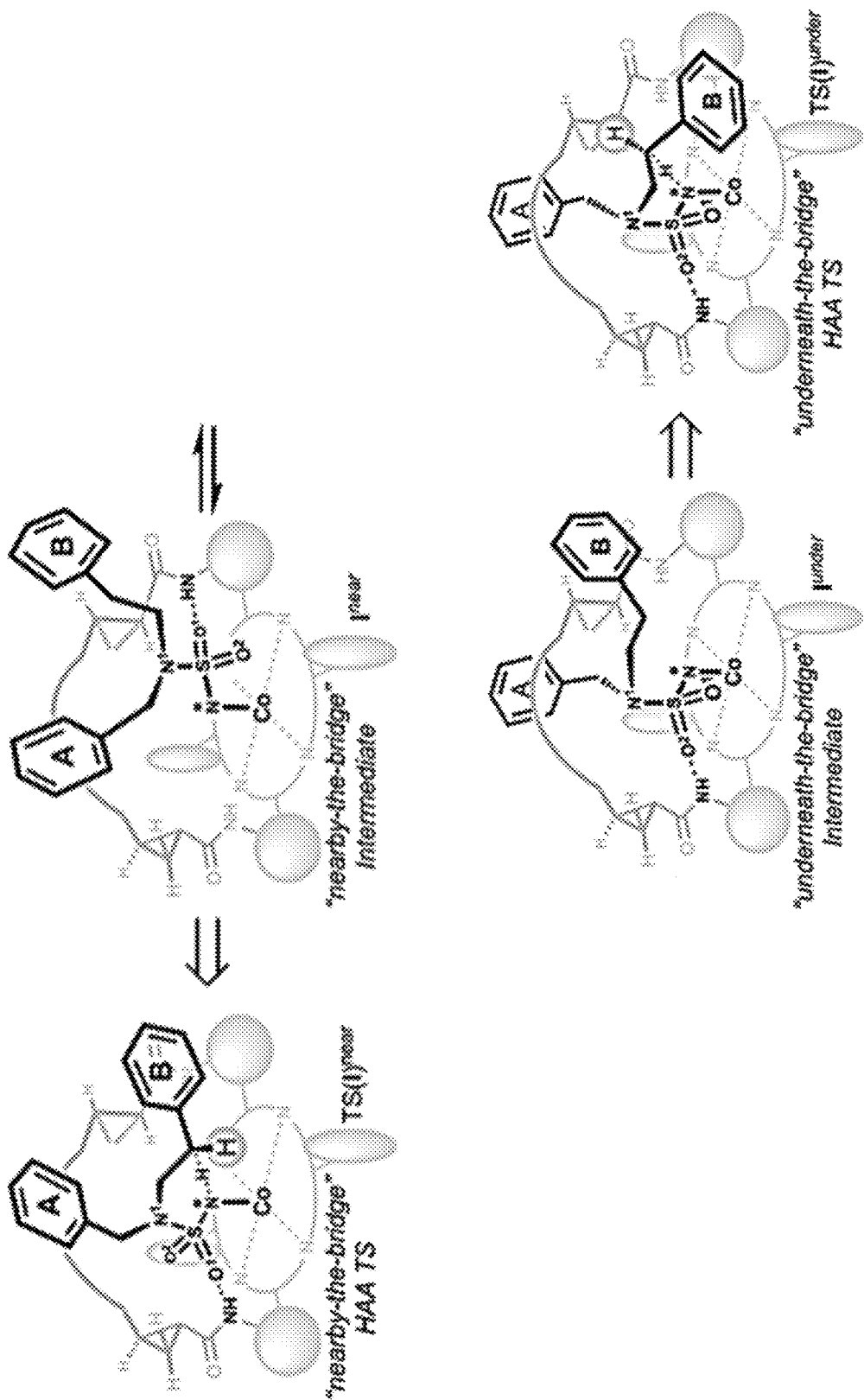
FIGS. 7A-7B show DFT-optimized stereochemical models of enantiodifferentiative H-atom abstraction.
Figure 7B:
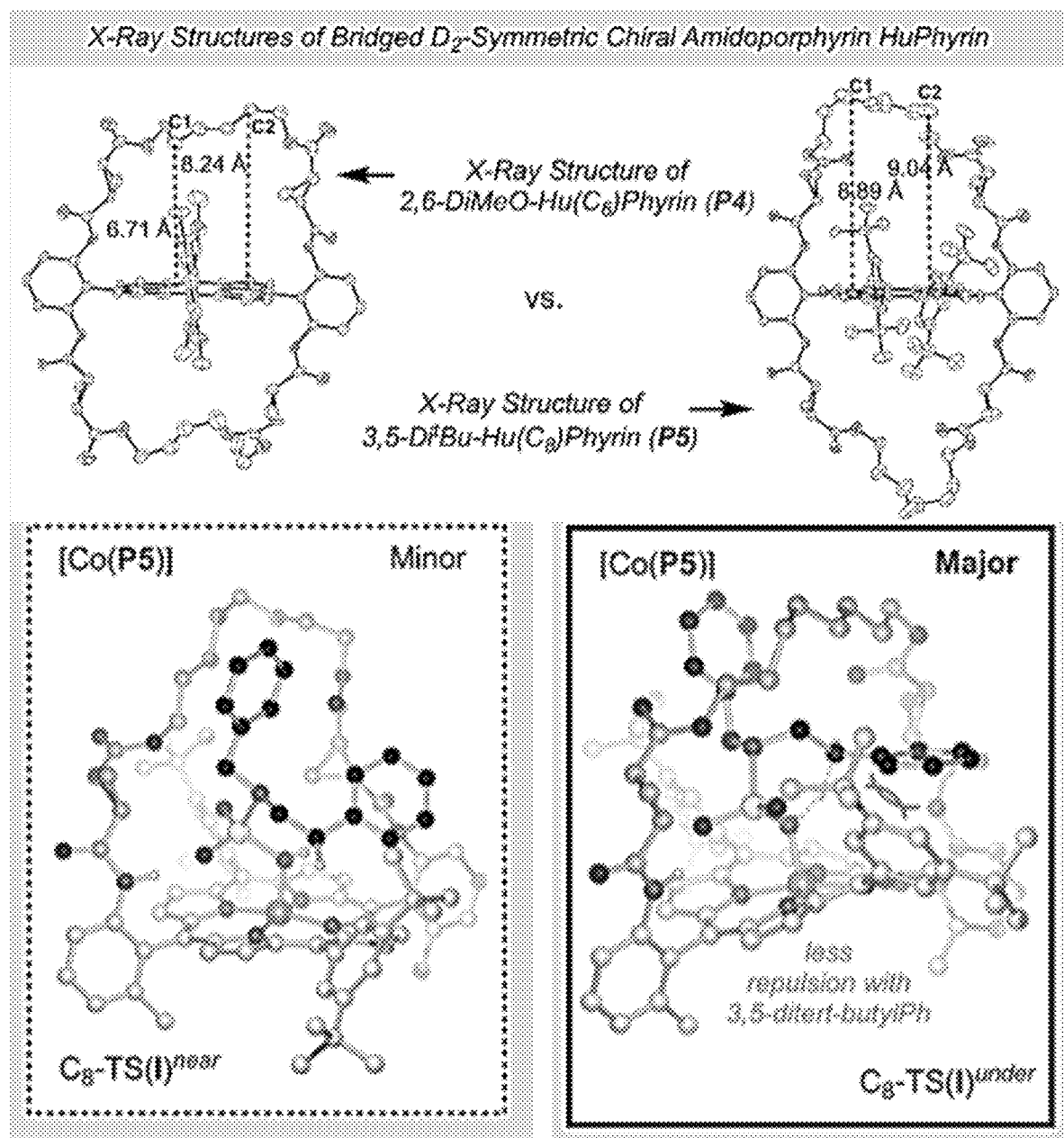
Figure 8A:
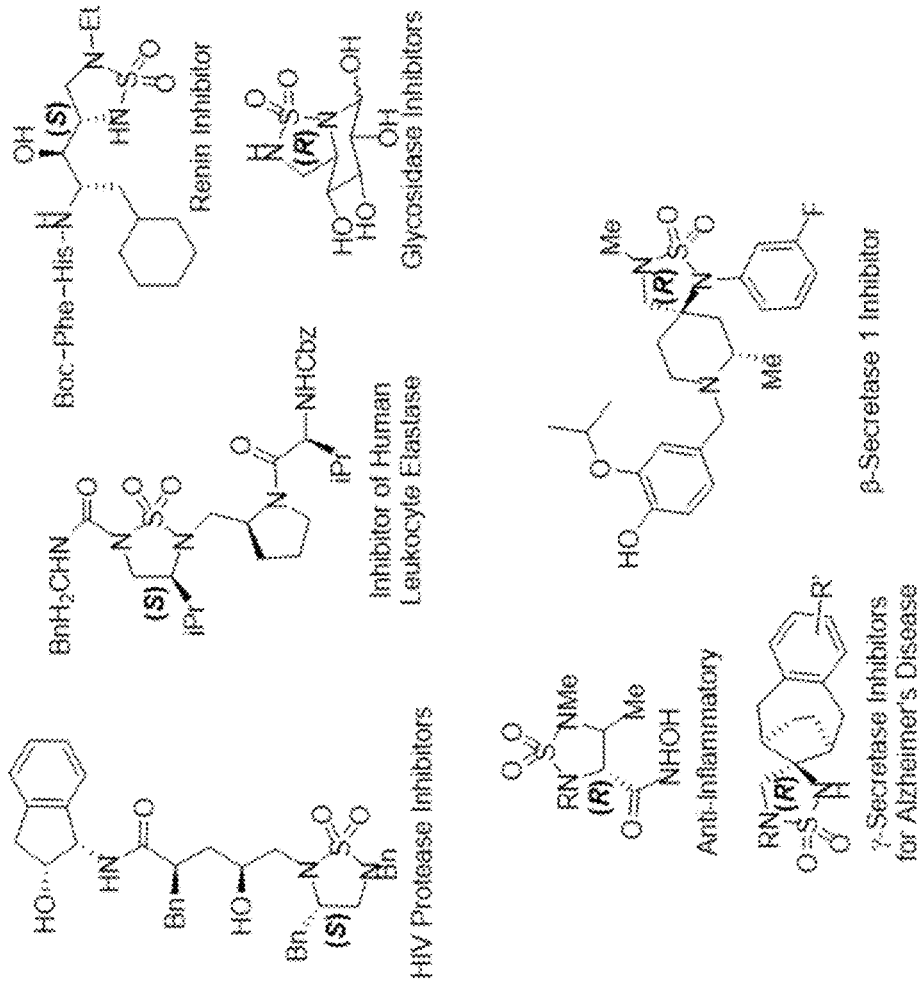
FIG. 8A shows examples of biologically active molecules carrying chiral five-membered cyclic sulfamide as the key motif.
Figure 8B:
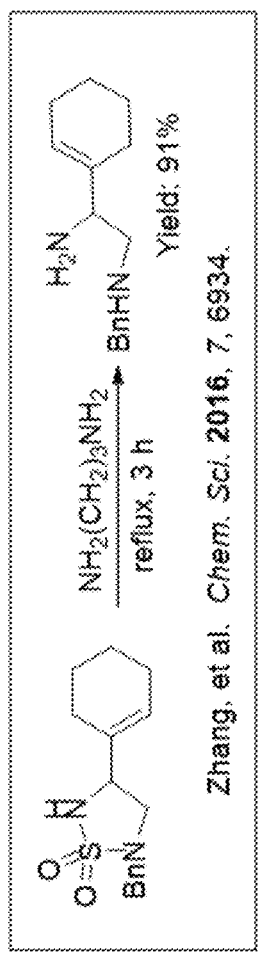
FIG. 8B shows a previously published method for converting cyclic sulfamides into diamines.
Figure 8B:
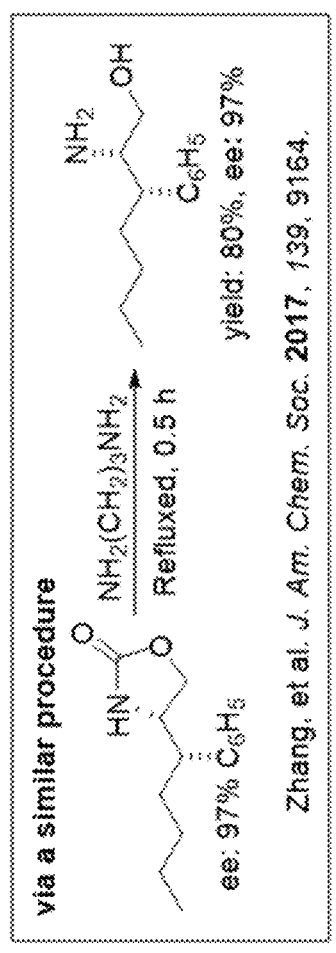
Figure 8B:
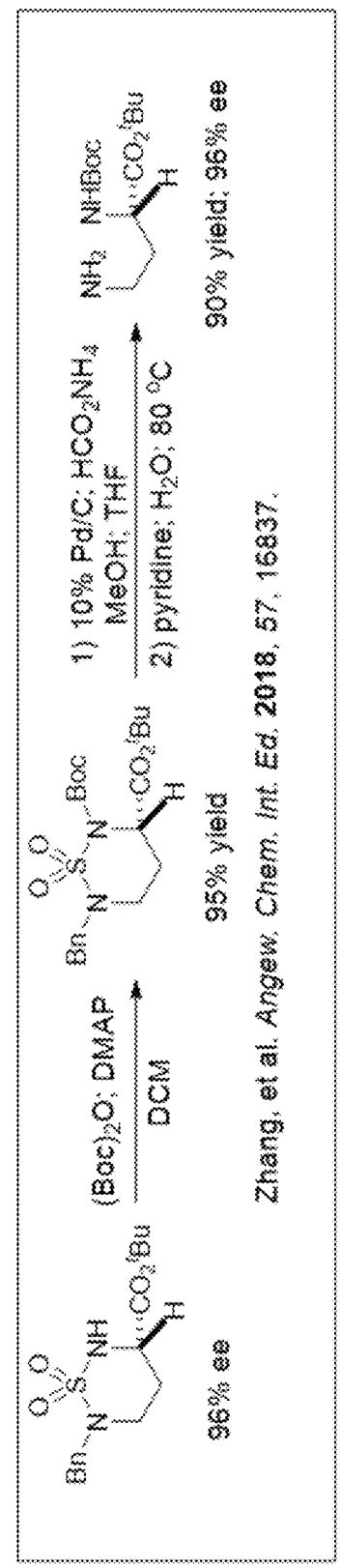

We tested the conformational preference in absence of a bridge, since we hypothesized that it is very likely that the herein identified least strained conformation will also play a significant role in the real systems with the bridge. This is thought to further support the finally proposed stereochemical model. Optimized stereochemical models of enantiodifferentiative H-atom abstraction by [Co(P4)] and [Co(P5)] are shown in FIGS. 7A-B.

Example 19: Results

Figure 5A:
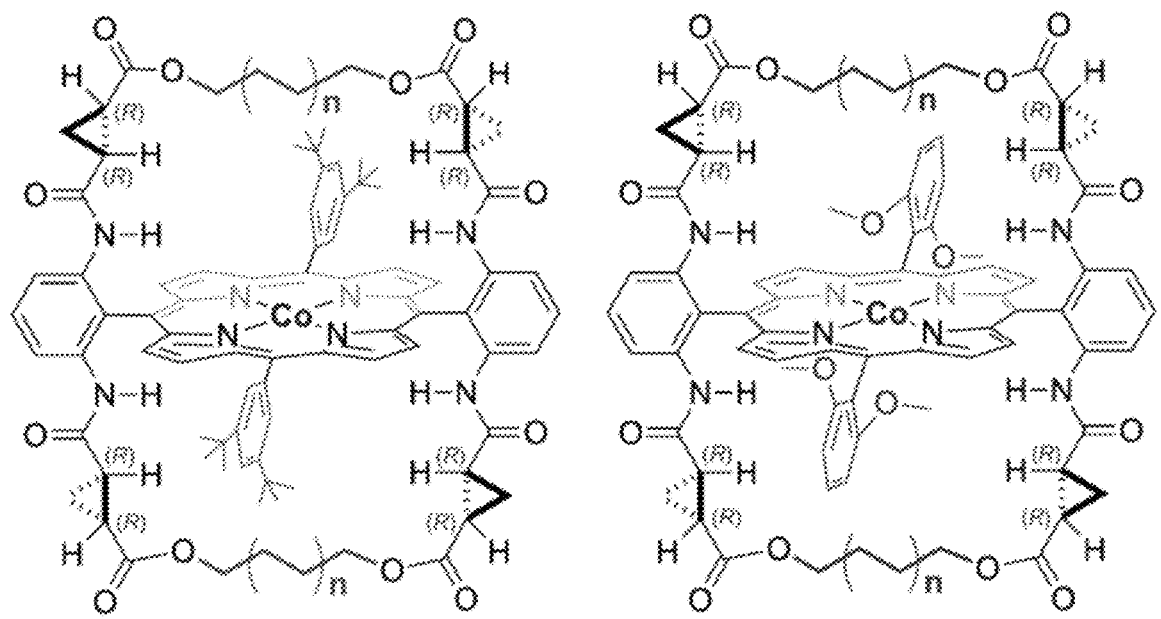
FIGS. 5A-5B shows systematic control of degree and sense of asymmetric induction in intramolecular radical 1,5-C—H amination of sulfamoyl azide by [Co[HuPhyrin]]. Reactions were performed using 0.10 mmol of sulfamoyl azide 1a using 2 mol % of [Co(HuPhyrin)] in 1.0 mL of methyl tert-butyl ether (MTBE) at 40° C. Absolute configuration determined by X-ray crystal analysis. Enantiomeric ratios determined by chiral HPLC analysis.
Figure 5B:
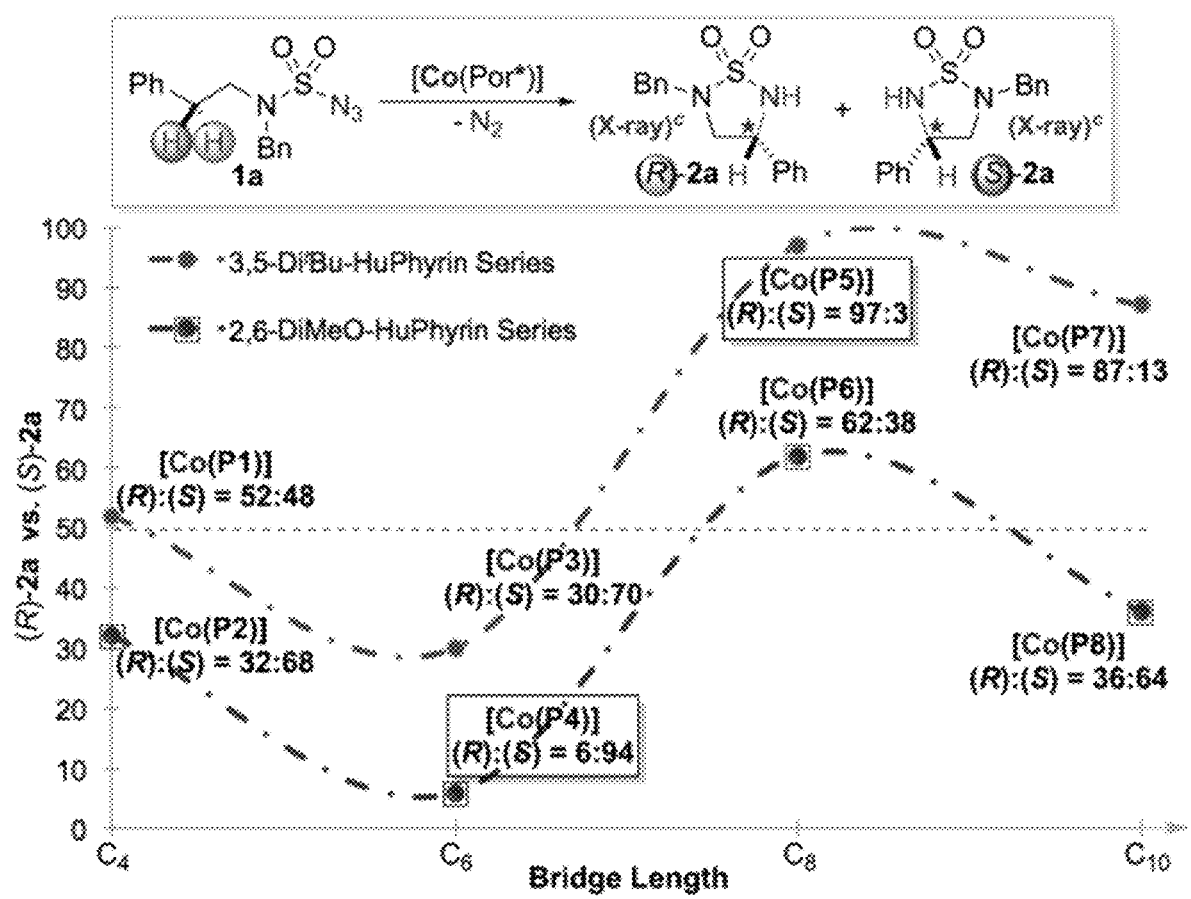

At the outset of this project, sulfamoyl azide 1a containing benzylic C—H bonds was selected as a test substrate for Co(II)-catalyzed radical 1,5-C—H amination. To explore the ligand effect on asymmetric induction during the Co(II)-catalyzed radical amination, we employed two series of HuPhyrin ligands that are based on 3,5-di-tert-butylphenyl and 2,6-dimethoxyphenyl groups as 5,15-aryl substituents, respectively. Both series of HuPhyrin contain the identical chiral amide element and the same type of alkyl bridge; they differ only by the bridge length varying from 4 to 6 to 8 to 10 methylene units (see FIG. 5). The length of the distal alkyl bridge in HuPhyrin could significantly affect the asymmetric induction of the Co(II)-catalyzed C—H amination of azide 1a. Variation of the bridge length by two methylene units each time resulted in systematic alteration in enantioselectivity and even led to the switch in the sense of asymmetric induction for the formation of 5-membered cyclic sulfamide 2a. For [Co(3,5-Di$^t$Bu-HuPhyrin)] catalyst series, C4-bridged [Co(P1)] slightly favored the formation of (R)-2a (52:48 er) while $C_6$-bridged [Co(P3)] produced (S)-2a as the major enantiomer (30:70 er). When the alkyl bridge was further extended to $C_8$-linker in [Co(P5)], the sense of asymmetric induction switched back again, forming (R)-2a in high enantioselectivity (97:3 er). The effect continued for $C_{10}$-bridged [Co(P7)], which still produced (R)-2a as the major enantiomer but with decreased enantioselectivity (87:13 er). Interestingly, a parallel trend in asymmetric induction was also observed for the reaction by [Co(2,6-DiMeO-HuPhyrin)] catalyst series, generating 2a with (R): (S) enantiomer ratio varied from 32:68 by $C_4$-bridged [Co(P2)] to 6:94 by $C_6$-bridged [Co(P4)] to 62:38 by $C_8$-bridged [Co(P6)] to 36:64 by $C_{10}$-bridged [Co(P8)]. Consequently, the 5-membered cyclic chiral sulfamide could be enantiodivergently constructed through C—H amination by the use of $C_6$-bridged [Co(P4)] and $C_8$-bridged [Co(P5)] as the catalysts, producing highly enantioenriched (S)-2a and (R)-2a, respectively. Considering that the only differences between [Co(P4)] and [Co(P5)] are the distal alkyl bridges and the remote non-chiral substituents, it is remarkable that such enantiodivergence could be realized under the same catalytic conditions.

Figure 2A:
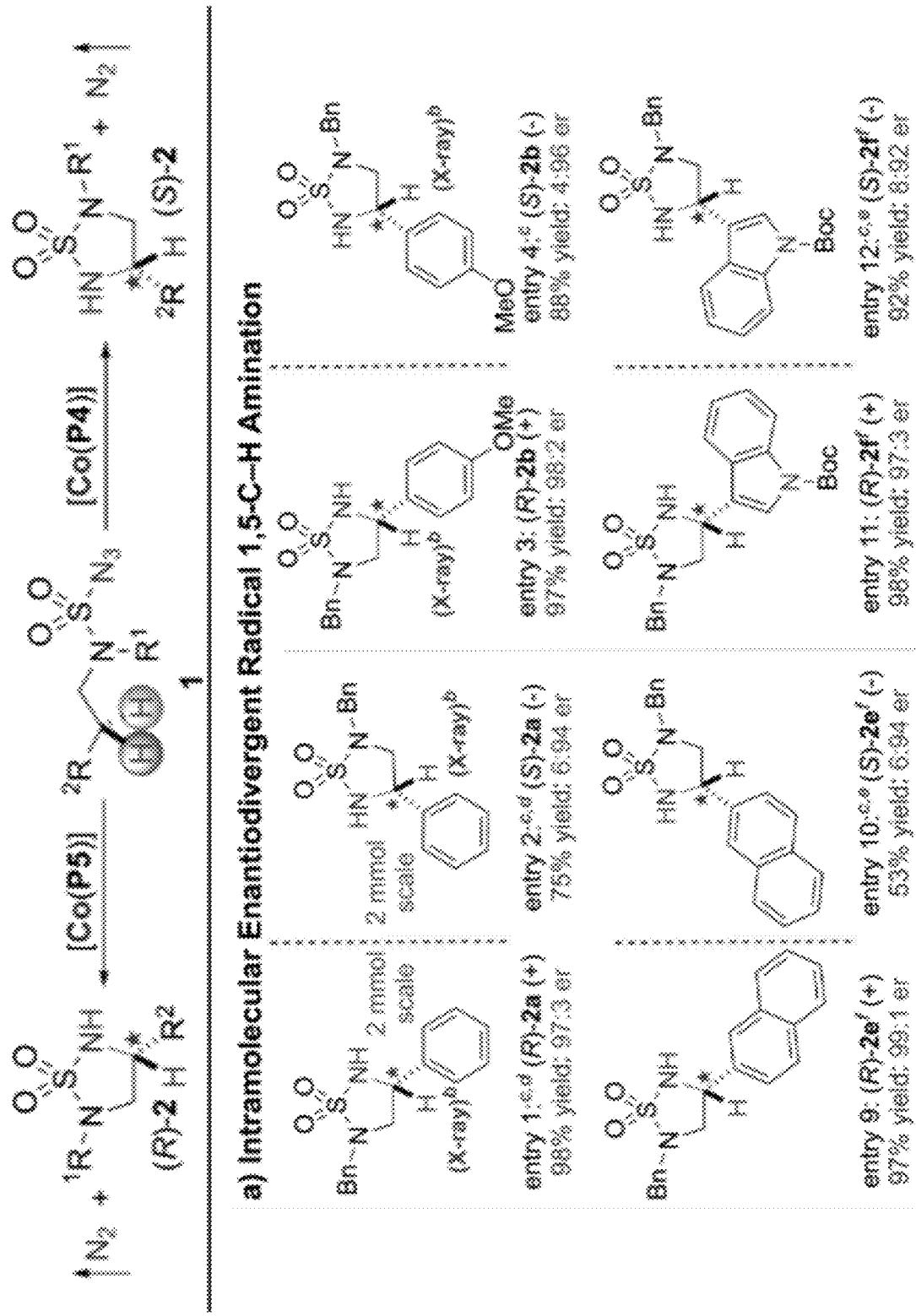
FIGS. 2A-2B show examples of intramolecular enantiodivergent radical 1,5-C—H amination of sulfamoyl azides.
Figure 2B:
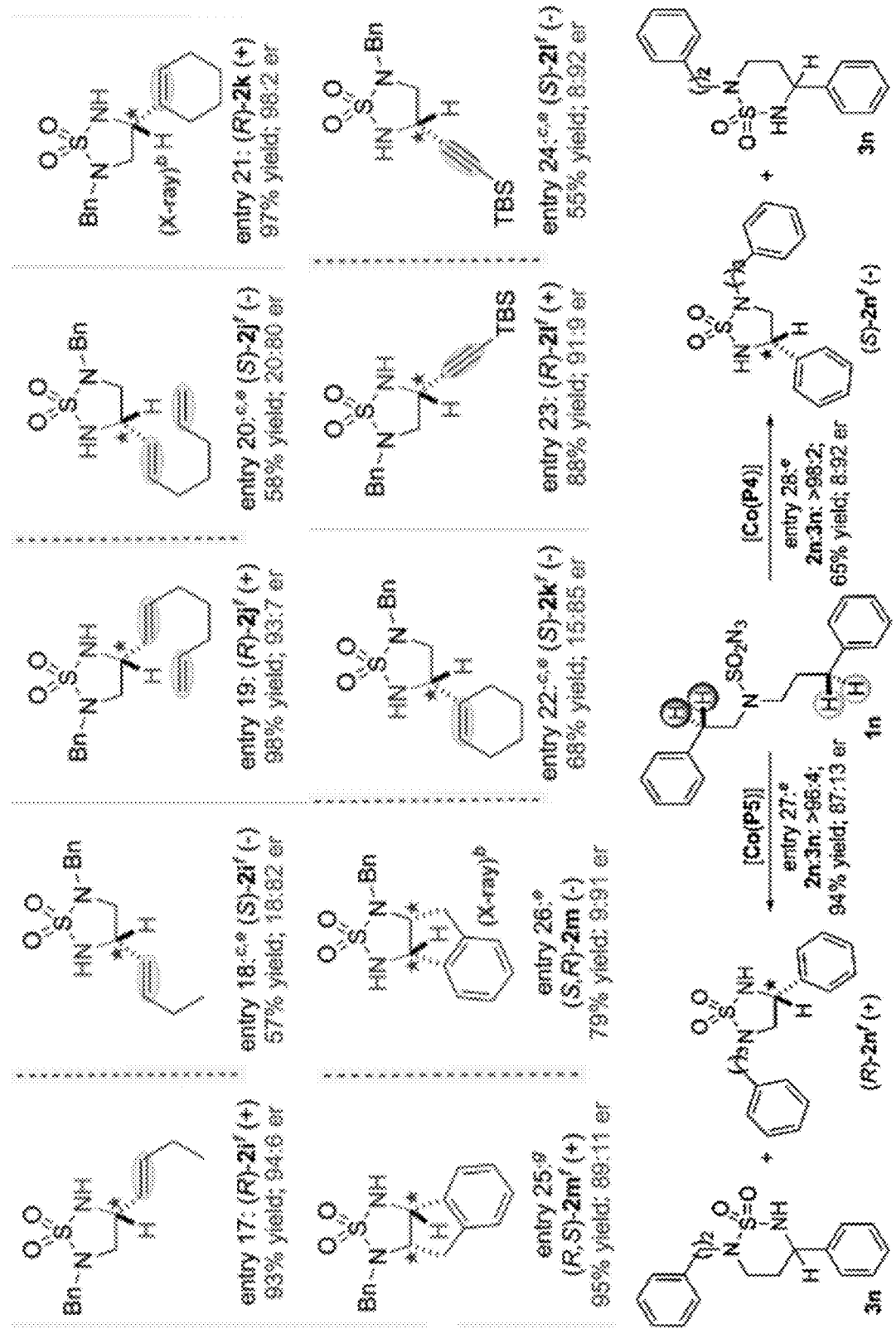
Figure 3A:
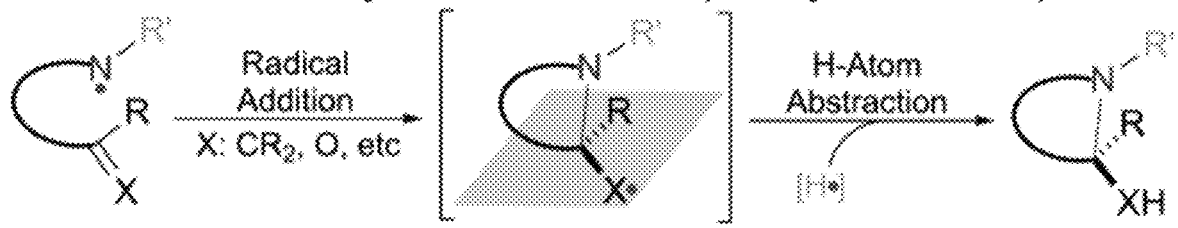
FIGS. 3A-3D show heterocyclization pathways of aminyl radicals and potential modes of asymmetric induction.
Figure 3B:
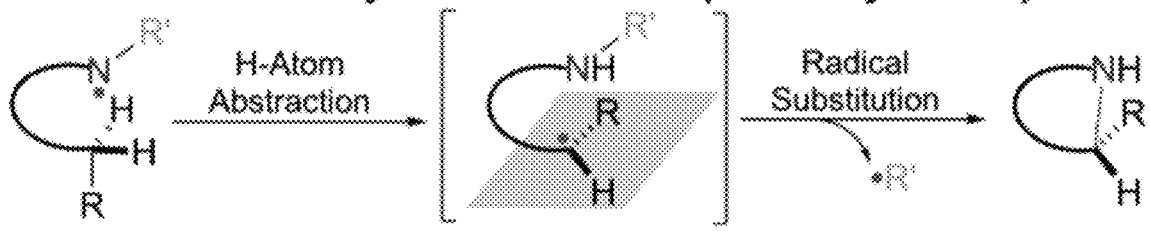
Figure 3C:
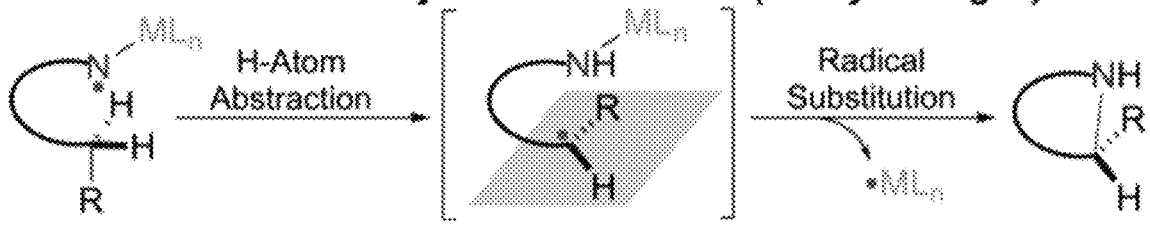
Figure 3D:
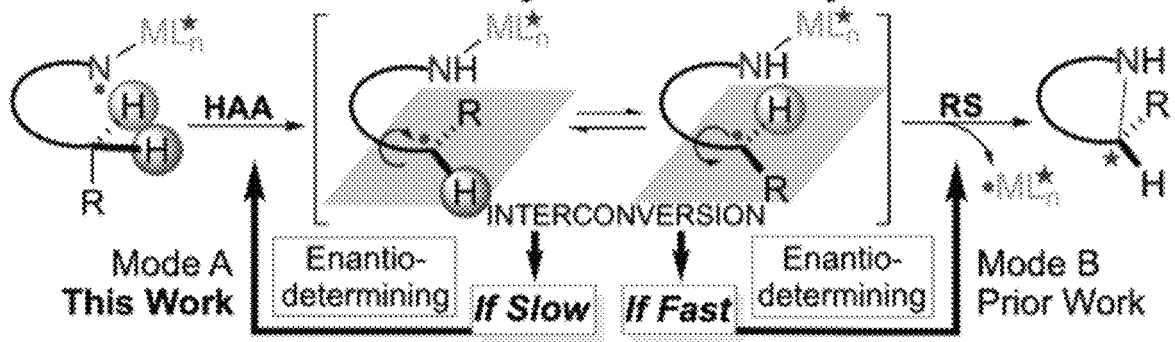

The enantiodivergent radical 1,5-C—H amination exerted by the pair of metalloradical catalysts [Co(P4)] and [Co(P5)] was found general and could be broadly applicable to various sulfamoyl azides with different types of C—H bonds (FIGS. 2A-B). For the catalytic amination reactions of azide 1a by [Co(P4)] and [Co(P5)], they could be scaled up 20 times (from 0.1 mmol to 2.0 mmol) under the standard conditions, producing (S)-2a and (R)-2a, respectively, in similarly high yields with the same excellent enantioselectivities (entries 1 and 2). Other benzylic C—H bonds with varied electronic properties could also be aminated in high yields with excellent enantioselectivities as shown for formation of both (R)- and (S)-cyclic sulfamides 2b-2d (entries 3-8). In addition, highly enantiodivergent stereocontrol was observed for amination of benzylic C—H bonds in both polyaromatic and heteroaromatic systems, as demonstrated for the productive formation of naphthalene-based 2e (entries 9 and 10), indole-based 2f (entries 11 and 12), dihydrobenzofuran-based 2 g (entries 13 and 14) and benzothiophen-based 2h (entries 15 and 16). Furthermore, this enantiodivergent system exhibited excellent chemoselectivity toward radical amination of allylic C—H bonds to afford allylic 1,2-diamine derivatives without affecting the C═C double bonds, including monoene (2i), diene (2j), and cyclic ene (2 k) (entries 17-22). Similarly, propargylic C—H bonds could be chemoselectively aminated as exemplified by enantiodivergent formation of propargylic 1,2-diamine derivative 2l without the involvement of the electron-rich C≡C bond (entries 23 and 24). Addition-ally, the Co(II)-based enantiodivergent system could be successfully applied for the desymmetrization of 2-indane-derived sulfamoyl azide to form the cis-fused tricyclic sulfamide 2m with effective control of the two newly-generated stereogenic centers (entries 25 and 26). Moreover, the cavity environment of [Co(P4)] and [Co(P5)] enabled the enantiodivergent system with uncommon regioselectivity. This was nicely illustrated by the reactions of sulfamoyl azide 1 n bearing sterically and electronically similar benzylic C—H bonds where both 1,5- and 1,6-C—H amination could potentially occur (entries 27 and 28). Remarkably, 5-membered cyclic sulfamides 2n were regioselectively constructed in high enantiodivergent selectivities over the less-strained 6-membered cyclic sulfamides 3n.

A set of mechanistic experiments were performed to obtain direct evidence for the proposed stepwise radical pathway of the Co(II)-catalyzed 1,5-C—H amination. The corresponding α-Co(III)-aminyl radical I from the reaction of azide 1a could be directly detected by EPR and HRMS. In the presence of excess TEMPO (10 equiv.), the resulting ε-Co(III)-alkyl radical II after 1,5-H-atom abstraction could be successfully trapped, generating a TEMPO-substituted product along with the amination product 2a. To determine the mode of asymmetric induction in the enantiodivergent system by [Co(P4)] and [Co(P5)], isotopomeric sulfamoyl azides in optically pure form (S)-1$a_D$ and (R)-1$a_D$ were prepared as substrates to study kinetic isotope effects (KIE) on C—H radical amination (Table 2). With the achiral non-bridged catalyst [Co(P9)] (P9=3,5-Di$^t$Bu-IbuPhyrin; see SI for structure), the intramolecular KIE was measured to have the same high value of 23.0 for reactions of both azides (S)-1$a_D$ and (R)-1$a_D$, which suggests significant tunneling that might be related to the high-strained transition state of the HAA process. When chiral catalysts are employed, alteration of this intrinsic KIE will be expected because of chirality match and mismatch between the catalyst and substrate. Accordingly, the use of chiral catalyst [Co(P4)] resulted in a lower KIE value of 2.0 for (S)-1$a_D$ while a higher KIE value of 61.0 for (R)-1$a_D$ (entry 5) was obtained, indicating enantiodifferentiative abstraction of pro-(S) H-atom by [Co(P4)]. On the other hand, chiral catalyst [Co(P5)] raised the KIE to a value of 96.0 for (S)-1$a_D$ but lowered it a value of 0.8 for (R)-1$a_D$, suggesting that [Co(P5)] abstracted pro-(R) H-atom enantiodifferentiatively. Based on the measured KIE values, the ratios of the initially-established two chiral faces (Re)-IIa to (Si)-IIa could be deduced. And in turn, it permits the calculation of predicted enantiomeric excess (ee) of the amination products 2a based on the assumption that there is no racemization of the face chirality during the subsequent RS step. The fact that the measured ee of product 2a by HPLC for the amination reaction of (S)-1a$_D$ by [Co(P5)] agreed near completely with the predicted value revealed stereoretentive RS during the catalytic process. Likewise, the RS step for catalytic amination reaction of (R)-1a$_D$ by [Co(P4)] was also concluded to be stereoretentive. In contrast to [Co(P4)] and [Co(P5)], however, the data suggested that the RS in the catalytic process by the non-bridged catalyst [Co(P9)] is non-stereoretentive. Presumably due to less geometric constraints exerted by the open catalyst [Co(P9)], the highly enantioenriched facial chirality established in the first HAA step from both reactions of (S)-1a$_D$ (entry 1) and (R)-1a$_D$ was near completely racemized through low-barrier rotation of the α-C—C bond in the corresponding radical intermediate IIa. Clearly, the cavity environment in [Co(P4)] and [Co(P5)] created by bridging is primarily contributed to the realization of this unprecedented mode of asymmetric induction in the catalytic radical process by combining highly enantiodifferentiative HAA with completely retentive RS.

DFT Results

To shed light on the origin of this new mode of asymmetric induction, the transition states (TS) of the HAA step in the reaction of azide 1a by C$_6$-bridged [Co(P4)] and C$_8$-bridged [Co(P5)] catalysts were calculated with density functional theory (DFT) at the ω-B97XD/Def2TZVPP// M06L/Def2SVP$_{benzene(SMD)}$ level. The DFT calculations revealed two possible low-energy conformers I$^{under}$ and I$^{near}$ for α-Co(III)-aminyl radical intermediate I, where phenyl ring A is located "underneath-the-bridge" and "nearby-the-bridge", respectively. Accordingly, two major TS were identified for HAA: the most stable "underneath-the-bridge" TS(I)$^{under}$ and the next stable "nearby-the-bridge" TS(I)$^{near}$, enabling pro-(R) HAA to generate ε-Co(III)-alkyl radical intermediate (Re)-II$^{under}$ and pro-(S) HAA to form ε-Co (III)-alkyl radical intermediate (Si)-II$^{near}$, respectively. In both TS, the chiral cyclopropane unit on the left serves as a primary source for asymmetric induction by forcing phenyl ring B into the front right quadrant. Consistent with the experimental observations, the bridge lengths (C$_6$ vs. C$_8$) as well as the identity of the non-chiral substituents (2,6-DiMeO vs. 3,5-Di$^t$Bu) appear to be pivotal to reach specific TS. The larger cavity created by the C$_8$-bridge in [Co(P5)] significantly favors C$_8$-TS(I)$^{under}$ (−6.6 kcal/mol below C$_8$-TS(I)$^{near}$), where the pro-(R) benzylic hydrogen is oriented in closer proximity to the nitrogen radical for HAA so as to avoid the steric interaction of phenyl ring B with the distal 3,5-Di$^t$Bu groups. In the smaller [Co(P4)] system, C$_6$-TS(I)$^{under}$ is also lower in energy than C$_6$-TS(I)$^{near}$, albeit to a lesser degree (−1.8 kcal/mol). Considering that the C$_6$-bridge is too small to allow isomerization from C$_6$−I$^{near}$ to C$_6$−I$^{under}$ we propose that access to C$_6$-TS(I)$^{under}$ is kinetically difficult. This is well illustrated by the DFT-optimized ball-and-stick models of C$_6$-TS(I) and C$_8$-TS(I), which are in consistency with the structural details of P4 and P5 provided by single-crystal X-ray diffraction analysis. Consequently, [Co(P4)] is governed to adopt C$_6$-TS(I)$^{near}$, in which the pro-(S) benzylic hydrogen is better positioned to approach the nitrogen radical for HAA in order to prevent steric clash between the protruding phenyl ring B and the proximal 2,6-DiMeO moieties. Collectively, the DFT studies allowed us to establish agreeable stereochemical models where productive HAA can be achieved enantiodifferentiatively through TS(I)$^{near}$ or TS(I)$^{under}$, depending on the cavity size underneath the distal bridge, which turns on and off the isomerization from intermediate I$^{near}$ to I$^{under}$, eventually leading to the opposite asymmetric induction. The low barriers associated with radical substitution (TS(I)$^{near}$ and TS(I)$^{under}$) together with the hindered racemization of the chiral face in ε-Co(III)-alkyl radical intermediate II are consistent with a stereoretentive RS step.

These stereochemical models were further substantiated by additional experiments that employed substrates with unique steric or electronic properties to probe difference in reactivity and stereoselectivity (FIG. 2B, entries 29-35). First, when azides 1o-1q bearing heteroatoms in proximity to the C—H site were used as the substrates, the catalytic reactions by [Co(P4)] were inefficient (<10% yields even at 40° C.) while [Co(P5)] could catalyze the high-yielding formation of the desired amination products 2o-2q with high (R)-enantioselectivities (entries 29-31). The negative outcomes of these catalytic reactions by [Co(P4)] are attributed to the high barrier to reach the dominated C$_6$-TS(I)$^{near}$ owing to the lone-pair repulsion between heteroatom in the substrates and the oxygen of 2,6-DiMeO groups in the catalyst. Such unfavorable repulsive interactions are absent with the 3,5-Di$^t$Bu groups in [Co(P5)] through C$_8$-TS(I)$^{under}$. The productive formation of (R)-2o (entry 29) is particularly noteworthy both fundamentally and practically in view of the difficulty associated with amination of the electron-deficient α-C—H bonds of ester by C—H insertion via electrophilic metallonitrenes as well as the importance of the resulting α,β-diamino acid ester as a recurring core unit in a variety of bioactive compounds. As a probe for steric effect, azide 1 r carrying a less sterically hindered cyclopropyl moiety adjacent to the C—H site was found to be efficiently aminated by [Co(P5)] to afford the desired 2r with high (R)-enantioselectivity (entry 32) whereas the use of [Co(P4)] led to the formation of 2r with moderate (R)-enantioselectivity (58:42 er). Considering the similar size of the two N-substituents (cyclopropylethyl vs. phenylmethyl), such low and anomalous (R)-enantioselectivity by [Co(P4)] agrees well with the general models because of the decreased preference for the cyclopropyl moiety to stay in the front right quadrant to react in the dominated C$_6$-TS(I)$^{near}$. On the other hand, azides 1s-1u bearing bulky groups could be productively aminated by [Co(P4)] to produce the desired 2s-2u with high (S)-enantiocontrol (entries 33-35), indicating that the majority of steric bulkiness in these substrates was effectively directed outside the catalyst cavity in the corresponding C$_6$-TS(I)$^{near}$. In addition to demonstrating the suitability for large substrates, the productive formation of cyclic sulfamides 2t containing densely functionalized deoxyuridine highlights the remarkable degree of functional group tolerance by the catalytic system (entry 34). It is also notable that [Co(P4)] could effectively desymmetrize the two benzyl groups in azide 1s, leading to trans-(S,S)-2s with effective control of the two newly-generated stereogenic centers (entry 33). However, when [Co(P5)] was used as the catalyst, the catalytic reactions of azides 1s-1u afforded the amination products 2s-2u with moderate (R)-enantioselectivity (~58:42 er) (see SI). As well, these results are considered to be consistent with the general models in view of the decreased preference for C$_8$-TS(I)$^{under}$ over C$_8$-TS(I)$^{near}$ as a result of the large size associated with these substrates. Furthermore, the observed systematic variation in enantiodivergence described herein appears to be well consistent with the stereochemical models.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A catalyst for the stereoselective synthesis of chiral sulfamides, the catalyst having Formula I:

Formula I

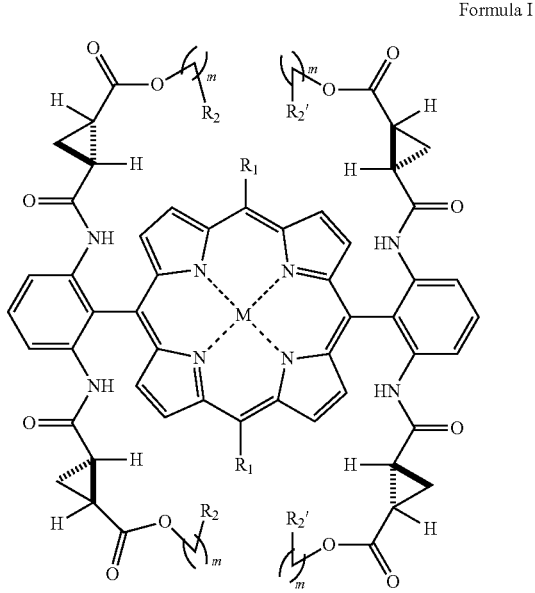

wherein M comprises cobalt;
wherein m is 1;
wherein R₁ is selected from

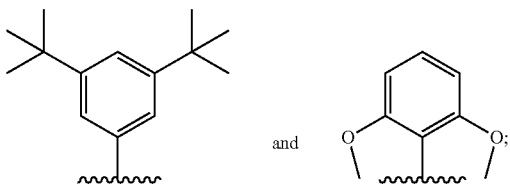 [SMILES: *c1cc(C(C)(C)C)cc(C(C)(C)C)c1 ; "and" ; *c1c(OC)cccc1OC]

and
wherein each $R_2$ and $R_2'$ is independently —CH₂— and each $R_2$ is chemically linked to an adjoining $R_2'$ with a bridge having a structure

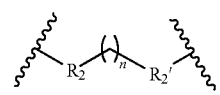

wherein n is 0, 2, 4, or 6.

2. The catalyst of claim 1, wherein n is 4 and R₁ is

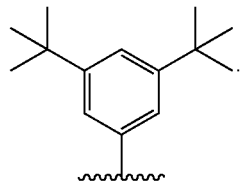 [SMILES: *c1cc(C(C)(C)C)cc(C(C)(C)C)c1 ; "."]

3. The catalyst of claim 1, wherein n is 2 and R₁ is

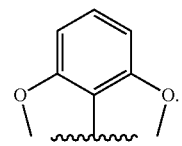

4. A method for the stereoselective synthesis of a chiral sulfamide, the method comprising contacting a sulfamoyl azide substrate with the catalyst of claim 1 in a solvent.

5. The method of claim 4, wherein the solvent comprises methyl tert-butyl ether (MTBE).

6. The method of claim 4, wherein the substrate has Formula II:

Formula II

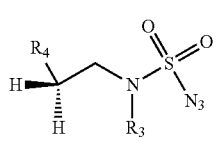

wherein $R_3$ is a benzoyl group, and
wherein $R_4$ is selected from:

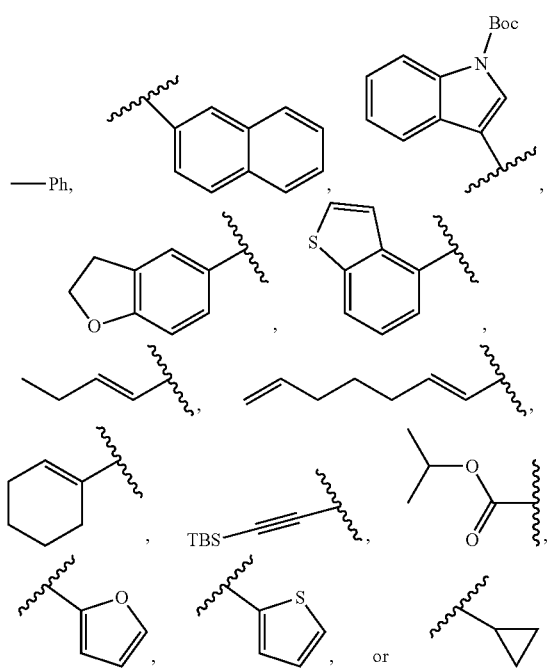

or wherein $R_3$ is —(CH₂)₃-Ph and $R_4$ is -Ph.

7. The method of claim 6, wherein the chiral sulfamide consists of the following structures:
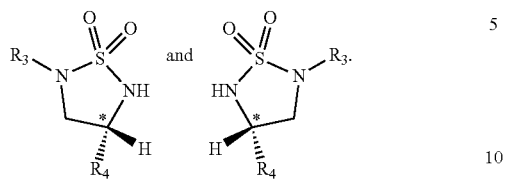
8. The method of claim 7, wherein the ratio of (R) enantiomer at * to (S) enantiomer at * is from about 4:96 to about 99:1.
* * * * *